United States Patent
Lassner et al.

(10) Patent No.: US 10,030,245 B2
(45) Date of Patent: Jul. 24, 2018

(54) METHODS FOR PRODUCING A COMPLEX TRANSGENIC TRAIT LOCUS

(75) Inventors: Michael Lassner, Urbandale, IA (US); Derek Jantz, Durham, NC (US); James Jefferson Smith, Durham, NC (US); Mark Cigan, Johnston, IA (US); Carl Falco, Wilmington, DE (US); Huirong Gao, Johnston, IA (US); Zhongsen Li, Hockessin, DE (US); Zhan-Bin Liu, West Chester, PA (US); Sergei Svitashev, Johnston, IA (US)

(73) Assignees: E I DU PONT DE NEMOURS AND COMPANY, Wilmington, DE (US); PIONEER HI-BRED INTERNATIONAL, INC. IA (US)

( * ) Notice: Subject to any disclaimer, the term of this patent is extended or adjusted under 35 U.S.C. 154(b) by 761 days.

(21) Appl. No.: 13/427,138

(22) Filed: Mar. 22, 2012

(65) Prior Publication Data
US 2013/0263324 A1 Oct. 3, 2013

Related U.S. Application Data

(60) Provisional application No. 61/466,602, filed on Mar. 23, 2011, provisional application No. 61/499,443, filed on Jun. 21, 2011.

(51) Int. Cl.
C12N 15/82 (2006.01)
A01H 1/06 (2006.01)
C12N 9/22 (2006.01)

(52) U.S. Cl.
CPC ........... *C12N 15/8202* (2013.01); *A01H 1/06* (2013.01); *C12N 9/22* (2013.01); *C12N 15/8213* (2013.01)

(58) Field of Classification Search
None
See application file for complete search history.

(56) References Cited

U.S. PATENT DOCUMENTS

| 7,223,601 | B2 * | 5/2007 | Baszczynski et al. | 435/462 |
| 2003/0050258 | A1 * | 3/2003 | Calos | A61K 48/00 514/44 R |
| 2009/0133152 | A1 * | 5/2009 | Lyznik et al. | 800/275 |
| 2010/0100980 | A1 * | 4/2010 | Bull | A01H 1/02 800/260 |

FOREIGN PATENT DOCUMENTS

| WO | WO 2008/148559 A1 | 12/2008 |
| WO | WO 2009/006297 A2 | 1/2009 |
| WO | WO 2009/042164 A1 | 4/2009 |
| WO | WO 2009/114321 A2 | 9/2009 |
| WO | WO 2010/077319 A1 | 7/2010 |
| WO | WO 2011/117249 A1 | 9/2011 |

OTHER PUBLICATIONS

Lyznik et al., 2012, In: Transgenic Plants: Methods and Protocols, Methods in Molecular Biology 847: 399-416.*
Cai et al., 2009, Plant. Mol. Biol. 69: 699-709.*
Zeevi et al., 2009, Proc. Natl. Acad. Sci. USA 105: 12785-12790.*
Gilbertson, 2003, Trends in Biotechnology 21: 550-555.*
Civardi et al., 1994, Proc. Natl. Acad. Sci. USA 91: 8268-8272.*
Civardi et al., 1994, Proc. Natl. Acad. Sci. USA 91: 8268-8271.*
Que, Q., et al., "Trait stacking in transgenic crops—Challenges and opportunities," *GM Crops*, 2010, vol. 1(4), pp. 220-229.
Townsend, J., et al., "High-frequency modification of plant genes using engineered zinc-finger nucleases," *Nature*, 2009, vol. 459(7245), pp. 442-446.
International Search Report of the International Searching Authority dated Jun. 11, 2012 for PCT/US2012/030061, filed on Mar. 22, 2012 and published as WO 2012/129373 on Sep. 9, 2012 (Applicant—Pioneer Hi-Bred Int'l, Inc. // Inventors—Lassner, et al.) (7 pages).
Written Opinion of the International Searching Authority dated Sep. 23, 2013 for PCT/US2012/030061, filed on Mar. 22, 2012 and published as WO 2012/129373 on Sep. 9, 2012 (Applicant—Pioneer Hi-Bred Int'l, Inc. // Inventors—Lassner, et al.) (9 pages).
International Preliminary Report on Patentability dated Sep. 24, 2013 for PCT/US2012/030061, filed on Mar. 22, 2012 and published as WO 2012/129373 on Sep. 9, 2012 (Applicant—Pioneer Hi-Bred Int'l, Inc. // Inventor—Lassner, et al.) (10 pages).

* cited by examiner

*Primary Examiner* — Amjad Abraham
*Assistant Examiner* — Bratislav Stankovic
(74) *Attorney, Agent, or Firm* — Pioneer Hi-Bred Int'l, Inc.

(57) ABSTRACT

Methods for producing in a plant a complex transgenic trait locus comprising at least two altered target sequences in a genomic region of interest are disclosed. The methods involve the use of two or more double-strand-break-inducing agents, each of which can cause a double-strand break in a target sequence in the genomic region of interest which results in an alteration in the target sequence. Also disclosed are complex transgenic trait loci in plants. A complex transgenic trait locus comprises at least two altered target sequences that are genetically linked to a polynucleotide of interest. Plants, plant cells, plant parts, and seeds comprising one or more complex transgenic trait loci are also disclosed.

3 Claims, 14 Drawing Sheets

Figure 1:
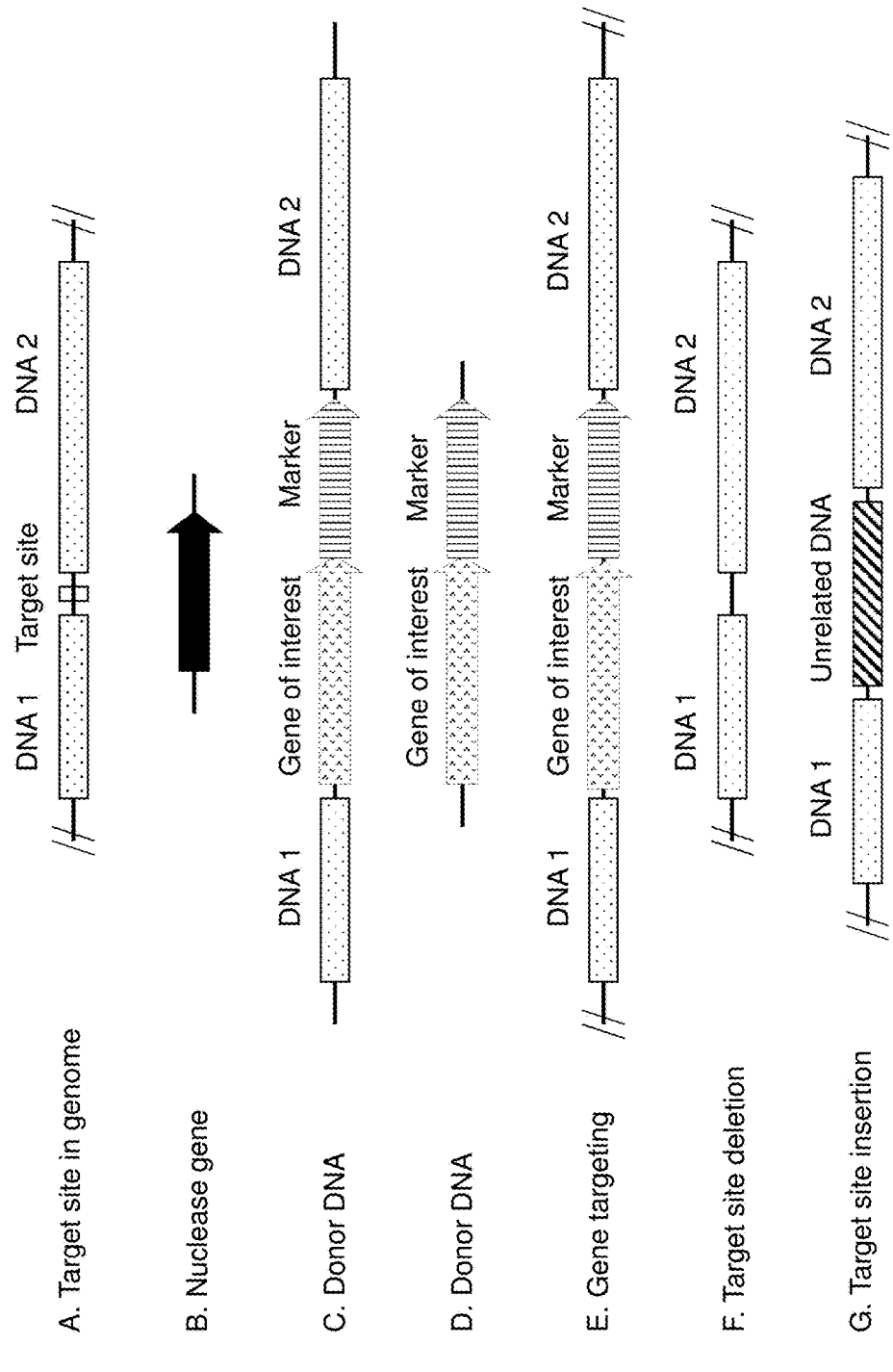

Genetic / physical Distance Between Target Sites and Transgene of Interest

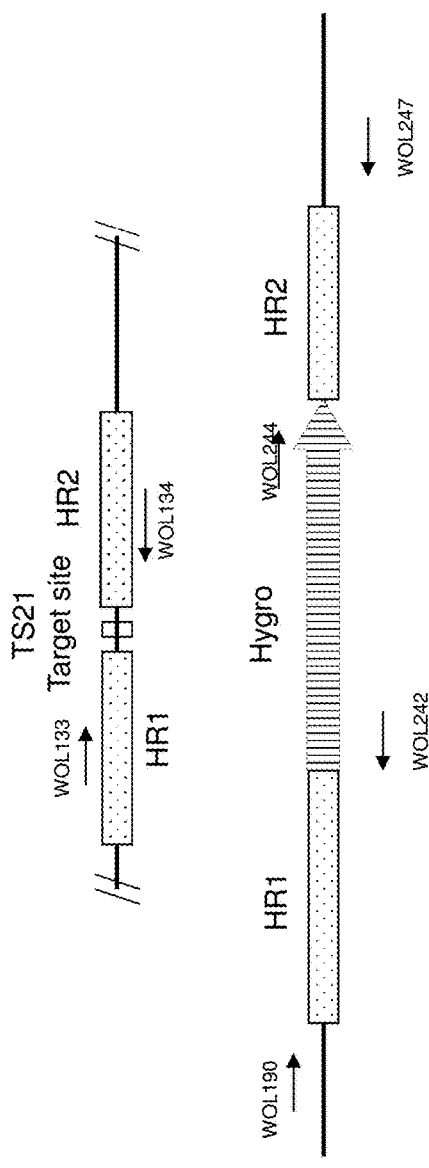

FIG. 4

A: Alignment of sequences of TS5 transgenic events (TS5 target sites underlined)

```
                                                                BssSI
Deletion/insertion event
WT     TAATGATCACATTTTTTTTTCTCACACTCACCTAAGTGCACGAGTACGAGTAAGTCTTAGGTTAAAGTTCATGCCCCCCCCCCCAAAA
P2A6   TAATGATCACATTTTTTTTTCTCACACTCACCTAAGTGCACGAGTACGAGTACACGT......326bp deletion with 42bp filler DNA..........
P1B9   TAATGATCACATTTTTTTTTCTCACACTCACCTAAGTGCACGAGTACGAGTACACAC▼ GTAAGTCTTAGGTTAAAGTTCATGCCCCCCCCCCCCAAAA
P2C5   TAATGATCACATTTTTTTTTCTCACACTCACCTCACACTCACCTAAGTGCACGAG......94bp deletion with 193bp filler DNA..........
```

▼ indicates a 161 bp insertion into the target site

B: Alignment of sequences of selected TS14 transgenic event (TS5 target sites underlined)

```
                                                                         BsiWI
Deletion/insertion event
WT      TAATGATCACATTTTTTTTTTTTCTCACACTCACCTAAGTGCAGACGTACGCAAGTAGCTTTGTTACTTTCGTATTGACAATTCAAAATCGTCTTTTATTTTTATT
P4G10   TAATGATCACATTTTTTTTTTTTCTCACACTCACCTAAGTGCAGACGTA▼ CAAGTAGCTTTGTTACTTTCGTATTGACAATTCAAAATCGTCTTTTATTTTTATT
```

HO Mega14 target sites are underlined with the cut sites in bold

▶ indicates a 115 bp insertion into the target site

Gene Integration by Homologous Recombination Enabled by Double-Strand Breaks with Meganuclease Near a Transgenic Event (TE) of Interest Location of Target Sites Near a Herbicide-Resistant Transgenic Event in Soybean

FIG. 9
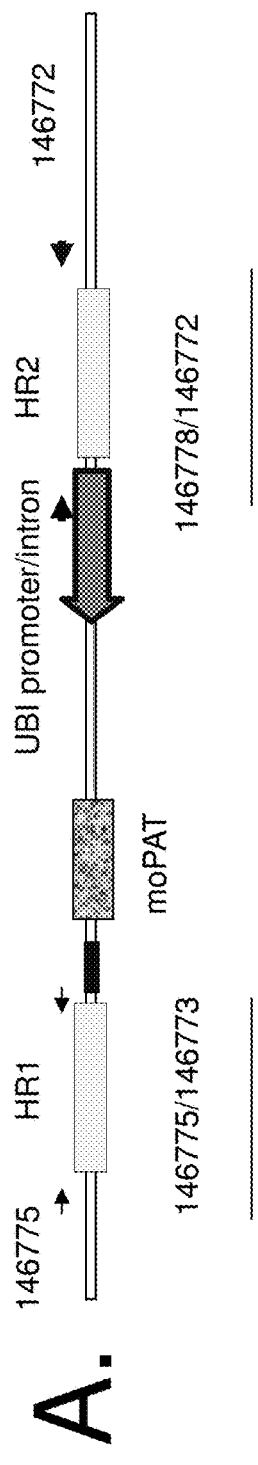
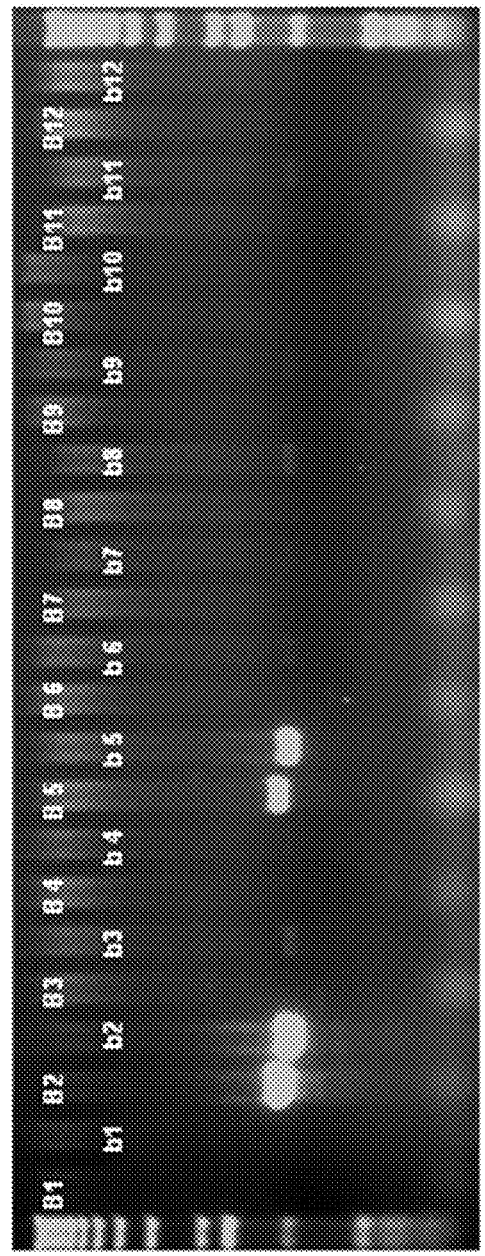

SEQUENCE LISTING

<160> NUMBER OF SEQ ID NOS: 129

<210> SEQ ID NO 1
<211> LENGTH: 22
<212> TYPE: DNA
<213> ORGANISM: Glycine max

<400> SEQUENCE: 1
ggcactctcg tgtgtgatta aa                                            22

<210> SEQ ID NO 2
<211> LENGTH: 22
<212> TYPE: DNA
<213> ORGANISM: Glycine max

<400> SEQUENCE: 2
cagacgtacg caagtagctt tg                                            22

<210> SEQ ID NO 3
<211> LENGTH: 22
<212> TYPE: DNA
<213> ORGANISM: Glycine max

<400> SEQUENCE: 3
gagtcccacg caagagcata aa                                            22

<210> SEQ ID NO 4
<211> LENGTH: 22
<212> TYPE: DNA
<213> ORGANISM: Glycine max

<400> SEQUENCE: 4
aagacttacg tgtgtactcg tg                                            22

<210> SEQ ID NO 5
<211> LENGTH: 22
<212> TYPE: DNA
<213> ORGANISM: Glycine max

<400> SEQUENCE: 5
gacattgtcg tgagaaaaga ga                                            22

<210> SEQ ID NO 6
<211> LENGTH: 22
<212> TYPE: DNA
<213> ORGANISM: Glycine max

<400> SEQUENCE: 6
aaatctgtct tgcgaaacgg ca                                            22

<210> SEQ ID NO 7
<211> LENGTH: 22
<212> TYPE: DNA
<213> ORGANISM: Glycine max

<400> SEQUENCE: 7
tattctctca taaataaact tt                                            22

<210> SEQ ID NO 8
<211> LENGTH: 22
<212> TYPE: DNA
<213> ORGANISM: Glycine max

<400> SEQUENCE: 8

<210> SEQ ID NO 9
<211> LENGTH: 1272
<212> TYPE: DNA
<213> ORGANISM: Artificial Sequence
<220> FEATURE:
<223> OTHER INFORMATION: synthetic construct; plant optimized nucleotide sequence of TS21 meganuclease

<400> SEQUENCE: 9

```
atggcaccga agaagaagcg caaggtgcat atgaacacca agtacaacaa ggagttcctg        60
ctctacctgg ccggcttcgt ggacggcgac ggctccatca tggcgcagat caagccgcag       120
cagtcctgca agttcaagca cgcgctccag ctgaccttca ccgtgaccca gaagacgcag       180
aggcgctggt tcctcgacaa gctggtcgac gagatcgggg tgggcaaggt ctacgaccgc       240
gggtcggtgt ccgactacat cctctcccag atcaagcccc tgcacaactt cctcacccag       300
ctccagccgt tcctcaagct gaagcagaag caggcgaacc tcgtcctgaa gatcatcgag       360
cagctcccct cggccaagga gtccccggac aagttcctgg aggtaagttt ctgcttctac       420
ctttgatata tatataataa ttatcattaa ttagtagtaa tataatattt caaatatttt       480
tttcaaaata aagaatgta gtatatagca attgcttttc tgtagtttat aagtgtgtat       540
attttaattt ataacttttc taatatatga ccaaaacatg gtgatgtgca ggtgtgcacg       600
tgggtcgacc agatcgcggc cctcaacgac agcaagaccc gcaagacgac ctcggagacg       660
gtgcgggcgg tcctggactc cctcccagga tccgtgggag gtctatcgcc atctcaggca       720
tccagcgccg catcctcggc ttcctcaagc ccgggttcag ggatctccga agcactcaga       780
gctggagcaa ctaagtccaa ggaattcctg ctctacctgg ccggcttcgt ggacggcgac       840
ggctccatca aggcgcagat caagccgcgc cagtcccgca agttcaagca cgagctctcc       900
ctgaccttcc aggtgaccca gaagacgcag aggcgctggt tcctcgacaa gctggtcgac       960
gagatcgggg tgggctacgt ctacgaccgc gggtcggtgt ccgactacat cctctcccag      1020
atcaagcccc tgcacaactt cctcacccag ctccagccgt tcctcaagct gaagcagaag      1080
caggcgaacc tcgtcctgaa gatcatcgag cagctcccct cggccaagga gtccccggac      1140
aagttcctgg aggtgtgcac gtgggtcgac cagatcgcgg ccctcaacga cagcaagacc      1200
cgcaagacga cctcggagac ggtgcgggcg gttctagact ccctcagcga agaagaagaag    1260
tcgtccccct ga                                                         1272
```

<210> SEQ ID NO 10
<211> LENGTH: 1272
<212> TYPE: DNA
<213> ORGANISM: Artificial Sequence
<220> FEATURE:
<223> OTHER INFORMATION: synthetic construct; plant optimized nucleotide sequence of TS14 meganuclease

<400> SEQUENCE: 10

```
atggcaccga agaagaagcg caaggtgcat atgaacacca agtacaacaa ggagttcctg        60
ctctacctgg ccggcttcgt ggacggcgac ggctccatca tcgcgtccat caagccggag       120
cagtcctaca agttcaagca ccgcctctcc ctgaccttca ccgtgaccca gaagacgcag       180
aggcgctggt tcctcgacaa gctggtcgac gagatcgggg tgggcaaggt ctacgaccgc       240
gggtcggtgt ccgactaccg cctctcccag atcaagcccc tgcacaactt cctcacccag       300
```

```
ctccagccgt tcctgaagct caagcagaag caggccaacc tcgtgctgaa gatcatcgag    360
cagctgccct ccgccaagga atccccggac aagttcctgg aggtaagttt ctgcttctac    420
ctttgatata tatataataa ttatcattaa ttagtagtaa tataatattt caaatatttt    480
tttcaaaata aaagaatgta gtatatagca attgcttttc tgtagtttat aagtgtgtat    540 atttttaattt ataacttttc taatatatga ccaaaacatg gtgatgtgca ggtgtgcacg    600
tgggtggacc agatcgcggc cctcaacgac agcaagaccc gcaagacgac ctcggagacg    660
gtgcgggcgg tcctggactc cctcccagga tccgtgggag gtctatcgcc atctcaggca    720
tccagcgccg catcctcggc ttcctcaagc ccgggttcag ggatctccga agcactcaga    780
gctggagcaa ctaagtccaa ggaattcctg ctctacctgg ccggcttcgt ggacggcgac    840
ggctccatca tcgcgaagat cacccccgaac cagtcctaca agttcaagca ccagctccag    900
ctgcgcttca ccgtgaccca aagacgcag aggcgctggt cctcgacaa gctggtcgac    960 gagatcgggg tgggcaaggt ctacgaccgc gggtcggtgt ccgactacat cctctcccag   1020
atcaagcccc tgcacaactt cctcacccag ctccagccgt tcctcaagct gaagcagaag   1080
caggcgaacc tcgtcctgaa gatcatcgag cagctcccct cggccaagga gtccccggac   1140
aagttcctgg aggtgtgcac gtgggtcgac cagatcgcgg ccctcaacga cagcaagacc   1200
cgcaagacga cctcggagac ggtgcgggcg gttctagact ccctcagcga gaagaagaag   1260 tcgtcccct ga                                                        1272

<210> SEQ ID NO 11
<211> LENGTH: 1272
<212> TYPE: DNA
<213> ORGANISM: Artificial Sequence
<220> FEATURE:
<223> OTHER INFORMATION: synthetic construct; plant optimized nucleotide
      sequence of TS30 meganuclease

<400> SEQUENCE: 11
atggcaccga agaagaagcg caaggtgcat atgaacacca agtacaacaa ggagttcctg     60
ctctacctgg ccggcttcgt ggacggcgac ggctccatca tggcgaagat caagccggag    120
cagtcctaca agttcaagca ccgcctcatg ctgaccttca ccgtgaccca aagacgcag    180 aggcgctggt cctcgacaa gctggtcgac gagatcgggg tgggctacgt ctacgaccgc    240
gggtcggtgt ccgactacat cctctcccag atcaagcccc tgcacaactt cctcacccag    300
ctccagccgt tcctcaagct gaagcagaag caggcgaacc tcgtcctgaa gatcatcgag    360
cagctcccct cggccaagga gtccccggac aagttcctgg aggtaagttt ctgcttctac    420
ctttgatata tatataataa ttatcattaa ttagtagtaa tataatattt caaatatttt    480
tttcaaaata aaagaatgta gtatatagca attgcttttc tgtagtttat aagtgtgtat    540 atttttaattt ataacttttc taatatatga ccaaaacatg gtgatgtgca ggtgtgcacg    600
tgggtcgacc agatcgcggc cctcaacgac agcaagaccc gcaagacgac ctcggagacg    660
gtgcgggcgg tcctggactc cctcccagga tccgtgggag gtctatcgcc atctcaggca    720
tccagcgccg catcctcggc ttcctcaagc ccgggttcag ggatctccga agcactcaga    780
gctggagcaa ctaagtccaa ggaattcctg ctctacctgg ccggcttcgt ggacggcgac    840
ggctccatca aggcgtccat caccccgcag cagtcctgca agttcaagca cgcgctccag    900
ctgaccttcc aggtgaccca aagacgcag aggcgctggt cctcgacaa gctggtcgac    960 gagatcgggg tgggcaaggt ctacgaccgc gggtcggtgt ccgactaccg cctctcccag   1020
```

```
atcaagcccc tgcacaactt cctcacccag ctccagccgt tcctcaagct gaagcagaag    1080
caggcgaacc tcgtcctgaa gatcatcgag cagctcccct cggccaagga gtccccggac    1140
aagttcctgg aggtgtgcac gtgggtcgac cagatcgcgg ccctcaacga cagcaagacc    1200
cgcaagacga cctcggagac ggtgcgggcg gttctagact ccctcagcga agaagaag     1260 tcgtccccct ga                                                        1272

<210> SEQ ID NO 12
<211> LENGTH: 1272
<212> TYPE: DNA
<213> ORGANISM: Artificial Sequence
<220> FEATURE:
<223> OTHER INFORMATION: synthetic construct; Plant optimized nucleotide
      sequence of TS5 meganuclease

<400> SEQUENCE: 12
atggcaccga agaagaagcg caaggtgcat atgaacacca agtacaacaa ggagttcctg      60
ctctacctgg ccggcttcgt ggacggcgac ggttccatca tcgcgcagat caagccggag    120
cagtcctaca agttcaagca ccgcctctcc ctgaccttca ccgtgaccca agagacgcag    180
aggcgctggt tcctcgacaa gctggtcgac gagatcgggg tgggctacgt ctacgaccgc    240
gggtcggtgt ccgactaccg cctctcccag atcaagcccc tgcacaactt cctcacccag    300
ctccagccgt tcctgaagct caagcagaag caggccaacc tcgtgctgaa gatcatcgag    360
cagctgccct ccgccaagga atccccggac aagttcctgg aggtaagttt ctgcttctac    420
ctttgatata tatataataa ttatcattaa ttagtagtaa tataatatttt caaatatttt    480 tttcaaaata aagaatgta gtatatagca attgcttttc tgtagtttat aagtgtgtat     540
attttaattt ataacttttc taatatatga ccaaaacatg gtgatgtgca ggtgtgcacg     600
tgggtggacc agatcgcggc cctcaacgac agcaagaccc gcaagacgac ctcggagacg    660
gtgcgggcgg tcctggactc cctcccagga tccgtgggag gtctatcgcc atctcaggca     720
tccagcgccg catcctcggc ttcctcaagc ccgggttcag ggatctccga gcactcaga     780 gctggagcaa ctaagtccaa ggaattcctg ctctacctgg ccggcttcgt ggacggcgac    840
ggctccatca tcgcgtccat ctccccgcgc cagtcctaca agttcaagca cgagctccgc    900
ctgaccttca ccgtgaccca gaagacgcag aggcgctggt tcctcgacaa gctggtcgac    960
gagatcgggg tgggctacgt ctacgaccgc gggtcggtgt ccgactaccg cctctcccag   1020
atcaagcccc tgcacaactt cctcacccag ctccagccgt tcctcaagct gaagcagaag   1080
caggcgaacc tcgtcctgaa gatcatcgag cagctcccct cggccaagga gtccccggac   1140
aagttcctgg aggtgtgcac gtgggtcgac cagatcgcgg ccctcaacga cagcaagacc   1200
cgcaagacga cctcggagac ggtgcgggcg gttctagact ccctcagcga agaagaag    1260 tcgtccccct ga                                                       1272

<210> SEQ ID NO 13
<211> LENGTH: 1272
<212> TYPE: DNA
<213> ORGANISM: Artificial Sequence
<220> FEATURE:
<223> OTHER INFORMATION: synthetic construct; Plant optimized nucleotide
      sequence of TS7 meganuclease

<400> SEQUENCE: 13
atggcaccga agaagaagcg caaggtgcat atgaacacca agtacaacaa ggagttcctg      60
ctctacctgg ccggcttcgt ggacggcgac ggctccatca tcgcgcagat caccccgcgc    120
```

```
cagtcctaca agttcaagca ctccctccag ctgaccttcc aggtgaccca gaagacgcag      180
aggcgctggt tcctcgacaa gctggtcgac gagatcgggg tgggcaaggt ccgcgaccgc      240
gggtcggtgt ccgactacat cctctcccag atcaagcccc tgcacaactt cctcacccag      300
ctccagccgt tcctcaagct gaagcagaag caggcgaacc tcgtcctgaa gatcatcgag      360
cagctccctt cggccaagga gtccccggac aagttcctgg aggtaagttt ctgcttctac      420
ctttgatata tatataataa ttatcattaa ttagtagtaa tataatattt caaatatttt      480
tttcaaaata aagaatgta gtatatagca attgcttttc tgtagtttat aagtgtgtat       540
attttaattt ataacttttc taatatatga ccaaaacatg gtgatgtgca ggtgtgcacg      600
tgggtcgacc agatcgcggc cctcaacgac agcaagaccc gcaagacgac ctcggagacg      660
gtgcgggcgg tcctggactc cctcccagga tccgtgggag gtctatcgcc atctcaggca      720
tccagcgccg catcctcggc ttcctcaagc ccgggttcag ggatctccga agcactcaga      780
gctggagcaa ctaagtccaa ggaattcctg ctctacctgg cgggcttcgt ggacggcgac      840
ggctccatca tcgcgcagat ctccccgcag cagtccgcga agttcaagca catcctctcc      900
ctgaccttcc aggtgaccca gaagacgcag aggcgctggt tcctcgacaa gctggtcgac      960
gagatcgggg tgggcaaggt ctacgaccgc gggtcggtgt ccgactaccg cctctcccag     1020
atcaagcccc tgcacaactt cctcacccag ctccagccgt tcctcaagct gaagcagaag     1080
caggcgaacc tcgtcctgaa gatcatcgag cagctcccct cggccaagga gtccccggac     1140
aagttcctgg aggtgtgcac gtgggtcgac cagatcgcgg ccctcaacga cagcaagacc     1200
cgcaagacga cctcggagac ggtgcgggcg gttctagact ccctcagcga agaagaag      1260 tcgtccccct ga                                                           1272

<210> SEQ ID NO 14
<211> LENGTH: 1272
<212> TYPE: DNA
<213> ORGANISM: Artificial Sequence
<220> FEATURE:
<223> OTHER INFORMATION: synthetic construct; Plant optimized nucleotide
      sequence of TS4 meganuclease

<400> SEQUENCE: 14
atggcaccga agaagaagcg caaggtgcat atgaacacca agtacaacaa ggagttcctg       60
ctctacctgg ccggcttcgt ggacggcgac ggctccatca tcgcgcagat ccgcccgcgc      120
cagtcccgca agttcaagca cgagctcgag ctgcgcttcc aggtgaccca gaagacgcag      180
aggcgctggt tcctcgacaa gctggtcgac gagatcgggg tgggctacgt ctacgaccgc      240
gggtcggtgt ccgactacat cctctcccag atcaagcccc tgcacaactt cctcacccag      300
ctccagccgt tcctcaagct gaagcagaag caggcgaacc tcgtcctgaa gatcatcgag      360
cagctcccct cggccaagga gtccccggac aagttcctgg aggtaagttt ctgcttctac      420
ctttgatata tatataataa ttatcattaa ttagtagtaa tataatattt caaatatttt      480
tttcaaaata aagaatgta gtatatagca attgcttttc tgtagtttat aagtgtgtat       540
attttaattt ataacttttc taatatatga ccaaaacatg gtgatgtgca ggtgtgcacg      600
tgggtcgacc agatcgcggc cctcaacgac agcaagaccc gcaagacgac ctcggagacg      660
gtgcgggcgg tcctggactc cctcccagga tccgtgggag gtctatcgcc atctcaggca      720
tccagcgccg catcctcggc ttcctcaagc ccgggttcag ggatctccga agcactcaga      780
gctggagcaa ctaagtccaa ggaattcctg ctctacctgg cgggcttcgt ggacggcgac      840
```

```
ggctccatca tcgcgcagat caagccgaac cagtcctaca agttcaagca ccagctcatg      900
ctgaccttcc aggtgaccca gaagacgcag aggcgctggt tcctcgacaa gctggtcgac      960
gagatcgggg tgggctacgt ccgcgaccgc gggtcggtgt ccgactacat cctctccgag     1020
atcaagcccc tgcacaactt cctcacccag ctccagccgt tcctcaagct gaagcagaag     1080
caggcgaacc tcgtcctgaa gatcatcgag cagctcccct cggccaagga gtccccggac     1140
aagttcctgg aggtgtgcac gtgggtcgac cagatcgcgg cctcaacga cagcaagacc     1200 cgcaagacga cctcggagac ggtgcgggcg gttctagact ccctcagcga agaagaag      1260 tcgtcccct ga                                                          1272
```

<210> SEQ ID NO 15
<211> LENGTH: 1272
<212> TYPE: DNA
<213> ORGANISM: Artificial Sequence
<220> FEATURE:
<223> OTHER INFORMATION: synthetic construct; Plant optimized nucleotide sequence of TS22 meganuclease

<400> SEQUENCE: 15

```
atggcaccga agaagaagcg caaggtgcat atgaacacca agtacaacaa ggagttcctg       60
ctctacctgg cgggcttcgt ggacggcgac ggctccatca tcgcgcagat ctccccgaac      120
cagtcctaca agttcaagca ccagctccgc ctgaccttca ccgtgaccca gaagacgcag      180
aggcgctggt tcctcgacaa gctggtcgac gagatcgggg tgggcatggt ctacgaccag      240
gggtcggtgt cccactaccg cctctcccag atcaagcccc tgcacaactt cctcacccag      300
ctccagccgt tcctcaagct gaagcagaag caggcgaacc tcgtcctgaa gatcatcgag      360
cagctcccct cggccaagga gtccccggac aagttcctgg aggtaagttt ctgcttctac      420
ctttgatata tatataataa ttatcattaa ttagtagtaa tataatattt caaatatttt      480
tttcaaaata aaagaatgta gtatatagca attgcttttc tgtagtttat aagtgtgtat      540
attttaattt ataacttttc taatatatga ccaaaacatg gtgatgtgca ggtgtgcacg      600
tgggtcgacc agatcgcggc cctcaacgac agcaagaccc gcaagacgac ctcggagacg      660
gtgcgggcgg tcctggactc cctcccagga tccgtgggag gtctatcgcc atctcaggca      720
tccagcgccg catcctcggc ttcctcaagc ccggggttcag ggatctccga agcactcaga      780
gctggagcaa ctaagtccaa ggaattcctg ctctacctgg cgggcttcgt ggacggcgac      840
ggctccatca aggcgcagat caagccgcag cagtgctaca agttcaagca cgcgctcatg      900
ctgaccttcc aggtgaccca gaagacgcag aggcgctggt tcctcgacaa gctggtcgac      960
gagatcgggg tgggctacgt ctacgaccgc gggtcggtgt ccgactacat cctctcccag     1020
atcaagcccc tgcacaactt cctcacccag ctccagccgt tcctcaagct gaagcagaag     1080
caggcgaacc tcgtcctgaa gatcatcgag cagctcccct cggccaagga gtccccggac     1140
aagttcctgg aggtgtgcac gtgggtcgac cagatcgcgg cctcaacga cagcaagacc     1200 cgcaagacga cctcggagac ggtgcgggcg gttctagact ccctcagcga agaagaag      1260 tcgtcccct ga                                                          1272
```

<210> SEQ ID NO 16
<211> LENGTH: 1272
<212> TYPE: DNA
<213> ORGANISM: Artificial Sequence
<220> FEATURE:
<223> OTHER INFORMATION: synthetic construct; Plant optimized nucleotide sequence of TS24 meganuclease

<400> SEQUENCE: 16

```
atggcaccga agaagaagcg caaggtgcat atgaacacca agtacaacaa ggagttcctg      60
ctctacctgg cgggcttcgt ggacggcgac ggctccatca tcgcgtccat caccccgaac     120
cagtcccgca agttcaagca ccagctccag ctgaccttca ccgtgaccca agagacgcag     180
aggcgctggt tcctcgacaa gctggtcgac gagatcgggg tgggcaaggt ccgcgaccgc     240
gggtcggtgt ccgactaccg cctctcccag atcaagcccc tgcacaactt cctcacccag     300
ctccagccgt tcctcaagct gaagcagaag caggcgaacc tcgtcctgaa gatcatcgag     360
cagctcccct cggccaagga gtccccggac aagttcctgg aggtaagttt ctgcttctac     420
ctttgatata tatataataa ttatcattaa ttagtagtaa tataatattt caaatatttt     480
tttcaaaata aagaatgta gtatatagca attgcttttc tgtagtttat aagtgtgtat      540
attttaattt ataacttttc taatatatga ccaaaacatg gtgatgtgca ggtgtgcacg     600
tgggtcgacc agatcgcggc cctcaacgac agcaagaccc gcaagacgac ctcggagacg     660
gtgcgggcgg tcctggactc cctcccagga tccgtgggag gtctatcgcc atctcaggca     720
tccagcgccg catcctcggc ttcctcaagc ccgggttcag ggatctccga agcactcaga     780
gctggagcaa ctaagtccaa ggaattcctg ctctacctgg cgggcttcgt ggacggcgac     840
ggctccatca aggcgcagat caccccgaac cagtcctgca agttcaagca ccagctccgc     900
ctgaccttcc aggtgaccca agagacgcag aggcgctggt tcctcgacaa gctggtcgac     960
gagatcgggg tgggcaaggt ctacgaccgc gggtcggtgt ccgactacat cctctcccag    1020
atcaagcccc tgcacaactt cctcacccag ctccagccgt tcctcaagct gaagcagaag    1080
caggcgaacc tcgtcctgaa gatcatcgag cagctcccct cggccaagga gtccccggac    1140
aagttcctgg aggtgtgcac gtgggtcgac cagatcgcgg ccctcaacga cagcaagacc    1200
cgcaagacga cctcggagac ggtgcgggcg gttctagact ccctcagcga agaagaagaag   1260
tcgtcccccct ga                                                       1272
```

<210> SEQ ID NO 17
<211> LENGTH: 1020
<212> TYPE: DNA
<213> ORGANISM: Glycine max

<400> SEQUENCE: 17

```
ttatttatcc cctataaagg gcaccagtta gttcaatctg atgtctaacc taatttggat      60
acatgccttt tattgcagct gccgtccgtg cacagaggag tcttaggagg aacaactgta     120
gagaaaagga tctgccaaat tcgctagaaa attcaccaga acaccaccc gttatccaat      180
taaacaagat ttttggatca cttgtgaagt tgaattgcta tccaactgct attcccattt     240
ctaaaccttg ttacacgagc atcttgatca atggtctaga aagggaaata gcagttgagt     300
ggtgcttcaa cgataagtta ttggatttag tatttatctt agcctgtttt cgtgtacttt     360
gttttgccgg atggaggtat gtgatttgt ctatgattct taatacaata acctacactt      420
actctcattg atagtttgtg cagatctaat agctatgaag caccgatacc ggacatgaca     480
cggtcaggtg gacacatgta atgtctaaaa tattaaaata tagaacgtag tacgagtgtc     540
gtgtcggtgt tagatactga tagggacgcg tgtcggacac cggacatgac aaaggactga     600
agtgcttaga attgttttatg tttgagatct tgttgatgag aggcagatag aggtcaactt     660
gccaagataa cctacagttc tatattagat gctttgtgca aaaacgatca tccaaaggct     720
```

```
attggattat tcaagaaaac taaagaccaa ggagttcaaa accgccatgt tacacatgca    780
ctatacttat ggatggattg tgcgaagtgg aagacttcag aatgcaaaaa tgattttca     840 ggatctactg attaaaggct atcaactaag tgtctgtctg tactctgtat aatgttatga    900
ttcataggct ttgtaaagag ggattttttg atgaagcatt gatctagaaa tctaaaatgg    960
aaaacagatc ttaaagaaga tacactgtgt aaatgtgtaa tggcactggc actctcgtgt   1020
```

<210> SEQ ID NO 18
<211> LENGTH: 1000
<212> TYPE: DNA
<213> ORGANISM: Glycine max

<400> SEQUENCE: 18

```
gtgtgtgatt aaaagtcata tatggtttaa gatactttt tttataaaga tagtagtggt     60 caattttcg atattacaca agtgtttctt tttcttctca ttgtactgta gatctgattt    120
actttcaatg attgtttaag tcactggtgt aattgtttgt gtttcaaata tcaaaccaag   180
ctgaaactga gatgatgatg atttgaaatg cttatctca tgtagtcgac tcaattttcc    240
tgtatatttc ttgttctttt taaagaaaca ggagcttta agatttaaaa caccagcata    300
ttttgtttgc ataatccaaa ttgtcttagg tgtaaagttg ctgacatttc ccttgatgtc    360
attgctgcat aattaattgg agccttttca aaacctatgg tttatttgt tggggattat    420 tcaaggaacg cgtgtctcag tctcaagtgt tatgattgct gatatcagtg atatattgct   480
gcacaatgaa gtggaactat tttaaatttc aattgatgat tctgcattca atttatcatc   540
tgaccttttt atcttttacc tcatctggca tttagtctt ttaccagata aaggaccaa    600 acacatgaga taatcacc aaatgaaaag aatgaaagac gagatataaa gatgtggttt     660 ttcttttat tcctggaaga tttagatgat gttttcaatt aagttgtttg tggatgcttt    720
tagatgattt tgttttgcat acatatgttt acttttttgt tctcaacttc tcattcattt    780
tccatgattt catcccgtga aaaagtgatt tagcagaaaa cgttttccc ctgttgtctt    840 tgtcctaaac ttttggattc taagtttttt tatatgaaaa ttagatcatt tggcacatgg    900
ttttccaaag acacaagtag actctttcta tgaaatcaat cttaaatccc tttagagga    960 aaaacatttt aaaggaggtg aacatgttgt ggagtgggaa                        1000
```

<210> SEQ ID NO 19
<211> LENGTH: 1000
<212> TYPE: DNA
<213> ORGANISM: Glycine max

<400> SEQUENCE: 19

```
attttgtcag tcttgtaact tttgaaaact tttttctttt tttttataga ccaataatat    60
aatatattat attaaaaaaa ccaaacttat aacaacatgt aacacgttag caaacagtag   120
atctcaacca aacgttcgaa aacttttgga tattatatat gtggctgttg gcactgctaa   180
actcagcagt atatctccat tattgatgag tctctcctaa aattatcttt ccaagtctta    240
ttttttattt aattggttag atattaaatt gaaaaataaa ataaaagttg tgttgttgtg    300
tagttttcgt cacttttact cataagaaaa tatatatact acgttagca tctttaaact    360 gaaaacttt cagttgaaat gcataacaaa atattggcca agtaattagt acacaaaatc    420
ttgctcaaag tgtttgccac catagattta ggttgtgttt aggacgatta cttaaaatat    480
cattaattga taattgaaac ttcaaataaa atttaaaagt ttaaaagttg aatagttaaa    540
```

| | |
|---|---|
| aatgaaagct gaaaataaat aagctaatgg attcaatttg aagtatttaa tagtatcaac | 600 |
| tagtgaaatt tattcataaa ttctctttta aatatatacc gattttatta gttaatataa | 660 |
| aaaaaaaata gtatgaacta ataaaattga tcaaaagtaa attaatataa atataaaatt | 720 |
| ttatatgatg aataatcagt agaaataata aaaaagttag ctctagaaaa gataaattga | 780 |
| tttaattagg gtcatgacaa aattttgcta gcttctattt tagtctgctt tgctttagaa | 840 |
| tatttacatt caaatagctc ttttatagca taacaaacat aaaaaaagct attgattcta | 900 |
| cataaaaaaa aaagattaat tatgctattc tttgggacaa aactttttaga tgaatgccaa | 960 |
| tttaaaataa ttattaaggt attcaagcag acgtacgcaa | 1000 |

<210> SEQ ID NO 20
<211> LENGTH: 928
<212> TYPE: DNA
<213> ORGANISM: Glycine max

<400> SEQUENCE: 20

| | |
|---|---|
| gcaagtagct ttgttacttt cgtattgaca attcaaaatc gtcttttatt tttattttgt | 60 |
| tttgtttaat tagaggactt tttgaagtcg tccatcatgt gtttcttatt ttgtcagttt | 120 |
| tgtcacttat gaacactttt tttacagaca aataatatat tatattaaaa aaaccatact | 180 |
| tataacaaca acatgtaaca cgttggcaaa cagttaatct caaccaaacg ctcgaaaact | 240 |
| tttggatatt atatatatat atgcatggct attggcagtg ctaaagtcat cattatcatt | 300 |
| ctaaagtcat cagtatcatt ctaattctca tattgagtgg attcatttca tcaatcactt | 360 |
| tgcctttctc atcataacca ccaaaatgcc aaccattaat ccagtggtt tgaaattcat | 420 |
| ggaaggcata ataacatta tgatgatgat gttgcaggtt gttgtttctg ctcaagacca | 480 |
| tattatgtgc attcagactg agagagaagc actcctccaa ttcaaggctg cacttctgga | 540 |
| tcactatggc atgctctctt cttggaccac ttctgattgc tgccaatggc aagggattcg | 600 |
| ctgctccaac ctcaccgccc atgttctaat gctcgacctt cacagtttag gcctcagagg | 660 |
| agagatccac cagtcgttga tggagttgca acaattaaac tatttaaacc tcagttggaa | 720 |
| ttcttttcaa ggcagaggaa tcccagagtt tcttggttct ctcaccaact tgagatacct | 780 |
| tgatctgtca cattctgatt tgaaggaaa aattccaact cagtttggct ctcttttctca | 840 |
| tttgaaatac ttaaatcttg ctgggaatta ttatctggag ggttcaatcc cacgtcaact | 900 |
| tggaaatctc tcccagttgc agcatctt | 928 |

<210> SEQ ID NO 21
<211> LENGTH: 1000
<212> TYPE: DNA
<213> ORGANISM: Glycine max

<400> SEQUENCE: 21

| | |
|---|---|
| tcatgccagc tcagccagc ttccaaatca tttccctcgt attggtagaa ggtccaatgg | 60 |
| tgcacactat cttcgtcttg cgcctaaacg ttggcttaga ccacattcca acagagttct | 120 |
| caccaaatgg ctgcaccca cgtaaatgtt gcaaatgctc ctcaatctaa acaccaaaac | 180 |
| acaaaaaggg tcacaagaat tatcccttaa aaactcaaaa aatgcaaaaa acacgaactt | 240 |
| ttggatcatc ttcgggtgac atggggatga cttcagaagg ggcagatttc cttgcactga | 300 |
| tctgaaggct tctgagcctg agtttggagc gtttgttatt gttctctccc aaagggaaca | 360 |
| ccttggaagc aaaagatgga ggctttaaca ggttttgggt tctgtcacgt gcagatccag | 420 |
| aagtggggca caatggggtg ctttgaatgg atcgtgaagc cacgacctga gccattgtta | 480 |

```
gaaagagaga gaaatggggt ggatgaggaa aagagagtg tgaggggtat aagaagaagg      540
tgagggggga aatggaagtt ggaaaaatcg ccgctaagtt tggcggaggt tctgagaagg      600
aagccttgtt cgtatcgaaa cacaaaggac actactgtgt tgaattctg ttcaacgtgt      660 ttgttgttgt aatttattg aaatggactg tacttctttt ctgttttttt ttttcacagt      720
aaaaatgcac tgtatttcct taaatctgct cataaacaat tacacatatt ttattagcta      780
aaatttaata taaattacaa aatatttaca aatatgttga tcaataaaaa agtgaaacac      840 ataatttat tatttctaac aaatttatct tatgataaag agtgtatttg aaagattatt       900
attaagggac aatttctgtt gttgtggaca actttcataa gtgatccatg aaacaccaca      960
ttttatagtc accagattga tctcagattt atgctcttgc                          1000
```

<210> SEQ ID NO 22
<211> LENGTH: 1009
<212> TYPE: DNA
<213> ORGANISM: Glycine max

<400> SEQUENCE: 22

```
ttgcgtggga ctcagatcct gagggaggac atggaagatg tgtcgaaccc aacaagtggt       60
gctactcatg gcagctccaa caagaagagc tttaaaacta agttcatgca ggaacaaaag      120
gacaggatga aagatgcacc accagagtgt cctgcaggag ttttgttccc aaagtgacgt      180
tcaacgccac gtcatgagtt tgaatgctca acacaactaa cacacccttg ctaagaagtc      240
ctagaaaaat aaaaatctaa ggttagaaa tggactaatg atgtacatgt aaaaataata      300
tgctgaagcc ccttgagtta aaagatgtgg attctaacga ctttgataat ttttaatggg      360
attttttata agttaattta ttgattattt ttaataattt tcttatattt ttttattcac      420
aaaacttaaa tctaaaatct tatttatagg aataaggaat tgagtttaat aacaccgata      480
tgttgataat gatttaaatc atgggaatct gtgtttataa atagagaaaa aaaaaccctt      540
atgatataaa accttcctta gtctaaactc cctagctttg tgttaatttg attgtccaaa      600
aggaggctag ctagttttgtt ccttcctcgt ccttacttct aaatgcatgg attaaggaaa      660
gaagcttctt tttgtttggt gttatatgtt tttggggtca ttatagtatg ggcaacttaa      720
cactcactct aagaggtgtt accttggcta ttcctagatg gctagacatc aaaactttga      780
atacaaaatt attaaagatc aataaaatat gattttatta taatactgag attaaattgt      840
aattttaatc tctctttaat tcatggtatg caattttaga ttttattttt tcatgtaatt      900
ttaatcatca cattttaaaa aattcataat tttaaattga ttttttaatttt tgtatatgtt      960 ttatttttaa ttttttatcta gttaaactgt atatttaaca tattgattt              1009
```

<210> SEQ ID NO 23
<211> LENGTH: 1006
<212> TYPE: DNA
<213> ORGANISM: Glycine max

<400> SEQUENCE: 23

```
attgaaagat tctatttgc ttgtttggtt gtcatttgga taaatgaatg agtactataa       60
acttttgaaa acatatatac tttgagcagt tctatgacct aattttgctt gtttgattag      120
aattttgaat gaatacaaac gaattgctttt gataaatgtg ttatgaattg aacagataat      180
ttcaatgaaa atagatcaaa attagatcgg tttcaattta tatatatata tatatatata      240
tatatatata tatatatata tatattggta taaaatattt ttacacaaaa tttaataaag      300
```

```
ttttaacatt ttataatatt attttgttca ttaatataag gtaatacagt ataaattcct    360
attatgtgtt tatataaatt tctattttta gtccttaatt ttgataattg tcaattaatt    420
ataatttagt cttcaaaatt tgatattact agtcaactta aacttaaata ttaataaatt    480
agtcaattta atttaaaaat ttgactatat atatatataa atcaaaaggg ttaaacaatt    540
catttatcat aaaactcggg ttaagatcac atgatagcaa agcaattcgt ttgacaattt    600
aaaaattcgg maaatatagt cttagtcata aacaaaatc aaaagggtta agattaaatc     660
ataaaactat attttttta aatgatatcr tgtgatcaat taaaaaagac aactttaatt     720
ataatmatct attcactaaa aaaacctaac tcatttgatt gagtagaata tatatrttat    780
tgtactttrt ttatctttga ttcctaccaa taattaaaaa caaataatca tctatctatt    840
ttatatagtc tagttttatt cttctcataa cactaaaaaa ttatttaatg atgatatgat    900
cacttaaaaa aattacataa tttatatttc tatatcgtaa ccattcatgt gatataatga    960
tcacatttt tttttctcac actcacctaa gtgcacgagt acacac                  1006
```

<210> SEQ ID NO 24
<211> LENGTH: 1007
<212> TYPE: DNA
<213> ORGANISM: Glycine max

<400> SEQUENCE: 24

```
acacgtaagt cttaggttaa agtttcatgc cccccccccc cccccccccc aaaattacat     60
tttttccat taaaataact ccaaactact ctacttctct cgctttggcg gaaccaccat    120
tgctctatga aaaggccatt ttattttcaa ccgcattgtt ttggaactat acaacgcaaa    180
agccttccat cctctatcat tgagctactt caaatcttgg tttctcttcg tcttctacca    240
gttatgtaag ctttcttcct ttcctctttt tggtttgggca gcacgaaatt atttttcttc    300
ttgttattag ctagaagcac tattctagaa caagcttgca aaaaggactc aagttatctt    360
tggtaaggga agctttagac ctcaagtcta gcttggagac tttttgatttt gaagctttgt    420
atttttgtatc ttggctaaag aatatatgtt ggaaaaagtc ttcttgaaga gctcttaaag    480
tgttgatttt gatgaaagtt cgttcaaaca taaattgttg atcttgaata ttttttctat    540
ttatttgcac caaaaacgtt atgtttatta tgttccacta taatttattg ttttgaggac    600
gggaaaagga tcggagttgg ttaagcttga tcttgagaat atatgtcttt tgtatttgaa    660
gtctttctga tggtgattct agatgacatg tcttatgggt ggagtaatag cgtaagtatc    720
tagagtatgt gagttgtaat gatctctaaa aatactcgtg gaagtaatga cttttacttg    780
aagaaaagac tattatgtga agagactta acttgaaag agattattga aatacaagtg      840
tggagtaaag ttttacttta aataaaaata aaaaagttaa atacaagtaa aaaaatactc    900
ataaatttaa ctttaaaatt ttaaattaag atgtaatgta atattcactt atatggttac    960
tcataattca tgaatataac tctcctcggt tacatagtcg ttaaatg                1007
```

<210> SEQ ID NO 25
<211> LENGTH: 993
<212> TYPE: DNA
<213> ORGANISM: Glycine max

<400> SEQUENCE: 25

```
agccgataac ttatagataa cgttacagat aacattaact taaagataat tgtaccttgt     60
agataatgtg tagtcctgta gataattgaa tatatatcaa gagataaagg gatgacaaca    120
tattcaaata ataaaagtta gagataactt gtggtttggg gagttcaact gcgaagggtt    180
```

-continued

```
ggacgtctgt gctcctacac caggattgac atggaggatt gacgtgtgtc ttggagtgtc      240
acatggtatg atacatgtat tttgtggatt atgaacaaca caattgctta aagttctact      300
caatttactt attacttcag gtgatgtctt ggtagttcac agatataagt ttttgtctgc      360 tatcttcat gtggacacac aagtatgtgt aaatagagat ttttttttgaa agtttgagat      420 ccagggggcgc accaatgtat aggggagggg accttggcgg tttaaatcac cataaaattt      480
taaaaatctt ttaaaaaaat ttaagccaaa caaattttga cttttttaca tcacctaaaa      540
atgaaccact agaaagtata atattgtcag atcctaattc tatttgggca aaaaaaaaca      600 aaaaaaaga aggaaagaaa aagtattaag aaaaagaaaa caaaaaaata aacaaaaaaa       660
caaaagaata aaaacaaaa aagagaaga aacaaaaca aaaaaaaaag aagaaaaaat         720
aaaacaaaaa agtattaaga aaaaaaaga acagtaaaaa aacaaaagaa agaaaatgta       780
aaaaaaagaa aaaatagaa gaaaaagga aagttaaaa aaaagatt  tgtgacctat          840 tggcttctca aggagagccc attaggtcaa gaggagaaca ttgtataaaa aaataaagaa      900
ggaaagtctg tgcaattaag gcacatagga ggcaacatga atcccaagga gaacaatgga     960
ccaatctgtt ggcgtcattt gacattgtcg tga                                   993
```

<210> SEQ ID NO 26
<211> LENGTH: 1118
<212> TYPE: DNA
<213> ORGANISM: Glycine max

<400> SEQUENCE: 26

```
gtgagaaaag agagagggat cactaggtaa cccctcattt cctcactctc tcagtttccc      60
tctagtcttt tcttctttct ttcttttctt cccccttttct ttcttcttc tttatgtttt     120 caatctactg cttcgttatg tcccatctcg tcggtgggca ccttggccgt cggcgatgtt     180
tttgtgaatt gaattgggat tttctttcg ttgggtttc acgcattcct tcatctcctt      240
tgttcttctt cttttttcgt ttgcgccacc gtcgtgcctc cttcgcatca tcgctatcgt     300
ggtcgtgcca tcgctgtccc cgtggcggcc tcgcaccgtt ggatcttgga tcaatggtgt     360
cgaggacggg gcgccaccct ctgtgctggt tcacccttt atcgtgtcgt ttggaggcta      420
ggacatctag gttttttcaa ccctgttgtc taattgcggg ttgggtcagg tcaccctgac      480
cgagttccaa cccacaaaaa aatggaattt ttttttacta tttacaccac cttttcaaat     540
atgcaccatt ttctcatttt gggtctagcc cgttttatg aagtatgaaa taaaataaaa      600
aacactattt gcaccaattt tttacacatc accttcttc atgttatgcc tagcccgttt      660
ttgtgaagtc taaagtaaaa taataaccgt tattcacactt ttttctttaa tacaagcacc    720
ttcttctatt ttgggcataa catgtatttt ttagtctgaa agaaaataaa aagtgctact     780
cacagctgct ttttcaacac atgcaccttc ttttgtttg ggcctagcgt gtgttttttt      840
tattattaag tccgaagtaa aataaaactg atgattacac cactttttt atatatgcac      900 ccctgaaact taggatgatg actaggtcca ccatgtctgc actccgttag tgttaattaa     960
gtcaaagtca atcctttga ctttgaaaaa aaatataaat attagtggat gaatctttat     1020
tttatttaat ttctttattg tttatatcat ttatttcatt cttcaatgtg attttatttt    1080
tattattgcc tagttagtta gtttaattaa taatgtat                             1118
```

<210> SEQ ID NO 27
<211> LENGTH: 1002
<212> TYPE: DNA

<213> ORGANISM: Glycine max

<400> SEQUENCE: 27

```
cctctcacga aacggaagcc tctatcagac ttagcttgcc tgataactct ttgtatatat        60
attctcaggg gttaaaatta aaatagtgtt ttgatacttg ttttgttttc catgttgtta       120
tttatattga tgagggaacc aatcttggtg aaaatgtggg agatatatgc catggttagt       180
tttgtgaaat taagttgctt acaatgtgtt taacgaaatg cccttgaatg cattctctcg       240
ttagtcattt aaattatgag ctatcatgaa ttttagttta aagttcattt aaattatgct       300
atttgttaca gacttttaatt taaattatgc taagagtctt ttgttatgct ataattggtg       360
tggtttctaa cattttatgtt ggaatagaag taatgtcaat tataattagc ttaatcagcc       420
caaaacattc actgtatttg tgtgcaaatt aagtgagctt aaccttggtt ttgtgaatga       480
tataccttac ctctaatcat gttaaaatag aacctaagtg tagattattt aaatcctaag       540
ttctacatat taatacacta tgcaagttat gcaatatagg tgcttatata tgttgctgaa       600
aacatgttac acttctgctc tgtgatacga gctgcattgt gattgacgca gatcttagtt       660
tttaatgacc tgtggaattg ttgtaggctt gtgtgtactc tttgtgaaac aattgatccc       720
atttcatttc aattttttgta cattttttta tgattttttat agtgtaacat gctctgctga       780
gtgatttact gtgtggctgc tgtaataaag caataaaatg ctatgttttg aatatcttga       840
cacttggttt gtattttagt tgaaaataga cttaaaaagg gttctataga atttggaact       900
actcaaattg cttttatctt caatttatac caatgtcatc tttaaggcat gttaatcata       960
tatcttaaca agcggtaatc tatatcttga aatctgtctt gc                         1002
```

<210> SEQ ID NO 28
<211> LENGTH: 1001
<212> TYPE: DNA
<213> ORGANISM: Glycine max

<400> SEQUENCE: 28

```
ttgcgaaacg gcagataaaa tttgctttgt cttagaacaa ttcatgaaaa cagcccctag        60
tgagtcaaag tatccccttt tgtttcaatt taaaaaatta atttctcact attcttattg       120
tgtaaatttt ttaaggaaat tgtgtaatct ttattcatat gttaatgtta atttgatata       180
taatatttaa tagaattata ttgttgatgt cataatgtta atcatgctaa tatagatgtt       240
ttaatcttaa tttatttatt ataaaaatgtt aaatgttaat tattgttagc aaagacaaat      300
tcaaggaagg acaagaaagg atcttgcact ccccttcctaa ggatccttta tatacatgtg       360
aaaaaagaaa aataataga agaaaatgaa ttaaagaaat aagttgttga atttatgttt       420
gtttaatatt ttttattcta gtaatggatc tatcttaatt tttcatacaa atttttctca       480
caaaattaat aatgttttat tttataaaaa cttattattt attaagggtt agatataaat       540
aattgcacaa aaaagaaag aaaaatagtt ccctttaaaa atgttttttgg atttgttctt       600
cattgttagt aagaggattt gaacccataa ttttttttcct tttttttatta ctaagttaat      660
cttataagtc ttagttaact tgaatgtcaa tcataccaat agagtattat gtgaatattt       720
ttcataaaat attaattatc aagtctatgg atgtagaaaa atagtttaat taaaaaaatg       780
acgataataa aaatgttcaa ttatgtgttg attatactac acctcactta ttaaaaaaaa       840
ataccacacc tcacattttt ttcgcttaat tgacatcaag aatgagaatg caaacaaaaa       900
atatgaatta gaccagaaaa caatccatcc atcgtatgcc atatagatca tctcataaac       960
cacctgtgta aggaaaattt ttattgtcaa ttgggcttag c                         1001
```

<210> SEQ ID NO 29
<211> LENGTH: 1002
<212> TYPE: DNA
<213> ORGANISM: Glycine max

<400> SEQUENCE: 29

```
acaaatacga atcatgtacc tgcatggaag aaataaccac acaacacaca atgatcagaa      60
taagcaaatg catataatta agcatgatac aatatcaata ttcatggaag taacaatgac     120
ttgtcaaaaa tttggatgaa attcaatatg taaatcaaag ctttgtccct gaaaccctct     180
atataaatca aagctttgtc cctgaaaccc tctatgtaaa tgtgacagcc tcatgtctcc     240
cttcctgaaa acccactaaa aactgcctaa ccccctgct gttactccat aatttattct      300
acaataactg cttaaggcag ttacatatgg tcctaaatca ctacacattc agttacgatt     360
aacccttgt gcctaactac ggtttcgaaa catcacaaca gagacagacc attgaacaat      420
ggattttcat cattaacata caacagagac ataccttcga tggaagcgta gacacgaact     480
ccacaaacgc gaactcgaca atgtggttgc agttacagaa gcatagccca gtttgcgaca    540
aacacgaact caggcagaag gagaaacaac aataaagccc tgggttaaaa cgacgaacgc    600
ctaatgttaa aacgacgaac gcctaatgtt aaaacgaaag gacgtacctc aatggataag    660
tgccaaagac gatctccaca aacacaatct ccacaatgtg gttgcagtca cagaagcaca    720
agatcaagag atcaagagaa aagattcacg ttagtccatt atttgttaaa agaatctctt    780
aatggttgaa aaggtttggc cttaaaaata actaaaaata attgtgtaat cgattatcaa    840
agatctataa tcgattacta atgagaaaat ttcaaaaata actctgaaaa gtcacatccc    900
tttatgagtt tttgaaaagc caccaaaggt ctatatatat gtgaattgtg ttcgaaaatc    960
tttagaattt tttcaaaact tctttgtctt attctctcat aa                       1002
```

<210> SEQ ID NO 30
<211> LENGTH: 1000
<212> TYPE: DNA
<213> ORGANISM: Glycine max

<400> SEQUENCE: 30

```
ataaataaac ttttggtcaa acacttgcaa atcaattaaa gattctttta agttttcaa       60
tttgtattat acttctctag aagagagaaa aacttttgta cttcaaaaag aaaactatta    120
ttgtgatcaa gaggtagtga gtctcttgat ttgtgagttt ttctgaacac aagagaaatg    180
tatccctagg tggttcagaa gttgtaaagg aatttacaag aacaatagaa atctcaaatg    240
agttgcttga agattgaacg taaactgagt ttgcaattct ctctttcctt aattatctca    300
tttacataat tgcaatttaa ttttgtcttg tgcatttaaa gagtgtcaat taaattgttc    360
gttgtttctt attctgcata ttaagtttgc atatatcatt taagagaga attaaaattt    420
gttagggaa aattttaaaa cttaattcac ctcgctctta aattattgat gccacttgtt     480
taaccatatg ttatcaattg aaataaatta atttttaat agaaatatga aataattat     540
ataacaaaaa aaccaaaaa aagaagaaa ataatcaata tattatcgac aactactatt      600
atcatattat taacataaaa aatatcaaca tattattaac aactatttta aattaatatg    660
aaaacaatta tataactaaa aaataataa gaaagtaatg aaaaaaatca aatattata      720
aactaatcca atatattaaa actactattt tgactgatca acataagaga caacaaaaaa    780
tttcatatta ttaacaagag tgtggctcaa gttgtcaatc cataatttat agaataattt    840
```

```
attaaagcaa actacgaatg aatatggttt aagcagatac taacataagt ttacaaaact       900
taacaaaatg catgcatttt ctttactcta gaaatataaa agcctatttt aaaagacagt       960
aataaaatta ctaagaacta caccattcaa aatagtgccg                            1000

<210> SEQ ID NO 31
<211> LENGTH: 1002
<212> TYPE: DNA
<213> ORGANISM: Glycine max

<400> SEQUENCE: 31
agctttaatt ttgttccgta catagtggcc acctattcta tccatgtcat aaccaataag        60
gtccaacata attgacagat aactgaattt tttaaatata ttaggagttc gattactgat       120
catgtgcata cagaagattt tgagaaagac aaaactcact ttagtgatat ctatgtttcg       180
aaagaaatta attttcgact acccattaga agatatcttt ggtacaaaca aaaaagaaga      240
aaaaaattct atcaatatca tagatattat actcaaatta taagactcat atattccacc       300
attcatccac ttgcttttgt gatgccccctt gaaaaagaga ttggttgcaa tctcttatgt      360
tgttctgatt cctactcgga agacgtcatg tgctcctcac gagactaaga aaaggtcatg       420
aagataaagg atctatactc taaattgcta accaatgttg tggttggtaa attctgttct       480
tatataatgt tagatatttc tgaagagtca tggttcagaa tcgggatcc atcacatgcc        540 cctatgctaa taggttatat acaatgcttt tcgttgagga tgcttacaat attttacgta      600
agagcacaat taaataaaa aaagtaattg ttagaagatg catagttaaa gttaaagtat        660
gaggacagac aacatggata aatactcctt ctgtgtccgc acaaatgcag agcatcgaat       720
atagaacctc ggttgatatg actaatgtat gtagaacaca tactaagtaa taatagatta       780
gtctaagttt gatggatttt tttttattca taggaaatga aaatagtgtc aggagattta       840
taatataata gttatgtat tctacttaac catttaaatt agatctcttg acaagttaca       900
atagttaaga gaacaaaact ctcctcatgt tttttatttt ttttatttac atacaagatt       960
cggacaagac aacttaaaga aaaagccttg gaatggacat aa                          1002

<210> SEQ ID NO 32
<211> LENGTH: 1002
<212> TYPE: DNA
<213> ORGANISM: Glycine max

<400> SEQUENCE: 32
ataagagaac tgtttttat attattatta tttcctttct aattcataga gaacccagta        60
tgttgaccat atcaccctga aatgaaattt aaatacccta accataatt actaaaataa       120 ccttgaaatg gctaaattgc tagctactct tttatatgta actgaggtgt tacttcatca      180
aaaggatata tattgagatc actcactaat tactagtaca ttgtaacatt gtaacactat      240
ggatgtgttt gaataagtat ttttcatcta gtttcacttg acaatgggaa cagcagcatt      300
gagttgtatt gattggatga gatcagagtc tagcaagttc agtggtggca gagagaaagg     360
gctctctgtg gaactacctt ttcggatttc ttgcattgta agcaaagccg caactgtgtt     420
tctgaaaatc ccttctcctg ccacagttat tgcatctttt gcttcctttg ctctctcagc      480
ttcttcctct gccgggaaca ctgcatcgat tatgctctca cactccttca ccagctttga     540
gatcaaatct gttgtgaaaa atggctgctc caacactttc tggatgaatg gcaaacgcag     600 aagccccccct gtcctcttgt cgtatttctt cagaattttt gccaacccctg caaaattcag     660 tgttgtcact tgttcaaggt agcatcaaat tctgtagaga aagctgcatc aaagtctatg     720
```

```
gcaatgcatt tcctagcctt tttatcaata gcaaaccatg ttttaacatt ggagtttaat    780
tttcatgcac tgtaaagagt tttatgggtg aaacacgaga aattattaga tggtttaaga    840
ctgttacatt catggtcccc attagtttct acattatata tatatattga tttttctgaa    900
aactcaatta tgtctcgtgt aaaaattatt aatttgagac tgtaatctta tattatgtaa    960
taatttcacg tcaatcaatt agaaattacc ttagatataa ag                       1002
```

<210> SEQ ID NO 33
<211> LENGTH: 1083
<212> TYPE: DNA
<213> ORGANISM: Artificial Sequence
<220> FEATURE:
<223> OTHER INFORMATION: synthetic construct; Plant optimized nucleotide sequence of TS21 meganuclease

<400> SEQUENCE: 33

```
atggcaccga agaagaagcg caaggtgcat atgaacacca agtacaacaa ggagttcctg     60
ctctacctgg ccggcttcgt ggacggcgac ggctccatca tggcgcagat caagccgcag    120
cagtcctgca agttcaagca cgcgctccag ctgaccttca ccgtgaccca agaagacgcag   180 aggcgctggt tcctcgacaa gctggtcgac gagatcgggg tgggcaaggt ctacgaccgc    240
gggtcggtgt ccgactacat cctctcccag atcaagcccc tgcacaactt cctcacccag    300
ctccagccgt tcctcaagct gaagcagaag caggcgaacc tcgtcctgaa gatcatcgag    360 cagctccccct cggccaagga gtccccggac aagttcctgg aggtgtgcac gtgggtcgac    420
cagatcgcgg ccctcaacga cagcaagacc cgcaagacga cctcggagac ggtgcgggcg    480
gtcctggact ccctcccagg atccgtggga ggtctatcgc catctcaggc atccagcgcc    540
gcatcctcgg cttcctcaag cccggggttca gggatctccg aagcactcag agctggagca    600
actaagtcca aggaattcct gctctacctg gccggcttcg tggacggcga cggctccatc    660
aaggcgcaga tcaagccgcg ccagtcccgc aagttcaagc acgagctctc cctgaccttc    720
caggtgaccc agaagacgca gaggcgctgg ttcctcgaca agctggtcga cgagatcggg    780
gtgggctacg tctacgaccg cgggtcggtg tccgactaca tcctctccca gatcaagccc    840
ctgcacaact tcctcaccca gctccagccg ttcctcaagc tgaagcagaa gcaggcgaac    900
ctcgtcctga gatcatcga gcagctcccc tcggccaagg agtccccgga caagttcctg    960
gaggtgtgca cgtgggtcga ccagatcgcg gccctcaacg acagcaagac ccgcaagacg   1020
acctcggaga cggtgcgggc ggttctagac tccctcagcg agaagaagaa gtcgtccccc   1080
tga                                                                 1083
```

<210> SEQ ID NO 34
<211> LENGTH: 10
<212> TYPE: PRT
<213> ORGANISM: Simian virus 40

<400> SEQUENCE: 34

```
Met Ala Pro Lys Lys Lys Arg Lys Val His
1               5                   10
```

<210> SEQ ID NO 35
<211> LENGTH: 5937
<212> TYPE: DNA
<213> ORGANISM: Artificial Sequence
<220> FEATURE:
<223> OTHER INFORMATION: synthetic construct; Expression cassette RTW317, comprising the TS21 meganuclease plant optimized nucleotide sequence without an intron and operably linked to the soybean EF1A promoter

<400> SEQUENCE: 35

```
cacatggtta acctagactt gtccatcttc tggattggcc aacttaatta atgtatgaaa     60
taaaaggatg cacacatagt gacatgctaa tcactataat gtgggcatca aagttgtgtg    120
ttatgtgtaa ttactagtta tctgaataaa agagaaagag atcatccata tttcttatcc    180
taaatgaatg tcacgtgtct ttataattct ttgatgaacc agatgcattt cattaaccaa    240
atccatatac atataaatat taatcatata taattaatat caattgggtt agcaaaacaa    300
atctagtcta ggtgtgtttt gcgaatgcgg ccgccaccgc ggtggagctc gaattctagt    360
ggccggccca gctgatatcc atcacactgg cggccgcact cgactgaatt ggttccggcg    420
ccagcctgct tttttgtaca aagttggcat tataaaaaag cattgcttat caatttgttg    480
caacgaacag gtcactatca gtcaaaataa aatcattatt tggggcccga gcttaagtaa    540
ctaactaaca ggaagagttt gtagaaacgc aaaaaggcca tccgtcagga tggccttctg    600
cttagtttga tgcctggcag tttatggcgg gcgtcctgcc cgccaccctc cgggccgttg    660
cttcacaacg ttcaaatccg ctcccggcgg atttgtccta ctcaggagag cgttcaccga    720
caaacaacag ataaaacgaa aggcccagtc ttccgactga gcctttcgtt ttatttgatg    780
cctggcagtt ccctactctc gcttagtagt tagacgtccc cgagatccat gctagcggta    840
atacggttat ccacagaatc aggggataac gcaggaaaga acatgtgagc aaaaggccag    900
caaaaggcca ggaaccgtaa aaaggccgcg ttgctggcgt ttttccatag gctccgcccc    960
cctgacgagc atcacaaaaa tcgacgctca agtcagaggt ggcgaaaccc gacaggacta   1020
taaagatacc aggcgtttcc ccctggaagc tccctcgtgc gctctcctgt tccgaccctg   1080
ccgcttaccg gatacctgtc cgcctttctc ccttcgggaa gcgtggcgct ttctcatagc   1140
tcacgctgta ggtatctcag ttcggtgtag gtcgttcgct ccaagctggg ctgtgtgcac   1200
gaaccccccg ttcagcccga ccgctgcgcc ttatccggta actatcgtct tgagtccaac   1260
ccggtaagac acgacttatc gccactggca gcagccactg gtaacaggat tagcagagcg   1320
aggtatgtag gcggtgctac agagttcttg aagtggtggc ctaactacgg ctacactaga   1380
agaacagtat ttggtatctg cgctctgctg aagccagtta ccttcggaaa aagagttggt   1440
agctcttgat ccggcaaaca aaccaccgct ggtagcggtg ttttttttgt ttgcaagcag   1500
cagattacgc gcagaaaaaa aggatctcaa gaagatcctt tgatcttttc tacggggtct   1560
gacgctcagt ggaacggggc ccaatctgaa taatgttaca accaattaac caattctgat   1620
tagaaaaact catcgagcat caaatgaaac tgcaatttat tcatatcagg attatcaata   1680
ccatattttt gaaaaagccg tttctgtaat gaaggagaaa actcaccgag gcagttccat   1740
aggatggcaa gatcctggta tcggtctgcg attccgactc gtccaacatc aatacaacct   1800
attaatttcc cctcgtcaaa ataaggtta tcaagtgaga atcaccatg agtgacgact   1860
gaatccggtg agaatggcaa aagtttatgc atttcttttcc agacttgttc aacaggccag   1920
ccattacgct cgtcatcaaa atcactcgca tcaaccaaac cgttattcat tcgtgattgc   1980
gcctgagcga gacgaaatac gcgatcgctg ttaaaaggac aattacaaac aggaatcgaa   2040
tgcaaccggc gcaggaacac tgccagcgca tcaacaatat tttcacctga atcaggatat   2100
tcttctaata cctggaatgc tgttttccg gggatcgcag tggtgagtaa ccatgcatca   2160
tcaggagtac ggataaaatg cttgatggtc ggaagaggca taaattccgt cagccagttt   2220
```

```
agtctgacca tctcatctgt aacatcattg gcaacgctac ctttgccatg tttcagaaac    2280
aactctggcg catcgggctt cccatacaag cgatagattg tcgcacctga ttgcccgaca    2340
ttatcgcgag cccatttata cccatataaa tcagcatcca tgttggaatt taatcgcggc    2400
ctcgacgttt cccgttgaat atggctcata acaccccttg tattactgtt tatgtaagca    2460
gacagtttta ttgttcatga tgatatattt ttatcttgtg caatgtaaca tcagagattt    2520
tgagacacgg gccagagctg cagctggatg gcaaataatg atttattttt gactgatagt    2580
gacctgttcg ttgcaacaaa ttgataagca atgctttctt ataatgccaa ctttgtacaa    2640
gaaagctggg tctagatatc tcgacccggg caatcaaatt atatatgtaa agcaattaca    2700
gtttatcaaa ctttatttat ggaaataatt tattatcaca tttattttgg tttataaatt    2760
ttaaattaaa atatcaccta aataaaaata attttttaaca tgacttattg tcctaaataa    2820
attatttccg taaattaaat aaaatgaagt ttttttcttt caaagaatct aaatggtcat    2880
aatgagaatt ctctaaaaaa atacataatg agaataatta tggaatttat ttattaataa    2940
aaattaatag cattttgata gacaattaat aaaattttaa aaataaccat atagaaataa    3000
taattttttt actatcggtt ccaattaaaa taatgataaa aaataaaata gattattaat    3060
tgatattgat atgaaattta aataaagaat ataatcatat attttattga tatatgatat    3120
gatatagatt aattgatatt gattttgata tggaatttaa aaataatata ataattgttt    3180
ttatttatta atacgtgtaa tcaaataatt ctcacttttt gaatcaatca gtgtacttaa    3240
agataatatc agttgaatat ttttttatcct tttacgtgtg ctgtgagaca ttatcatcaa    3300
ttgtgttgta tatgatatat agatatagat atataaatat atagattgag tgatataata    3360
tatttaaaat ataattata tatatgtttt aatatatttt tgcatatata tatatatttg    3420
taaaaactag aagtatttttt tcatgagata attattatcg agttgaataa gtctattatt    3480
tgtgagagcc aaccatattt atatatgtga ttaaattttta tctttgtgaa attaaaaata    3540
ataaaaaata ccttaaaatc ataataatag aaaaacttat atttataatt taccattata    3600
cttaaaaaaa attaaataaa tattataaat ataaatacta tcgagtaatg gccgcgctag    3660 ggttttttgag aaaaaatctt cccacgcact caactgcact gtacggcgtc gttttcacag    3720
ccgcataata gaagccgcgt tccccaaccc ttcctcacaa cattctcgga ccctccagca    3780
ccgtcaccca aacaaatatc cacgcggtag taggcgcgtg aaacaaactc taatccgaac    3840
tacgagacgt gagaagcacg cgctttagcg agcgtttcaa ttgtcgctac gaaagcagag    3900
aaggatacaa acggaactag ggtaaattag taagggtaat ttcgtaaaca gaagaaaaga    3960
gttgtagcta taaataaacc ctctaacccct cgtcgcatta cttctcttca cacctttgtt    4020
cactcttctt ctcttgcggc tagggttttta gcgcagcttc ttctaggttc gttatctacc    4080
accgttctat ggatttttatt ccttctattc gtgtttattc tattggttta tgttgcttgc    4140
aatatgtttt ttctgaatct gtcgtcgttg tcttcaattt tatccatgtt tcagagatca    4200
attttgtttg tgtagtatgt gcttattctt cttcttttcg ttcgagttgt taataacggt    4260
gctatggtgt tttcaaaagt gttttttttta ttacttttga tttaaagttt ttttggtaag    4320
gcttttattt gcttgttata ttcaaatctt tggatccaga tcttatataa gttttttggtt    4380 caagaaagtt tttggttact gatgaataga tctattaact gttactttaa tcgattcaag    4440
ctaaagtttt ttggttactg atgaatagat ctattatctg ttactttttaa tcggttcaag    4500 ctcaagtttt ttggttactg atgaatagat ctatatacgt cacagtgtgc taaacatgcc    4560
cttgttttat ctcgatctta tgtatgggag tgccataaat tttgttatgt ctattttttt    4620
```

```
atctgttgga atcatactga gtttgatgcg ttacgattga gcatacctat tttttgggctt    4680 gttgtatggt gggtatttag atcttaatct ttttatgctt atgaaaggtt ttgtaatgac    4740
aaaggtctta atgttgttaa acttttattt ttactttata tggtgtgttg atgtgttatg    4800
gttttgacaa cttttttttt ttctggattt ttgcagattt aaggaagcca tggcaccgaa    4860
gaagaagcgc aaggtgcata tgaacaccaa gtacaacaag gagttcctgc tctacctggc    4920
cggcttcgtg gacggcgacg gctccatcat ggcgcagatc aagccgcagc agtcctgcaa    4980
gttcaagcac gcgctccagc tgaccttcac cgtgacccag aagacgcaga ggcgctggtt    5040
cctcgacaag ctggtcgacg agatcggggt gggcaaggtc tacgaccgcg gtcggtgtc    5100 cgactacatc ctctcccaga tcaagcccct gcacaacttc ctcacccagc tccagccgtt    5160
cctcaagctg aagcagaagc aggcgaacct cgtcctgaag atcatcgagc agctcccctc    5220
ggccaaggag tccccggaca gttcctgga ggtgtgcacg tgggtcgacc agatcgcggc    5280
cctcaacgac agcaagaccc gcaagacgac ctcggagacg gtgcgggcgg tcctggactc    5340
cctcccagga tccgtgggag gtctatcgcc atctcaggca tccagcgccg catcctcggc    5400
ttcctcaagc ccgggttcag ggatctccga agcactcaga gctggagcaa ctaagtccaa    5460
ggaattcctg ctctacctgg ccggcttcgt ggacggcgac ggctccatca aggcgcagat    5520
caagccgcgc cagtcccgca agttcaagca cgagctctcc ctgaccttcc aggtgaccca    5580
gaagacgcag aggcgctggt tcctcgacaa gctggtcgac gagatcgggg tgggctacgt    5640
ctacgaccgc gggtcggtgt ccgactacat cctctcccag atcaagcccc tgcacaactt    5700
cctcacccag ctccagccgt tcctcaagct gaagcagaag caggcgaacc tcgtcctgaa    5760
gatcatcgag cagctcccct cggccaagga gtccccggac aagttcctgg aggtgtgcac    5820
gtgggtcgac cagatcgcgg ccctcaacga cagcaagacc cgcaagacga cctcggagac    5880
ggtgcgggcg gttctagact ccctcagcga agaagaagaag tcgtcccct gaggtac    5937
```

<210> SEQ ID NO 36
<211> LENGTH: 6126
<212> TYPE: DNA
<213> ORGANISM: Artificial Sequence
<220> FEATURE:
<223> OTHER INFORMATION: synthetic construct; Expression cassette RTW322, comprising the TS21 meganuclease plant optimized nucleotide sequence ST-LS1 intron2 and operably linked to the soybean EF1A promoter

<400> SEQUENCE: 36

```
cacatggtta acctagactt gtccatcttc tggattggcc aacttaatta atgtatgaaa     60
taaaaggatg cacacatagt gacatgctaa tcactataat gtgggcatca aagttgtgtg    120
ttatgtgtaa ttactagtta tctgaataaa agagaaagag atcatcccata tttcttatcc    180 taaatgaatg tcacgtgtct ttataattct ttgatgaacc agatgcattt cattaaccaa    240
atccatatac atataaatat taatcatata taattaatat caattgggtt agcaaaacaa    300
atctagtcta ggtgtgtttt gcgaatgcgg ccgccaccgc ggtggagctc gaattctagt    360
ggccggccca gctgatatcc atcacactgg cggccgcact cgactgaatt ggttccggcg    420
ccagcctgct tttttgtaca aagttggcat tataaaaaag cattgcttat caatttgttg    480
caacgaacag gtcactatca gtcaaaataa aatcattatt tgggccccga gcttaagtaa    540
ctaactaaca ggaagagttt gtagaaacgc aaaaaggcca tccgtcagga tggccttctg    600
cttagtttga tgcctggcag tttatggcgg gcgtcctgcc cgccaccctc cgggccgttg    660
```

```
cttcacaacg ttcaaatccg ctcccggcgg atttgtccta ctcaggagag cgttcaccga    720
caaacaacag ataaaacgaa aggcccagtc ttccgactga gcctttcgtt ttatttgatg    780
cctggcagtt ccctactctc gcttagtagt tagacgtccc cgagatccat gctagcggta    840
atacggttat ccacagaatc aggggataac gcaggaaaga acatgtgagc aaaaggccag    900
caaaaggcca ggaaccgtaa aaaggccgcg ttgctggcgt ttttccatag gctccgcccc    960
cctgacgagc atcacaaaaa tcgacgctca agtcagaggt ggcgaaaccc gacaggacta   1020
taaagatacc aggcgtttcc ccctggaagc tccctcgtgc gctctcctgt tccgaccctg   1080
ccgcttaccg gatacctgtc cgcctttctc ccttcgggaa gcgtggcgct ttctcatagc   1140
tcacgctgta ggtatctcag ttcggtgtag gtcgttcgct ccaagctggg ctgtgtgcac   1200
gaaccccccg ttcagcccga ccgctgcgcc ttatccggta actatcgtct tgagtccaac   1260
ccggtaagac acgacttatc gccactggca gcagccactg gtaacaggat tagcagagcg   1320
aggtatgtag gcggtgctac agagttcttg aagtggtggc ctaactacgg ctacactaga   1380
agaacagtat ttggtatctg cgctctgctg aagccagtta ccttcggaaa aagagttggt   1440
agctcttgat ccggcaaaca aaccaccgct ggtagcggtg gtttttttgt ttgcaagcag   1500
cagattacgc gcagaaaaaa aggatctcaa gaagatcctt tgatcttttc tacggggtct   1560
gacgctcagt ggaacggggc ccaatctgaa taatgttaca accaattaac caattctgat   1620
tagaaaaact catcgagcat caaatgaaac tgcaatttat tcatatcagg attatcaata   1680
ccatattttt gaaaaagccg tttctgtaat gaaggagaaa actcaccgag gcagttccat   1740
aggatggcaa gatcctggta tcggtctgcg attccgactc gtccaacatc aatacaacct   1800
attaatttcc cctcgtcaaa aataaggtta tcaagtgaga aatcaccatg agtgacgact   1860
gaatccggtg agaatggcaa aagtttatgc atttctttcc agacttgttc aacaggccag   1920
ccattacgct cgtcatcaaa atcactcgca tcaaccaaac cgttattcat tcgtgattgc   1980
gcctgagcga gacgaaatac gcgatcgctg ttaaaaggac aattacaaac aggaatcgaa   2040
tgcaaccggc gcaggaacac tgccagcgca tcaacaatat tttcacctga atcaggatat   2100
tcttctaata cctggaatgc tgttttttccg gggatcgcag tggtgagtaa ccatgcatca   2160
tcaggagtac ggataaaatg cttgatggtc ggaagaggca taaattccgt cagccagttt   2220
agtctgacca tctcatctgt aacatcattg gcaacgctac ctttgccatg tttcagaaac   2280
aactctggcg catcgggctt cccatacaag cgatagattg tcgcacctga ttgcccgaca   2340
ttatcgcgag cccatttata cccatataaa tcagcatcca tgttggaatt taatcgcggc   2400
ctcgacgttt cccgttgaat atggctcata caccccttg tattactgtt tatgtaagca   2460 gacagttta ttgttcatga tgatatattt ttatcttgtg caatgtaaca tcagagattt   2520
tgagacacgg gccagagctg cagctggatg gcaaataatg attttatttt gactgatagt   2580
gacctgttcg ttgcaacaaa ttgataagca atgcttcctt ataatgccaa ctttgtacaa   2640
gaaagctggg tctagatatc tcgacccggg caatcaaatt atatatgtaa agcaattaca   2700
gtttatcaaa ctttatttat ggaaataatt tattatcaca tttattttgg tttataaatt   2760
ttaaattaaa atatcaccta ataaaaaata atttttaaca tgacttattg tcctaaataa   2820
attatttccg taaattaaat aaaatgaagt ttttttcttt caaagaatct aaatggtcat   2880
aatgagaatt ctctaaaaaa atacataatg agaataatta tggaatttat ttattaataa   2940
aaattaatag cattttgata gacaattaat aaaatttaa aaataaccat atagaaataa   3000
```

```
taatttttttt actatcggtt ccaattaaaa taatgataaa aaataaaata gattattaat    3060
tgatattgat atgaaattta aataaagaat ataatcatat attttattga tatatgatat    3120
gatatagatt aattgatatt gattttgata tggaatttaa aaataatata ataattgttt    3180
ttatttatta atacgtgtaa tcaaataatt ctcactttttt gaatcaatca gtgtacttaa    3240 agataaatatc agttgaatat tttttatcct tttacgtgtg ctgtgagaca ttatcatcaa    3300
ttgtgttgta tatgatatat agatatagat atataaatat atagattgag tgatataata    3360
tatttaaaat ataaattata tatatgtttt aatatattttt tgcatatata tatatatttg    3420
taaaaactag aagtattttt tcatgagata attattatcg agttgaataa gtctattatt    3480
tgtgagagcc aaccatattt atatatgtga ttaaatttta tctttgtgaa attaaaaata    3540
ataaaaaata ccttaaaatc ataataatag aaaaacttat atttataatt taccattata    3600
cttaaaaaaa attaaataaa tattataaat ataaatacta tcgagtaatg gccgcgctag    3660 ggttttttgag aaaaaatctt cccacgcact caactgcact gtacggcgtc gttttcacag    3720
ccgcataata gaagccgcgt tccccaaccc ttcctcacaa cattctcgga ccctccagca    3780
ccgtcaccca aacaaatatc cacgcggtag taggcgcgtg aaacaaactc taatccgaac    3840
tacgagacgt gagaagcacg cgctttagcg agcgtttcaa ttgtcgctac gaaagcagag    3900
aaggatacaa acggaactag ggtaaattag taagggtaat ttcgtaaaca gaagaaaaga    3960
gttgtagcta taaataaacc ctctaaccct cgtcgcatta cttctcttca cacctttgtt    4020
cactcttctt ctcttgcggc tagggttttta gcgcagcttc ttctaggttc gttatctacc    4080
accgttctat ggatttttatt ccttctattc gtgtttattc tattggttta tgttgcttgc    4140
aatatgtttt ttctgaatct gtcgtcgttg tcttcaattt tatccatgtt tcagagatca    4200
attttgtttg tgtagtatgt gcttattctt cttcttttcg ttcgagttgt taataacggt    4260
gctatggtgt tttcaaaagt gttttttttta ttactttttga tttaaagtttt ttttggtaag    4320 gcttttattt gcttgttata ttcaaatctt tggatccaga tcttatataa gttttttggtt    4380 caagaaagtt tttggttact gatgaataga tctattaact gttactttaa tcgattcaag    4440
ctaaagtttt ttggttactg atgaatagat ctattatctg ttactttttaa tcggttcaag    4500 ctcaagtttt ttggttactg atgaatagat ctatatacgt cacagtgtgc taaacatgcc    4560
cttgttttat ctcgatctta tgtatgggag tgccataaat tttgttatgt ctattttttt    4620
atctgttgga atcatactga gtttgatgcg ttacgattga gcatacctat ttttgggctt    4680
gttgtatggt gggtatttag atcttaatct ttttatgctt atgaaaggtt ttgtaatgac    4740
aaaggtctta atgttgttaa acttttatttt ttactttata tggtgtgttg atgtgttatg    4800
gttttgacaa cttttttttt ttctggattt ttgcagattt aaggaagcca tggcaccgaa    4860
gaagaagcgc aaggtgcata tgaacaccaa gtacaacaag gagttcctgc tctacctggc    4920
cggcttcgtg gacggcgacg gctccatcat ggcgcagatc aagccgcagc agtcctgcaa    4980
gttcaagcac gcgctccagc tgaccttcac cgtgacccag aagacgcaga ggcgctggtt    5040
cctcgacaag ctggtcgacg agatcggggt gggcaaggtc tacgaccgcg ggtcggtgtc    5100
cgactacatc ctctccccaga tcaagcccct gcacaacttc ctcacccagc tccagccgtt    5160
cctcaagctg aagcagaagc aggcgaacct cgtcctgaag atcatcgagc agctcccctc    5220
ggccaaggag tccccggaca agttcctgga ggtaagtttc tgcttctacc tttgatatat    5280
atataataat tatcattaat tagtagtaat ataaatttc aaatattttt ttcaaaataa    5340
aagaatgtag tatatagcaa ttgctttttct gtagtttata agtgtgtata ttttaattta    5400
```

```
taacttttct aatatatgac caaaacatgg tgatgtgcag gtgtgcacgt gggtcgacca    5460
gatcgcggcc ctcaacgaca gcaagacccg caagacgacc tcggagacgg tgcgggcggt    5520
cctggactcc ctcccaggat ccgtgggagg tctatcgcca tctcaggcat ccagcgccgc    5580
atcctcggct tcctcaagcc cgggttcagg gatctccgaa gcactcagag ctggagcaac    5640
taagtccaag gaattcctgc tctacctggc cggcttcgtg gacggcgacg gctccatcaa    5700
ggcgcagatc aagccgcgcc agtcccgcaa gttcaagcac gagctctccc tgaccttcca    5760
ggtgacccag aagacgcaga ggcgctggtt cctcgacaag ctggtcgacg agatcggggt    5820
gggctacgtc tacgaccgcg gtcggtgtc cgactacatc ctctcccaga tcaagcccct    5880
gcacaacttc ctcacccagc tccagccgtt cctcaagctg aagcagaagc aggcgaacct    5940
cgtcctgaag atcatcgagc agctcccctc ggccaaggga tccccggaca agttcctgga    6000
ggtgtgcacg tgggtcgacc agatcgcggc cctcaacgac agcaagaccc gcaagacgac    6060
ctcggagacg gtgcgggcgg ttctagactc cctcagcgag aagaagaagt cgtccccctg    6120
aggtac                                                               6126

<210> SEQ ID NO 37
<211> LENGTH: 5056
<212> TYPE: DNA
<213> ORGANISM: Artificial Sequence
<220> FEATURE:
<223> OTHER INFORMATION: synthetic construct; Nucleotide sequence of
      RTW328A, which is the repair DNA fragment for TS21 meganuclease

<400> SEQUENCE: 37
cgcgcctcta gttgaagaca cgttcatgtc ttcatcgtaa gaagacactc agtagtcttc      60
ggccagaatg gccatctgga ttcagcaggc ctagaaggcc atttaaatcc tgaggatctg     120
gtcttcctaa ggacccggga tatcgctatc aactttgtat agaaaagttg ggccgaattc     180
gagctcggta cggccagaat ccggtaagtg actagggtca cgtgacccta gtcacttaaa     240
ttcggccaga atggccatct ggattcagca ggcctagaag gcccggaccg attaaacttt     300
aattcggtcc gggttacctc gagttattta tcccctataa agggcaccag ttagttcaat     360
ctgatgtcta acctaatttg gatacatgcc ttttattgca gctgccgtcc gtgcacagag     420
gagtcttagg aggaacaact gtagagaaaa ggatctgcca aattcgctag aaaattcacc     480
agaaacacca cccgttatcc aattaaacaa gatttttgga tcacttgtga agttgaattg     540
ctatccaact gctattccca tttctaaacc ttgttacacg agcatcttga tcaatggtct     600
agaaagggaa atagcagttg agtggtgctt caacgataag ttattggatt tagtatttat     660
cttagcctgt tttcgtgtac tttgttttgc cggatggagg tatgtgattt tgtctatgat     720
tcttaataca ataacctaca cttactctca ttgatagttt gtgcagatct aatagctatg     780
aagcaccgat accggacatg acacggtcag gtggacacat gtaatgtcta aatattaaa     840 atatagaacg tagtacgagt gtcgtgtcgg tgttagatac tgatagggac gcgtgtcgga     900
caccggacat gacaaaggac tgaagtgctt agaattgttt atgtttgaga tcttgttgat     960
gagaggcaga tagaggtcaa cttgccaaga taacctacag ttctatatta gatgctttgt    1020
gcaaaaacga tcatccaaag gctattggat tattcaagaa aactaaagac caaggagttc    1080
aaaaccgcct atgtacacat gcactatact tatggatgga ttgtgcgaag tggaagactt    1140
cagaatgcaa aaatgatttt tcaggatcta ctgattaaag gctatcaact aagtgtctgt    1200
ctgtactctg tataatgtta tgattcatag gctttgtaaa gagggattt ttgatgaagc    1260
```

```
attgatctag aaatctaaaa tggaaaacag atcttaaaga agatacactg tgtaaatgtg      1320
taatggcact ggcactctcg tgtactagtg gtcacctaag tgactagggt cacgtgaccc      1380
tagtcactta ttcccaacag aagttcctat tccgaagttc ctattctcta gaaagtatag      1440
gaacttccac tagtacccaa caagcttgca tgcctgcagg tttaaacagt cgactctaga      1500
gatccgtcaa catggtggag cacgacactc tcgtctactc caagaatatc aaagatacag      1560
tctcagaaga ccaaagggct attgagactt tcaacaaag gtaatatcg ggaaacctcc        1620
tcggattcca ttgcccagct atctgtcact tcatcaaaag gacagtagaa aaggaaggtg      1680
gcacctacaa atgccatcat tgcgataaag gaaaggctat cgttcaagat gcctctgccg      1740
acagtggtcc caaagatgga cccccaccca cgaggagcat cgtggaaaaa gaagacgttc      1800
caaccacgtc ttcaaagcaa gtggattgat gtgatgatcc tatgcgtatg gtatgacgtg      1860
tgttcaagat gatgacttca aacctaccta tgacgtatgg tatgacgtgt gtcgactgat      1920
gacttagatc cactcgagcg gctataaata cgtacctacg caccctgcgc taccatccct      1980
agagctgcag cttatttta caacaattac caacaacaac aaacaacaaa caacattaca       2040
attactattt acaattacag tcgacccca gtccatgaaa aagcctgaac tcaccgcgac       2100
gtctgtcgag aagtttctga tcgaaaagtt cgacagcgtc tccgacctga tgcagctctc      2160
ggagggcgaa gaatctcgtg cttttcagctt cgatgtagga gggcgtggat atgtcctgcg    2220
ggtaaatagc tgcgccgatg gtttctacaa agatcgttat gtttatcggc actttgcatc     2280
ggccgcgctc ccgattccgg aagtgcttga cattggggaa ttcagcgaga gcctgaccta     2340
ttgcatctcc cgccgtgcac agggtgtcac gttgcaagac ctgcctgaaa ccgaactgcc     2400
cgctgttctg cagccggtcg cggaggccat ggatgcgatc gctgcggccg atcttagcca    2460
gacgagcggg ttcggcccat tcggaccgca aggaatcggt caatacacta catggcgtga     2520
tttcatatgc gcgattgctg atccccatgt gtatcactgg caaactgtga tggacgacac     2580
cgtcagtgcg tccgtcgcgc aggctctcga tgagctgatg ctttgggccg aggactgccc     2640
cgaagtccgg cacctcgtgc acgcggattt cggctccaac aatgtcctga cggacaatgg     2700
ccgcataaca gcggtcattg actggagcga ggcgatgttc ggggattccc aatacgaggt     2760
cgccaacatc ttcttctgga ggccgtggtt ggcttgtatg gagcagcaga cgcgctactt     2820
cgagcggagg catccggagc ttgcaggatc gccgcggctc cgggcgtata tgctccgcat     2880
tggtcttgac caactctatc agagcttggt tgacggcaat ttcgatgatg cagcttgggc     2940
gcagggtcga tgcgacgcaa tcgtccgatc cggagccggg actgtcgggc gtacacaaat     3000
cgcccgcaga agcgcggccg tctggaccga tggctgtgta aagtactcg ccgatagtgg      3060
aaaccgacgc cccagcactc gtccgagggc aaaggaatag tgaggtacct aaagaaggag     3120
tgcgtcgaag cagatcgttc aaacatttgg caataaagtt tcttaagatt gaatcctgtt     3180
gccggtcttg cgatgattat catataattt ctgttgaatt acgttaagca tgtaataatt     3240
aacatgtaat gcatgacgtt atttatgaga tgggttttta tgattagagt cccgcaatta    3300
tacatttaat acgcgataga aaacaaaata tagcgcgcaa actaggataa attatcgcgc    3360
gcggtgtcat ctatgttact agatcgatgt cgacccggga tcatggctag cgaagttcct    3420
attccgaagt tcctattctc tagaaagtat aggaacttca gatcctctag agtcgacctg    3480
caggcatgcc cgcggatatc gatgggccc ggccgaagct tcaagtttgt acaaaaaagc    3540
aggctccggc cagaatccgg taagtgacta gggtcacgtg accctagtca cttaaattcg    3600
```

```
gccagaatgg ccatctggat tcagcaggcc tagaaggccc ggaccgatta aactttaatt    3660
cggtccggaa gcttggatcc gtcgacgaat tcactagtgt taccagagct ggtcacctaa    3720
gtgactaggg tcacgtgacc ctagtcactt attcccgggc acccagcttt cttgtacaaa    3780
gtggccgtta acggatcggc cagaatccgg taagtgacta gggtcacgtg accctagtca    3840
cttaaattcg gccagaatgg ccatctggat tcagcaggcc tagaaggccc ggaccgatta    3900
aactttaatt cggtccgggt tacctctaga aagcttgtcg acctgcaggt gtgtgattaa    3960
aagtcatata tggtttaaga tactttttt tataaagata gtagtggtca atttttcgat    4020
attacacaag tgtttctttt tcttctcatt gtactgtaga tctgatttac tttcaatgat    4080
tgtttaagtc actggtgtaa ttgtttgtgt ttcaaatatc aaaccaagct gaaactgaga    4140
tgatgatgat ttgaaatgct ttatctcatg tagtcgactc aattttcctg tatatttctt    4200
gttcttttta agaaacagg agcttttaag atttaaaaca ccagcatatt ttgtttgcat    4260
aatccaaatt gtcttaggtg taaagttgct gacatttccc ttgatgtcat tgctgcataa    4320
ttaattggag ccttttcaaa acctatggtt tattttgttg gggattattc aaggaacgcg    4380
tgtctcagtc tcaagtgtta tgattgctga tatcagtgat atattgctgc acaatgaagt    4440
ggaactattt taaatttcaa ttgatgattc tgcattcaat ttatcatctg acctttttat    4500
cttttacctc atctggcatt ttagtctttt accagataaa aggaccaaac acatgagata    4560
taatcaccaa atgaaaagaa tgaaagacga gatataaaga tgtggttttt cttttattc    4620 ctggaagatt tagatgatgt tttcaattaa gttgtttgtg gatgcttta gatgattttg    4680 ttttgcatac atatgtttac tttttgttc tcaacttctc attcattttc catgatttca    4740
tcccgtgaaa aagtgattta gcagaaaacg ttttcccct gttgtctttg tcctaaactt    4800
ttggattcta agttttttta tatgaaaatt agatcatttg gcacatggtt ttccaaagac    4860
acaagtagac tctttctatg aaatcaatct taaatccctt ttagaggaaa aacattttaa    4920
aggaggtgaa catgttgtgg agtgggaagg atccggtcac ctaagtgact agggtcacgt    4980
gaccctagtc acttattccc gggcaacttt attatacaaa gttgatagat ctcgaattca    5040
ttccgattaa tcgtgg                                                   5056
```

<210> SEQ ID NO 38
<211> LENGTH: 24
<212> TYPE: DNA
<213> ORGANISM: Artificial Sequence
<220> FEATURE:
<223> OTHER INFORMATION: synthetic construct; Primer Mega21-190F

<400> SEQUENCE: 38
ggcactctcg tgtgtgatta aaag                                           24

<210> SEQ ID NO 39
<211> LENGTH: 27
<212> TYPE: DNA
<213> ORGANISM: Artificial Sequence
<220> FEATURE:
<223> OTHER INFORMATION: synthetic construct; Primer Mega21-301R

<400> SEQUENCE: 39
caatgagaag aaaaagaaac acttgtg                                        27

<210> SEQ ID NO 40
<211> LENGTH: 16
<212> TYPE: DNA
<213> ORGANISM: Artificial Sequence

```
<220> FEATURE:
<223> OTHER INFORMATION: synthetic construct; Probe mega21-250T

<400> SEQUENCE: 40
agtagtggtc aattt                                                         16

<210> SEQ ID NO 41
<211> LENGTH: 23
<212> TYPE: DNA
<213> ORGANISM: Artificial Sequence
<220> FEATURE:
<223> OTHER INFORMATION: synthetic construct; Primer Mega14-13F

<400> SEQUENCE: 41
aacacatgat ggacgacttc aaa                                                23

<210> SEQ ID NO 42
<211> LENGTH: 23
<212> TYPE: DNA
<213> ORGANISM: Artificial Sequence
<220> FEATURE:
<223> OTHER INFORMATION: synthetic construct; Primer Mega14-128R

<400> SEQUENCE: 42
caagcagacg tacgcaagta gct                                                23

<210> SEQ ID NO 43
<211> LENGTH: 19
<212> TYPE: DNA
<213> ORGANISM: Artificial Sequence
<220> FEATURE:
<223> OTHER INFORMATION: synthetic construct; Probe Mega14-85T

<400> SEQUENCE: 43
ttgtcaatac gaaagtaac                                                     19

<210> SEQ ID NO 44
<211> LENGTH: 21
<212> TYPE: DNA
<213> ORGANISM: Artificial Sequence
<220> FEATURE:
<223> OTHER INFORMATION: synthetic construct; Primer Mega30-30F

<400> SEQUENCE: 44
tgccatgagt agcaccactt g                                                  21

<210> SEQ ID NO 45
<211> LENGTH: 23
<212> TYPE: DNA
<213> ORGANISM: Artificial Sequence
<220> FEATURE:
<223> OTHER INFORMATION: synthetic construct; Primer Mega30-87R

<400> SEQUENCE: 45
ctcagattta tgctcttgcg tgg                                                23

<210> SEQ ID NO 46
<211> LENGTH: 16
<212> TYPE: DNA
<213> ORGANISM: Artificial Sequence
<220> FEATURE:
<223> OTHER INFORMATION: synthetic construct; Probe Mega30-52T

<400> SEQUENCE: 46
tgggttcgac acatct                                                        16
```

```
<210> SEQ ID NO 47
<211> LENGTH: 28
<212> TYPE: DNA
<213> ORGANISM: Artificial Sequence
<220> FEATURE:
<223> OTHER INFORMATION: synthetic construct; Primer Mega5-F1

<400> SEQUENCE: 47
tcgtaaccat tcatgtgata taatgatc                                      28

<210> SEQ ID NO 48
<211> LENGTH: 22
<212> TYPE: DNA
<213> ORGANISM: Artificial Sequence
<220> FEATURE:
<223> OTHER INFORMATION: synthetic construct; Primer Mega5-R1

<400> SEQUENCE: 48
tgcttacgtg tgtactcgtg ca                                            22

<210> SEQ ID NO 49
<211> LENGTH: 18
<212> TYPE: DNA
<213> ORGANISM: Artificial Sequence
<220> FEATURE:
<223> OTHER INFORMATION: synthetic construct; Probe Mega5-T1

<400> SEQUENCE: 49
ttctcacact cacctaag                                                 18

<210> SEQ ID NO 50
<211> LENGTH: 32
<212> TYPE: DNA
<213> ORGANISM: Artificial Sequence
<220> FEATURE:
<223> OTHER INFORMATION: synthetic construct; Primer WOL133

<400> SEQUENCE: 50
gttgatgaga ggcagataga ggtcaacttg cc                                 32

<210> SEQ ID NO 51
<211> LENGTH: 33
<212> TYPE: DNA
<213> ORGANISM: Artificial Sequence
<220> FEATURE:
<223> OTHER INFORMATION: synthetic construct; Primer WOL134

<400> SEQUENCE: 51
ttatgcagca atgacatcaa gggtaatgtc agc                                33

<210> SEQ ID NO 52
<211> LENGTH: 27
<212> TYPE: DNA
<213> ORGANISM: Artificial Sequence
<220> FEATURE:
<223> OTHER INFORMATION: synthetic construct; Primer WOL190

<400> SEQUENCE: 52
ctaatgacac gtgtatcaag taactgg                                       27

<210> SEQ ID NO 53
<211> LENGTH: 27
<212> TYPE: DNA
<213> ORGANISM: Artificial Sequence
<220> FEATURE:
<223> OTHER INFORMATION: synthetic construct; Primer WOL242
```

```
<400> SEQUENCE: 53
tcgaactttt cgatcagaaa cttctcg                                        27

<210> SEQ ID NO 54
<211> LENGTH: 34
<212> TYPE: DNA
<213> ORGANISM: Artificial Sequence
<220> FEATURE:
<223> OTHER INFORMATION: synthetic construct; Primer WOL153

<400> SEQUENCE: 54
gattagagtc ccgcaattat acatttaata cgcg                                34

<210> SEQ ID NO 55
<211> LENGTH: 27
<212> TYPE: DNA
<213> ORGANISM: Artificial Sequence
<220> FEATURE:
<223> OTHER INFORMATION: synthetic construct; Primer WOL247

<400> SEQUENCE: 55
aactgagaga ctgagcgaca atcacag                                        27

<210> SEQ ID NO 56
<211> LENGTH: 31
<212> TYPE: DNA
<213> ORGANISM: Artificial Sequence
<220> FEATURE:
<223> OTHER INFORMATION: synthetic construct; Primer WOL121

<400> SEQUENCE: 56
gctaatggat tcaatttgaa gtatttaata g                                   31

<210> SEQ ID NO 57
<211> LENGTH: 34
<212> TYPE: DNA
<213> ORGANISM: Artificial Sequence
<220> FEATURE:
<223> OTHER INFORMATION: synthetic construct; Primer WOL150

<400> SEQUENCE: 57
actttagaat gataatgatg actttagcac tgcc                                34

<210> SEQ ID NO 58
<211> LENGTH: 27
<212> TYPE: DNA
<213> ORGANISM: Artificial Sequence
<220> FEATURE:
<223> OTHER INFORMATION: synthetic construct; Primer WOL192

<400> SEQUENCE: 58
gtacgcaaac agcttgttta cctttcg                                        27

<210> SEQ ID NO 59
<211> LENGTH: 28
<212> TYPE: DNA
<213> ORGANISM: Artificial Sequence
<220> FEATURE:
<223> OTHER INFORMATION: synthetic construct; Primer WOL193

<400> SEQUENCE: 59
ttccaatttg agagggtata tttccttc                                       28

<210> SEQ ID NO 60
```

```
<211> LENGTH: 30
<212> TYPE: DNA
<213> ORGANISM: Artificial Sequence
<220> FEATURE:
<223> OTHER INFORMATION: synthetic construct; Primer WOL113

<400> SEQUENCE: 60
ggaagccttg ttcgtatcga aacacaaagg                                    30

<210> SEQ ID NO 61
<211> LENGTH: 29
<212> TYPE: DNA
<213> ORGANISM: Artificial Sequence
<220> FEATURE:
<223> OTHER INFORMATION: synthetic construct; Primer WOL114

<400> SEQUENCE: 61
ccacatcttt taactcaagg ggcttcagc                                     29

<210> SEQ ID NO 62
<211> LENGTH: 28
<212> TYPE: DNA
<213> ORGANISM: Artificial Sequence
<220> FEATURE:
<223> OTHER INFORMATION: synthetic construct; Primer WOL194

<400> SEQUENCE: 62
ccaagtcaat aactttctga tgagaagc                                      28

<210> SEQ ID NO 63
<211> LENGTH: 29
<212> TYPE: DNA
<213> ORGANISM: Artificial Sequence
<220> FEATURE:
<223> OTHER INFORMATION: synthetic construct; Primer WOL195

<400> SEQUENCE: 63
ggttaggcaa attagatagt gtttgattt                                     29

<210> SEQ ID NO 64
<211> LENGTH: 29
<212> TYPE: DNA
<213> ORGANISM: Artificial Sequence
<220> FEATURE:
<223> OTHER INFORMATION: synthetic construct; Primer WOL105

<400> SEQUENCE: 64
ctcgggttaa gatcacatga tagcaaagc                                     29

<210> SEQ ID NO 65
<211> LENGTH: 31
<212> TYPE: DNA
<213> ORGANISM: Artificial Sequence
<220> FEATURE:
<223> OTHER INFORMATION: synthetic construct; Primer WOL144

<400> SEQUENCE: 65
cttaaccaac tccgatcctt ttcccgtcct c                                  31

<210> SEQ ID NO 66
<211> LENGTH: 27
<212> TYPE: DNA
<213> ORGANISM: Artificial Sequence
<220> FEATURE:
<223> OTHER INFORMATION: synthetic construct; Primer WOL196

<400> SEQUENCE: 66
```
attctatgaa aaggatgtct tgtggcg                                    27

<210> SEQ ID NO 67
<211> LENGTH: 25
<212> TYPE: DNA
<213> ORGANISM: Artificial Sequence
<220> FEATURE:
<223> OTHER INFORMATION: synthetic construct; Primer WOL197

<400> SEQUENCE: 67
acaccaagcc caatcgccat acatc                                     25

<210> SEQ ID NO 68
<211> LENGTH: 22
<212> TYPE: DNA
<213> ORGANISM: Zea mays

<400> SEQUENCE: 68
tggattgact tgcgagataa ac                                        22

<210> SEQ ID NO 69
<211> LENGTH: 22
<212> TYPE: DNA
<213> ORGANISM: Zea mays

<400> SEQUENCE: 69
caaacagatt cacgtcagat tt                                        22

<210> SEQ ID NO 70
<211> LENGTH: 22
<212> TYPE: DNA
<213> ORGANISM: Zea mays

<400> SEQUENCE: 70
ttacatgacg taggacatta cg                                        22

<210> SEQ ID NO 71
<211> LENGTH: 22
<212> TYPE: DNA
<213> ORGANISM: Zea mays

<400> SEQUENCE: 71
gtttctcacg cgtgagagcc tt                                        22

<210> SEQ ID NO 72
<211> LENGTH: 22
<212> TYPE: DNA
<213> ORGANISM: Zea mays

<400> SEQUENCE: 72
ccaaccgtcg tgagacctgc cc                                        22

<210> SEQ ID NO 73
<211> LENGTH: 22
<212> TYPE: DNA
<213> ORGANISM: Zea mays

<400> SEQUENCE: 73
agatcggacg caagagggtt ta                                        22

<210> SEQ ID NO 74
<211> LENGTH: 22
<212> TYPE: DNA

<213> ORGANISM: Zea mays

<400> SEQUENCE: 74
gggcggtatg tatgtcatac ta                                               22

<210> SEQ ID NO 75
<211> LENGTH: 22
<212> TYPE: DNA
<213> ORGANISM: Zea mays

<400> SEQUENCE: 75
caagctctcg cgaaaagggc ag                                               22

<210> SEQ ID NO 76
<211> LENGTH: 22
<212> TYPE: DNA
<213> ORGANISM: Zea mays

<400> SEQUENCE: 76
ctagtatacg tgagagacct tg                                               22

<210> SEQ ID NO 77
<211> LENGTH: 22
<212> TYPE: DNA
<213> ORGANISM: Zea mays

<400> SEQUENCE: 77
aagaaataca tgcgagccag tc                                               22

<210> SEQ ID NO 78
<211> LENGTH: 1083
<212> TYPE: DNA
<213> ORGANISM: Artificial Sequence
<220> FEATURE:
<223> OTHER INFORMATION: synthetic construct; Plant optimized nucleotide
      sequence of MHP14 containing a nuclear localization signal and no
      intron

<400> SEQUENCE: 78
atggcaccga agaagaagcg caaggtgcat atgaacacca agtacaacaa ggagttcctg      60
ctctacctgg ccggcttcgt ggacggcgac ggctccatca tcgcgcagat caagccgaac     120
cagtcctaca agttcaagca ccagctcatg ctgaccttca ccgtgaccca gaagacgcag     180
aggcgctggt tcctcgacaa gctggtcgac gagatcgggg tgggctacgt ccgcgaccgc     240
gggtcggtgt ccgactacat cctctcccag atcaagcccc tgcacaactt cctcacccag     300
ctccagccgt tcctcaagct gaagcagaag caggcgaacc tcgtcctgaa gatcatcgag     360
cagctcccct cggccaagga gtccccggac aagttcctgg agtgtgcac gtgggtcgac      420 cagatcgcgg ccctcaacga cagcaagacc cgcaagacga cctcggagac ggtgcgggcg     480
gtcctggact cctcccagg atccgtggga ggtctatcgc catctcaggc atccagcgcc      540
gcatcctcgg cttcctcaag cccgggttca gggatctccg aagcactcag agctggagca     600
actaagtcca aggaattcct gctctacctg gccggcttcg tggacggcga cggctccatc     660
atcgcggcga tcaagccgaa ccagtcctac aagttcaagc accagctctc cctgaccttc    720
accgtgaccc agaagacgca gaggcgctgg ttcctcgaca gctggtcga cgagatcggg      780 gtgggctacg tccgcgacca ggggtcggtg tccgactacc agctctccca gatcaagccc    840
ctgcacaact tcctcaccca gctccagccg ttcctcaagc tgaagcagaa gcaggcgaac    900
ctcgtcctga agatcatcga gcagctcccc tcggccaagg agtccccgga caagttcctg    960

```
gaggtgtgca cgtgggtcga ccagatcgcg gccctcaacg acagcaagac ccgcaagacg    1020
acctcggaga cggtgcgggc ggttctagac tccctcagcg agaagaagaa gtcgtccccc    1080
tga                                                                 1083
```

<210> SEQ ID NO 79
<211> LENGTH: 1083
<212> TYPE: DNA
<213> ORGANISM: Artificial Sequence
<220> FEATURE:
<223> OTHER INFORMATION: synthetic construct; Plant plant optimized
      nucleotide sequence of MHP14+ containing a nuclear localization
      signal and no intron

<400> SEQUENCE: 79

```
atggcaccga agaagaagcg caaggtgcat atgaacacca agtacaacaa ggagttcctg    60
ctctacctgg ccggcttcgt ggacggcgac ggctccatca tcgcgcagat caagccgaac   120
cagtcctaca agttcaagca ccagctcatg ctgaccttca ccgtgaccca gaagacgcag   180
aggcgctggt tcctcgacaa gctggtcgac gagatcgggg tgggcaaggt ccgcgaccgc   240
gggtcggtgt ccgactacat cctctcccag atcaagcccc tgcacaactt cctcacccag   300
ctccagccgt tcctcaagct gaagcagaag caggcgaacc tcgtcctgaa gatcatcgag   360
cagctcccct cggccaagga gtccccggac aagttcctgg aggtgtgcac gtgggtcgac   420
cagatcgcgg ccctcaacga cagcaagacc cgcaagacga cctcggagac ggtgcgggcg   480
gtcctggact ccctcccagg atccgtggga ggtctatcgc catctcaggc atccagcgcc   540
gcatcctcgg cttcctcaag cccgggttca gggatctccg aagcactcag agctggagca   600
actaagtcca aggaattcct gctctacctg gccggcttcg tggacggcga cggctccatc   660
atcgcggcga tcaagccgaa ccagtcctac aagttcaagc accagctctc cctgaccttc   720
accgtgaccc agaagacgca gaggcgctgg ttcctcgaca gctggtcga cgagatcggg   780 gtgggctacg tccgcgacca ggggtcggtg tcccactacc agctctccca gatcaagccc   840
ctgcacaact tcctcaccca gctccagccg ttcctcaagc tgaagcagaa gcaggcgaac   900
ctcgtcctga gatcatcga gcagctcccc tcggccaagg agtccccgga caagttcctg   960
gaggtgtgca cgtgggtcga ccagatcgcg gccctcaacg acagcaagac ccgcaagacg  1020
acctcggaga cggtgcgggc ggttctagac tccctcagcg agaagaagaa gtcgtccccc  1080
tga                                                                1083
```

<210> SEQ ID NO 80
<211> LENGTH: 1273
<212> TYPE: DNA
<213> ORGANISM: Artificial Sequence
<220> FEATURE:
<223> OTHER INFORMATION: synthetic construct; Plant optimized nucleotide
      sequence of MHP55 containing a nuclear localization signal and an
      intron

<400> SEQUENCE: 80

```
atggcaccga agaagaagcg caaggtgcat atgaacacca agtacaacaa ggagttcctg    60
ctctacctgg ccggcttcgt ggacggcgac ggatccatca tcgcgcagat caagccgaac   120
cagtcctgca agttcaagca ccagctctcc ctgaccttcc aggtgaccca gaagacgcag   180
aggcgctggt tcctcgacaa gctggtcgac gagatcgggg tgggctacgt ccgcgaccgc   240
gggtcggtgt ccgactacat cctctcccag atcaagcccc tgcacaactt cctcacccag   300
```

| | |
|---|---|
| ctgcagccgt tcctcaagct gaagcagaag caggcgaacc tcgtcctgaa gatcatcgag | 360 |
| cagctcccct cggccaagga gtccccggac aagttcctgg aggtaagttt ctgcttctac | 420 |
| ctttgatata tatataataa ttatcattaa ttagtagtaa tataatattt caaatatttt | 480 |
| tttcaaaata aaagaatgta gtatatagca attgcttttc tgtagtttat aagtgtgtat | 540 |
| atttttaattt ataacttttc taatatatga ccaaaacatg gtgatgtgca ggtgtgcacg | 600 |
| tgggtcgacc agatcgcggc cctcaacgac agcaagaccc gcaagacgac ctcggagacg | 660 |
| gtgcgggcgg tcctggactc cctcccagga tccgtgggag gtctatcgcc atctcaggca | 720 |
| tccagcgccg catcctcggc ttcctcaagc ccgggttcag ggatctccga agcactcaga | 780 |
| gctggagcaa ctaagtccaa ggaattcctg ctctacctgg ccggcttcgt ggacggcgac | 840 |
| ggctccatca tcgcgtccat caagccggag cagtcccgca agttcaagca ccgcctcgag | 900 |
| ctgaccttcc aggtgaccca agagacgcag aggcgctggt tcctcgacaa gctggtcgac | 960 |
| gagatcgggg tgggctacgt ccgcgaccgc gggtcggtgt ccgactaccg cctctcccag | 1020 |
| atcaagcccc tgcacaactt cctcacccag ctccagccgt tcctcaagct taagcagaag | 1080 |
| caggcgaacc tcgtcctgaa gatcatcgag cagctcccct cggccaagga gtccccggac | 1140 |
| aagttcctgg aggtgtgcac gtgggtcgac cagatcgcgg ccctcaacga cagcaagacc | 1200 |
| cgcaagacga cctcggagac ggtgcgggcg gttctagact ccctcagcga agaagaag | 1260 |
| tcgtcccct gaa | 1273 |

<210> SEQ ID NO 81
<211> LENGTH: 1083
<212> TYPE: DNA
<213> ORGANISM: Artificial Sequence
<220> FEATURE:
<223> OTHER INFORMATION: synthetic construct; Plant optimized nucleotide
      sequence of MHP55 containing a nuclear localization signal and
      without an intron

<400> SEQUENCE: 81

| | |
|---|---|
| atggcaccga agaagaagcg caaggtgcat atgaacacca gtacaacaa ggagttcctg | 60 |
| ctctacctgg ccggcttcgt ggacggcgac ggctccatca tcgcgcagat caagccgaac | 120 |
| cagtcctgca gttcaagca ccagctctcc ctgaccttcc aggtgaccca agagacgcag | 180 |
| aggcgctggt tcctcgacaa gctggtcgac gagatcgggg tgggctacgt ccgcgaccgc | 240 |
| gggtcggtgt ccgactacat cctctcccag atcaagcccc tgcacaactt cctcacccag | 300 |
| ctccagccgt tcctcaagct gaagcagaag caggcgaacc tcgtcctgaa gatcatcgag | 360 |
| cagctcccct cggccaagga gtccccggac aagttcctgg aggtgtgcac gtgggtcgac | 420 |
| cagatcgcgg ccctcaacga cagcaagacc cgcaagacga cctcggagac ggtgcgggcg | 480 |
| gtcctggact ccctcccagg atccgtggga ggtctatcgc catctcaggc atccagcgcc | 540 |
| gcatcctcgg cttcctcaag cccgggttca gggatctccg aagcactcag agctggagca | 600 |
| actaagtcca aggaattcct gctctacctg gccggcttcg tggacggcga cggctccatc | 660 |
| atcgcgtcca tcaagccgga gcagtcccgc aagttcaagc accgcctcga gctgaccttc | 720 |
| caggtgaccc agaagacgca gaggcgctgg ttcctcgaca gctggtcga cgagatcggg | 780 |
| gtgggctacg tccgcgaccg cgggtcggtg tccgactacc gcctctccca gatcaagccc | 840 |
| ctgcacaact tcctcaccca gctccagccg ttcctcaagc tgaagcagaa gcaggcgaac | 900 |
| ctcgtcctga agatcatcga gcagctcccc tcggccaagg agtccccgga caagttcctg | 960 |
| gaggtgtgca cgtgggtcga ccagatcgcg gccctcaacg acagcaagac cgcaagacg | 1020 |

```
acctcggaga cggtgcgggc ggttctagac tccctcagcg agaagaagaa gtcgtccccc    1080
tga                                                                 1083

<210> SEQ ID NO 82
<211> LENGTH: 1083
<212> TYPE: DNA
<213> ORGANISM: Artificial Sequence
<220> FEATURE:
<223> OTHER INFORMATION: synthetic construct; Plant optimized nucleotide
      sequence of MHP55-2 containing a nuclear localization signal and
      without an intron

<400> SEQUENCE: 82
atggcaccga agaagaagcg caaggtgcat atgaacacca agtacaacaa ggagttcctg     60
ctctacctgg ccggcttcgt ggacggcgac ggctccatca tcgcgcagat caagccgaac    120
cagtcctgca gttcaagca ccagctctcc ctgaccttcc aggtgaccca agagacgcag     180
aggcgctggt cctcgacaa gctggtcgac gagatcgggg tgggctacgt ccgcgaccgc    240
gggtcggtgt ccgactacat cctctcccga gatcaagcccc tgcacaactt cctcacccag    300
ctccagccgt tcctcaagct gaagcagaag caggcgaacc tcgtcctgaa gatcatcgag    360
cagctcccct cggccaagga gtccccggac aagttcctgg aggtgtgcac gtgggtcgac    420
cagatcgcgg ccctcaacga cagcaagacc cgcaagacga cctcggagac ggtgcgggcg    480
gtcctggact ccctcccagg atccgtggga ggtctatcgc catctcaggc atccagcgcc    540
gcatcctcgg cttcctcaag cccgggttca gggatctccg aagcactcag agctggagca    600
actaagtcca aggaattcct gctctacctg gccggcttcg tggacggcga cggctccatc    660
atcgcgtcca tcaagccgga gcagtcccgc aagttcaagc accgcctcga gctgaccttc    720
caggtgaccc agaagacgca gaggcgctgg ttcctcgaca gctggtcga cgagatcggg    780 gtgggctacg tccgcgaccg cgggtcggtg tccgactacc gcctctccca gatcaagccc    840
ctgcacaact tcctcaccca gctccagccg ttcctcaagc tgaagcagaa gcaggcgaac    900
ctcgtcctga gatcatcga gcagctcccc tcggccaagg agtccccgga caagttcctg    960
gaggtgtgca cgtgggtcga ccagatcgcg gccctcaaca cagcaagac ccgcaagacg    1020 acctcggaga cggtgcgggc ggttctagac tccctcagcg agaagaagaa gtcgtccccc    1080
tga                                                                 1083

<210> SEQ ID NO 83
<211> LENGTH: 1083
<212> TYPE: DNA
<213> ORGANISM: Artificial Sequence
<220> FEATURE:
<223> OTHER INFORMATION: synthetic construct; Plant optimized nucleotide
      sequence of MHP77 containing a nuclear localization signal and
      without an intron

<400> SEQUENCE: 83
atggcaccga agaagaagcg caaggtgcat atgaacacca agtacaacaa ggagttcctg     60
ctctacctgg ccggcttcgt ggacggcgac ggctccatca tcgcgcagat caagccggag    120
cagtgctaca gttcaagca ccgcctcatg ctgaccttca ccgtgaccca agagacgcag     180
aggcgctggt cctcgacaa gctggtcgac gagatcgggg tgggctacgt ccgcgaccgc    240
gggtcggtgt ccgactacat cctctcccag atcaagcccc tgcacaactt cctcacccag    300
ctccagccgt tcctcaagct gaagcagaag caggcgaacc tcgtcctgaa gatcatcgag    360
```

| | |
|---|---|
| cagctcccct cggccaagga gtccccggac aagttcctgg aggtgtgcac gtgggtcgac | 420 |
| cagatcgcgg ccctcaacga cagcaagacc cgcaagacga cctcggagac ggtgcgggcg | 480 |
| gtcctggact ccctcccagg atccgtggga ggtctatcgc catctcaggc atccagcgcc | 540 |
| gcatcctcgg cttcctcaag cccgggttca gggatctccg aagcactcag agctggagca | 600 |
| actaagtcca aggaattcct gctctacctg gccggcttcg tggacggcga cggctccatc | 660 |
| atcgcgtcca tccgcccgga gcagtccgc aagttcaagc accgcctcga gctgcgcttc | 720 |
| accgtgaccc agaagacgca gaggcgctgg ttcctcgaca gctggtcga cgagatcggg | 780 |
| gtgggctacg tctacgacca ggggtcggtg tcccactacc gcctctccca gatcaagccc | 840 |
| ctgcacaact tcctcaccca gctccagccg ttcctcaagc tgaagcagaa gcaggcgaac | 900 |
| ctcgtcctga agatcatcga gcagctcccc tcggccaagg agtccccgga caagttcctg | 960 |
| gaggtgtgca cgtgggtcga ccagatcgcg gccctcaacg acagcaagac ccgcaagacg | 1020 |
| acctcggaga cggtgcgggc ggttctagac tccctcagcg agaagaagaa gtcgtccccc | 1080 |
| tga | 1083 |

<210> SEQ ID NO 84
<211> LENGTH: 1041
<212> TYPE: DNA
<213> ORGANISM: Zea mays

<400> SEQUENCE: 84

| | |
|---|---|
| gtgaatctgt ttggaattga aaacaagtg cttccttta tacaccacta tgtcgcttca | 60 |
| atgtttgcga accaaggtaa agaaatgtaa aatcttacaa tttccgtgca tccgacataa | 120 |
| atctgtggtc acatagctat tgttaaacgg ttgcaaatcc taaggaggac cattattgtg | 180 |
| caacaactac atatgtaga agcgcttgtt ttgatgtgtg cacattttgt tgctaaaagg | 240 |
| atcacgatgc ccaagagggg ggtgaattgg ctttcctaa aaatcaacac taattaaaac | 300 |
| ctaagcaaga gcccaacttc accccgacaa ctagcaataa gagaatatga aagggaaata | 360 |
| ggatcaaacc ttttcctaaa tgattttggt ggttgaattg cccaacacaa ataattggac | 420 |
| taactagttt gctctagatc atacattcta caggtgccaa aggttcaaca caaccaatc | 480 |
| aaagaacaa gttaggcttc aaaagaaagg agcaaaaagg aaaccgaagt gtgcctggtc | 540 |
| tggcgcaccg ggctgtccgg tgtgccacca gacagtgtcc ggtgcaccag ggtgaatcag | 600 |
| ctcaagctcc tcaacttcgg gtttcccaga cgcagctcca ctataattca ttggactgtc | 660 |
| cggtgcaccc gcagagcaac ggctacttgc gcgcaacggt cgactctgca aagtgaacag | 720 |
| tgcaattcag aagtcagagc agatggtcag aggggcaccg gattgtccgg tgtagcaccg | 780 |
| gactgtccgg tgccgcatga ggacaaagcc tccaacggtc gaccagctcc aagccctaac | 840 |
| tacaagatga cgtggcggcg caccggacac tgtccggtgg tgcaccggac tgttcggtgc | 900 |
| gcccatcgcc agtagccttc tccaacggct acaatttggt tggtggctat aaataccacc | 960 |
| ccaaccggcc actttaaggt gtgggagccc aagcaacatt ccaagtcata tagttgacat | 1020 |
| attcaagcca tcccaaccac c | 1041 |

<210> SEQ ID NO 85
<211> LENGTH: 906
<212> TYPE: DNA
<213> ORGANISM: Zea mays

<400> SEQUENCE: 85

| | |
|---|---|
| tcactttccc ccctatttttt ctccctattt tttcatctcc cgcagcggtt cccctaaat | 60 |

```
actcctatat accccaatac aactataaaa tatcatttc tatatcaact atcaattttt      120
tatctactaa caattactcg tggacccaca tcacaatgtt tagggtgatg aacagtgaca      180
cgctagatct gaggggagag agaaaagggt cggcgcgtag ggggcgctgt aggggggcacc     240 gctgcggctg tggagtgccc cctacagccc ccatgcaagg ggaggggat actgaggggg      300 ctgcgttgcg tacagcctga caggctctcc ttcgcatttg cgcgggacag aaatgacttg      360
ccgaggatgg aagcagagag acggatttgg ccgagcgcac agcagctcgc caaagacggc      420
gtcgaagcag cagtgaccgc ggtcgagtga gggagtcatc ctggattcgc ggtttatcga      480
ctcggcacgg gggcaaccat ggcgttgaag gtaggcaaca tgaggagcca tcgattgaca      540
ccggtcttcg gaatcggcgg atctcgacga tggtgacaag gaggaggcca cgaagcgtcg      600
tcgagcagag cgcgacaagc aaatcgagtc ggccacgagc gtggatttgg atctgacccc      660 caagttttg tatggatcct attccccaat ttgtagatct tcaatttcct tactttaatt      720
ttccatagca caaacgatgt ttgcatgcac gattcggaca atcttgactt gttcgtccac      780
ggttggagtt tagggttgga atgtgtaaaa cacgtgataa actgtgtaca actcgagaac      840
tagataattc attttggatt gtaatatgtg tacctcatgc tatagttttg gttaaatctg      900
acgtga                                                                 906

<210> SEQ ID NO 86
<211> LENGTH: 979
<212> TYPE: DNA
<213> ORGANISM: Zea mays

<400> SEQUENCE: 86
tcacgacggt tgggctggag agccggctgg taggggagga cctcaacggc tgcgccttcg       60
tctactgctc cctcagcttc ctggacaaga tcttctgcgg gatcgccctg tttgccctgg      120
aatcgtacga aggtaagtga cgccgagatc ggcagagatg cttgaaaatt tgtgttttc      180 cttctgctgc gaaggccggc aactgatcgg gcgggcgcaa caccgtcgtc ttccgctgca      240
gatacgatga gctgcggcga gacgggggc ctcaacacgg tgagcaggta cggaacgggc      300
ctgatccccc ctcctgcttc gccgtccta ctccgagagc cactgcactg gaagcccgc       360 tgcttgtctg acggactgaa gaaaccggtg gatgtcgatc gggttgggag aagaaatgcg      420
catcctcttc aattagattt gatttgaaga ggaacatgtc actcgctttt ttttccaatt      480
agaatcctct tcgattaggt ttgaagaggg gggaaatgcc actagttttt tttccaatta      540
gatttgaaag caggccactt tgtaataata ttcgccatgc cgtcgtgttg gcacatcaca      600
tatgcatagt tttggtgtgc taatagatga cattaagttg ttgtacgtat aactcgaatt      660
tctgcgaagt ttgtgtgcat gtcatcagat tattgtacta agagcaggaa cagcatatgg      720
tcgaggctga aacagaagac tagtatacag atccgtgtag gaaagaaaaa aaaactagc      780 tttgaacacg ctgaaaacga cctggacact gaatgcaaac atcacccgcc gcggcgggct      840
ctcctcacag ctcgtcctcc gactccgacc ggtacttgtc cacgtccgcc ctccggtgct      900
tccccttgcc gtcgacggcg gcgacgtcgg gcccagcgac cctctccttc acctcctcca      960
gcctctcctt ggccgtgtc                                                  979

<210> SEQ ID NO 87
<211> LENGTH: 734
<212> TYPE: DNA
<213> ORGANISM: Zea mays
```

<400> SEQUENCE: 87

```
tagagtatga gtcctgctgc ggtgcgtgga gtcgcttgag agcgttggcg gcgagaagtc      60
cgccaacggc actgtggatc tcggccacgg aagagaaaaa gaaaaggcaa aaattgcatt     120
gtcgaatacg tgaacaggaa aatccaattt tcgtatcatg acctctgtat atgtatccat     180
atatataaaa aaaattctaa tatataaaca gactcaatat tttgtaaaaa atgccatttt     240
aaatttgtat taatatatgt tggaaaatgt aaagaatgag atatagagaa cgaaatttag     300
agaaggttgc tgaagatata aaagattaaa tcttttagag tgtgctataa aggatagaga     360
atatttgttt aatggatgaa atttagaaaa cgttattgga gataggctaa aaaatatact     420
gcattgcaaa attcagcctt cccttcactc acccatctct ggaactgcct gcctgcctcg     480
aacgtaggag atcaagtgga acgaccggcg cctcaagtcc ctcctcaccg tcggcgcgac     540
gctctgggtc atctccggcg tcaccgtctt cgtcttcccg agccagatgc acaacaccct     600
ctcgccatgg tcatcggcgc tgccaacgcg ctcgtcatgg taaaacgcgg gcgcctagct     660
agcacgccac gctgcacgtc caaatcctac cggtttcgcg tgctctggct ttacattaca     720
tgggcaggtc tcac                                                       734
```

<210> SEQ ID NO 88
<211> LENGTH: 1016
<212> TYPE: DNA
<213> ORGANISM: Zea mays

<400> SEQUENCE: 88

```
atacataccg ccctaaggac ctagatagtg tgttggtcca aaaaaccaac atagaaacat      60
caaagttttt gccattaata gaaaagattg atggacaact catttccaaa gccatacagt     120
caattgtaat catcttcaac ccaatcaaaa actcatagtt tataaccgtt ctttggccag     180
cttcacggat agtctgtccc tctgagactg aaagtagcct agaagtgggt gaataggcta     240
aacctaaaat ttccaccaca aactttgaaa taatgtcaaa taagcagttc aactggtgca     300
ggccagttca accgctatta aggccggttg aaccactcta aaccggccca accgtgagag     360
aggatcaagg ctatgaacaa cgcagagact aatgagagat tcctttaaga aaagagctca     420
cgggataaat taggcataaa tagggaaaat ttgtgtggat aagatccaca cacaagacaa     480
ctcgatcgat gtcttctttg ctaaagataa ttcacaacga tttgaattaa agcaaagaca     540
caaagacgca aggatttatc ctgaggttcg gccacaccat aaaggtgccc tactccctgt     600
tgaggagccc acaaaggacc aagtctttc caactctaat cctccacaaa tcgaccacaa     660
aggtcaaggc aaactctttc tcaactttgc tcaacgagtg agtgaaacaa acttcttggg     720
gtcgtccaca aatttggaga ctcccaagca acctcaaact gccaaggaac tcgaaggttc     780
caagggcaac aaatctgcac aagaagtgtt tgcagtgggc tcaagagatg agaaaggggg     840
gggagagaaa actaagtcta aaagtgaaaa actcaaactt tacaccaagg gcccttcaat     900
caagcgatga gggagcgatt tggggtgtga gagagttggg agcttttatc tcaagttagg     960
tcagcaatga atgcgtggag caaccataat gaatgaggag agagacatga ggggt         1016
```

<210> SEQ ID NO 89
<211> LENGTH: 898
<212> TYPE: DNA
<213> ORGANISM: Zea mays

<400> SEQUENCE: 89

```
ctttggcaag caattgcatg cgagtaaaca agtaattaag agtaaggttc accggttagg      60
```

```
ttccttacct cggtgtaaag cttggaacat ggttgttgag gttagttagg ttccttaccc      120
acaagtcaca ctctcccaca tggtgtgctc atacctaagt tatacttgat cagcctagac      180
cacttggcgc tcttcacacc ccactctact aatgtgctct tcgtgtctcc tgtggggcga      240
gcacggtacc ccttacaatg cctcctttag agccacacac gatttcatgc aggattccat      300
ggagccataa cctccaaggc acctaggagg tggaaacctc taaaagtaac aagacaatga      360
tcttcctagt gataacttga taatgtgagt tagtaagagg tttggggcga aggctcaagc      420
atgctcaaca agtgctccta ttgctcagct tagggagcac acatttacac tcctactttt      480
tatagcccca cttcccacaa ctagacacta taacactttt tgagaaaact acacattagt      540
ggacactcca taatacaacc cacggatagc ccatatttga attccgatga ctatatttca      600
attaaatgcg tgttagtcgt catagaaagt gtttagtgaa cagtctatct gttaattttt      660
aacatgtcta taaacttcct aatttatgtc ccctttaag aatgtgcgac agatagtctg       720
cctttgaggc ccatatagta caccgaccaa atatttgcat tcaccgaaac tcccaagttt      780
ctatccacta tctaaaacag tgtagagaca gtctacatga ggggcccaa tagtccatcg       840 gtcaaaaaac acataaactt taagttttt gtccatcact tgaattagta tgacatac         898
```

<210> SEQ ID NO 90
<211> LENGTH: 260
<212> TYPE: DNA
<213> ORGANISM: Zea mays

<400> SEQUENCE: 90

```
agggcaagtc aatccatgca acaccactca cgaatatgtt acgttaatac caaaaccata      60
tattgacaca catgcacaac atcatatatt atgttaatca ctttataaat ccaattttaa     120
tctaaaacaa tgttttatca cacacgattt cgcaatatac atcggtgata aagatacgcc     180
ggttgaccat gtaagtcaac aaagggtcga taacgtcgtg acacttaaaa ggaggcgagt     240
cacacatcta tatgggtgct                                                  260
```

<210> SEQ ID NO 91
<211> LENGTH: 900
<212> TYPE: DNA
<213> ORGANISM: Zea mays

<400> SEQUENCE: 91

```
cgtacaactt taggaatcac accagccgcc tactctaagc ttgggcctca cttctgtggt      60
ccctatcagg ttctggagga aattgggaca gtatcttaca ggcttgccct gccatctcac     120
gcccgcatcc ataatgtgtt tcatgtctct ttactaaaga aatatattgg ggctcccccg     180
gctgcaatag ttcctctacc cccaatatta catggcagag tcctgcctca gcctgagaag     240
gttactaagg cacgcaagaa ccgaggcgtg tgggaactgc ttgtgcaatg ctgggacaa      300 tcagccgctg atgcaacgtg ggttcagctg gaggactttc gtcgccgttt tcctggtgtc     360
caggtcgcgg acgacttgtt tttgggggag ggggaaatg ataccgatgc atttgtagga      420
aaggtatacc agagaaggaa tcgccaggaa taaaggaaac aacagataag gaataaaaga     480
gacaacagat aattttctat atttagtcag tcagcagatt aggaataaaa gagacagcag     540
ataagtttct atatttagtc agtctatttt ctagcaagtt gagagtgata tgatttgttt     600
ctatattaac ctgggctcag tctataagag accaggggta gtttgtacta gggattatca     660
aaagaagaaa atctcctagt cctaggaggt tgcctgggcc cctggggtgc actggaggaa     720
```

```
ctctccagcg tccggaacgc caccaggaat cctcctcccc cttcccactc ctatttcctg    780
cgttcattgt ccacaacctc ctgctgagcc cccaacgaaa gcagggagtt tgcgtcactc    840
gacccccaac tgataagggt ttaaggtcgg gaaatctcac ccgtgaagtt tatctcgcaa    900
```

<210> SEQ ID NO 92
<211> LENGTH: 931
<212> TYPE: DNA
<213> ORGANISM: Zea mays

<400> SEQUENCE: 92

```
ctacgtcatg taagtttcta gtggttgtat tgctctgggt ttgaagatta taggtgattg     60
ttgaaggtag aatatgaaag tagcctacga gtctaatgga gtctcccgtt tcagcattat    120
atggccaaat gaagagataa ccctgtatag atcataatcc tatatgcatc taaccacttt    180
cactatagac gcaacgcatt ttccggcgtt cggttggttc cctgcgaggc ttgtgtacgg    240
ctgcatgcat gggacatgcc ttcgaagatc cccttgactc ggtgtgtgac cgctttactc    300
ggcttcggtt gcatcttgca gaggcccacg atgcacccta tggacgaccc atcaggggcc    360
ttataagcgt cacatggagc gcatccatgc atggtgacct aggggatatc catgtaacac    420
cccaggtgtt agctagaagt aataacccaa ccacttggac cattatcaca tgtggataac    480
ttaaggtaaa agtcactaaa attaatgacc atattcctaa taaggtgaaa aacacccctag   540 aagaattaac ttacccaccc catggtgatc aaaggaaagg ggagtaacca accccctaaa    600
cctactctct tgagcccaag agcaccaata caaagtgtca agagaaagtt aaccaaaatc    660
cttaaccaca agtggaccct taacaaaagt tatagctaac taaatacctat acaaaagttc    720 ttgagggtta agcaccaaaa ggggtgctag agtcccaatc aagtcacaca tgtgggagaa    780
ggggagagaa atcaagattt tttcataaat ccaaaaacag ccctatccca aaaacataaa    840
atctccaatt atgaaatgtg tgcctaattg tcctaggaac accctcgtaa agtttgaact    900
cgagccctca ctgtttgaca tgacaagtca t                                   931
```

<210> SEQ ID NO 93
<211> LENGTH: 922
<212> TYPE: DNA
<213> ORGANISM: Zea mays

<400> SEQUENCE: 93

```
cgccgcatta aatgcgcggc agagagccgt tggcgcggag atgaccgttg cttcggagtc     60
gcaccggaca gtccggtgaa ttatagcgga ctagccgttg gagtttcccg aagctggcga    120
gttcctgagg ccgtcctccc ttggcgcacc ggacactgtc cggtgtacac cggacagtcc    180
ggtgaattat agccgagtcg cctctgcgaa ttcccgaagg tgacgagatt gagtctgagt    240
ccccctagtg caccggacat gtccggtggc gcaccggaca gtccggtgcg ccagaccagg    300
ggtgccttcg gttgcccctt tgcttctttg ttgaatccaa aactcggtct ttttattggc    360
tgagtgtgaa cctttacac ctgtataatc tatacacttg ggcaaactag ttagtccaaa     420
gatttgtgtt gggcaactca accaccaaaa ttatttagga actaggtgta agcctaattc    480
cctttcaagg cttcacttcg gaccactcta gaagtctatg gatggtctag cctcttagca    540
tgaacgatcc acgacaatga tacttagccc actttccaaa acacgctttt gaaaatattt    600
taactcacga attcagaaga attgttaata atcttgctaa tgcatcatct aaaagctcta    660
tgaggcatta agtttcacat aagaaattgt cattgactcc tcttgacagt atggctatct    720
atccgactaa cccagacaat tttcttctct aaacaccttg tgactggtgt cggtgtttgg    780
```

```
taccaatggc gcactatggg atataccatg tagtgctttt gggaggatag cgatgtcgat      840
caaaacttga tggttcatgc caggcacgat ggaacagagc agattatata ggtttgaacc      900
acctagaggc gtaatgtcct ac                                              922
```

<210> SEQ ID NO 94
<211> LENGTH: 994
<212> TYPE: DNA
<213> ORGANISM: Zea mays

<400> SEQUENCE: 94

```
acgcgtgaga aactgagaat cgcctgcggg ccgcgaatgg cgagcgagca cggcttgaga       60
atctgacgat ggaggaagct tggatagtgg aagggtattt ttggagatca atttgtagat      120
gctggtggaa gcgttttctt tcctatactg gccttctcga aacctgtagg agttgctcta      180
acaggtaagc atcatcagcc cctccttgtc cctcagtttg taatacagca atttcagata      240
tggacataga aaaactctag gtccaccact gatagtaatc ctctaccatc aaaatatatt      300
ttatttgttt tcgaaaataa ataagacaat gttaagagta catgtagaac cttctaaaca      360
tctgaacttc agattcaaca ccaaatcaac atgatgagtt caacatgtg agttaaatga      420 caaagtgggt tgctttagaa agcaacacaa gttacctagt tagggcttaa gcagacaatt      480
atttttgggg tagtgattta caaaataatt tattttccga ttgcaactat gttacact       540 caatttaaa aaatatgttt tataatcaga ccacacatcg aagtacaggt gtgtattatc      600
gaggtacatg attatttcaa tatttgagag agccttttca acttggtaca attgggacac      660
ccaaatggaa agaaacagta tgatcaaagg acctgaatag gtgggcacaa taactgaagt      720
tatctggcca attattaagt aacacttttt tagaattcct ggggcctggt cagcatgtac      780
gattgaccat aaattgttct ggtcagcata gttattgaca actccggaaa ctatctgata      840
agacatactt gggacctgtt tgtttgagat tataaatatg tttagattat aaccccaaac      900
aaacaaaccc ttcatattcc taaaacaagt ctaaaattta attaaatata taataaatgt      960
tacatatgct atttgtcacc taggtgcgac tggg                                  994
```

<210> SEQ ID NO 95
<211> LENGTH: 1048
<212> TYPE: DNA
<213> ORGANISM: Zea mays

<400> SEQUENCE: 95

```
ctgccgatgc tatataagtt gagtcgccct gccgatcgtt gacgctcgaa cgtcgaccct       60
cctgaagaat aggctcctgt tgcgtgtctc ctaaccacgg ccacctcgac ttcggctaac      120
tcggcatcca ggggctatcg ccttatcaga atccacaccg gtctcttctc cagccacaac      180
attggcaccc tcacgacgct gcgaccgcag gggggttcaa cccgtcgact cctaccttcg      240
gcctctactc cagtttcatc gtgtgtggtg ccccgttgc gactgcgggg atgttagact       300
gtgtgtgtag gccggcacca ctgttgggct gccggcccat tagggttagg gttgtgagtc      360
tatatattat accccatctc ttatcaatac aaccaccact tgatacttct acatagagga      420
tagaggtagg agcagcccct aatcttcagc tttcatagcc aactgcccaa gaatatccat      480
aaacctagcc aattcacttc tccaatcgcc ttagtctagt aaaagcaaat gccctatgca      540
tgtaacttta ccttgcactt tcttttccac ttctgcactt ccatccatca tcttcacatg      600
ttgagcactt gcacttcatg gtccttgcca tctccacttc acggttctat atatgtggct      660
```

```
caactatctt gtacactaaa tcgcctattc atctcacatg aaataaatta gtctggcatt    720
caattatcaa agccaaatca ggtctttcac tccagagctc ctgcttgact agttgccgct    780
cttccgtgat gtttgccacc tcttccaccc ccagactgca gtggtatact ttcccccaat    840
ctatttttag tgctaaaatt ggggcttttct caaattgaat tatttgcttc tccatatgcg   900
catcttactg taatacgcgg tggtggccta tgaccgccag gatgtgtcta caacgcagta    960
cctatggcta aagttgcag cttcctccac aactggtagg ccaatctccc ccatgcaggc    1020
gcgcacagga gagggaaggc tctcacgc                                      1048
```

<210> SEQ ID NO 96
<211> LENGTH: 901
<212> TYPE: DNA
<213> ORGANISM: Zea mays

<400> SEQUENCE: 96

```
ttgcgtccga tctcatccac ccgctcctga tccaacgacc cagatccttg ataccggtt    60 cgagcgcgcg ccccctacccc taggcccac acgttgccgc ctgcgcccct gatgctaggc    120
ctgaactgtc agtccaccct caccctggc cgctgaccgc tctgtcaccg cttgctcgcg    180
cccccgtgcg cttgcccgca gatctgatct cggcagttga tctgtgatcg gatggccgag    240
agcgcccgat accccttcat ttggaaattt tgttaaagag atccccggtt tcttagaaat    300
caacccgcag tctagtttta ttgcgcctga gtccctggtt ttttgcagag agacccagta    360
actttatttt tatcacaaaa attggtttaa tttagggttt tgaattccaa aacttgtaaa    420
tttcatatct tttgcatatg aactccaaat tgggtggttc aaattgcaaa atgttcataa    480
tgttattctc tatgtgttta aattatattc atttactatt ttcatgtctc aatttttgtgg   540 ctaatcccta ggttaattta aagtgataga atatttatta aagggtaaaa taaaaggtaa    600
agccctaatg aatgtccatg tgcttaactt tgtaaactta atttcattta atgtaatccc    660
atccctagaa tctgtttatt taagtaagta atttattgag atagacttag ttagaaaata    720 gtagacctt aaacatagtg atctacccta ataccagag ttcacttgtg tgtttgtact    780
tttctactga acctttgttt gatcggttgc acatgtttgg tgtgctgttc tttgttgttc    840
cccaagtgtg ttgaatgaat gattgcttg cgtacacaac gagcaatccg aggttccgag     900
t                                                                   901
```

<210> SEQ ID NO 97
<211> LENGTH: 1083
<212> TYPE: DNA
<213> ORGANISM: Zea mays

<400> SEQUENCE: 97

```
atggcaccga agaagaagcg caaggtgcat atgaacacca agtacaacaa ggagttcctg    60
ctctacctgg ccggcttcgt ggacggcgac ggctccatca tcgcgtccat caagccgaac    120
cagtcccgca agttcaagca ccagctcatg ctgaccttca ccgtgaccca aagacgcag    180 aggcgctggt tcctcgacaa gctggtcgac gagatcgggg tgggcaaggt ccgcgaccgc    240
gggtcggtgt ccgactaccg cctctgccag atcaagcccc tgcacaactt cctcacccag    300
ctccagccgt tcctcaagct gaagcagaag caggcgaacc tcgtcctgaa gatcatcgag    360
cagctcccct cggccaagga gtccccggac aagttcctgg aggtgtgcac gtgggtcgac    420
cagatcgcgg ccctcaacga cagcaagacc cgcaagacga cctcggagac ggtgcgggcg    480
gtcctggact ccctcccagg atccgtggga ggtctatcgc catctcaggc atccagcgcc    540
```

```
gcatcctcgg cttcctcaag cccgggttca gggatctccg aagcactcag agctggagca    600
actaagtcca aggaattcct gctctacctg gccggcttcg tggacggcga cggctccatc    660
aaggcgcaga tcaagccgaa ccagtcctac aagttcaagc accagctctc cctgaccttc    720
caggtgaccc agaagacgca gaggcgctgg ttcctcgaca agctggtcga cgagatcggg    780
gtgggctacg tctacgaccg cgggtcggtg tccgactaca tcctctccca gatcaagccc    840
ctgcacaact tcctcaccca gctccagccg ttcctcaagc tgaagcagaa gcaggcgaac    900
ctcgtcctga agatcatcga gcagctcccc tcggccaagg agtccccgga caagttcctg    960
gaggtgtgca cgtgggtcga ccagatcgcg ccctcaacg acagcaagac cgcaagacg     1020 acctcggaga cggtgcgggc ggttctagac tccctcagcg agaagaagaa gtcgtccccc   1080
tga                                                                 1083

<210> SEQ ID NO 98
<211> LENGTH: 1026
<212> TYPE: DNA
<213> ORGANISM: Zea mays

<400> SEQUENCE: 98
tcgcgagagc ttggggggcc ttgacgactg agtgagtgtc tttcgtgctc ggccttcctg    60
ctctcgtttg cgtcttcgcg caaggaaacg ggaagagaaa aagagggacc gtcccgtccg   120
tgcggacgtt gtcgtgcatg ggtgggtctt gcatgatttg tgcctgccgt cctgtggtcg   180
acgggaagcg acggcgagtc ggcgaagccc agctggagcg tagagccaag agcccgtgct   240
gtgcgcgctg tgtgctgtag ctgtgccgtt gcagttgcag ttgcagttgc agttgcagcg   300
acgggttctc acttgatcac ttcggagttc aggcaaagct ctcgtggtgg ctgccatgcc   360
accactggct gatagcgtgt ggacccattc caggcccata cccactttac ctacccgggc   420
acccaaaggc cgaagcctgc tattgtagta ttgtcggcct cgcagcaga gcgctgagtg   480 tctactgatt ataccgctga aattaaatgc ggtattcgct tttcagacca aaccagacca   540
gatcagccag tgcaaagccc gcagtgggat ccaggcaaac gttttctcca ctgcaatcga   600
tctgctgcta cgtagaggcc ggtagtctac tgagcgcaac gcgtacaagt tgctgttgct   660
ggatcgctag ctcacatacc tctcgacgca ctcggttgtt ggcttacat gcatggccgc    720 ccaccacctt ctcggtgacc acctacatgg tctctctagc agaccccgtc agtgccgcgc   780
gcattcggtg catgcatgcc tgtatggaca tgacgtgcgt tctcgagcaa taattagatc   840
catgttggca ccagagatgg gtagacctgg cgtgcacgaa ataactggta ccatcagtga   900
acaaaacaag cattcctcgt ggcgttcatg gcggtgatgg cagtgggaat gtacaactga   960
cttcagggac cgtgacggac cgtgggataa agacgcagta gagcaggaaa gatacttcct  1020
accaaa                                                             1026

<210> SEQ ID NO 99
<211> LENGTH: 856
<212> TYPE: DNA
<213> ORGANISM: Zea mays

<400> SEQUENCE: 99
caaaggagtc aaggacagac actgtcgatg atatgagaca acaacaaca aagcacactc     60 cgtttcaata aaagaagat tatcggactc cctcatacca gccctaccta cgacacgtgt    120
aacgcctcag gggaggaacg ggacacaccc atgcatgcgg atgcgggcgc agcatatcct   180
```

```
gacacgcgcg gcgtgacccg cctgtcagtg agtctgcacc gtccgatcga gccgcgcggg      240
tcacgtcgag gccgcgctgg tcggtccttt tttcttcgtt ccccggtcc  ctcctgcccc      300 tggtatgtaa tattttctt  gccctcgtgg agtaccgacc gcgagaaagg aacggccgtg      360
ggaagaaagc gacgggaggg ggcgggcgct tggatcggcg gcatctgtag aaagatggga      420
atcctcctgc aggacaacta gacaagtgtc caccggaaca gaagacctta tctagtagta      480
gcagaagagt ggtagcagta caccttccta aagtttgatt taaaaaaaat tgaaagtatc      540
aaatatctat ttaacaatat gtaatgcttc tactacaaag tatttttttgt aatggagaat     600 ttagtaatac tcattttatt tataagtact aaaatttcat ataaattagg ttaaaccttaa     660 aaataacttg actgagtcga cgctctatta taaaattttt tttctcagac cgagggagta      720
aataaaacta acaaagcga ggagctgcgc ggaggacatg tcaacgaggg agacgacgac       780
gagagaaacc aacgagattt tttgccagac atgaaagcga gagaggcctt gtatgttcct      840
cgcctgccct tttcgc                                                      856

<210> SEQ ID NO 100
<211> LENGTH: 1068
<212> TYPE: DNA
<213> ORGANISM: Zea mays

<400> SEQUENCE: 100
tcacgtatac tagctgaccc atggagccca ttgccagtag ctgctcccgc tttacgctcg       60
gatcaggtga ctcaatagaa tccggctgag atcctcgcta gtgaccgtta ccttcctcta      120
ggggaacctg cctctctatg tatataagaa accacgccct ctcgcctcct aatcctaccc      180
atgttgagcg tcaccgaaag ctgagagcct cgccatcgag tgaggggggg gggggagat       240 tgccgccacg gtcaacccat tagtgtgccg catccccgcc ttcggagcat ggtctagggg      300
catccacggg tcgtggcgga gctatccgtg gcattatcaa gcaggatggg tcctcggacc      360
aatgggaatt tctcgccgta gtccttcgcc atagatccgc ctgcaccgtg gtcggaggac      420
atcacctact tcatcgctgg tacataaccc ctataccgtt agctagggtc ccctatccat      480
gtagctctcc tccgatcaag atctaaagca tcaaagcgct aacctgaaag ggaaatggtt      540
aaccatttcc tataatcgat tttggtgttt gacgactatc acaaaccata tggactaact      600
agtttgccta gtcaatattt tccttaggt  gcataaagtt catatacaca ttgtcgggta      660
ccgtaattag gggtaccccc aacactccta aacacgacta gtaaacacct tcaaagcaaa      720
ccatgaagac caacagttcg ggtcaaagtc aaagcttcgt ctaccaaggg acacgatctc      780
gcctcggccg agcccgaccc caggcgggaa cagtagtccc ggacggattc acgtctcgcc      840
cgagggtctc ctcaggcagt gagcacaccc tcggctcagc caaaggcaag ccttgtcgtg      900
caagcgaccc tggccaaatc gccttaccag tcgaccgtat tgcatgcgca tttaatgctg      960
ggatcgcctg acaccttatc ctgacacgcg tgcctcagtt gacaaggtcg aagtgaccgc     1020
agtcgcttcg cccttccact gaccgatctg acagaaaaat agcaccgc                  1068

<210> SEQ ID NO 101
<211> LENGTH: 982
<212> TYPE: DNA
<213> ORGANISM: Zea mays

<400> SEQUENCE: 101
tttctgacag cccaacgaat ttcgttgatg aaatatgcaa ctttcatgat ctctgaagtc       60
gtaaatgcat cttcatatat cttcaagcct ttcacgacat agcaaaaggg tattgtcggt      120
```

-continued

```
accttataac taagtatcct cttctactgt attaagatag agacctccgc ggttaacttt       180
aaacgcgtac taaggtaatg agtggccggt cctacgggac tggacctgtc tgtcaggacc       240
cctggcttca agttccgctc ttcacctcga atttgtaaca cccaaaaatc ataattttg        300 gatttagaaa aaatatatta tcctgaaatc taaataagaa tattttctca taaaagattt       360
aagtaaaagt atttcataaa agagattata tattagaaag tatttcctcg taaaacaaaa       420
caagtaataa atattaaagt tttttttaatg aacttttaat gtgactacac attcaaaata      480
ttttcgtaaa ataaatatta tgtgtgttgc atattgaaaa cattgcctaa ataaataaat       540
aaggtaataa attaatgaat aaacttaata cacaaacctt gcattcatgc tggatatttt       600
tttgtgcaaa ttagaacttt gtttgaatct aaatctaatt ggaattggaa aatagaaaat       660
agaaaaagaa taaaaaagga aaggaaaact ttacatgcat cgtgggccga gtaacgcagc       720
acgctccacc cgcggtctct tttccttttc tactagtcac tgacacgcga gccccacagt       780
gcagcctcac catctcgcac tcgaatgggc tctagaagtc gctcccaaat ggggccaagg       840
tgccaacacc ttcttctcta atcaatgggg atcacaatg aatcctttcg taaccgccat        900
gtaacggcct ccatagatcc cgaccaccag tactttctct attcgtgcgc gcctgcccga       960
gggaccgttg tggcaaggtc tc                                                982
```

<210> SEQ ID NO 102
<211> LENGTH: 1052
<212> TYPE: DNA
<213> ORGANISM: Zea mays

<400> SEQUENCE: 102

```
agaatgacga ttgctggact gggagacatt gggttggcgt aactgttcag gacttcgggt        60
acccgtgggt cacccgtggg tgaagtgaga acccggacc cgaacccgaa aaggtgcggg        120
tcgggttcgg gtcacacccg tgggtgaaaa aacacacccg cgcccgcacc cgtcgggtcg       180
ggtacccgac gggtacccga acctgtgggt gaaattgcca tgcctacagc tggctgtggc       240
gtcaggctcg ggagcccatg ccaattgggc taaaagccca aaattttcca atgcacgcca       300
ttggggctgc acagttctag cactagactg gcttttcttc agtgaaactg aggctgcact       360
ttgcaactgc ttcttcaggc aaaacactaca tatgattgga cgtccagctc gtgggcgcaa      420
ggctcgcggc ggcctggatg cgcagggatg ctccctcttc gtatctccat gcgtacaaac       480
tgacacaaca aaaagccatt gagttgcatc ggtgcgtgca ggctcgtctc cattcataca       540
gcgcccacca atcaccggct aagtgcggtc aacggaacgt ggagagcctg acgcacgcg        600 cctaggtatc caatcacgcg gagtactgtg tccagccgaa gccttccaca gcggccgagg       660
accgaggtat agttcaacgg aacgttgccg tgctcgatcc ggcagtgaga ctccggcctg       720
catcgttgtc gtctttgctt cagaactgac aaaacatgga tgtggacctg gcctagaagg       780
tcatacaata caaaactaga attatttttag aattgacagt ggcagagtat taggaatcat      840
cagctgcgat aacataaccg acagttaata ctccatccat ttcaatttat aattcactta      900
tcttttttat cctaaatttg ataggttcgt cttattcaaa aaaaattata attatcatta      960
atttttactg tgatatagtt taacatataa tacattttaa gcgtggtttt caatttttta     1020
tttttcacaa aaacatggta agaaatacat gc                                    1052
```

<210> SEQ ID NO 103
<211> LENGTH: 792
<212> TYPE: DNA

<213> ORGANISM: Zea mays

<400> SEQUENCE: 103

```
atgcgagcca gtcaaacttg ttaagaaaaa tcaaacgaat tagaaattag gacagtggga    60
gtatacaaac gggagtatat aaacgactat cactattaat ttagtgttga gtgagcaatt   120
atcggttcgt gtctatcact atcactcatg atatgaatca acggtgataa ctgctaagca   180
taaatggttt ataattttc atatgagatc gaacgaagat atactctata ttgaaattat   240
ttagtttaaa ggaatctaaa actttacagt cgataacttc ttaattaatt cgagatggtt   300
tacccgtgta aatattcaat atgattttg aatcatattt gacatgatta acaatgtcaa   360
attcgcaata tcgaatgaag acaaactcaa cattaaagtt gtgctagtat aatgctcgtg   420
tgttgtgaca aaacataaat atttgatagt ataacgatta catgaaaatg aacaatagat   480
atattaccat cgatcgacct taatatctga caaattattt gtcaacaacc aatacaaaac   540
taaacttgga attcagaacg cctcctcctc tcccttagct gttcagtcac gcatcacggg   600
tggcagagcc tcctcctcct atccagggaa ggtcgatgtg ctttatggtg gtgcggactg   660
cggaagaatc tgggtgaaga aggtggagac gagaaagaga tgagaagtta gagggttaat   720
aacttaatat acgatgacaa gagcgatgaa gaggaggatg aagcgcttat ggtggtgcat   780
gattggttgc at                                                       792
```

<210> SEQ ID NO 104
<211> LENGTH: 15574
<212> TYPE: DNA
<213> ORGANISM: Artificial Sequence
<220> FEATURE:
<223> OTHER INFORMATION: synthetic construct; plasmid PHP44285

<400> SEQUENCE: 104

```
gtttacccgc caatatatcc tgtcaaacac tgatagttta aactgaaggc gggaaacgac    60
aatctgatca tgagcggaga attaagggag tcacgttatg accccgccg atgacgcggg   120
acaagccgtt ttacgtttgg aactgacaga accgcaacgt tgaaggagcc actcagcaag   180
ctggtacgat tgtaatacga ctcactatag ggcgaattga gcgctgttta aacgctcttc   240
aactggaaga gcggttacta ccggctggat ggcggggcct tgatcgtgca ccgccggcgt   300
ccggactaac taactagtcg agctagttac cctatgaggt gacatgaagc gctcacggtt   360
actatgacgg ttagcttcac gactgttggt ggcagtagcg tacgacttag ctatagttcc   420
ggacttaccc ttaagataac ttcgtatagc atacattata cgaagttatg gcccaccgg   480
tggtaccgag ctcgtttaaa cgctcttcaa ctggaagagc ggttaccaga gctggtcacc   540
tttgtccacc aagatggaac tggcgcgcct cattaattaa gtcagcggcc gctctagttg   600
aagacacgtt catgtcttca tcgtaagaag acactcagta gtcttcggcc agaatggcca   660
tctggattca gcaggcctag aaggccattt aaatcctgag gatctggtct tcctaaggac   720
ccgggatagc ttgcatgcct gcagtgcagc gtgacccggt cgtgcccctc tctagagata   780
atgagcattg catgtctaag ttataaaaaa ttaccacata tttttttgt cacacttgtt   840
tgaagtgcag tttatctatc tttatacata tatttaaact ttactctacg aataatataa   900
tctatagtac tacaataata tcagtgtttt agagaatcat ataaatgaac agttagacat   960
ggtctaaagg acaattgagt attttgacaa caggactcta cagttttatc tttttagtgt  1020
gcatgtgttc tccttttttt ttgcaaatag cttcacctat ataatacttc atccatttta  1080
ttagtacatc catttagggt ttagggttaa tggtttttat agactaattt ttttagtaca  1140
```

```
tctattttat tctatttag cctctaaatt aagaaaacta aaactctatt ttagttttt     1200 tatttaataa tttagatata aaatagaata aaataaagtg actaaaaatt aaacaaatac   1260
cctttaagaa attaaaaaaa ctaaggaaac atttttcttg tttcgagtag ataatgccag   1320
cctgttaaac gccgtcgacg agtctaacgg acaccaacca gcgaaccagc agcgtcgcgt   1380
cgggccaagc gaagcagacg gcacggcatc tctgtcgctg cctctggacc cctctcgaga   1440
gttccgctcc accgttggac ttgctccgct gtcggcatcc agaaattgcg tggcggagcg   1500
gcagacgtga gccggcacgg caggcggcct cctcctcctc tcacggcacc ggcagctacg   1560
ggggattcct ttcccaccgc tccttcgctt tcccttcctc gcccgccgta ataaatagac   1620 acccccctcca caccctcttt ccccaacctc gtgttgttcg gagcgcacac acacacaacc   1680
agatctcccc caaatccacc cgtcggcacc tccgcttcaa ggtacgccgc tcgtcctccc   1740
ccccccccct ctctaccttc tctagatcgg cgttccggtc catgcatggt tagggcccgg   1800
tagttctact tctgttcatg tttgtgttag atccgtgttt gtgttagatc cgtgctgcta   1860
gcgttcgtac acggatgcga cctgtacgtc agacacgttc tgattgctaa cttgccagtg   1920
tttctctttg gggaatcctg ggatggctct agccgttccg cagacgggat cgatttcatg   1980 atttttttg tttcgttgca tagggtttgg tttgcccttt tcctttattt caatatatgc    2040
cgtgcacttg tttgtcgggt catctttca tgcttttttt tgtcttggtt gtgatgatgt    2100
ggtctggttg ggcggtcgtt ctagatcgga gtagaattct gtttcaaact acctggtgga   2160
tttattaatt ttggatctgt atgtgtgtgc catacatatt catagttacg aattgaagat   2220
gatggatgga aatatcgatc taggataggt atacatgttg atgcgggttt tactgatgca   2280
tatacagaga tgcttttttgt tcgcttggtt gtgatgatgt ggtgtggttg ggcggtcgtt  2340
cattcgttct agatcggagt agaatactgt tcaaactac ctggtgtatt tattaatttt    2400
ggaactgtat gtgtgtgtca tacatcttca tagttacgag tttaagatgg atggaaatat   2460
cgatctagga taggtataca tgttgatgtg ggttttactg atgcatatac atgatggcat   2520
atgcagcatc tattcatatg ctctaacctt gagtacctat ctattataat aaacaagtat   2580
gttttataat tattttgatc ttgatatact tggatgatgg catatgcagc agctatatgt   2640 ggatttttt agccctgcct tcatacgcta tttatttgct tggtactgtt tcttttgtcg    2700
atgctcaccc tgttgtttgg tgttacttct gcaggtcgac tctagaggat ccatggcacc   2760
gaagaagaag cgcaaggtgc atatgaacac caagtacaac aaggagttcc tgctctacct   2820
ggccggcttc gtgacggcg acggctccat catcgcgcag atcaagccga accagtccta    2880
caagttcaag caccagctca tgctgacctt caccgtgacc cagaagacgc agaggcgctg   2940
gttcctcgac aagctggtcg acgagatcgg ggtgggctac gtccgcgacc gcgggtcggt   3000
gtccgactac atcctctccc agatcaagcc cctgcacaac ttcctcaccc agctccagcc   3060
gttcctcaag ctgaagcaga agcaggcgaa cctcgtcctg aagatcatcg agcagctccc   3120
ctcggccaag gagtccccgg acaagttcct ggaggtgtgc acgtgggtcg accagatcgc   3180
ggccctcaac gacagcaaga cccgcaagac gacctcggag acggtgcggg cggtcctgga   3240
ctccctccca ggatccgtgg gaggtctatc gccatctcag gcatccagcg ccgcatcctc   3300
ggcttcctca gcccgggtt cagggatctc cgaagcactc agagctggag caactaagtc    3360
caaggaattc ctgctctacc tggccggctt cgtggacggc gacggctcca tcatcgcggc   3420
gatcaagccg aaccagtcct acaagttcaa gcaccagctc tccctgacct tcaccgtgac   3480
```

```
ccagaagacg cagaggcgct ggttcctcga caagctggtc gacgagatcg gggtgggcta      3540
cgtccgcgac caggggtcgg tgtcccacta ccagctctcc cagatcaagc ccctgcacaa      3600
cttcctcacc cagctccagc cgttcctcaa gctgaagcag aagcaggcga acctcgtcct      3660
gaagatcatc gagcagctcc cctcggccaa ggagtccccg gacaagttcc tggaggtgtg      3720
cacgtgggtc gaccagatcg cggccctcaa cgacagcaag acccgcaaga cgacctcgga      3780
gacggtgcgg gcggttctag actccctcag cgagaagaag aagtcgtccc cctgaggtac      3840
cacatggtta acctagactt gtccatcttc tggattggcc aacttaatta atgtatgaaa      3900
taaaaggatg cacacatagt gacatgctaa tcactataat gtgggcatca aagttgtgtg      3960
ttatgtgtaa ttactagtta tctgaataaa agagaaagag atcatccata tttcttatcc      4020
taaatgaatg tcacgtgtct ttataattct ttgatgaacc agatgcattt cattaaccaa      4080
atccatatac atataaatat taatcatata taattaatat caattgggtt agcaaaacaa      4140
atctagtcta ggtgtgtttt gcgaatgcgg ccatcggacc gattaaactt taattcggtc      4200
cgataacttc gtatagcata cattatacga agttatacct ggtggcgtca ctttccccc       4260 tattttctc cctattttt catctcccgc agcggttccc cctaaatact cctatatacc        4320
ccaatacaac tataaaatat cattttctat atcaactatc aattttttat ctactaacaa      4380
ttactcgtgg acccacatca caatgtttag ggtgatgaac agtgacacgc tagatctgag      4440
gggagagaga aaagggtcgg cgcgtagggg gcgctgtagg gggcaccgct gcggctgtgg      4500
agtgccccct acagccccca tgcaagggga gggggatact gaggggggctg cgttgcgtac     4560 agcctgacag gctctccttc gcatttgcgc gggacagaaa tgacttgccg aggatggaag     4620
cagagagacg gatttggccg agcgcacagc agctcgccaa agacggcgtc gaagcagcag     4680
tgaccgcggt cgagtgaggg agtcatcctg gattcgcggt ttatcgactc ggcacggggg    4740
caaccatggc gttgaaggta ggcaacatga ggagccatcg attgacaccg gtcttcggaa      4800
tcggcggatc tcgacgatgg tgacaaggag gaggccacga agcgtcgtcg agcagagcgc      4860
gacaagcaaa tcgagtcggc cacgagcgtg gatttggatc tgacccccaa gtttttgtat     4920
ggatcctatt ccccaatttg tagatcttca atttccttac tttaattttc catagcacaa      4980
acgatgtttg catgcacgat tcggacaatc ttgacttgtt cgtccacggt tggagtttag     5040
ggttggaatg tgtaaaacac gtgataaact gtgtacaact cgagaactag ataattcatt     5100
ttggattgta atatgtgtac ctcatgctat agttttggtt aaatctgacg tgaaagggcg     5160
aattcgccgc tagcctgcag tgcagcgtga cccggtcgtg cccctctcta gagataatga    5220
gcattgcatg tctaagttat aaaaaattac cacatatttt ttttgtcaca cttgtttgaa     5280
gtgcagttta tctatcttta tacatatatt taaactttac tctacgaata atataatcta     5340
tagtactaca ataatatcag tgttttagag aatcatataa atgaacagtt agacatggtc     5400
taaaggacaa ttgagtattt tgacaacagg actctacagt tttatctttt tagтgтgcat     5460 gtgттстсст тттттттгс aaatagcтtс acctatataa tacttcatcc attttattag     5520
tacatccatt taggгттаg ggttaatggt tttatagac taatttttt agtacatcta     5580

ttttattcta ttttagcctc taattaaga aaactaaaac tctattttag ttttttatt     5640 taataattta gatataaaat agaataaaat aaagtgacta aaattaaac aaataccctt     5700 taagaaatta aaaaaactaa ggaaacattt tctttgttc gagtagataa tgccagcctg     5760

ttaaacgccg tcgacgagtc taacggacac caaccagcga accagcagcg tcgcgtcggg     5820
ccaagcgaag cagacggcac ggcatctctg tcgctgcctc tggacccctc tcgagagttc    5880
```

-continued

```
cgctccaccg ttggacttgc tccgctgtcg gcatccagaa attgcgtggc ggagcggcag    5940
acgtgagccg gcacggcagg cggcctcctc ctcctctcac ggcaccggca gctacggggg    6000
attcctttcc caccgctcct tcgctttccc ttcctcgccc gccgtaataa atagacaccc    6060
cctccacacc ctctttcccc aacctcgtgt tgttcggagc gcacacacac acaaccagat    6120
ctcccccaaa tccacccgtc ggcacctccg cttcaaggta cgccgctcgt cctcccccc    6180 ccccctctct accttctcta gatcggcgtt ccggtccatg catggttagg gcccggtagt    6240
tctacttctg ttcatgtttg tgttagatcc gtgtttgtgt tagatccgtg ctgctagcgt    6300
tcgtacacgg atgcgacctg tacgtcagac acgttctgat tgctaacttg ccagtgtttc    6360
tctttgggga tcctgggat ggctctagcc gttccgcaga cgggatcgat ttcatgattt    6420
tttttgtttc gttgcatagg gtttggtttg cccttttcct ttatttcaat atatgccgtg    6480
cacttgtttg tcgggtcatc ttttcatgct tttttttgtc ttggttgtga tgatgtggtc    6540
tggttgggcg gtcgttctag atcggagtag aattctgttt caaactacct ggtggattta    6600
ttaattttgg atctgtatgt gtgtgccata catattcata gttacgaatt gaagatgatg    6660
gatggaaata tcgatctagg ataggtatac atgttgatgc gggtttact gatgcatata    6720 cagagatgct ttttgttcgc ttggttgtga tgatgtggtg tggttgggcg gtcgttcatt    6780
cgttctagat cggagtagaa tactgtttca aactacctgg tgtatttatt aattttggaa    6840
ctgtatgtgt gtgtcataca tcttcatagt tacgagttta agatggatgg aaatatcgat    6900
ctaggatagg tatacatgtt gatgtgggtt ttactgatgc atatacatga tggcatatgc    6960
agcatctatt catatgctct aaccttgagt acctatctat tataataaac aagtatgttt    7020
tataattatt ttgatcttga tatacttgga tgatggcata tgcagcagct atatgtggat    7080 tttttagcc ctgccttcat acgctattta tttgcttggt actgtttctt ttgtcgatgc    7140
tcaccctgtt gtttggtgtt acttctgcag gtcgactcta gaggatcaat tcgctagcga    7200
agttcctatt ccgaagttcc tattctctag aaagtatagg aacttcagat ccaccgggat    7260
ccacacgaca ccatgtcccc cgagcgccgc ccgtcgaga tccgcccggc caccgccgcc    7320
gacatggccg ccgtgtgcga catcgtgaac cactacatcg agacctccac cgtgaacttc    7380
cgcaccgagc cgcagacccc gcaggagtgg atcgacgacc tggagcgcct ccaggaccgc    7440
tacccgtggc tcgtggccga ggtggagggc gtggtggccg gcatcgccta cgccggcccg    7500
tggaaggccc gcaacgccta cgactggacc gtggagtcca ccgtgtacgt gtcccaccgc    7560
caccagcgcc tcggcctcgg ctccacccctc tacacccacc tcctcaagag catggaggcc    7620
cagggcttca gtccgtggt ggccgtgatc ggcctcccga acgacccgtc cgtgcgcctc    7680
cacgaggccc tcggctacac cgcccgcgg accctccgcg ccgccggcta caagcacggc    7740
ggctggcacg acgtcggctt ctggcagcgc gacttcgagc tgccggcccc gccgcgcccg    7800
gtgcgcccgg tgacgcagat ctgagtcgaa acctagactt gtccatcttc tggattggcc    7860
aacttaatta atgtatgaaa taaaaggatg cacacatagt gacatgctaa tcactataat    7920
gtgggcatca aagttgtgtg ttatgtgtaa ttactagtta tctgaataaa agagaaagag    7980
atcatccata tttcttatcc taaatgaatg tcacgtgtct ttataattct ttgatgaacc    8040
agatgcattt cattaaccaa atccatatac atataaatat taatcatata taattaatat    8100 caattggggtt agcaaaacaa atctagtcta ggtgtgtttt gcgaatgcgg ccctagcgta    8160
tacgaagttc ctattccgaa gttcctattc tccagaaagt ataggaactt ctgtacacct    8220
```

```
gagctgattc cgatgacttc gtaggttcct agctcaagcc gctcgtgtcc aagcgtcact    8280
tacgattagc taatgattac ggcatctagg accgactagc taactaacta gtacaattcg    8340
cccttgtgaa tctgtttgga attgaaaaac aagtgcttcc ttttatacac cactatgtcg    8400
cttcaatgtt tgcgaaccaa ggtaaagaaa tgtaaaatct tacaatttcc gtgcatccga    8460
cataaatctg tggtcacata gctattgtta acggttgca aatcctaagg aggaccatta    8520
ttgtgcaaca actacatatg gtagaagcgc ttgttttgat gtgtgcacat tttgttgcta    8580
aaaggatcac gatgcccaag agggggggtga attgggcttt tctaaaaatc aacactaatt    8640
aaaacctaag caagagccca acttcacccc gacaactagc aataagagaa tatgaaaggg    8700
aaataggatc aaacctttc ctaaatgatt ttggtggttg aattgcccaa cacaaataat    8760
tggactaact agtttgctct agatcataca ttctacaggt gccaaaggtt caacacaaac    8820
caatcaaaag aacaagttag gcttcaaaag aaaggagcaa aaaggaaacc gaagtgtgcc    8880
tggtctggcg caccgggctg tccggtgtgc caccagacag tgtccggtgc accagggtga    8940
atcagctcaa gctcctcaac ttcgggtttc ccagacgcag ctccactata attcattgga    9000
ctgtccggtg caccgcaga gcaacggcta cttgcgcgca acggtcgact ctgcaaagtg    9060
aacagtgcaa ttcagaagtc agagcagatg gtcagagggg caccggattg tccggtgtag    9120
caccggactg tccggtgccg catgaggaca aagcctccaa cggtcgacca gctccaagcc    9180
ctaactacaa gatgacgtgg cggcgcaccg gacactgtcc ggtggtgcac cggactgttc    9240
ggtgcgccca tcgccagtag ccttctccaa cggctacaat ttggttggtg gctataaata    9300
ccaccccaac cggccacttt aaggtgtggg agcccaagca acattccaag tcatatagtt    9360
gacatattca agccatccca accaccgtag aattaattca ttccgattaa tcgtggcctc    9420
ttgctcttca ggatgaagag ctatgtttaa acgtgcaagc gctactagac aattcagtac    9480
attaaaaacg tccgcaatgt gttattaagt tgtctaagcg tcaatttgtt tacaccacaa    9540
tatatcctgc caccagccag ccaacagctc cccgaccggc agctcggcac aaaatcacca    9600
ctcgatacag gcagcccatc agtccgggac ggcgtcagcg ggagagccgt tgtaaggcgg    9660
cagactttgc tcatgttacc gatgctattc ggaagaacgg caactaagct gccgggtttg    9720
aaacacggat gatctcgcgg agggtagcat gttgattgta acgatgacag agcgttgctg    9780
cctgtgatca aatatcatct ccctcgcaga gatccgaatt atcagccttc ttattcattt    9840
ctcgcttaac cgtgacaggc tgtcgatctt gagaactatg ccgacataat aggaaatcgc    9900
tggataaagc cgctgaggaa gctgagtggc gctatttctt tagaagtgaa cgttgacgat    9960
cgtcgaccgt accccgatga attaattcgg acgtacgttc tgaacacagc tggatactta    10020
cttgggcgat tgtcatacat gacatcaaca atgtacccgt ttgtgtaacc gtctcttgga    10080
ggttcgtatg acactagtgg ttcccctcag cttgcgacta gatgttgagg cctaacattt    10140
tattagagag caggctagtt gcttagatac atgatcttca ggccgttatc tgtcagggca    10200
agcgaaaatt ggccatttat gacgaccaat gccccgcaga agctcccatc tttgccgcca    10260
tagacgccgc gccccccttt tggggtgtag aacatccttt tgccagatgt ggaaaagaag    10320
ttcgttgtcc cattgttggc aatgacgtag tagccggcga aagtgcgaga cccatttgcg    10380
ctatatataa gcctacgatt tccgttgcga ctattgtcgt aattggatga actattatcg    10440
tagttgctct cagagttgtc gtaatttgat ggactattgt cgtaattgct tatggagttg    10500
tcgtagttgc ttggagaaat gtcgtagttg gatggggagt agtcataggg aagacgagct    10560
tcatccacta aaacaattgg caggtcagca agtgcctgcc ccgatgccat cgcaagtacg    10620
```

```
aggcttagaa ccaccttcaa cagatcgcgc atagtcttcc ccagctctct aacgcttgag    10680
ttaagccgcg ccgcgaagcg gcgtcggctt gaacgaattg ttagacatta tttgccgact    10740
accttggtga tctcgccttt cacgtagtga acaaattctt ccaactgatc tgcgcgcgag    10800
gccaagcgat cttcttgtcc aagataagcc tgcctagctt caagtatgac gggctgatac    10860
tgggccggca ggcgctccat tgcccagtcg gcagcgacat ccttcggcgc gattttgccg    10920
gttactgcgc tgtaccaaat gcgggacaac gtaagcacta catttcgctc atcgccagcc    10980
cagtcgggcg gcgagttcca tagcgttaag gtttcattta gcgcctcaaa tagatcctgt    11040
tcaggaaccg gatcaaagag ttcctccgcc gctggaccta ccaaggcaac gctatgttct    11100
cttgcttttg tcagcaagat agccagatca atgtcgatcg tggctggctc gaagatacct    11160
gcaagaatgt cattgcgctg ccattctcca aattgcagtt cgcgcttagc tggataacgc    11220
cacggaatga tgtcgtcgtg cacaacaatg gtgacttcta cagcgcggag aatctcgctc    11280
tctccagggg aagccgaagt ttccaaaagg tcgttgatca aagctcgccg cgttgtttca    11340
tcaagcctta cagtcaccgt aaccagcaaa tcaatatcac tgtgtggctt caggccgcca    11400
tccactgcgg agccgtacaa atgtacggcc agcaacgtcg gttcgagatg gcgctcgatg    11460
acgccaacta cctctgatag ttgagtcgat acttcggcga tcaccgcttc cctcatgatg    11520
tttaactcct gaattaagcc gcgccgcgaa gcggtgtcgg cttgaatgaa ttgttaggcg    11580
tcatcctgtg ctcccgagaa ccagtaccag tacatcgctg tttcgttcga gacttgaggt    11640
ctagttttat acgtgaacag gtcaatgccg ccgagagtaa agccacattt tgcgtacaaa    11700
ttgcaggcag gtacattgtt cgtttgtgtc tctaatcgta tgccaaggag ctgtctgctt    11760
agtgcccact ttttcgcaaa ttcgatgaga ctgtgcgcga ctcctttgcc tcggtgcgtg    11820
tgcgacacaa caatgtgttc gatagaggct agatcgttcc atgttgagtt gagttcaatc    11880
ttcccgacaa gctcttggtc gatgaatgcg ccatagcaag cagagtcttc atcagagtca    11940
tcatccgaga tgtaatcctt ccggtagggg ctcacacttc tggtagatag ttcaaagcct    12000
tggtcggata ggtgcacatc gaacacttca cgaacaatga aatggttctc agcatccaat    12060
gtttccgcca cctgctcagg gatcaccgaa atcttcatat gacgcctaac gcctggcaca    12120
gcggatcgca aacctggcgc ggcttttggc acaaaaggcg tgacaggttt gcgaatccgt    12180
tgctgccact tgttaaccct tttgccagat ttggtaacta taatttatgt tagaggcgaa    12240
gtcttgggta aaaactggcc taaaattgct ggggatttca ggaaagtaaa catcaccttc    12300
cggctcgatg tctattgtag atatatgtag tgtatctact tgatcggggg atctgctgcc    12360
tcgcgcgttt cggtgatgac ggtgaaaacc tctgacacat gcagctcccg gagacggtca    12420
cagcttgtct gtaagcggat gccgggagca gacaagcccg tcaggcgcg tcagcgggtg    12480 ttggcgggtg tcgggcgca gccatgaccc agtcacgtag cgatagcgga gtgtatactg    12540
gcttaactat gcggcatcag agcagattgt actgagagtg caccatatgc ggtgtgaaat    12600
accgcacaga tgcgtaagga gaaaataccg catcaggcgc tcttccgctt cctcgctcac    12660
tgactcgctg cgctcggtcg ttcggctgcg gcgagcggta tcagctcact caaaggcggt    12720
aatacggtta tccacagaat caggggataa cgcaggaaaa acatgtgag caaaaggcca    12780 gcaaaaggcc aggaaccgta aaaaggccgc gttgctggcg ttttccata ggctccgccc    12840 ccctgacgag catcacaaaa atcgacgctc aagtcagagg tggcgaaacc cgacaggact    12900
ataaagatac caggcgtttc ccctggaag ctccctcgtg cgctctcctg ttccgaccct    12960
```

```
gccgcttacc ggatacctgt ccgcctttct cccttcggga agcgtggcgc tttctcatag   13020
ctcacgctgt aggtatctca gttcggtgta ggtcgttcgc tccaagctgg gctgtgtgca   13080
cgaacccccc gttcagcccg accgctgcgc cttatccggt aactatcgtc ttgagtccaa   13140
cccggtaaga cacgacttat cgccactggc agcagccact ggtaacagga ttagcagagc   13200
gaggtatgta ggcggtgcta cagagttctt gaagtggtgg cctaactacg gctacactag   13260
aaggacagta tttggtatct gcgctctgct gaagccagtt accttcggaa aaagagttgg   13320
tagctcttga tccggcaaac aaaccaccgc tggtagcggt ggttttttttg tttgcaagca   13380 gcagattacg cgcagaaaaa aaggatctca agaagatcct ttgatctttt ctacggggtc   13440
tgacgctcag tggaacgaaa actcacgtta agggattttg gtcatgagat tatcaaaaag   13500
gatcttcacc tagatccttt taaattaaaa atgaagtttt aaatcaatct aaagtatata   13560
tgagtaaact tggtctgaca gttaccaatg cttaatcagt gaggcaccta tctcagcgat   13620
ctgtctattt cgttcatcca tagttgcctg actccccgtc gtgtagataa ctacgatacg   13680
ggagggctta ccatctggcc ccagtgctgc aatgataccg cgagacccac gctcaccggc   13740
tccagattta tcagcaataa accagccagc cggaagggcc gagcgcagaa gtggtcctgc   13800
aactttatcc gcctccatcc agtctattaa ttgttgccgg gaagctagag taagtagttc   13860
gccagttaat agtttgcgca acgttgttgc cattgctgca gggggggggg ggggggggga   13920
cttccattgt tcattccacg gacaaaaaca gagaaaggaa acgacagagg ccaaaaagcc   13980
tcgctttcag cacctgtcgt ttcctttctt ttcagagggt attttaaata aaaacattaa   14040
gttatgacga agaagaacgg aaacgcctta accggaaaaa ttttcataaa tagcgaaaac   14100
ccgcgaggtc gccgccccgt aacctgtcgg atcaccggaa aggacccgta agtgataat    14160 gattatcatc tacatatcac aacgtgcgtg gaggccatca aaccacgtca ataatcaat    14220 tatgacgcag gtatcgtatt aattgatctg catcaactta acgtaaaaac aacttcagac   14280
aatacaaatc agcgacactg aatacggggc aacctcatgt ccccccccccc cccccccctg  14340 caggcatcgt ggtgtcacgc tcgtcgtttg gtatggcttc attcagctcc ggttcccaac   14400
gatcaaggcg agttacatga tccccatgt tgtgcaaaaa agcggttagc tccttcggtc    14460
ctccgatcgt tgtcagaagt aagttggccg cagtgttatc actcatggtt atggcagcac   14520
tgcataattc tcttactgtc atgccatccg taagatgctt ttctgtgact ggtgagtact   14580
caaccaagtc attctgagaa tagtgtatgc ggcgaccgag ttgctcttgc ccggcgtcaa   14640
cacgggataa taccgcgcca catagcagaa ctttaaaagt gctcatcatt ggaaaacgtt   14700
cttcggggcg aaaactctca aggatcttac cgctgttgag atccagttcg atgtaaccca   14760
ctcgtgcacc caactgatct tcagcatctt ttactttcac cagcgtttct gggtgagcaa   14820
aaacaggaag gcaaaatgcc gcaaaaaagg gaataagggc gacacggaaa tgttgaatac   14880
tcatactctt cctttttcaa tattattgaa gcatttatca gggttattgt ctcatgagcg   14940
gatacatatt tgaatgtatt tagaaaaata acaaataggg gttccgcgc acatttcccc     15000 gaaaagtgcc acctgacgtc taagaaacca ttattatcat gacattaacc tataaaaata   15060
ggcgtatcac gaggcccttt cgtcttcaag aattggtcga cgatcttgct gcgttcggat   15120
attttcgtgg agttcccgcc acagacccgg attgaaggcg agatccagca actcgcgcca   15180
gatcatcctg tgacggaact ttggcgcgtg atgactggcc aggacgtcgg ccgaaagagc   15240
gacaagcaga tcacgctttt cgacagcgtc ggatttgcga tcgaggattt tcggcgctg    15300 cgctacgtcc gcgaccgcgt tgagggatca agccacagca gcccactcga ccttctagcc   15360
```

```
gacccagacg agccaaggga tcttttttgga atgctgctcc gtcgtcaggc tttccgacgt    15420
ttgggtggtt gaacagaagt cattatcgta cggaatgcca agcactcccg aggggaaccc    15480
tgtggttggc atgcacatac aaatggacga acggataaac cttttcacgc ccttttaaat    15540
atccgttatt ctaataaacg ctcttttctc ttag                                15574

<210> SEQ ID NO 105
<211> LENGTH: 15585
<212> TYPE: DNA
<213> ORGANISM: Artificial Sequence
<220> FEATURE:
<223> OTHER INFORMATION: synthetic construct; plasmid PHP44779

<400> SEQUENCE: 105
gtttacccgc caatatatcc tgtcaaacac tgatagttta aactgaaggc gggaaacgac      60
aatctgatca tgagcggaga attaagggag tcacgttatg accccgccg atgacgcggg     120 acaagccgtt ttacgtttgg aactgacaga accgcaacgt tgaaggagcc actcagcaag    180
ctggtacgat tgtaatacga ctcactatag ggcgaattga gcgctgttta aacgctcttc    240
aactggaaga gcggttacta ccggctggat ggcggggcct tgatcgtgca ccgccggcgt    300
ccggactaac taactagtcg agctagttac cctatgaggt gacatgaagc gctcacggtt    360
actatgacgg ttagcttcac gactgttggt ggcagtagcg tacgacttag ctatagttcc    420
ggacttaccc ttaagataac ttcgtatagc atacattata cgaagttatg ggcccaccgg    480
tggtaccgag ctcgttttaaa cgctcttcaa ctggaagagc ggttaccaga gctggtcacc    540
tttgtccacc aagatggaac tggcgcgcct cattaattaa gtcagcggcc gctctagttg    600
aagacacgtt catgtcttca tcgtaagaag acactcagta gtcttcggcc agaatggcca    660
tctggattca gcaggcctag aaggccattt aaatcctgag gatctggtct tcctaaggac    720
ccgggatatc ggaccgaagc ttgcatgcct gcagtgcagc gtgacccggt cgtgcccctc    780
tctagagata atgagcattg catgtctaag ttataaaaaa ttaccacata ttttttttgt    840
cacacttgtt tgaagtgcag tttatctatc tttatacata tatttaaact ttactctacg    900
aataatataa tctatagtac tacaataata tcagtgtttt agagaatcat ataaatgaac    960
agttagacat ggtctaaagg acaattgagt attttgacaa caggactcta cagttttatc   1020 ttttagtgt gcatgtgttc tccttttttt ttgcaaatag cttcacctat ataatacttc   1080
atccatttta ttagtacatc catttagggt ttagggttaa tggttttat agactaattt    1140 ttttagtaca tctattttat tctattttag cctctaaatt aagaaaacta aaactctatt   1200
ttagtttttt tatttaataa tttagatata aaatagaata aaataaagtg actaaaaatt   1260
aaacaaatac cctttaagaa attaaaaaaa ctaaggaaac attttctttg tttcgagtag   1320
ataatgccag cctgttaaac gccgtcgacg agtctaacgg acaccaacca gcgaaccagc   1380
agcgtcgcgt cgggccaagc gaagcagacg gcacggcatc tctgtcgctg cctctggacc   1440
cctctcgaga gttccgctcc accgttggac ttgctccgct gtcggcatcc agaaattgcg   1500
tggcggagcg gcagacgtga gccggcacgg caggcggcct cctcctcctc tcacggcacc   1560
ggcagctacg ggggattcct ttcccaccgc tccttcgctt tccttcctc gcccgccgta    1620 ataaatagac accccctcca cacctcttt ccccaacctc gtgttgttcg gagcgcacac    1680
acacacaacc agatctcccc caaatccacc cgtcggcacc tccgcttcaa ggtacgccgc   1740
tcgtcctccc ccccccccct ctctaccttc tctagatcgg cgttccggtc catgcatggt   1800
```

```
tagggcccgg tagttctact tctgttcatg tttgtgttag atccgtgttt gtgttagatc    1860
cgtgctgcta gcgttcgtac acggatgcga cctgtacgtc agacacgttc tgattgctaa    1920
cttgccagtg tttctctttg gggaatcctg ggatggctct agccgttccg cagacgggat    1980
cgatttcatg attttttttg tttcgttgca tagggtttgg tttgcccttt tcctttattt    2040
caatatatgc cgtgcacttg tttgtcgggt catcttttca tgctttttt  tgtcttggtt    2100 gtgatgatgt ggtctggttg ggcggtcgtt ctagatcgga gtagaattct gtttcaaact    2160
acctggtgga tttattaatt ttggatctgt atgtgtgtgc catacatatt catagttacg    2220
aattgaagat gatggatgga aatatcgatc taggataggt atacatgttg atgcgggttt    2280
tactgatgca tatacagaga tgcttttgt  tcgcttggtt gtgatgatgt ggtgtggttg    2340
ggcggtcgtt cattcgttct agatcggagt agaatactgt ttcaaactac ctggtgtatt    2400
tattaatttt ggaactgtat gtgtgtgtca tacatcttca tagttacgag tttaagatgg    2460
atggaaatat cgatctagga taggtataca tgttgatgtg ggttttactg atgcatatac    2520
atgatggcat atgcagcatc tattcatatg ctctaacctt gagtacctat ctattataat    2580
aaacaagtat gttttataat tattttgatc ttgatatact tggatgatgg catatgcagc    2640
agctatatgt ggatttttt  agccctgcct tcatacgcta tttatttgct tggtactgtt    2700
tcttttgtcg atgctcaccc tgttgtttgg tgttacttct gcaggtcgac tctagaggat    2760
ccatggcacc gaagaagaag cgcaaggtgc atatgaacac caagtacaac aaggagttcc    2820
tgctctacct ggccggcttc gtggacggcg acggctccat catcgcgcag atcaagccga    2880
accagtccta caagttcaag caccagctca tgctgacctt caccgtgacc agaagacgc     2940 agaggcgctg gttcctcgac aagctggtcg acgagatcgg ggtgggcaag gtccgcgacc    3000
gcgggtcggt gtccgactac atcctctccc agatcaagcc cctgcacaac ttcctcaccc    3060
agctccagcc gttcctcaag ctgaagcaga agcaggcgaa cctcgtcctg aagatcatcg    3120
agcagctccc ctcggccaag gagtccccgg acaagttcct ggaggtgtgc acgtgggtcg    3180
accagatcgc ggccctcaac gacagcaaga cccgcaagac gacctcggag acggtgcggg    3240
cggtcctgga ctccctccca ggatccgtgg gaggtctatc gccatctcag gcatccagcg    3300
ccgcatcctc ggcttcctca gcccgggtt  cagggatctc cgaagcactc agagctggag    3360
caactaagtc caaggaattc ctgctctacc tggccggctt cgtggacggc gacggctcca    3420
tcatcgcggc gatcaagccg aaccagtcct acaagttcaa gcaccagctc tccctgacct    3480
tcaccgtgac ccagaagacg cagaggcgct ggttcctcga caagctggtc gacgagatcg    3540
gggtgggcta cgtccgcgac caggggtcgg tgtcccacta ccagctctcc cagatcaagc    3600
ccctgcacaa cttcctcacc cagctccagc cgttcctcaa gctgaagcag aagcaggcga    3660
acctcgtcct gaagatcatc gagcagctcc cctcggccaa ggagtccccg gacaagttcc    3720
tggaggtgtg cacgtgggtc gaccagatcg cggccctcaa cgacagcaag acccgcaaga    3780
cgacctcgga cggtgcgg  gcggttctag actccctcag cgagaagaag aagtcgtccc    3840
cctgaggtac cacatggtta acctagactt gtccatcttc tggattggcc aacttaatta    3900
atgtatgaaa taaaggatg  cacacatagt gacatgctaa tcactataat gtgggcatca    3960
aagttgtgtg ttatgtgtaa ttactagtta tctgaataaa agagaaagag atcatccata    4020
tttcttatcc taaatgaatg tcacgtgtct ttataattct ttgatgaacc agatgcattt    4080
cattaaccaa atccatatac atataaatat taatcatata taattaatat caattgggtt    4140
agcaaaacaa atctagtcta ggtgtgtttt gcgaatgcgg ccgccaccgc ggtggagctc    4200
```

```
gaattccggt ccgataactt cgtatagcat acattatacg aagttatacc tggtggcgtc    4260
actttccccc ctatttttct ccctattttt tcatctcccg cagcggttcc ccctaaatac    4320
tcctatatac cccaatacaa ctataaaata tcattttcta tatcaactat caattttta    4380 tctactaaca attactcgtg gacccacatc acaatgttta gggtgatgaa cagtgacacg    4440
ctagatctga ggggagagag aaaagggtcg gcgcgtaggg ggcgctgtag ggggcaccgc    4500
tgcggctgtg gagtgccccc tacagccccc atgcaagggg aggggatac tgaggggct     4560 gcgttgcgta cagcctgaca ggctctcctt cgcatttgcg cgggacagaa atgacttgcc    4620
gaggatggaa gcagagagac ggatttggcc gagcgcacag cagctcgcca aagacggcgt    4680
cgaagcagca gtgaccgcgg tcgagtgagg gagtcatcct ggattcgcgg tttatcgact    4740
cggcacgggg gcaaccatgg cgttgaaggt aggcaacatg aggagccatc gattgacacc    4800
ggtcttcgga atcggcggat ctcgacgatg gtgacaagga ggaggccacg aagcgtcgtc    4860
gagcagagcg cgacaagcaa atcgagtcgg ccacgagcgt ggatttggat ctgaccccca    4920 agttttttgta tggatcctat tccccaattt gtagatcttc aatttcctta cttaattttt    4980
ccatagcaca aacgatgttt gcatgcacga ttcggacaat cttgacttgt tcgtccacgg    5040
ttggagttta gggttggaat gtgtaaaaca cgtgataaac tgtgtacaac tcgagaacta    5100
gataattcat tttggattgt aatatgtgta cctcatgcta tagttttggt taaatctgac    5160
gtgaaagggc gaattcgccg ctagcctgca gtgcagcgtg acccggtcgt gcccctctct    5220
agagataatg agcattgcat gtctaagtta taaaaaatta ccacatattt ttttgtcac    5280 acttgtttga agtgcagttt atctatcttt atacatatat ttaaacttta ctctacgaat    5340
aatataatct atagtactac aataatatca gtgttttaga gaatcatata aatgaacagt    5400
tagacatggt ctaaaggaca attgagtatt ttgacaacag gactctacag ttttatcttt    5460
ttagtgtgca tgtgttctcc ttttttttg caaatagctt cacctatata atacttcatc     5520
cattttatta gtacatccat ttagggttta gggttaatgg ttttttataga ctaattttt    5580 tagtacatct atttatttct atttagcct ctaaattaag aaaactaaaa ctctatttta    5640 gttttttttat ttaataattt agatataaaa tagaataaaa taaagtgact aaaaattaaa    5700 caaatacccct ttaagaaatt aaaaaaacta aggaaacatt tttcttgttt cgagtagata    5760
atgccagcct gttaaacgcc gtcgacgagt ctaacgacga ccaaccagcg aaccagcagc    5820
gtcgcgtcgg gccaagcgaa gcagacggca cggcatctct gtcgctgcct ctggaccct    5880 ctcgagagtt ccgctccacc gttggacttg ctccgctgtc ggcatccaga aattgcgtgg    5940
cggagcggca gacgtgagcc ggcacggcag gcggcctcct cctcctctca cggcaccggc    6000
agctacgggg gattcctttc ccaccgctcc ttcgcttttcc cttcctcgcc cgccgtaata    6060
aatagacacc ccctccacac cctctttccc caacctcgtg ttgttcggag cgcacacaca    6120
cacaaccaga tctccccccaa atccacccgt cggcacctcc gcttcaaggt acgccgctcg    6180 tcctccccccc cccccctctc taccttctct agatcggcgt tccggtccat gcatggttag    6240
ggcccggtag ttctacttct gttcatgttt gtgttagatc cgtgtttgtg ttagatccgt    6300
gctgctagcg ttcgtacacg gatgcgacct gtacgtcaga cacgttctga ttgctaactt    6360
gccagtgttt ctcttttgggg aatcctggga tggctctagc cgttccgcag acgggatcga    6420
tttcatgatt tttttttgttt cgttgcatag ggttttggttt gcccttttcc tttatttcaa    6480
tatatgccgt gcacttgttt gtcgggtcat cttttcatgc ttttttttgt cttggttgtg    6540
```

```
atgatgtggt ctggttgggc ggtcgttcta gatcggagta gaattctgtt tcaaactacc    6600
tggtggattt attaattttg gatctgtatg tgtgtgccat acatattcat agttacgaat    6660
tgaagatgat ggatggaaat atcgatctag gataggtata catgttgatg cgggttttac    6720
tgatgcatat acagagatgc ttttgttcg cttggttgtg atgatgtggt gtggttgggc     6780
ggtcgttcat tcgttctaga tcggagtaga atactgtttc aaactacctg gtgtatttat    6840
taattttgga actgtatgtg tgtgtcatac atcttcatag ttacgagttt aagatggatg    6900
gaaatatcga tctaggatag gtatacatgt tgatgtgggt tttactgatg catatacatg    6960
atggcatatg cagcatctat tcatatgctc taaccttgag tacctatcta ttataataaa    7020
caagtatgtt ttataattat tttgatcttg atatacttgg atgatggcat atgcagcagc    7080
tatatgtgga tttttttagc cctgccttca tacgctattt atttgcttgg tactgtttct    7140
tttgtcgatg ctcaccctgt tgtttggtgt tacttctgca ggtcgactct agaggatcaa    7200
ttcgctagcg aagttcctat tccgaagttc ctattctcta gaaagtatag gaacttcaga    7260
tccaccggga tccacacgac accatgtccc ccgagcgccg ccccgtcgag atccgcccgg    7320
ccaccgccgc cgacatggcc gccgtgtgcg acatcgtgaa ccactacatc gagacctcca    7380
ccgtgaactt ccgcaccgag ccgcagaccc gcaggagtg gatcgacgac ctggagcgcc     7440
tccaggaccg ctacccgtgg ctcgtggccg aggtggaggg cgtggtggcc ggcatcgcct    7500
acgccggccc gtggaaggcc cgcaacgcct acgactggac cgtggagtcc accgtgtacg    7560
tgtcccaccg ccaccagcgc ctcggcctcg gctccaccct ctacacccac ctcctcaaga    7620
gcatggaggc ccagggcttc aagtccgtgg tggccgtgat cggcctcccg aacgacccgt    7680
ccgtgcgcct ccacgaggcc ctcggctaca ccgcccgcgg caccctccgc gccgccggct    7740
acaagcacgg cggctggcac gacgtcggct tctggcagcg cgacttcgag ctgccggccc    7800
cgccgcgccc ggtgcgcccg gtgacgcaga tctgagtcga aacctagact tgtccatctt    7860
ctggattggc caacttaatt aatgtatgaa ataaaaggat gcacacatag tgacatgcta    7920
atcactataa tgtgggcatc aaagttgtgt gttatgtgta attactagtt atctgaataa    7980
aagagaaaga gatcatccat atttcttatc ctaaatgaat gtcacgtgtc tttataattc    8040
tttgatgaac cagatgcatt tcattaacca aatccatata catataaata ttaatcatat    8100
ataattaata tcaattgggt tagcaaaaca aatctagtct aggtgtgttt tgcgaatgcg    8160
gccctagcgt atacgaagtt cctattccga agttcctatt ctccagaaag tataggaact    8220
tctgtacacc tgagctgatt ccgatgactt cgtaggttcc tagctcaagc cgctcgtgtc    8280
caagcgtcac ttacgattag ctaatgatta cggcatctag gaccgactag ctaactaact    8340
agtacaattc gcccttgtga atctgtttgg aattgaaaaa caagtgcttc cttttataca    8400
ccactatgtc gcttcaatgt ttgcgaacca aggtaaagaa atgtaaaatc ttacaatttc    8460
cgtgcatccg acataaatct gtggtcacat agctattgtt aaacggttgc aaatcctaag    8520
gaggaccatt attgtgcaac aactacatat ggtagaagcg cttgttttga tgtgtgcaca    8580
ttttgttgct aaaaggatca cgatgcccaa gagggggtg aattgggctt ttctaaaaat     8640
caacactaat taaaacctaa gcaagagccc aacttcaccc cgacaactag caataagaga    8700
atatgaaagg gaaataggat caaacctttt cctaaatgat tttggtggtt gaattgccca    8760
acacaaataa ttggactaac tagttttgctc tagatcatac attctacagg tgccaaaggt    8820
tcaacacaaa ccaatcaaaa gaacaagtta ggcttcaaaa gaaaggagca aaaggaaac     8880
cgaagtgtgc ctggtctggc gcaccgggct gtccggtgtg ccaccagaca gtgtccggtg    8940
```

```
caccagggtg aatcagctca agctcctcaa cttcgggttt cccagacgca gctccactat   9000
aattcattgg actgtccggt gcacccgcag agcaacggct acttgcgcgc aacggtcgac   9060
tctgcaaagt gaacagtgca attcagaagt cagagcagat ggtcagaggg gcaccggatt   9120
gtccggtgta gcaccggact gtccggtgcc gcatggagac aaagcctcca acggtcgacc   9180
agctccaagc cctaactaca agatgacgtg gcggcgcacc ggacactgtc cggtggtgca   9240
ccggactgtt cggtgcgccc atcgccagta gccttctcca acggctacaa tttggttggt   9300
ggctataaat accaccccaa ccggccactt taaggtgtgg gagcccaagc aacattccaa   9360
gtcatatagt tgacatattc aagccatccc aaccaccgta gaattaattc attccgatta   9420
atcgtggcct cttgctcttc aggatgaaga gctatgttta aacgtgcaag cgctactaga   9480
caattcagta cattaaaaac gtccgcaatg tgttattaag ttgtctaagc gtcaatttgt   9540
ttacaccaca atatatcctg ccaccagcca gccaacagct ccccgaccgg cagctcggca   9600
caaaatcacc actcgataca ggcagcccat cagtccggga cggcgtcagc gggagagccg   9660
ttgtaaggcg gcagactttg ctcatgttac cgatgctatt cggaagaacg gcaactaagc   9720
tgccgggttt gaaacacgga tgatctcgcg gagggtagca tgttgattgt aacgatgaca   9780
gagcgttgct gcctgtgatc aaatatcatc tccctcgcag agatccgaat tatcagcctt   9840
cttattcatt tctcgcttaa ccgtgacagg ctgtcgatct tgagaactat gccgacataa   9900
taggaaatcg ctggataaag ccgctgagga agctgagtgg cgctatttct ttagaagtga   9960
acgttgacga tcgtcgaccg taccccgatg aattaattcg gacgtacgtt ctgaacacag  10020
ctggatactt acttgggcga ttgtcataca tgacatcaac aatgtacccg tttgtgtaac  10080
cgtctcttgg aggttcgtat gacactagtg gttcccctca gcttgcgact agatgttgag  10140
gcctaacatt ttattagaga gcaggctagt tgcttagata catgatcttc aggccgttat  10200
ctgtcagggc aagcgaaaat tggccattta tgacgaccaa tgccccgcag aagctcccat  10260
cttttgccgcc atagacgccg cgcccccctt ttggggtgta gaacatcctt ttgccagatg  10320
tggaaaagaa gttcgttgtc ccattgttgg caatgacgta gtagccggcg aaagtgcgag  10380
acccatttgc gctatatata agcctacgat ttccgttgcg actattgtcg taattggatg  10440
aactattatc gtagttgctc tcagagttgt cgtaatttga tggactattg tcgtaattgc  10500
ttatggagtt gtcgtagttg cttggagaaa tgtcgtagtt ggatggggag tagtcatagg  10560
gaagacgagc ttcatccact aaaacaattg gcaggtcagc aagtgcctgc cccgatgcca  10620
tcgcaagtac gaggcttaga accaccttca acagatcgcg catagtcttc cccagctctc  10680
taacgcttga gttaagccgc gccgcgaagc ggcgtcggct tgaacgaatt gttagacatt  10740
atttgccgac taccttggtg atctcgcctt tcacgtagtg aacaaattct tccaactgat  10800
ctgcgcgcga ggccaagcga tcttcttgtc caagataagc ctgcctagct tcaagtatga  10860
cgggctgata ctgggccggc aggcgctcca ttgcccagtc ggcagcgaca tccttcggcg  10920
cgattttgcc ggttactgcg ctgtaccaaa tgcgggacaa cgtaagcact acatttcgct  10980
catcgccagc ccagtcgggc ggcgagttcc atagcgttaa ggtttcattt agcgcctcaa  11040
atagatcctg ttcaggaacc ggatcaaaga gttcctccgc cgctggacct accaaggcaa  11100
cgctatgttc tcttgctttt gtcagcaaga tagccagatc aatgtcgatc gtggctggct  11160
cgaagatacc tgcaagaatg tcattgcgct gccattctcc aaattgcagt tcgcgcttag  11220
ctggataacg ccacggaatg atgtcgtcgt gcacaacaat ggtgacttct acagcgcgga  11280
```

```
gaatctcgct ctctccaggg gaagccgaag tttccaaaag gtcgttgatc aaagctcgcc   11340
gcgttgtttc atcaagcctt acagtcaccg taaccagcaa atcaatatca ctgtgtggct   11400
tcaggccgcc atccactgcg gagccgtaca aatgtacggc cagcaacgtc ggttcgagat   11460
ggcgctcgat gacgccaact acctctgata gttgagtcga tacttcggcg atcaccgctt   11520
ccctcatgat gtttaactcc tgaattaagc cgcgccgcga agcggtgtcg gcttgaatga   11580
attgttaggc gtcatcctgt gctcccgaga accagtacca gtacatcgct gtttcgttcg   11640
agacttgagg tctagtttta tacgtgaaca ggtcaatgcc gccgagagta aagccacatt   11700
ttgcgtacaa attgcaggca ggtacattgt tcgtttgtgt ctctaatcgt atgccaagga   11760
gctgtctgct tagtgcccac ttttcgcaa attcgatgag actgtgcgcg actcctttgc    11820
ctcggtgcgt gtgcgacaca acaatgtgtt cgatagaggc tagatcgttc catgttgagt   11880
tgagttcaat cttcccgaca agctcttggt cgatgaatgc gccatagcaa gcagagtctt   11940
catcagagtc atcatccgag atgtaatcct tccggtaggg gctcacactt ctggtagata   12000
gttcaaagcc ttggtcggat aggtgcacat cgaacacttc acgaacaatg aaatggttct   12060
cagcatccaa tgtttccgcc acctgctcag ggatcaccga atcttcata tgacgcctaa    12120 cgcctggcac agcggatcgc aaacctggcg cggcttttgg cacaaaaggc gtgacaggtt   12180
tgcgaatccg ttgctgccac ttgttaaccc ttttgccaga tttggtaact ataatttatg   12240
ttagaggcga agtcttgggt aaaaactggc ctaaaattgc tggggatttc aggaaagtaa   12300
acatcacctt ccggctcgat gtctattgta gatatatgta gtgtatctac ttgatcgggg   12360
gatctgctgc ctcgcgcgtt tcggtgatga cggtgaaaac ctctgacaca tgcagctccc   12420
ggagacggtc acagcttgtc tgtaagcgga tgccgggagc agacaagccc gtcagggcgc   12480
gtcagcgggt gttggcgggt gtcggggcgc agccatgacc cagtcacgta gcgatagcgg   12540
agtgtatact ggcttaacta tgcggcatca gagcagattg tactgagagt gcaccatatg   12600
cggtgtgaaa taccgcacag atgcgtaagg agaaaatacc gcatcaggcg ctcttccgct   12660
tcctcgctca ctgactcgct gcgctcggtc gttcggctgc ggcgagcggt atcagctcac   12720
tcaaaggcgg taatacggtt atccacagaa tcaggggata acgcaggaaa gaacatgtga   12780
gcaaaaggcc agcaaaaggc caggaaccgt aaaaaggccg cgttgctggc gtttttccat   12840
aggctccgcc cccctgacga gcatcacaaa aatcgacgct caagtcagag gtggcgaaac   12900
ccgacaggac tataaagata ccaggcgttt ccccctggaa gctccctcgt gcgctctcct   12960
gttccgaccc tgccgcttac cggatacctg tccgcctttc tcccttcggg aagcgtggcg   13020
ctttctcata gctcacgctg taggtatctc agttcggtgt aggtcgttcg ctccaagctg   13080
ggctgtgtgc acgaaccccc cgttcagccc gaccgctgcg ccttatccgg taactatcgt   13140
cttgagtcca acccggtaag acacgactta tcgccactgg cagcagccac tggtaacagg   13200
attagcagag cgaggtatgt aggcggtgct acagagttct tgaagtggtg gcctaactac   13260
ggctacacta gaaggacagt atttggtatc tgcgctctgc tgaagccagt taccttcgga   13320
aaaagagttg gtagctcttg atccggcaaa caaaccaccg ctggtagcgg tggtttttttt   13380 gtttgcaagc agcagattac gcgcagaaaa aaaggatctc aagaagatcc tttgatcttt   13440
tctacggggt ctgacgctca gtggaacgaa aactcacgtt aagggatttt ggtcatgaga   13500
ttatcaaaaa ggatcttcac ctagatcctt ttaaattaaa aatgaagttt taaatcaatc   13560
taaagtatat atgagtaaac ttggtctgac agttaccaat gcttaatcag tgaggcacct   13620
atctcagcga tctgtctatt tcgttcatcc atagttgcct gactccccgt cgtgtagata   13680
```

```
actacgatac gggagggctt accatctggc cccagtgctg caatgatacc gcgagaccca    13740
cgctcaccgg ctccagattt atcagcaata accagccag ccggaagggc cgagcgcaga     13800
agtggtcctg caactttatc cgcctccatc cagtctatta attgttgccg ggaagctaga    13860
gtaagtagtt cgccagttaa tagtttgcgc aacgttgttg ccattgctgc agggggggg    13920 ggggggggg acttccattg ttcattccac ggacaaaaac agagaaagga aacgacagag    13980
gccaaaaagc ctcgctttca gcacctgtcg tttcctttct tttcagaggg tattttaaat    14040
aaaaacatta agttatgacg aagaagaacg gaaacgcctt aaaccggaaa attttcataa    14100
atagcgaaaa cccgcgaggt cgccgccccg taacctgtcg gatcaccgga aaggacccgt    14160
aaagtgataa tgattatcat ctacatatca aacgtgcgt ggaggccatc aaaccacgtc     14220
aaataatcaa ttatgacgca ggtatcgtat taattgatct gcatcaactt aacgtaaaaa    14280
caacttcaga caatacaaat cagcgacact gaatacgggg caacctcatg tccccccccc    14340 cccccccct gcaggcatcg tggtgtcacg ctcgtcgttt ggtatggctt cattcagctc     14400
cggttcccaa cgatcaaggc gagttacatg atccccatg ttgtgcaaaa aagcggttag     14460
ctccttcggt cctccgatcg ttgtcagaag taagttggcc gcagtgttat cactcatggt    14520
tatggcagca ctgcataatt ctcttactgt catgccatcc gtaagatgct tttctgtgac    14580
tggtgagtac tcaaccaagt cattctgaga atagtgtatg cggcgaccga gttgctcttg    14640
cccggcgtca acacgggata ataccgcgcc acatagcaga actttaaaag tgctcatcat    14700
tggaaaacgt tcttcgggc gaaaactctc aaggatctta ccgctgttga gatccagttc     14760
gatgtaaccc actcgtgcac ccaactgatc ttcagcatct tttactttca ccagcgtttc    14820
tgggtgagca aaaacaggaa ggcaaaatgc cgcaaaaaag gaataaggg cgacacggaa     14880 atgttgaata ctcatactct tccttttca atattattga agcatttatc agggttattg    14940
tctcatgagc ggatacatat ttgaatgtat ttagaaaaat aaacaaatag gggttccgcg    15000
cacatttccc cgaaaagtgc cacctgacgt ctaagaaacc attattatca tgacattaac    15060
ctataaaaat aggcgtatca cgaggccctt tcgtcttcaa gaattggtcg acgatcttgc    15120
tgcgttcgga tattttcgtg gagttcccgc cacagacccg gattgaaggc gagatccagc    15180
aactcgcgcc agatcatcct gtgacggaac tttggcgcgt gatgactggc caggacgtcg    15240
gccgaaagag cgacaagcag atcacgcttt tcgacagcgc cggatttgcg atcgaggatt    15300
tttcggcgct cgctacgtc cgcgaccgcg ttgagggatc aagccacagc agcccactcg    15360
accttctagc cgacccagac gagccaaggg atcttttgg aatgctgctc cgtcgtcagg     15420
ctttccgacg tttgggtggt tgaacagaag tcattatcgt acggaatgcc aagcactccc    15480
gaggggaacc ctgtgttgg catgcacata caaatgacg aacggataaa ccttttcacg     15540 ccctttaaa tatccgttat tctaataaac gctcttttct cttag                     15585
```

<210> SEQ ID NO 106
<211> LENGTH: 18
<212> TYPE: DNA
<213> ORGANISM: Artificial Sequence
<220> FEATURE:
<223> OTHER INFORMATION: synthetic construct; MHP14TS probe

<400> SEQUENCE: 106
cagattcacg tcagattt                                                      18

<210> SEQ ID NO 107

```
<211> LENGTH: 26
<212> TYPE: DNA
<213> ORGANISM: Artificial Sequence
<220> FEATURE:
<223> OTHER INFORMATION: synthetic construct; MHPTS14_Forward_MGB primer

<400> SEQUENCE: 107
agcgacatag tggtgtataa aaggaa                                      26

<210> SEQ ID NO 108
<211> LENGTH: 27
<212> TYPE: DNA
<213> ORGANISM: Artificial Sequence
<220> FEATURE:
<223> OTHER INFORMATION: synthetic construct; MHPTS14_Reverse_MGB primer

<400> SEQUENCE: 108
tggattgtaa tatgtgtacc tcatgct                                     27

<210> SEQ ID NO 109
<211> LENGTH: 27
<212> TYPE: DNA
<213> ORGANISM: Artificial Sequence
<220> FEATURE:
<223> OTHER INFORMATION: synthetic construct; primer 146775

<400> SEQUENCE: 109
gctttctatt ttgtggcact attgtgg                                     27

<210> SEQ ID NO 110
<211> LENGTH: 31
<212> TYPE: DNA
<213> ORGANISM: Artificial Sequence
<220> FEATURE:
<223> OTHER INFORMATION: synthetic construct; primer 146773

<400> SEQUENCE: 110
gctcgtgtcc aagcgtcact tacgattagc t                                31

<210> SEQ ID NO 111
<211> LENGTH: 23
<212> TYPE: DNA
<213> ORGANISM: Artificial Sequence
<220> FEATURE:
<223> OTHER INFORMATION: synthetic construct; primer 146772

<400> SEQUENCE: 111
accgctacca gcaacaatcg tct                                         23

<210> SEQ ID NO 112
<211> LENGTH: 21
<212> TYPE: DNA
<213> ORGANISM: Artificial Sequence
<220> FEATURE:
<223> OTHER INFORMATION: synthetic construct; primer 146778

<400> SEQUENCE: 112
tcacgctgca ctgcaggcta g                                           21

<210> SEQ ID NO 113
<211> LENGTH: 27
<212> TYPE: DNA
<213> ORGANISM: Artificial Sequence
<220> FEATURE:
<223> OTHER INFORMATION: synthetic construct; primer mopatF2

<400> SEQUENCE: 113
```
tcagatctgc gtcaccgggc gcaccgg                                              27

<210> SEQ ID NO 114
<211> LENGTH: 27
<212> TYPE: DNA
<213> ORGANISM: Artificial Sequence
<220> FEATURE:
<223> OTHER INFORMATION: synthetic construct; primer mopatR2

<400> SEQUENCE: 114
ccgccgtgtg cgacatcgtg aaccact                                             27

<210> SEQ ID NO 115
<211> LENGTH: 16
<212> TYPE: DNA
<213> ORGANISM: Artificial Sequence
<220> FEATURE:
<223> OTHER INFORMATION: synthetic construct; MHP55TS probe

<400> SEQUENCE: 115
aaccgtcgtg agacct                                                         16

<210> SEQ ID NO 116
<211> LENGTH: 17
<212> TYPE: DNA
<213> ORGANISM: Artificial Sequence
<220> FEATURE:
<223> OTHER INFORMATION: synthetic construct; MHPTS55_Forward_MGB primer

<400> SEQUENCE: 116
aaggcgcagc cgttgag                                                        17

<210> SEQ ID NO 117
<211> LENGTH: 20
<212> TYPE: DNA
<213> ORGANISM: Artificial Sequence
<220> FEATURE:
<223> OTHER INFORMATION: synthetic construct; MHP55TS_Reverse_MGB primer

<400> SEQUENCE: 117
ctaccggttt cgcgtgctct                                                     20

<210> SEQ ID NO 118
<211> LENGTH: 21
<212> TYPE: DNA
<213> ORGANISM: Artificial Sequence
<220> FEATURE:
<223> OTHER INFORMATION: synthetic construct; MHP77TS probe

<400> SEQUENCE: 118
tagtatgaca tacataccgc c                                                   21

<210> SEQ ID NO 119
<211> LENGTH: 23
<212> TYPE: DNA
<213> ORGANISM: Artificial Sequence
<220> FEATURE:
<223> OTHER INFORMATION: synthetic construct; MHP77TS_Forward_MGB primer

<400> SEQUENCE: 119
tccttagggc ggtatgtatg tca                                                 23

<210> SEQ ID NO 120
<211> LENGTH: 26
<212> TYPE: DNA

```
<213> ORGANISM: Artificial Sequence
<220> FEATURE:
<223> OTHER INFORMATION: synthetic construct; MHP77TS_Reverse_MGB primer

<400> SEQUENCE: 120
catcggtcaa aaacacata aacttt                                           26

<210> SEQ ID NO 121
<211> LENGTH: 105
<212> TYPE: DNA
<213> ORGANISM: Glycine max

<400> SEQUENCE: 121
tcttaaagaa gatacactgt gtaaatgtgt aatggcactg gcactctcgt gtgtgattaa     60
agtcatatat ggtttaagat actttttttt ataaagatag tagtg                    105

<210> SEQ ID NO 122
<211> LENGTH: 52
<212> TYPE: DNA
<213> ORGANISM: Glycine max

<400> SEQUENCE: 122
tcttaaagaa gatacactgt gtaaatgtgt aatggcactg gcactctcgt gt             52

<210> SEQ ID NO 123
<211> LENGTH: 28
<212> TYPE: DNA
<213> ORGANISM: Glycine max

<400> SEQUENCE: 123 gatactttt tttataaaga tagtagtg                                         28

<210> SEQ ID NO 124
<211> LENGTH: 100
<212> TYPE: DNA
<213> ORGANISM: Glycine max

<400> SEQUENCE: 124
taatgatcac atttttttt tctcacactc acctaagtgc acgagtacac acgtaagtct     60
taggttaaag tttcatgccc cccccccccc cccccaaaa                           100

<210> SEQ ID NO 125
<211> LENGTH: 54
<212> TYPE: DNA
<213> ORGANISM: Glycine max

<400> SEQUENCE: 125
taatgatcac atttttttt tctcacactc acctaagtgc acgagtacac acgt           54

<210> SEQ ID NO 126
<211> LENGTH: 100
<212> TYPE: DNA
<213> ORGANISM: Glycine max

<400> SEQUENCE: 126
taatgatcac atttttttt tctcacactc acctaagtgc acgagtacac acgtaagtct     60
taggttaaag tttcatgccc cccccccccc cccccaaaa                           100

<210> SEQ ID NO 127
<211> LENGTH: 45
<212> TYPE: DNA
<213> ORGANISM: Glycine max
```

```
<400> SEQUENCE: 127
taatgatcac attttttttt tctcacactc acctaagtgc acgag                45

<210> SEQ ID NO 128
<211> LENGTH: 104
<212> TYPE: DNA
<213> ORGANISM: Glycine max

<400> SEQUENCE: 128
taatgatcac attttttttt tctcacactc acctaagtgc agacgtacgc aagtagcttt    60
gttactttcg tattgacaat tcaaaatcgt cttttatttt tatt                    104

<210> SEQ ID NO 129
<211> LENGTH: 102
<212> TYPE: DNA
<213> ORGANISM: Glycine max
<220> FEATURE:
<221> NAME/KEY: misc_feature
<222> LOCATION: (47)..(48)
<223> OTHER INFORMATION: 115 bp insertion between position 47 and
      position 48 omitted below and in the alignment in Figure 4B

<400> SEQUENCE: 129
taatgatcac attttttttt tctcacactc acctaagtgc agacgtacaa gtagctttgt    60
tactttcgta ttgacaattc aaaatcgtct tttattttta tt                      102
```

METHODS FOR PRODUCING A COMPLEX TRANSGENIC TRAIT LOCUS

CROSS-REFERENCE TO RELATED APPLICATIONS

This application claims the benefit of U.S. Provisional Patent Application No. 61/499,443, filed Jun. 11, 2011 and U.S. Provisional Patent Application No. 61/466,602, filed Mar. 23, 2011; both of which are hereby incorporated herein in their entirety by reference.

REFERENCE TO SEQUENCE LISTING

The Sequence Listing submitted Oct. 5, 2016 as a text file named "36446_0002U3_Updated_Sequence_Listing.txt," created on Sep. 29, 2016, and having a size of 154,654 bytes is hereby incorporated by reference pursuant to 37 C.F.R. § 1.52(e)(5).

FIELD OF INVENTION

The invention relates to the field of plant molecular biology, in particular, to methods for altering the genome of a plant cell.

BACKGROUND

Recombinant DNA technology has made it possible to insert foreign DNA sequences into the genome of an organism, thus, altering the organism's phenotype. The most commonly used plant transformation methods are *Agrobacterium* infection and biolistic particle bombardment in which transgenes integrate into a plant genome in a random fashion and in an unpredictable copy number. Thus, efforts are undertaken to control transgene integration in plants.

One method for inserting or modifying a DNA sequence involves homologous DNA recombination by introducing a transgenic DNA sequence flanked by sequences homologous to the genomic target. U.S. Pat. No. 5,527,695 describes transforming eukaryotic cells with DNA sequences that are targeted to a predetermined sequence of the eukaryote's DNA. Specifically, the use of site-specific recombination is discussed. Transformed cells are identified through use of a selectable marker included as a part of the introduced DNA sequences.

It was shown that artificially induced site-specific genomic double-stranded breaks in plant cells were repaired by homologous recombination with exogenously supplied DNA using two different pathways. (Puchta et al., (1996) *Proc. Natl. Acad. Sci. USA* 93:5055-5060; U.S. Patent Application Publication No. 2005/0172365A1 published Aug. 4, 2005; U.S. Patent Application Publication No. 2006/0282914 published Dec. 14, 2006; WO 2005/028942 published Jun. 2, 2005).

Since the isolation, cloning, transfer and recombination of DNA segments, including coding sequences and non-coding sequences, is most conveniently carried out using restriction endonuclease enzymes. Much research has focused on studying and designing endonucleases such as WO 2004/067736 published Aug. 12, 2004; U.S. Pat. No. 5,792,632 issued to Dujon et al., Aug. 11, 1998; U.S. Pat. No. 6,610,545 B2 issued to Dujon et al., Aug. 26, 2003; Chevalier et al., (2002) *Mol Cell* 10:895-905; Chevalier et al., (2001) *Nucleic Acids Res* 29:3757-3774; Seligman et al., (2002) *Nucleic Acids Res* 30:3870-3879.

Although a plethora of approaches have been developed to target a specific site for modification in the genome of a plant, there still remains a need for methods for producing a fertile plant, having an altered genome comprising two or more site-specific modifications in defined region of the genome of the plant.

BRIEF SUMMARY OF THE INVENTION

The present invention provides methods for producing in a plant a complex transgenic trait locus comprising at least two altered target sequences in a genomic region of interest. The methods involve selecting a genomic region in a plant that comprises a first target sequence and a second target sequence and then providing a first double-strand-break-inducing agent and a second double-strand-break-inducing agent. The first double-strand-break-inducing agent is capable of inducing a first double-strand break in DNA comprising the first target sequence, and the second double-strand-break-inducing agent is capable of inducing a second double-strand break in DNA comprising the second target sequence. The methods further involve contacting at least one plant cell with the first double-strand-break-inducing agent, identifying a cell comprising a first alteration at the first target sequence, and then recovering a first fertile plant from the cell comprising the first alteration. The first fertile plant also comprises the first alteration. Additionally, the methods involve contacting at least one plant cell with the second double-strand-break-inducing agent, identifying a cell comprising a second alteration at the second target sequence, and then recovering a second fertile plant from the cell comprising the second alteration. The methods further involve obtaining a fertile progeny plant from the second fertile plant, wherein the fertile progeny plant comprises both the first and second alterations in physical linkage.

In a first embodiment of the methods for producing in a plant a complex transgenic trait locus, the fertile progeny plant is obtained by crossing the first fertile plant and the second fertile plant and selecting the fertile progeny plant comprising both the first and second alterations in physical linkage.

In second embodiment, a cell of the first fertile plant, or progeny thereof comprising the first alteration, is contacted with the second double-strand-break-inducing agent.

In third embodiment, the complex transgenic trait locus further comprises at least one polynucleotide of interest in the genomic region of interest. Such a polynucleotide of interest can be, for example, a transgene, a native gene, and a gene that was a native gene prior to a targeted mutation therein.

In a fourth embodiment, the first alteration comprises insertion of a first DNA sequence of interest, or part thereof, into the first target sequence, and/or the second alteration comprises insertion of a second DNA sequence of interest, or part thereof, into the second target sequence. Such a first and/or a second DNA sequence of interest can be, for example, a DNA for gene silencing, a DNA encoding a phenotypic marker and a DNA encoding a protein providing an agronomic advantage.

In a fifth embodiment, the first and second double-strand-break-inducing agents are selected from the group consisting of an endonuclease, a zinc finger nuclease, or a TAL effector nuclease.

In a sixth embodiment, the endonuclease is modified to specifically cut at the first target sequence or at the second target sequence and no longer cuts at its wild-type endonuclease target sequence.

In a seventh embodiment, the first target sequence and the second target sequence are separated from each other by about 0.1, 0.2, 0.3, 0.4, 0.5, 0.6, 0.7, 0.8, 0.9, 1, 2, 3, 4, or 5 centimorgans (cM) in the genome of the plant.

In an eighth embodiment, the methods can involve crossing the fertile progeny plant with an additional fertile plant that comprises at least a third altered target sequence in the genomic region of interest and then selecting from the crossing a fertile progeny plant comprising the first alteration, the second and the at least third alteration in physical linkage. Like the first and second altered target sequences, the third altered target sequence originated from a third target sequence that is recognized and cleaved by a third double-strand-break-inducing agent.

Additionally provided are complex trait loci in plants produced by the methods of the invention and plants, plant cells, plant parts, and seeds thereof comprising at least one complex transgenic trait locus of the invention.

The present invention further provides a complex transgenic trait locus comprising at least two altered target sequences that are genetically linked in the genome of a plant to a polynucleotide of interest. Such altered target sequences originated from a corresponding target sequence that is recognized and cleaved by a double-strand-break-inducing agent. The altered target sequences comprise an alteration such as, for example, replacement of at least one nucleotide in the target sequence, a deletion of at least one nucleotide in the target sequence, an insertion of at least one nucleotide in the target sequence, or any combination thereof. The polynucleotide interest can be, for example, a transgene, a native gene, and a mutated gene. The present invention further provides plants, plant parts, plant cells, and seeds comprising at least one complex transgenic trait locus of the invention.

In an embodiment of the complex transgenic trait locus of the invention, at least one altered target sequence comprises a recombinant DNA molecule. Recombinant DNA molecules include, but are not limited to, a DNA for gene silencing, a DNA encoding a phenotypic marker, and a DNA encoding a protein providing an agronomic advantage.

In another embodiment, the two altered target sequences of the complex transgenic trait locus are located within about 0.1, 0.2, 0.3, 0.4, 0.5, 0.6, 0.7, 0.8, 0.9, 1, 2, 3, 4, 5, 6, 7, 8, 9, 10, 11 or up to 21 centimorgan (cM) of the polynucleotide of interest.

The invention provides plants, plant parts, plant cells, and seeds comprising at least one complex transgenic trait locus of the invention.

Additionally provided is an alternative method for producing in a plant a complex transgenic trait locus comprising at least two altered target sequences in a genomic region of interest. This method involves obtaining a first fertile plant comprising a first altered target sequence at the genomic region of interest and a second fertile plant comprising a second altered target sequence at the genomic region of interest. In this method, the first altered target sequence originated from a first target sequence that is recognized and cleaved by a first double-strand-break-inducing agent, and the second altered target sequence originated from a second target sequence that is recognized and cleaved by a second double-strand-break-inducing agent. The alternative method further involves crossing the first fertile plant and the second fertile plant, and then selecting from the crossing a fertile progeny plant comprising the first alteration and the second alteration in physical linkage.

Also provided are plants produced by the second method of the invention and plant cells, plant parts, and seeds thereof comprising at least one complex transgenic trait locus.

In another embodiment, the present invention provides a plant comprising an expression construct, which comprises a promoter operably linked to a nucleotide sequence encoding an endonuclease. The endonuclease is capable of specifically binding to and creating a double strand break in a target sequence selected from the group consisting of SEQ ID NO:1, 2, 3, 4, 5, 6, 7, 8, 68, 69, 70, 71, 72, 73, 74, 75, 76, and 77, wherein the promoter is capable of driving expression of an operably linked nucleotide sequence in a plant cell. The nucleotide sequence encoding the endonuclease can comprise a coding sequence of a DNA binding domain of an endonuclease, wherein the coding sequence comprises nucleotides 100-261 and nucleotides 850-1011 of SEQ ID NO:9, 10, 11, 12, 13, 14, 15, 16, 78, 79, 80, 81, 82 or 83; or a degenerate coding sequence thereof. Preferably, the nucleotide sequence encoding the endonuclease is a nucleotide sequence selected from the group consisting of SEQ ID NO:9, 10, 11, 12, 13, 14, 15, 16, 78, 79, 80, 81, 82, and 83.

In yet another embodiment of the invention, a plant of the invention comprises at least one altered target sequence, wherein the at least one altered target sequence originated from a corresponding target sequence that was recognized and cleaved by a double-strand break-inducing agent. In this embodiment, the altered target sequence is in a genomic region of interest that extends from: the target sequence set forth in SEQ ID NO: 4 to the target sequence set forth in SEQ ID NO: 2; the target sequence set forth in SEQ ID NO: 5 to the target sequence set forth in SEQ ID NO: 8; or the target sequence set forth in SEQ ID NO: 68 to the target sequence set forth in SEQ ID NO: 77. Such a plant of the invention can be produced by a method comprising providing at least one double-strand-break-inducing agent that is capable of inducing a double-strand break in DNA comprising a target sequence, wherein the target sequence is in a genomic region of interest that extends from: the target sequence set forth in SEQ ID NO: 4 to the target sequence set forth in SEQ ID NO: 2; the target sequence set forth in SEQ ID NO: 5 to the target sequence set forth in SEQ ID NO: 8; or the target sequence set forth in SEQ ID NO: 68 to the target sequence set forth in SEQ ID NO: 77. The method further comprises contacting at least one plant cell with the double-strand-break-inducing agent, identifying a cell comprising an alteration at the target sequence, and recovering a fertile plant comprising the alteration. In one embodiment of this method, the double-strand-break-inducing agent is encoded by a nucleotide sequence comprising a coding sequence of a DNA binding domain of an endonuclease, and wherein the coding sequence is selected from the group consisting of nucleotides 100-261 and nucleotides 850-1011 of SEQ ID NO: 9, 10, 11, 12, 13, 14, 15, 16, and 80, and degenerate coding sequences thereof. In another embodiment of this method, the double-strand-break-inducing agent is encoded by a nucleotide sequence comprising a coding sequence of a DNA binding domain of an endonuclease, and wherein the coding sequence is selected from the group consisting of nucleotides 100-261 and nucleotides 661-822 of SEQ ID NO: 78, 79, 81, 82 and 83, and degenerate coding sequences thereof. In another embodiment of this method, the double-strand-break-inducing agent is encoded by a nucleotide sequence is selected from the group consisting of SEQ ID NO: 9, 10, 11, 12, 13, 14, 15, 16, 78, 79, 80, 81, 82, and 83.

Additional embodiments of the methods and compositions of the present invention are disclosed below.

BRIEF DESCRIPTION OF THE DRAWINGS AND THE SEQUENCE LISTING

The invention can be more fully understood from the following detailed description and the accompanying drawings and Sequence Listing, which form a part of this application. The sequence descriptions and sequence listing attached hereto comply with the rules governing nucleotide and amino acid sequence disclosures in patent applications as set forth in 37 C.F.R. §§ 1.821-1.825. The sequence descriptions contain the three letter codes for amino acids as defined in 37 C.F.R. §§ 1.821-1.825, which are incorporated herein by reference.

FIGURES

FIG. 1. DNA double-strand break induced DNA alteration of an endogenous target site. (A) A generalized endogenous target site with flanking genomic DNA sequences designated as DNA 1 and DNA 2 which can be used as DNA exchange regions by homologous recombination. (B) A generalized DNA construct that can be used to express a DNA endonuclease to recognize and cleave the endogenous target site. The DNA endonuclease gene can be physically linked to the donor DNA described in (C) or (D), or substituted by other double-strand break inducing agents. (C) A generalized donor DNA construct having two regions DNA1 and DNA 2 of homology to the genomic target which flank a polynucleotide of interest and/or marker gene. (D) A generalized donor DNA construct that does not have regions of homology to the genomic target to flank a polynucleotide of interest and/or marker gene. Insertion of the DNA fragment will produce an insertion of the polynucleotide of interest at or near the recognition site. (E) One expected outcome when the polynucleotide of interest and/or marker gene of donor construct described in (C) or (D) is inserted at the endogenous target site by homologous recombination or non-homologous recombination, respectively. (F) Another outcome when the endogenous target site is altered by a deletion during the repair of the DNA double-strand break cleaved by the DNA endonuclease. The polynucleotide of interest and/or marker gene of donor construct described in (C) or (D) can be inserted at unrelated sites by random DNA integration. (G) Another outcome when the endogenous target site is altered by the insertion of an unrelated DNA during the repair of the DNA double-strand breaks cleaved by the DNA endonuclease. The polynucleotide of interest and/or marker gene of donor construct described in (C) or (D) can be inserted at unrelated sites by random DNA integration.

Figure 2:
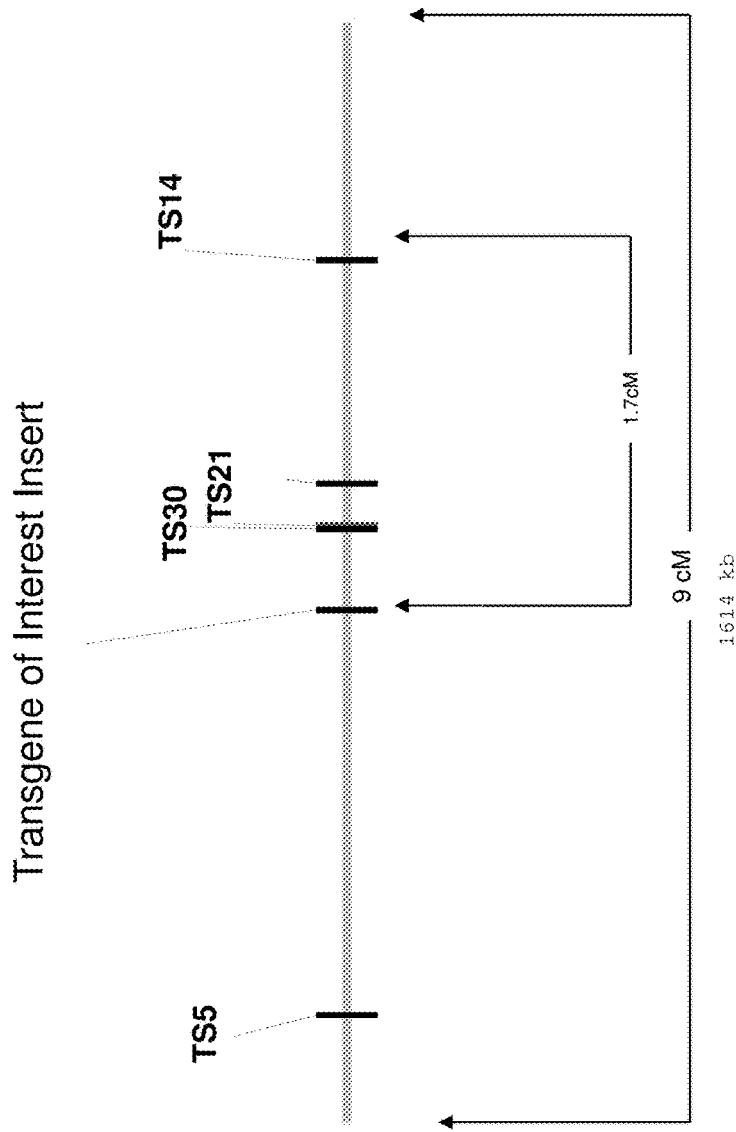

FIG. 2. Genetic distance between target sites and transgene of interest.

FIG. 3. A: Schematic diagram of PCR assays to detect TS21 target site modifications and transgenic integrations. B: Alignment of altered target sequences of selected TS21 transgenic event.

FIG. 4. A: Alignment of altered target sequences of selected TS5 transgenic events. B: Alignment of altered target sequences of selected TS14 transgenic events FIG. 5. Gene integration by homologous recombination enabled by double-strand breaks with custom designed meganuclease.

Figure 6:
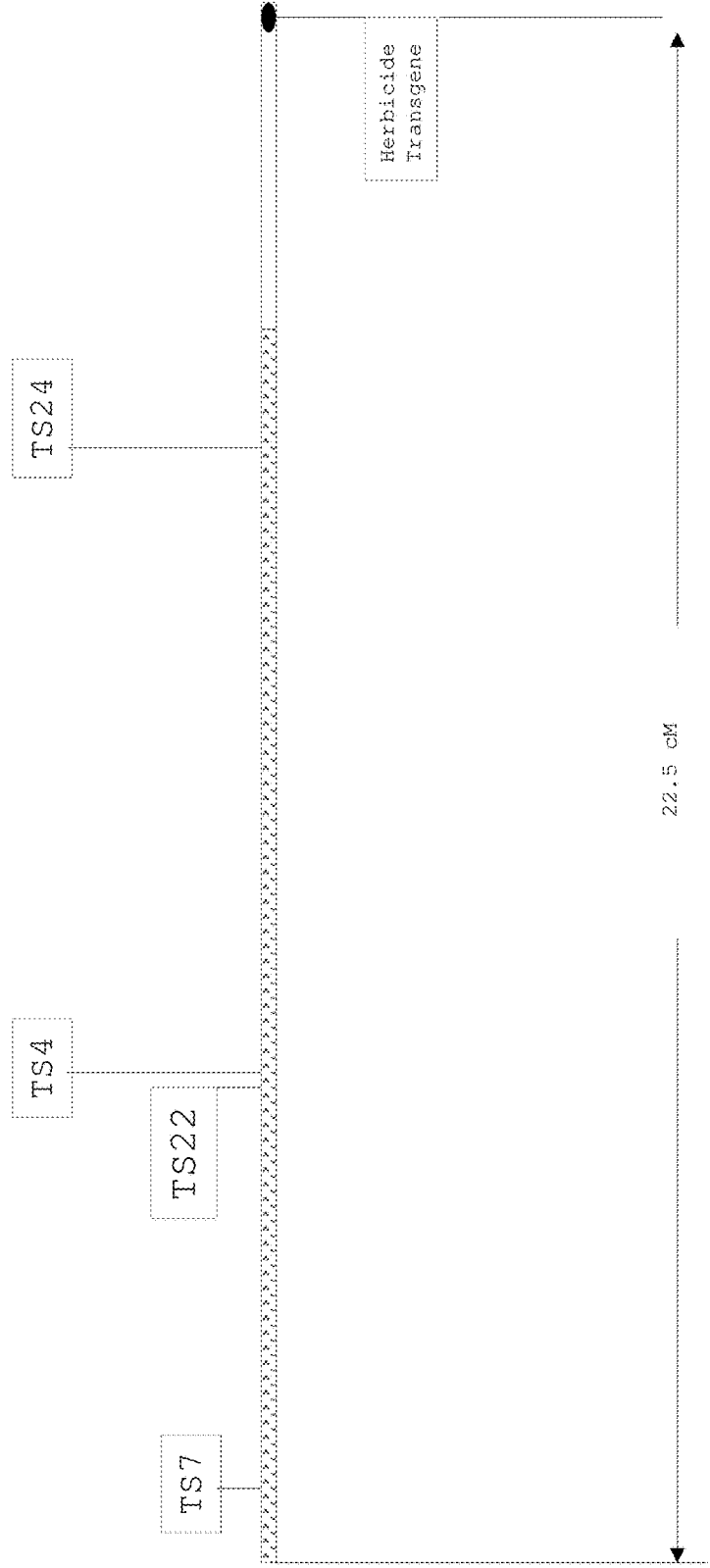

FIG. 6. Location of target sites near a herbicide resistant transgenic event in soybean.

Figure 7:
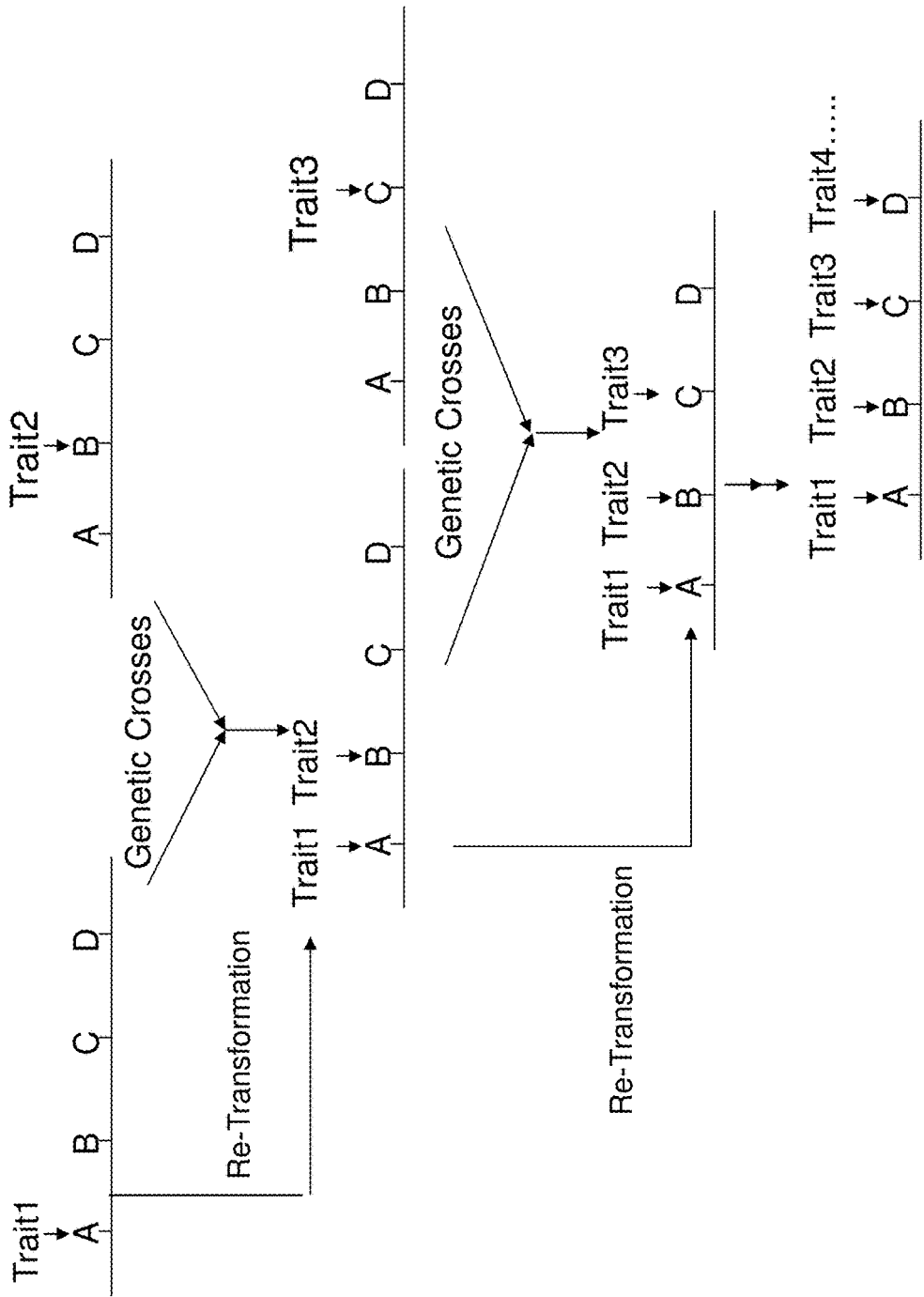

FIG. 7. Use of cluster of meganuclease target sites for stacking of multiple traits either by sequential transformation or genetic crosses.

Figure 8:
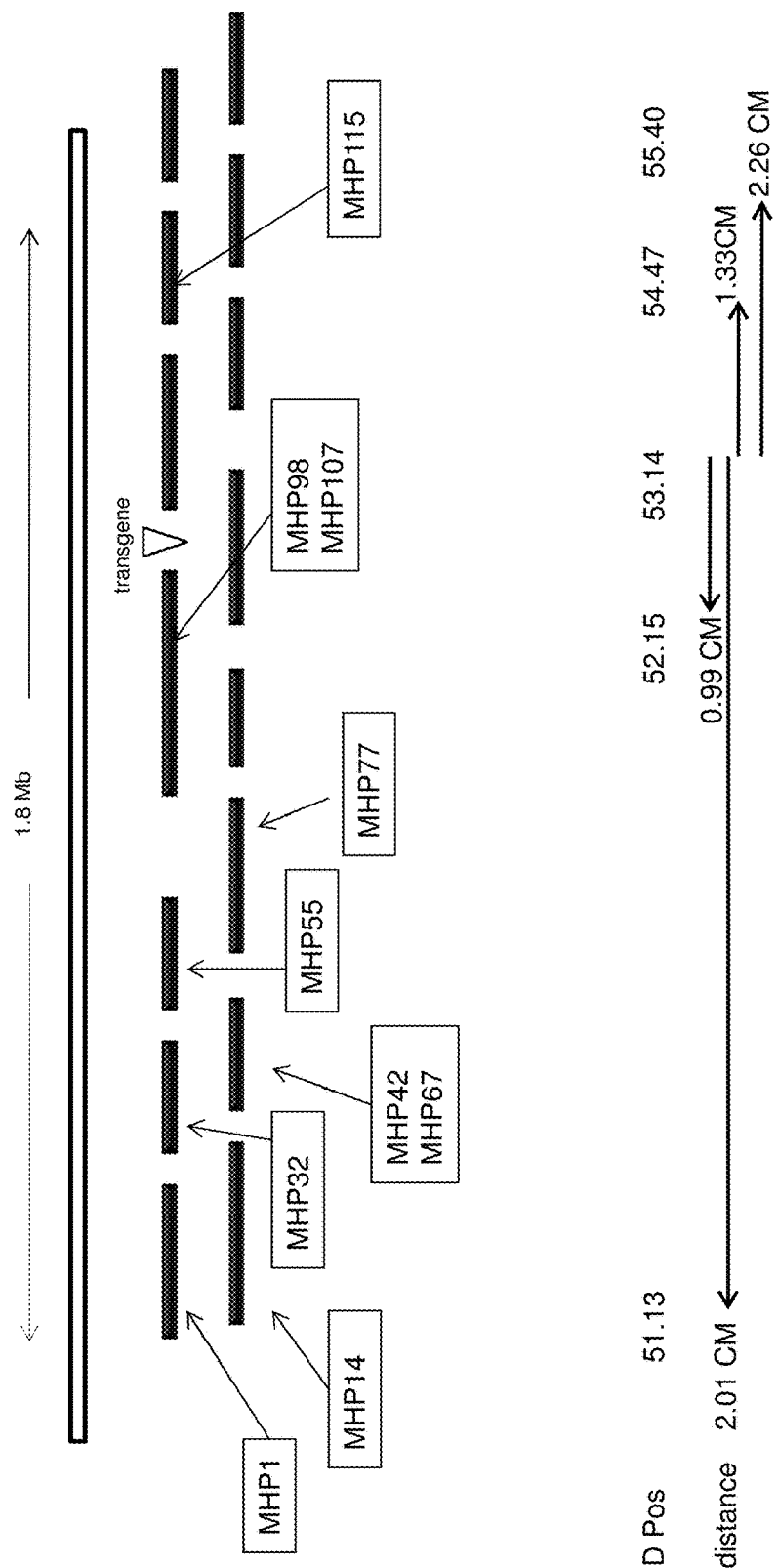

FIG. 8. The locations of various MHP target sites surrounding a transgenic DNA of interest integration site in a maize plant. Solid black rectangles represent BAC clones. Names and numbers in each box are the target sites. Arrows from box to BAC indicated the target site affiliated to BAC clones. Numbers and arrows on the bottom of the figure indicate the genetic distance of the target sites relative to the insertion location of the transgenic DNA of interest. As indicated at the top of the figure, the physical distance is about 1.8 Mb nucleotides in this region of the maize chromosome.

FIG. 9. A: Outline of PCR screening for integration of donor at MHP14 target site (donor was PHP44779) B: PCR of MHP14 events: B1-B12 junction PCR with primers 146773/146775; b1-b12 junction PCR with primers 146772/146778. Two events (B2 and B5) were positive for both junctions PCR. The arrows indicate the locations corresponding to the various primers used.

Figure 10:
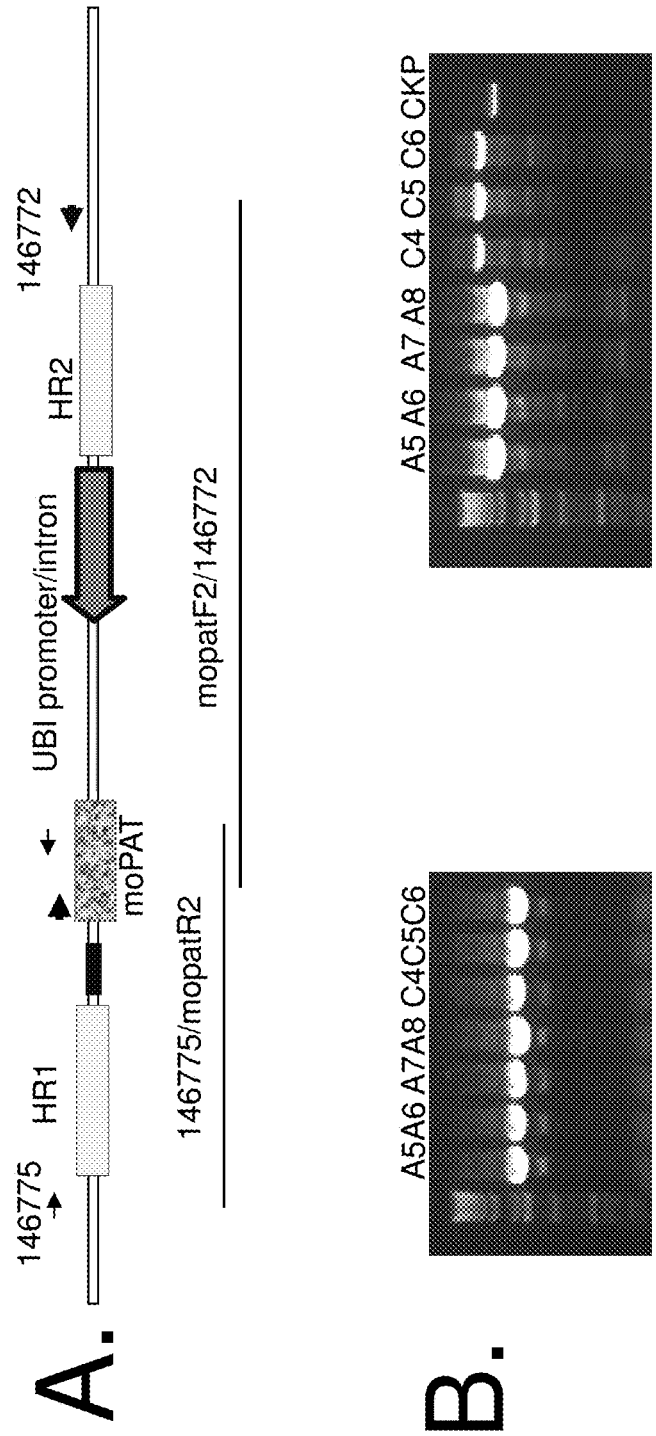

FIG. 10. A: Schematic outline of PCR to confirm ubi:mopat:pinII cassette integration at the endogenous MHP14 target. B: Long PCR on T0 plants from three events showed integration at the target site. The plant A5 was from event #1, A6-A8 event #2, and C4-C6 event #3. CKP: positive control from callus DNA. B: The left panel shows the results of junction PCR on the HR1 side using a genomic primer (146775) and a moPAT primer (mopatR2). The right panel shows the results of junction PCR on the HR2 side with a moPAT primer (mopatF2) a genomic primer (146772). The arrows indicate the locations corresponding to the various primers used.

Figure 11A:
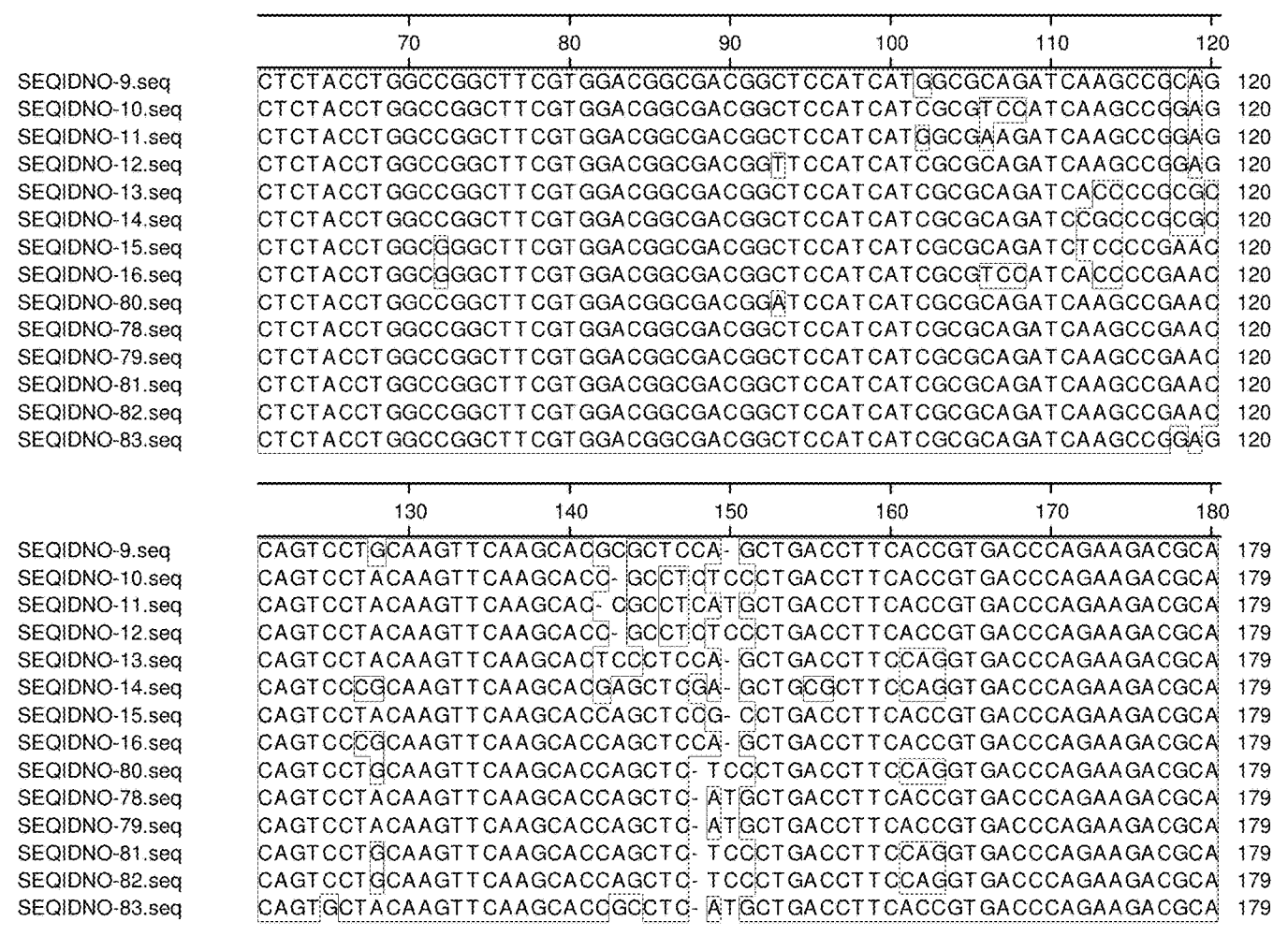
Figure 11B:
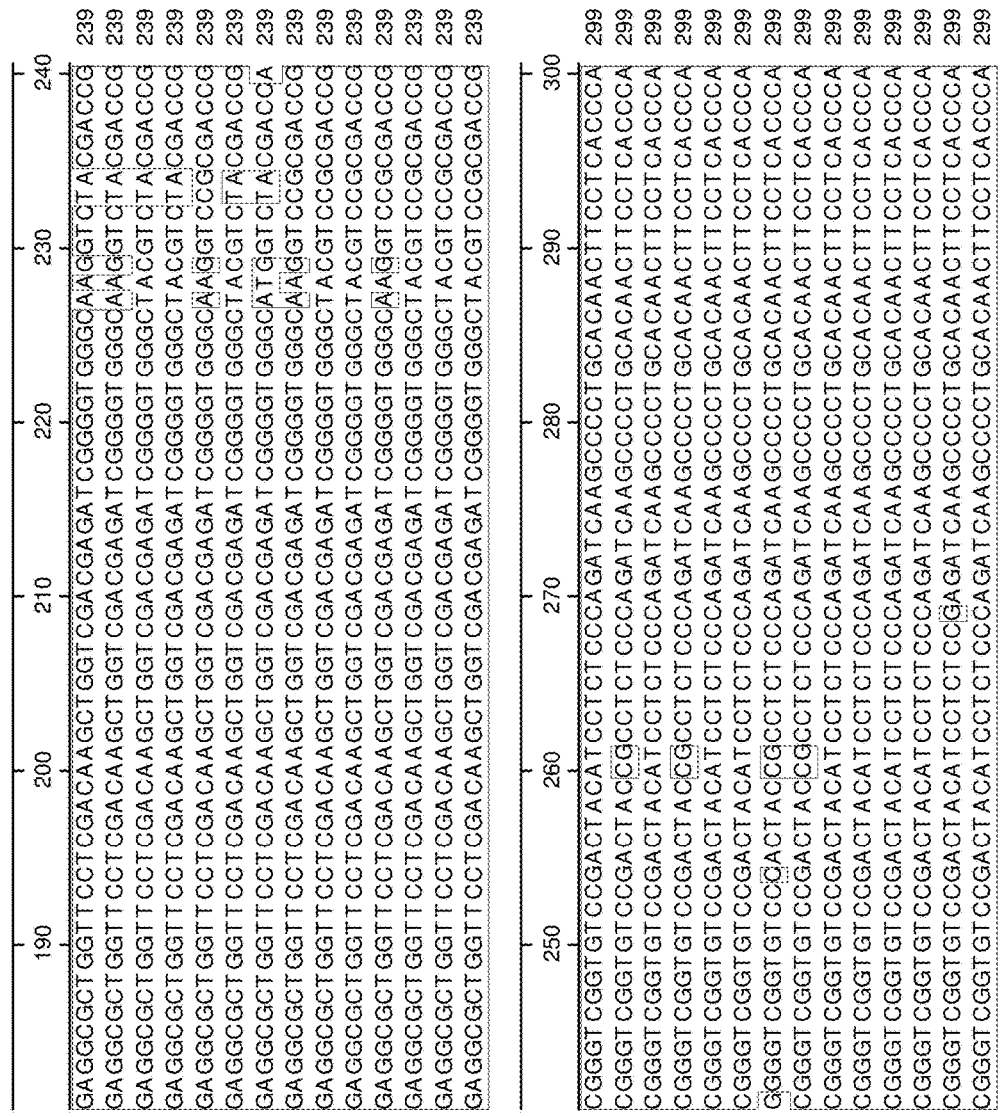
Figure 11C:
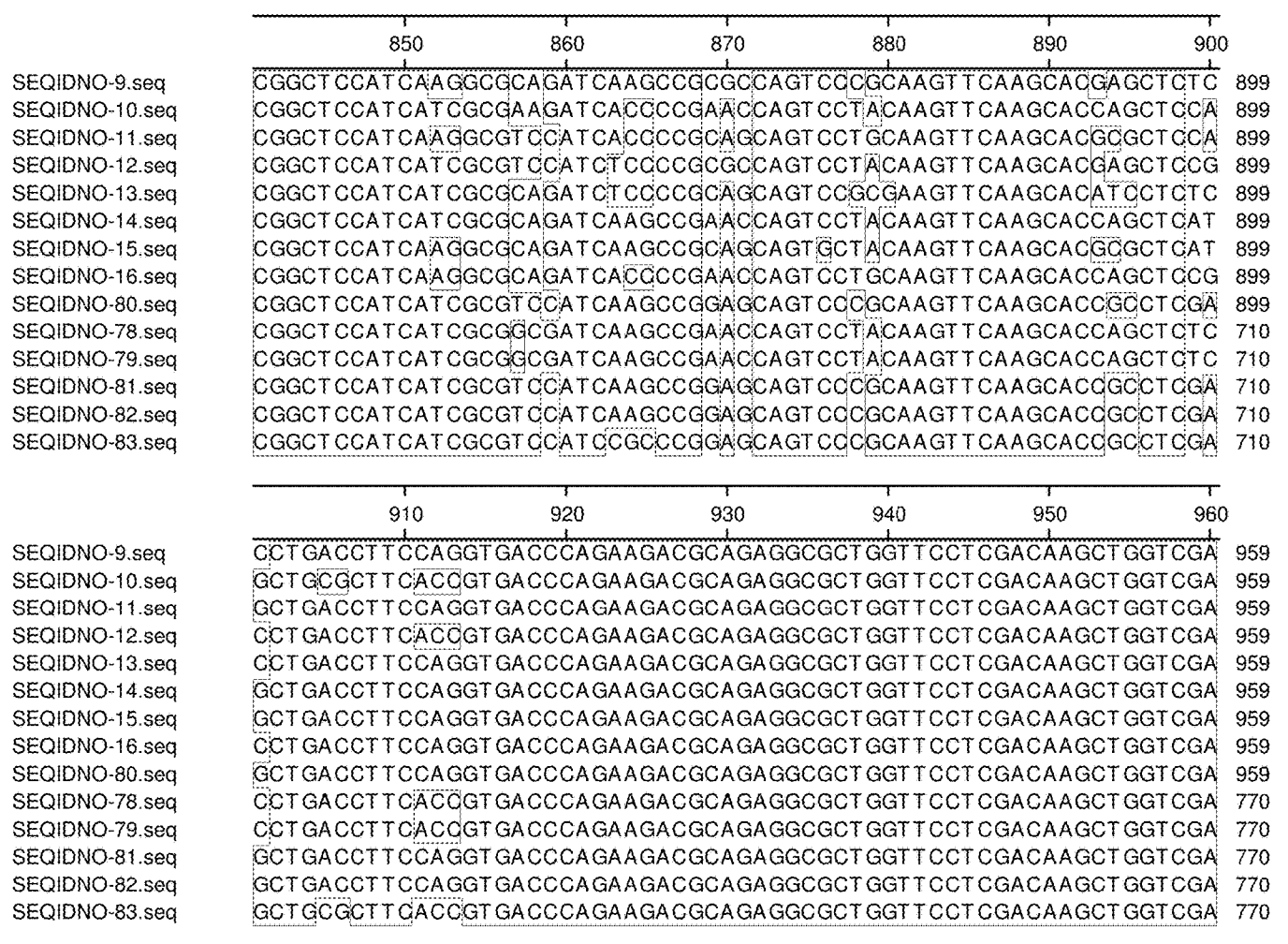
Figure 11D:
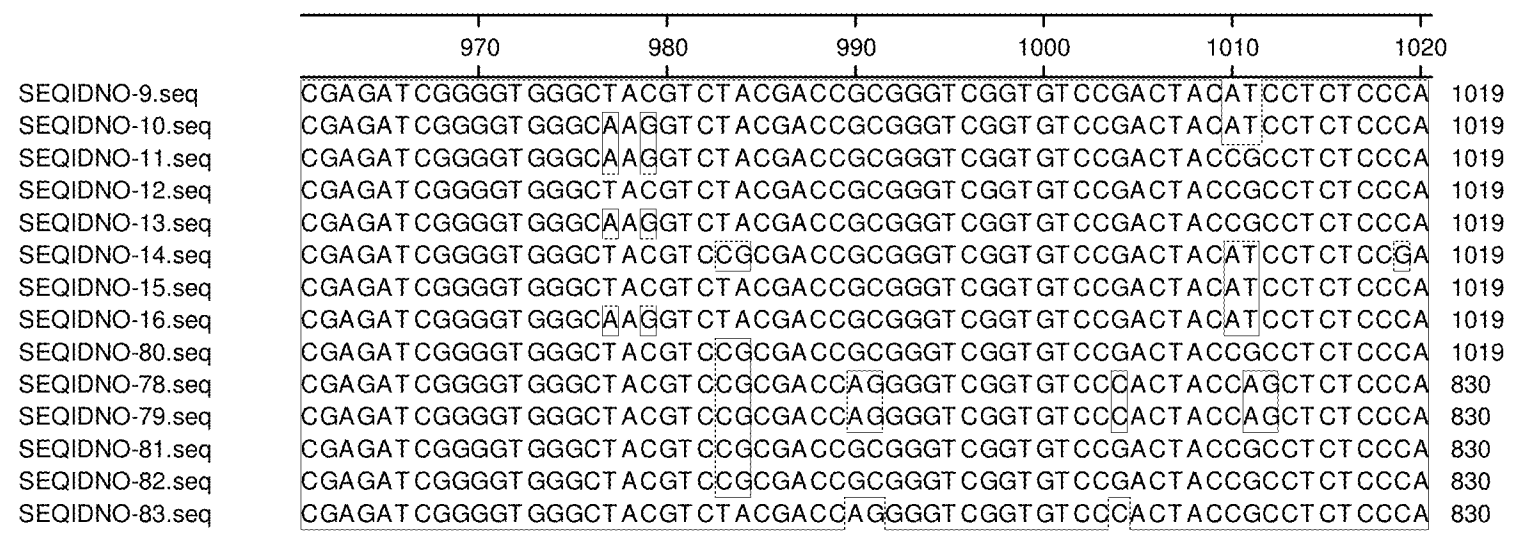

FIG. 11. Alignment of fragments from the plant-optimized nucleotide sequences of meganucleases comprising the nucleotides 100-261 and nucleotides 850-1011 of SEQ ID NO: 9, 10, 11, 12, 13, 14, 15, 16, and 80, and the nucleotides 100-261 and nucleotides 661-822 of SEQ ID NO: 78, 79, 81, 82 and 83. FIG. 11A shows SEQ ID NOs: 9-16 and 78-80 sequence positions 60-180, FIG. 11B shows SEQ ID NOs: 9-16 and 78-80 sequence positions 180-300, FIG. 11C shows SEQ ID NOs: 9-16 and 78-80 sequence positions 840-960, FIG. 11D shows SEQ ID NOs: 9-16 and 78-80 sequence positions 960-1020.

SEQUENCES

SEQ ID NO: 1 is the nucleotide sequence of the TS21 target site in soybean genome.

SEQ ID NO: 2 is the nucleotide sequence of the TS14 target site in soybean genome.

SEQ ID NO: 3 is the nucleotide sequence of the TS30 target site in soybean genome.

SEQ ID NO: 4 is the nucleotide sequence of the TS5 target site in soybean genome.

SEQ ID NO: 5 is the nucleotide sequence of the TS7 target site in soybean genome.

SEQ ID NO: 6 is the nucleotide sequence of the TS4 target site in soybean genome.

SEQ ID NO: 7 is the nucleotide sequence of the TS22 target site in soybean genome.

SEQ ID NO: 8 is the nucleotide sequence of the TS24 target site in soybean genome.

SEQ ID NO: 9 is the plant-optimized nucleotide sequence of the TS21 meganuclease containing a nuclear target site and an ST-LS1 intron.

SEQ ID NO: 10 is the plant-optimized nucleotide sequence of the TS14 meganuclease containing a nuclear target site and an ST-LS1 intron.

SEQ ID NO: 11 is the plant-optimized nucleotide sequence of the TS30 meganuclease containing a nuclear target site and an ST-LS1 intron.

SEQ ID NO: 12 is the plant-optimized nucleotide sequence of the TS5 meganuclease containing a nuclear target site and an ST-LS1 intron.

SEQ ID NO: 13 is the plant-optimized nucleotide sequence of the TS7 meganuclease containing a nuclear target site and an ST-LS1 intron.

SEQ ID NO: 14 is the plant-optimized nucleotide sequence of the TS4 meganuclease containing a nuclear target site and an ST-LS1 intron.

SEQ ID NO: 15 is the plant-optimized nucleotide sequence of the TS22 meganuclease containing a nuclear target site and an ST-LS1 intron.

SEQ ID NO: 16 is the plant-optimized nucleotide sequence of the TS24 meganuclease containing a nuclear target site and an ST-LS1 intron.

SEQ ID NO: 17 is the homologous region 1 (HR1) of the TS21 target site.

SEQ ID NO: 18 is the homologous region 2 (HR2) of the TS21 target site.

SEQ ID NO: 19 is the HR1 of the TS14 target site.

SEQ ID NO: 20 is the homologous region 2 of the TS14 target site.

SEQ ID NO: 21 is the HR1 of the TS30 target site.

SEQ ID NO: 22 is the homologous region 2 of the TS30 target site.

SEQ ID NO: 23 is the HR1 of the TS5 target site.

SEQ ID NO: 24 is the homologous region 2 of the TS5 target site.

SEQ ID NO: 25 is the HR1 of the TS7 target site.

SEQ ID NO: 26 is the homologous region 2 of the TS7 target site.

SEQ ID NO: 27 is the HR1 of the TS4 target site.

SEQ ID NO: 28 is the homologous region 2 of the TS4 target site.

SEQ ID NO: 29 is the HR1 of the TS22 target site.

SEQ ID NO: 30 is the homologous region 2 of the TS22 target site.

SEQ ID NO: 31 is the HR1 of the TS24 target site.

SEQ ID NO: 32 is the homologous region 2 of the TS24 target site.

SEQ ID NO: 33 is the plant-optimized nucleotide sequence of the TS21 meganuclease without a ST-LS1 intron.

SEQ ID NO: 34 is the amino acid sequence of the SV40 nuclear localization signal.

SEQ ID NO: 35: is the nucleotide sequences of expression cassette RTW317, comprising the TS21 meganuclease plant optimized sequence without an intron and operably linked to the soybean EF1A promoter.

SEQ ID NO: 36 is the nucleotide sequences of expression cassette RTW322, comprising the TS21 meganuclease plant optimized sequence with an intron and operably linked to the soybean EF1A promoter.

SEQ ID NO: 37 is the nucleotide sequence of RTW328A, which is the repair DNA fragment for TS21 meganuclease.

SEQ ID NO:38 is the nucleotide sequence of TS21 qPCR forward primer Mega21-190F.

SEQ ID NO:39 is the nucleotide sequence of TS21 qPCR reverse primer Mega21-301R.

SEQ ID NO:40 is the nucleotide sequence of TS21 qPCR probe mega21-250T. The fluorescent probe is labeled with FAM quenched with MGB.

SEQ ID NO:41 is the nucleotide sequence of TS14 qPCR forward primer Mega14-13F.

SEQ ID NO:42 is the nucleotide sequence of TS14 qPCR reverse primer Mega14-128R.

SEQ ID NO:43 is the nucleotide sequence of TS14 qPCR probe Mega14-85T. The fluorescent probe is labeled with FAM quenched with MGB.

SEQ ID NO:44 is the nucleotide sequence of TS30 qPCR forward primer Mega30-30F.

SEQ ID NO:45 is the nucleotide sequence of TS30 qPCR reverse primer Mega30-87R.

SEQ ID NO:46 is the nucleotide sequence of TS30 qPCR probe Mega30-52T. The fluorescent probe is labeled with FAM quenched with MGB.

SEQ ID NO:47 is the nucleotide sequence of TS5 qPCR forward primer Mega5-F1.

SEQ ID NO:48 is the nucleotide sequence of TS5 qPCR reverse primer Mega5-R1.

SEQ ID NO:49 is the nucleotide sequence of TS5 qPCR probe Mega5-T1. The fluorescent probe is labeled with FAM quenched with MGB.

SEQ ID NO:50 is the nucleotide sequence of the sense primer, WOL133, which is upstream of the TS21 target site in the soybean genome.

SEQ ID NO:51 is the nucleotide sequence of the antisense primer, WOL134, which is downstream of the TS21 target site in the soybean genome.

SEQ ID NO:52 is the nucleotide sequence of the sense primer, WOL190 which is further upstream of the TS21 target site beyond the TS21 HR1 fragment in the soybean genome.

SEQ ID NO:53 is the nucleotide sequence of the antisense primer, WOL242, which is specific to the hygromycin coding sequences.

SEQ ID NO:54 is the nucleotide sequence of the sense primer, WOL153, which is specific to the NOS Terminator.

SEQ ID NO:55 is the nucleotide sequence of the antisense primer, WOL247, which is further downstream of the TS21 target site beyond the TS21 HR2 fragment in the soybean genome.

SEQ ID NO:56 is the nucleotide sequence of the sense primer, WOL121, which is upstream of the TS14 target site in the soybean genome.

SEQ ID NO:57 is the nucleotide sequence of the antisense primer, WOL150, which is downstream of the TS21 target site in the soybean genome.

SEQ ID NO:58 is the nucleotide sequence of the sense primer, WOL192, which is further upstream of the TS14 target site beyond the TS14 HR1 fragment in the soybean genome.

SEQ ID NO:59 is the nucleotide sequence of the antisense primer, WOL193, which is further downstream of the TS14 target site beyond the TS14 HR2 fragment in the soybean genome.

SEQ ID NO:60 is the nucleotide sequence of the sense primer, WOL113, which is upstream of the TS30 target site in the soybean genome.

SEQ ID NO:61 is the nucleotide sequence of the antisense primer, WOL114, which is downstream of the TS30 target site in the soybean genome.

SEQ ID NO:62 is the nucleotide sequence of the sense primer, WOL194, which is further upstream of the TS30 target site beyond the TS30 HR1 fragment in the soybean genome.

SEQ ID NO:63 is the nucleotide sequence of the antisense primer, WOL195, which is further downstream of the TS30 target site beyond the TS30 HR2 fragment in the soybean genome.

SEQ ID NO:64 is the nucleotide sequence of the sense primer, WOL105, which is upstream of the TS5 target site in the soybean genome.

SEQ ID NO:65 is the nucleotide sequence of the antisense primer, WOL144, which is downstream of the TS5 target site in the soybean genome.

SEQ ID NO:66 is the nucleotide sequence of the sense primer, WOL196, which is further upstream of the TS5 target site beyond the TS5 HR1 fragment in the soybean genome.

SEQ ID NO:67 is the nucleotide sequence of the antisense primer, WOL197, which is further downstream of the TS5 target site beyond the TS5 HR2 fragment in the soybean genome.

SEQ ID NO:68 is the nucleotide sequence of the MHP1 target site in the maize genome.

SEQ ID NO:69 is the nucleotide sequence of the MHP14 target site sequence in the maize genome.

SEQ ID NO:70 is the nucleotide sequence of the MHP32 target site sequence in the maize genome.

SEQ ID NO:71 is the nucleotide sequence of the MHP42 target site sequence in the maize genome.

SEQ ID NO:72 is the nucleotide sequence of the MHP55 target site sequence in the maize genome.

SEQ ID NO:73 is the nucleotide sequence of the MHP67 target site sequence in the maize genome.

SEQ ID NO:74 is the nucleotide sequence of the MHP77 target site sequence in the maize genome.

SEQ ID NO:75 is the nucleotide sequence of the MHP98 target sit sequence in the maize genome.

SEQ ID NO:76 is the nucleotide sequence of the MHP107 target site sequence in the maize genome.

SEQ ID NO: 77 is the nucleotide sequence of the MHP115 target site sequence in the maize genome.

SEQ ID NO:78 is the plant-optimized nucleotide sequence of MHP14 comprising a nuclear localization signal and lacking an intron.

SEQ ID NO:79 is the plant-optimized nucleotide sequence of the MHP14+ comprising a nuclear localization signal and lacking an intron.

SEQ ID NO:80 is the plant-optimized nucleotide sequence of MHP55 comprising a nuclear localization signal and an intron.

SEQ ID NO:81 is the plant-optimized nucleotide sequence of MHP55 comprising a nuclear localization signal and lacking an intron.

SEQ ID NO:82 is the plant-optimized nucleotide sequence of MHP55-2 comprising a nuclear localization signal and lacking an intron.

SEQ ID NO:83 plant-optimized nucleotide sequence of MHP77 comprising a nuclear localization signal and lacking an intron.

SEQ ID NO:84 is the HR1 of the MHP14 target site.
SEQ ID NO:85 is the HR2 of the MHP14 target site.
SEQ ID NO:86 is the HR1 of the MHP55 target site.
SEQ ID NO:87 is the HR2 of the MHP55 target site.
SEQ ID NO:88 is the HR1 of the MHP77 target site.
SEQ ID NO:89 is the HR2 of the MHP77 target site.
SEQ ID NO: 90 is the HR1 of the MHP1 target site.
SEQ ID NO:91: is the HR2 of the MHP1 target site.
SEQ ID NO:92 is the HR1 of the MHP32 target site.
SEQ ID NO:93 is the HR2 of the MHP32 target site.
SEQ ID NO:94 is the HR1 of the MHP42 target site.
SEQ ID NO:95 is the HR2 of the MHP42 target site.
SEQ ID NO:96 is the HR1 of the MHP67 target site.
SEQ ID NO:97 is the HR2 of the MHP67 target site.
SEQ ID NO:98 is the HR1 of the MHP98 target site.
SEQ ID NO:99 is the HR2 of the MHP98 target site.
SEQ ID NO:100 is the HR1 of the MHP107 target site.
SEQ ID NO:101 is the HR2 of the MHP107 target site.
SEQ ID NO:102 is the HR1 of the MHP115 target site.
SEQ ID NO:103 is the HR2 of the MHP115 target site.
SEQ ID NO:104 is the nucleotide sequence of the plasmid PHP44285 (MHP14 and donor DNA).

SEQ ID NO:105 is the nucleotide sequence of the plasmid PHP44779 (MHP14+ and donor DNA).

SEQ ID NO:106 is the nucleotide sequence of the MHP14TS probe.

SEQ ID NO:107 is the nucleotide sequence of the MHPTS14TS_Forward_MGB primer.

SEQ ID NO:108 is the nucleotide sequence of the MHPTS14TS_Reverse_MGB primer.

SEQ ID NO:109 is the nucleotide sequence of the primer 146775 on genomic HR1 side.

SEQ ID NO:110 is the nucleotide sequence of the primer 146773 on vector HR1 side.

SEQ ID NO:111 is the nucleotide sequence of the primer 146772 on genomic HR2 side.

SEQ ID NO:112 is the nucleotide sequence of the primer 146778 on vector HR2 side.

SEQ ID NO:113 is the nucleotide sequence of the primer mopatF2.

SEQ ID NO:114 is the nucleotide sequence of the primer mopatR2.

SEQ ID NO:115 is the nucleotide sequence of the MHP55TS probe sequence.

SEQ ID NO:116 is the nucleotide sequence of the MHPTS55_Forward_MGB primer.

SEQ ID NO:117 is the nucleotide sequence of the MHP55TS_Reverse_MGB primer.

SEQ ID NO:118 is the nucleotide sequence of the MHP77TS probe.

SEQ ID NO:119 is the nucleotide sequence of the MHP77TS_Forward_MGB primer.

SEQ ID NO:120 is the nucleotide sequence of the MHP77TS_Reverse_MGB primer.

DETAILED DESCRIPTION OF THE INVENTION

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

In the context of this disclosure, a number of terms and abbreviations are used. The following definitions are provided.

As used herein a "complex transgenic trait locus" (plural: "complex transgenic trait loci") is a chromosomal segment within a genomic region of interest that comprises at least two altered target sequences that are genetically linked to each other and can also comprise one or more polynucleotides of interest as described hereinbelow. Each of the altered target sequences in the complex transgenic trait locus originates from a corresponding target sequence that was altered, for example, by a mechanism involving a double-strand break within the target sequence that was induced by a double-strand break-inducing agent of the invention. In certain embodiments of the invention, the altered target sequences comprise a transgene.

As used herein, a "genomic region of interest" is a segment of a chromosome in the genome of a plant that is desirable for producing a complex transgenic trait locus or the segment of a chromosome comprising a complex transgenic trait locus that was produced by the methods of the invention. The genomic region of interest can include, for example, one or more polynucleotides of interest prior to producing a complex transgenic trait locus therein. Generally, a genomic region of interest of the present invention comprises a segment of chromosome that is 0-15 cM.

The term "recognition sequence" or "recognition site" as used herein refers to a DNA sequence at which a double-strand break is induced in the plant cell genome by a double-strand break inducing agent. The terms "recognition sequence" and "recognition site" are used interchangeably herein.

The terms "target site", "target sequence", "target locus", "genomic target site", "genomic target sequence", and "genomic target locus" as used interchangeably herein refer to a polynucleotide sequence in the genome of a plant cell that comprises a recognition sequence for a double-strand break inducing agent.

An "artificial target sequence" is a target sequence that has been introduced into the genome of a plant. Such an artificial target sequence can be identical in sequence to an endogenous or native target sequence in the genome of a plant but be located in a different position (i.e., a non-endogenous or non-native position) in the genome of a plant.

The terms "endogenous target sequence" and "native target sequence" are used interchangeable herein to refer to a target sequence that is endogenous or native to the genome of a plant and is at the endogenous or native position of that target sequence in the genome of the plant.

An "altered target sequence" refers to a target sequence as disclosed herein that comprises at least one alteration of the invention when compared to non-altered target sequence. Such "alterations" of the invention include, for example: (i) replacement of at least one nucleotide, (ii) a deletion of at least one nucleotide, (iii) an insertion of at least one nucleotide, or (iv) any combination of (i)-(iii).

The term "double-strand-break-inducing agent" as used herein refers to any nuclease which produces a double-strand break in the target sequence. Producing the double-strand break in a target sequence or other DNA can be referred to herein as "cutting" or "cleaving" the target sequence or other DNA. In some embodiments of the invention, the double-strand-break-inducing agent has been engineered (or modified) to cut a specific endogenous target sequence, wherein the endogenous target sequence prior to being cut by the engineered double-strand-break-inducing agent was not a sequence that would have been recognized by a native (non-engineered or non-modified) double-strand-break-inducing agent.

As used herein, "physically linked," "in physical linkage", and "genetically linked" are used to refer to any two or more genes, transgenes, native genes, mutated genes, alterations, target sites, markers, and the like that are part of the same DNA molecule or chromosome.

As used herein, a "polynucleotide of interest" within a genomic region of interest is any coding and/or non-coding portion of the genomic region of interest including, but not limited to, a transgene, a native gene, a mutated gene, and a genetic marker such as, for example, a single nucleotide polymorphism (SNP) marker and a simple sequence repeat (SSR) marker.

"Open reading frame" is abbreviated ORF.

As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA that is single- or double-stranded, optionally containing synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

Polynucleotide and polypeptide sequences, variants thereof, and the structural relationships of these sequences can be described by the terms "homology", "homologous", "substantially identical", "substantially similar" and "corresponding substantially" which are used interchangeably herein. These refer to polypeptide or nucleic acid fragments wherein changes in one or more amino acids or nucleotide bases do not affect the function of the molecule, such as the ability to mediate gene expression or to produce a certain phenotype. These terms also refer to modification(s) of nucleic acid fragments that do not substantially alter the functional properties of the resulting nucleic acid fragment relative to the initial, unmodified fragment. These modifications include deletion, substitution, and/or insertion of one or more nucleotides in the nucleic acid fragment.

Substantially similar nucleic acid sequences encompassed may be defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence in an in vitro hybridization assay. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salt(s)) at pH 7.0 to 8.3, and at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth et al., (1984) *Anal Biochem* 138:267-284: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120 or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) *CABIOS* 5:151-153; Higgins et al., (1992) *Comput Appl Biosci* 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, (1989) *CABIOS* 5:151-153; Higgins et al., (1992) *Comput Appl Biosci* 8:189-191) and found in the MegAlign™ v6.1 program of the LASERGENE bioinformatics computing suite (DNASTAR Inc., Madison, Wis.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) *Proc. Natl. Acad. Sci. USA* 89:10915). GAP uses the algorithm of Needleman and Wunsch, (1970) *J Mol Biol* 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases.

BLAST® is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST® reports the identified sequences and their local alignment to the query sequence.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature, or at a different genetic locus than that found in nature. A "foreign" gene refers to a gene not normally found in the host organism, but that is introduced into the host organism by gene transfer. Foreign genes can comprise native genes inserted into a non-native organism, or chimeric genes.

A "mutated gene" is a native gene that has been altered through human intervention. Such a "mutated gene" has a sequence that differs from the sequence of the corresponding native gene by at least one nucleotide addition, deletion, or substitution. In certain embodiments of the invention, the mutated gene comprises an alteration that results from a double-strand-break-inducing agent as disclosed herein.

A "transgene" is a gene that has been introduced into the genome by a transformation procedure. A transgene can, for example encode one or more proteins or RNA that is not translated into protein. However, a transgene of the invention need not encode a protein and/or non-translated RNA. In certain embodiments of the invention, the transgene comprises one or more chimeric genes, including chimeric genes comprising, for example, a gene of interest, phenotypic marker, a selectable marker, and a DNA for gene silencing.

As used herein, a "targeted mutation" is mutation in a native gene that was made by altering a target sequence within the native gene using a method involving a double-strand-break-inducing agent that is capable of inducing a double-strand break in the DNA of the target sequence as disclosed herein or known in the art.

The term "genome" as it applies to a plant cells encompasses not only chromosomal DNA found within the nucleus, but organelle DNA found within subcellular components (e.g., mitochondria, or plastid) of the cell.

A "codon-modified gene" or "codon-preferred gene" or "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

"Coding sequence" refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, 5' untranslated sequences, 3' untranslated sequences, introns, polyadenylation recognition sequences, RNA processing sites, effector binding sites, and stem-loop structures.

"A plant-optimized nucleotide sequence" is nucleotide sequence that has been optimized for increased expression in plants, particularly for increased expression in plants or in one or more plants of interest. For example, a plant-optimized nucleotide sequence can be synthesized by modifying a nucleotide sequence encoding a protein such as, for example, double-strand-break-inducing agent (e.g., an endonuclease) as disclosed herein, using one or more plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference. Additional sequence modifications are known to enhance gene expression in a plant host. These include, for example, elimination of: one or more sequences encoding spurious polyadenylation signals, one or more exon-intron splice site signals, one or more transposon-like repeats, and other such well-characterized sequences that may be deleterious to gene expression. The G-C content of the sequence may be adjusted to levels average for a given plant host, as calculated by reference to known genes expressed in the host plant cell. When possible, the sequence is modified to avoid one or more predicted hairpin secondary mRNA structures. Thus, "a plant-optimized nucleotide sequence" of the present invention comprises one or more of such sequence modifications.

"Promoter" refers to a DNA sequence capable of controlling the expression of a coding sequence or functional RNA. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro and Goldberg, (1989) In *The Biochemistry of Plants*, Vol. 115, Stumpf and Conn, eds (New York, N.Y.: Academic Press), pp. 1-82.

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (e.g., Turner and Foster, (1995) *Mol Biotechnol* 3:225-236).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook et al., *Molecular Cloning: A Laboratory Manual; Cold Spring Harbor Laboratory*: Cold Spring Harbor, N.Y. (1989). Transformation methods are well known to those skilled in the art and are described infra.

"PCR" or "polymerase chain reaction" is a technique for the synthesis of specific DNA segments and consists of a series of repetitive denaturation, annealing, and extension cycles. Typically, a double-stranded DNA is heat denatured, and two primers complementary to the 3' boundaries of the target segment are annealed to the DNA at low temperature, and then extended at an intermediate temperature. One set of these three consecutive steps is referred to as a "cycle".

The term "recombinant" refers to an artificial combination of two otherwise separated segments of sequence, e.g., by chemical synthesis, or manipulation of isolated segments of nucleic acids by genetic engineering techniques.

The terms "plasmid", "vector" and "cassette" refer to an extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for expression of that gene in a foreign host.

The terms "recombinant DNA molecule", "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not all found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones et al., (1985) *EMBO J* 4:2411-2418; De Almeida et al., (1989) *Mol Gen Genetics* 218:78-86), and thus that multiple events are typically screened in order to obtain lines displaying the desired expression level and pattern. Such screening may be accomplished standard molecular biological, biochemical, and other assays including Southern analysis of DNA, Northern analysis of mRNA expression, PCR, real time quantitative PCR (qPCR), reverse transcription PCR (RT-PCR), immunoblotting analysis of protein expression, enzyme or activity assays, and/or phenotypic analysis.

The term "expression", as used herein, refers to the production of a functional end-product (e.g., an mRNA or a protein) in either precursor or mature form.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed (e.g., transfected mRNA).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or other DNA-containing organelle, of a host organism resulting in gene expression without integration or stable inheritance. Host organisms containing the transformed nucleic acid fragments are referred to as "transgenic" organisms.

As used herein, "transgenic" refers to a plant or a cell which comprises within its genome a heterologous polynucleotide. Typically, the heterologous polynucleotide is stably integrated within the genome such that the polynucleotide is passed on to successive generations. The heterologous polynucleotide may be integrated into the genome alone or as part of an expression construct. Transgenic is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollens, seeds, tumor tissue and various forms of cells and culture (e.g., single cells, protoplasts, embryos, and callus tissue). The plant tissue may be in plant or in a plant organ, tissue or cell culture. The term "plant organ" refers to plant tissue or a group of tissues that constitute a morphologically and functionally distinct part of a plant. The term "genome" refers to the entire complement of genetic material (genes and non-coding sequences) that is present in each cell of an organism, or virus or organelle; and/or a complete set of chromosomes inherited as a (haploid) unit from one parent. "Progeny" comprises any subsequent generation of a plant.

A "fertile plant" is a plant that is capable of producing a progeny plant. In certain embodiments of the invention, a fertile plant is a plant that produces viable male and female gametes and is self fertile. Such a self-fertile plant can produce a progeny plant without the contribution from any other plant of a gamete and the genetic material contained therein. Other embodiments of the invention can involve the use of a plant that is not self fertile because the plant does not produce male or female gametes that are viable or otherwise capable of fertilization. As used herein, a "male sterile plant" is a plant that does not produce male gametes that are viable or otherwise capable of fertilization. As used herein, a "female sterile plant" is a plant that does not produce female gametes that are viable or otherwise capable of fertilization. It is recognized that male and female sterile plants can be female and mail fertile, respectively. It is further recognized that a male fertile (but female sterile) plant can produce viable progeny when crossed with a female fertile plant and that a female fertile (but male sterile) plant can produce viable progeny when crossed with a male fertile plant.

A "centimorgan" (cM) or "map unit" is the distance between two linked genes, markers, target sites, loci, or any pair thereof, wherein 1% of the products of meiosis are recombinant. Thus, a centimorgan is equivalent to a distance equal to an 1% average recombination frequency between the two linked genes, markers, target sites, loci, or any pair thereof.

The present invention finds use in the breeding of plants comprising two to more transgenic traits. Currently, transgenic traits are randomly inserted throughout the plant genome as a consequence of transformation systems based on *Agrobacterium*, biolistics, or other commonly used procedures. More recently, gene targeting protocols have been developed that enable directed transgene insertion. One important technology, site-specific integration (SSI) enables the targeting of a transgene to the same chromosomal location as a previously inserted transgene. Custom-designed meganucleases and custom-designed zinc finger meganucleases allow researchers to design nucleases to target specific chromosomal locations, and these reagents allow the targeting of transgenes at the chromosomal site cleaved by these nucleases.

As disclosed herein, nuclease-mediated gene targeting can be used in methods for producing complex transgenic trait loci comprising multiple transgenes. In one embodiment of the invention, a complex transgenic trait locus is a locus that has multiple transgenes genetically linked to each other. By inserting independent transgenes within 1, 2 or even 5 centimorgans (cM) from each other, the transgenes can be bred as single genetic locus. FIG. 7 depicts the process of how two traits could be integrated into the genome at a genetic distance of, for example, 0.2 cM from each other in independent transformation runs or in sequential transformations (e.g., transformation and re-transformation). After selecting the events, plants containing the two events can be crossed to form an F1 that contains the events on different chromosomes. In progeny from these F1 (F2 or BC1) 1/500 progeny would have the two different transgenes recombined onto the same chromosome. The complex locus could then be bred as single genetic locus with both transgene traits. This process could be repeated to stack as many traits as desired.

The present invention provides methods for producing complex transgenic trait loci at selected genomic regions to simplify breeding with multiple transgenes. To initiate the development of a complex transgenic trait locus, a region of the genome is first selected. Second, the sequence of nearby genomic regions is compiled and nuclease reagents designed to facilitate targeting additional transgenes to those closely linked sites. Subsequently, algorithms for nuclease design such as, for example, those described in U.S. Patent Application Publication No. 2007/0117128 A1 are used to select potential target sites. Additional bioinformatic analysis such as, for example, copy number of the site in the target genome, location of the site relative to known gene coding regions and other factors could be used to filter the sites to a subset of preferred sites. Nucleases could then be used to target new transgenes to these preferred sites using published protocols See, for example, Halluin et al. (2008) *Plant Biotechnol. J.* 6:93-102; Shukla et al. (2009) *Nature* doi: 10.1038/nature07992; Wright et al. *Plant J.* (2005) 44:693-705; and WO 2009/006297); all of which are herein incorporated by reference.

In a first aspect, the present invention provides methods for producing in a plant a complex transgenic trait locus comprising at least two altered target sequences in a genomic region of interest. In one embodiment, the methods involve selecting a genomic region in a plant that comprises a first target sequence and a second target sequence. Generally, the first target sequence and the second target sequence are separated from each other by about 0.1, 0.2, 0.3, 0.4, 0.5, 0.6, 0.7, 0.8, 0.9, 1, 2, 3, 4, or 5 centimorgans (cM) in the genome of the plant. In certain embodiments of the invention, the first and second target sequences are physically linked to a polynucleotide of interest such as, for example, a transgene, native gene, or a gene with a targeted mutation, that is within about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, or 21 cM of the first and/or the second target sequence.

The methods of the invention further involve providing a first double-strand-break-inducing agent and a second double-strand-break-inducing agent. The first double-strand-break-inducing agent is capable of inducing a first double-strand break in DNA comprising the first target sequence, and the second double-strand-break-inducing agent is capable of inducing a second double-strand break in DNA comprising the second target sequence. The methods of the invention do not depend on a particular double-strand-break-inducing agent but only that the double-strand-break-inducing agent is capable of inducing a double-strand break in DNA in a target sequence of the invention. Any such double-strand-break-inducing agent that is disclosed herein or known in the art can be used in the methods of the present invention.

Additionally, the methods involve contacting at least one plant cell with the first double-strand-break-inducing agent, identifying a cell comprising a first alteration at the first target sequence, and then recovering a first fertile plant from the cell comprising the first alteration. The first fertile plant also comprises the first alteration. Additionally, the method involves contacting at least one plant cell with the second double-strand-break-inducing agent, identifying a cell comprising a second alteration at the second target sequence, and then recovering a second fertile plant from the cell comprising the second alteration. The method further involves obtaining a fertile progeny plant from the second fertile plant, wherein the fertile progeny plant comprises both the first and second alterations in physical linkage.

In one embodiment of this method, the fertile progeny plant is obtained by crossing the first fertile plant and the second fertile plant and selecting for a fertile progeny plant comprising both the first and second alterations in physical linkage. In another embodiment, a cell of the first fertile plant, or progeny thereof comprising the first alteration, is contacted with the second double-strand-break-inducing agent, and the second fertile plant comprises both the first and second alterations, which may or may not be physically linked. If necessary, the second fertile plant can be selfed and a fertile progeny plant selected comprising both the first and second alterations in physical linkage.

The first and second alterations are selected from the group consisting of (i) replacement of at least one nucleotide, (ii) a deletion of at least one nucleotide, (iii) an insertion of at least one nucleotide, and (iv) any combination of (i)-(iii). In one embodiment of the invention, the first and/or the second alterations comprise insertion of a DNA sequence of interest including, but not limited to, a DNA for gene silencing, a DNA encoding a phenotypic marker, and a DNA encoding a protein providing an agronomic advantage. In another embodiment, the first and/or the second alterations comprise a targeted mutation in a native gene.

In a like manner, the methods disclosed herein can be used to produce in a plant a complex transgenic trait locus comprising 1, 2, 3, 4, 5, 6, 7, 8, 9, 10, or more altered target sequences in physical linkage in a genomic region of interest comprising 1, 2, 3, 4, 5, 6, 7, 8, 9, 10, or more target sequences of interest. Each additional target sequence of interest in the genomic region of interest can be recognized and cleaved by a double-strand-break-inducing agent essentially as described above.

For example, a third DNA sequence of interest is inserted into a third target sequence by contacting at least one cell of a plant with a third double-strand-break-inducing agent and a third DNA molecule comprising the DNA sequence of interest, and then identifying a cell comprising the DNA sequence of interest. The method can further comprising recovering a fertile plant comprising the third DNA sequence of interest. In one embodiment, the cell comprising the third DNA sequence of interest comprises the first alteration, the second alteration, or both the first alteration and the second alteration. The method of the invention can further comprising producing a fertile plant comprising the first alteration, the second alteration, and the third DNA sequence of interest in physical linkage. In another embodiment, the fertile plant comprising the first alteration, the second alteration, and the third DNA sequence of interest is produced by crossing the fertile plant comprising the first and second alterations with a second fertile plant comprising the third DNA sequence of interest, and selecting a fertile progeny plant from the crossing, wherein the fertile progeny plant comprises the first alteration, the second alteration, and the third DNA sequence of interest in physical linkage.

The fertile plant comprising the first alteration, the second alteration, and the third DNA sequence of interest can be produced, for example, by: (i) contacting a cell comprising the first alteration and the second alteration with the third double-strand-break-inducing agent; (ii) identifying a cell from (i) comprising the third DNA sequence of interest, wherein the cell comprises the first alteration and the second alteration, and wherein the first alteration, the second alteration, and the third DNA sequence of interest are physically linked; and (iii) recovering a fertile plant comprising in physical linkage the first alteration, the second alteration, and the third DNA sequence of interest.

In another embodiment of the invention, the methods for producing in a plant a complex transgenic trait locus comprising at least two altered target sequences in a genomic region of interest that involve obtaining a first fertile plant comprising a first altered target site at the genomic region of interest and a second fertile plant comprising a second altered target site at the genomic region of interest. In this method, the first altered target sequence originated from a first target sequence that is recognized and cleaved by a first double-strand-break-inducing agent, and the second altered target sequence originated from a second target sequence that is recognized and cleaved by a second double-strand-break-inducing agent. The second method further involves crossing the first fertile plant and the second fertile plant, and then selecting from the crossing a fertile progeny plant comprising the first alteration and the second alteration in physical linkage.

The second method can optionally involve crossing the fertile progeny plant with an additional fertile plant that comprises at least a third altered target sequence in the genomic region of interest and then selecting from the crossing a fertile progeny plant comprising the first alteration, the second and the at least third alteration in physical linkage. Like the first and second altered target sequences, the third altered target sequence originated from a third target sequence that is recognized and cleaved by a third double-strand-break-inducing agent. In a like manner, a complex transgenic trait locus can be produced comprising 4, 5, 6, 7, 8, 9, 10, or more altered target sequences in physical linkage in the genomic region of interest.

In another aspect, the present invention provides complex transgenic trait loci in plants as well as plants, plant parts, plant cells, and seeds comprising at least one complex transgenic trait locus of the invention. A complex transgenic trait locus of the invention comprises at least two altered target sequences that are genetically linked to a polynucleotide of interest. Such altered target sequences originated from a corresponding target sequence that is recognized and cleaved by a double-strand-break-inducing agent using, for example, the methods disclosed herein. The altered target sequences comprise an alteration such as, for example, replacement of at least one nucleotide in the target sequence, a deletion of at least one nucleotide in the target sequence, an insertion of at least one nucleotide in the target sequence, or any combination thereof. The polynucleotide interest can be, for example, a transgene, a native gene, and a mutated gene. The present invention provides plants, plant parts, plant cells, and seeds comprising at least one complex transgenic trait locus of the invention.

In one embodiment, a complex transgenic trait locus of the invention comprises at least one altered target sequence comprising a recombinant DNA molecule. Recombinant DNA molecules of the invention include, but are not limited to, a DNA for gene silencing, a DNA encoding a phenotypic marker, and a DNA encoding a protein providing an agronomic advantage.

Generally, each of the altered target sites of the complex transgenic trait locus are located within about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, or 21 centimorgan (cM) of the polynucleotide of interest.

The methods of the present invention involve the use of one or more double-strand break inducing agents. A double-strand break inducing agent of the present invention is any agent that recognizes and/or binds to a specific polynucleotide recognition sequence to produce a break in the target sequence at or near the recognition sequence. Examples of double-strand break inducing agents include, but are not limited to, endonucleases, TAL effector nucleases, and zinc finger nucleases, and include modified derivatives, variants, and fragments thereof.

A recognition sequence is any polynucleotide sequence that is specifically recognized and/or bound by a double-strand break inducing agent. The length of the recognition site sequence can vary, and includes, for example, sequences that are at least 4, 6, 8, 10, 12, 14, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more nucleotides in length.

It is possible that the recognition site could be palindromic, that is, the sequence on one strand reads the same in the opposite direction on the complementary strand. The nick/cleavage site could be within the recognition sequence or the nick/cleavage site could be outside of the recognition sequence. In another variation, the cleavage could occur at nucleotide positions immediately opposite each other to produce a blunt end cut or, in other cases, the incisions could be staggered to produce single-stranded overhangs, also called "sticky ends", which can be either 5' overhangs, or 3' overhangs. The recognition sequence can be endogenous or exogenous. When the recognition site is an endogenous sequence, it may be a recognition sequence recognized by a naturally-occurring, or native double-strand break inducing agent. Alternatively, an endogenous recognition site could be recognized and/or bound by a modified or engineered double-strand break inducing agent designed or selected to specifically recognize the endogenous recognition sequence to produce a double-strand break. A modified double-strand break inducing agent can be derived from a native, naturally-occurring double-strand break inducing agent or it could be artificially created or synthesized.

A variety of methods are available to identify those cells having an altered genome at or near the recognition sequence without using a screenable marker phenotype. Such methods can be viewed as directly analyzing a recognition sequence to detect any change in the recognition sequence, including but not limited to PCR methods, sequencing methods, nuclease digestion, Southern blots, and any combination thereof.

Proteins may be altered in various ways including amino acid substitutions, deletions, truncations, and insertions. Methods for such manipulations are generally known. For example, amino acid sequence variants of the protein(s) can be prepared by mutations in the DNA. Methods for mutagenesis and nucleotide sequence alterations include, for example, Kunkel, (1985) *Proc. Natl. Acad. Sci. USA* 82:488-92; Kunkel et al., (1987) *Meth Enzymol* 154:367-82; U.S. Pat. No. 4,873,192; Walker and Gaastra, eds. (1983) *Techniques in Molecular Biology* (MacMillan Publishing Company, New York) and the references cited therein. Guidance regarding amino acid substitutions not likely to affect biological activity of the protein is found, for example, in the model of Dayhoff et al., (1978) *Atlas of Protein Sequence and Structure* (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double-strand-break-inducing activity are known and generally measure the overall activity and specificity of the agent on DNA substrates containing recognition sites.

Endonucleases are enzymes that cleave the phosphodiester bond within a polynucleotide chain, and include restriction endonucleases that cleave DNA as specific sites without damaging the bases. Restriction endonucleases include Type I, Type II, Type III, and Type IV endonucleases, which further include subtypes. In the Type I and Type III systems, both the methylase and restriction activities are contained in a single complex.

Type I and Type III restriction endonucleases recognize specific recognition sites, but typically cleave at a variable position from the recognition site, which can be hundreds of base pairs away from the recognition site. In Type II systems the restriction activity is independent of any methylase activity, and cleavage typically occurs at specific sites within or near to the recognition site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site.

Type IV restriction enzymes target methylated DNA. Restriction enzymes are further described and classified, for example in the REBASE database (webpage at rebase.neb.com; Roberts et al., (2003) *Nucleic Acids Res* 31:418-20), Roberts et al., (2003) *Nucleic Acids Res* 31:1805-12, and Belfort et al., (2002) in *Mobile DNA II*, pp. 761-783, Eds. Craigie et al., (ASM Press, Washington, D.C.).

Endonucleases also include meganucleases, also known as homing endonucleases (HEases), which like restriction endonucleases, bind and cut at a specific recognition sequence, however the recognition sites for meganucleases are typically longer, about 18 bp or more. Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFS, introns, and inteins, respectively. For example, intron-, intein-, and freestanding gene encoded meganuclease from *Saccharomyces cerevisiae* are denoted I-SceI, PI-SceI, and F-SceII, respectively. Meganuclease domains, structure and function are known, see for example, Guhan and Muniyappa (2003) *Crit. Rev Biochem Mol Biol* 38:199-248; Lucas et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure et al., (2002) *Nat Struct Biol* 9:764. In some examples a naturally occurring variant, and/or engineered derivative meganuclease is used. Methods for modifying the kinetics, cofactor interactions, expression, optimal conditions, and/or recognition site specificity, and screening for activity are known, see for example, Epinat et al., (2003) *Nucleic Acids Res* 31:2952-62; Chevalier et al., (2002) *Mol Cell* 10:895-905; Gimble et al., (2003) *Mol Biol* 334:993-1008; Seligman et al., (2002) *Nucleic Acids Res* 30:3870-9; Sussman et al., (2004) *J Mol Biol* 342:31-41; Rosen et al., (2006) *Nucleic Acids Res* 34:4791-800; Chames et al., (2005) *Nucleic Acids Res* 33:e178; Smith et al., (2006) *Nucleic Acids Res* 34:e149; Gruen et al., (2002) *Nucleic Acids Res* 30:e29; Chen and Zhao, (2005) *Nucleic Acids Res* 33:e154; WO2005105989; WO2003078619; WO2006097854; WO2006097853; WO2006097784; and WO2004031346.

Any meganuclease can be used as a double-strand break inducing agent including, but not limited to, I-SceI, I-SceI, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-Scat, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any variant or derivative thereof.

The endonuclease can be a modified endonuclease that binds a non-native or exogenous recognition sequence and does not bind a native or endogenous recognition sequence. Modification of the endonuclease can be as little as one nucleotide. A modified endonuclease is not capable of making a double-strand break within a wild-type target sequence. A wild-type (i.e., prior to being modified) endonuclease is capable of making a double-strand break within the wild-type target sequence.

The endonuclease can be provided via a polynucleotide encoding the endonuclease. Such a polynucleotide encoding an endonuclease can be modified to substitute codons having a higher frequency of usage in a plant, as compared to the naturally occurring polynucleotide sequence. For example the polynucleotide encoding the endonuclease can be modified to substitute codons having a higher frequency of usage in a maize or soybean plant, as compared to the naturally occurring polynucleotide sequence.

A site-specific recombinase, also referred to as a recombinase, is a polypeptide that catalyzes conservative site-specific recombination between its compatible recombination sites, and includes native polypeptides as well as derivatives, variants and/or fragments that retain activity, and native polynucleotides, derivatives, variants, and/or fragments that encode a recombinase that retains activity.

One step in the recombination process involves polynucleotide cleavage at or near the recognition site. This cleaving activity can be used to produce a double-strand break. For reviews of site-specific recombinases and their recognition sites, see, Sauer (1994) *Curr Op Biotechnol* 5:521-7; and Sadowski (1993) *FASEB* 7:760-7. In some examples the recombinase is from the Integrase or Resolvase families.

The Integrase family of recombinases has over one hundred members and includes, for example, FLP, Cre, lambda integrase, and R. The Integrase family has been grouped into two classes based on the structure of the active sites, serine recombinases and tyrosine recombinases. The tyrosine family, which includes Cre, FLP, SSV1, and lambda (λ) integrase, uses the catalytic tyrosine's hydroxyl group for a nucleophilic attack on the phosphodiester bond of the DNA. Typically, members of the tyrosine family initially nick the DNA, which later forms a double-strand break. In the serine recombinase family, which includes phiC31 (ΦC31) integrase, a conserved serine residue forms a covalent link to the DNA target site (Grindley et al., (2006) *Ann Rev Biochem* 16:16). For other members of the Integrase family, see for example, Esposito et al., (1997) *Nucleic Acids Res* 25:3605-14 and Abremski et al., (1992) *Protein Eng* 5:87-91.

Other recombination systems include, for example, the streptomycete bacteriophage phiC31 (Kuhstoss et al., (1991) *J Mol Biol* 20:897-908); the SSV1 site-specific recombination system from *Sulfolobus shibatae* (Maskhelishvili et al., (1993) *Mol Gen Genet* 237:334-42); and a retroviral integrase-based integration system (Tanaka et al., (1998) *Gene* 17:67-76).

Sometimes the recombinase is one that does not require cofactors or a supercoiled substrate, including but not limited to Cre, FLP, and active derivatives, variants or fragments thereof. FLP recombinase catalyzes a site-specific reaction during DNA replication and amplification of the two-micron plasmid of *S. cerevisiae*. FLP recombinase catalyzes site-specific recombination between two FRT sites. The FLP protein has been cloned and expressed (Cox (1993) *Proc. Natl. Acad. Sci. USA* 80:4223-7). Functional derivatives, variants, and fragments of FLP are known (Buchholz et al., (1998) *Nat Biotechnol* 16:617-8, Hartung et al., (1998) *J Biol Chem* 273:22884-91, Saxena et al., (1997) *Biochim Biophys Acta* 1340:187-204, and Hartley et al., (1980) *Nature* 286:860-4).

The bacteriophage recombinase Cre catalyzes site-specific recombination between two lox sites (Guo et al., (1997) *Nature* 389:40-6; Abremski et al., (1984) *J Biol Chem* 259:1509-14; Chen et al., (1996) *Somat Cell Mol Genet* 22:477-88; Shaikh et al., (1977) *J Biol Chem* 272:5695-702; and Buchholz et al., (1998) *Nat Biotechnol* 16:617-8). Examples of site-specific recombinases that can be used to produce a double-strand break at a recognition sequence, including for example FLP, Cre, SSV1, lambda Int, phi C31, HK022, and R. Examples of site-specific recombination systems used in plants can be found in U.S. Pat. No. 5,929,301; U.S. Pat. No. 6,175,056; WO99/25821; U.S. Pat. No. 6,331,661; WO99/25855; WO99/25841, and WO99/25840, the contents of each are herein incorporated by reference.

Methods for modifying the kinetics, cofactor interaction and requirements, expression, optimal conditions, and/or recognition site specificity, and screening for activity of recombinases and variants are known, see for example Miller et al., (1980) *Cell* 20:721-9; Lange-Gustafson and Nash, (1984) *J Biol Chem* 259:12724-32; Christ et al., (1998) *J Mol Biol* 288:825-36; Lorbach et al., (2000) *J Mol Biol* 296:1175-81; Vergunst et al., (2000) *Science* 290:979-82; Dorgai et al., (1995) *J Mol Biol* 252:178-88; Dorgai et al., (1998) *J Mol Biol* 277:1059-70; Yagu et al., (1995) *J Mol Biol* 252:163-7; Sclimente et al., (2001) *Nucleic Acids Res* 29:5044-51; Santoro and Schultze, (2002) *Proc. Natl. Acad. Sci. USA* 99:4185-90; Buchholz and Stewart, (2001) *Nat Biotechnol* 19:1047-52; Voziyanov et al., (2002) *Nucleic Acids Res* 30:1656-63; Voziyanov et al., (2003) *J Mol Biol* 326:65-76; Klippel et al., (1988) *EMBO J* 7:3983-9; Arnold et al., (1999) *EMBO J* 18:1407-14; WO03/08045; WO99/25840; and WO99/25841. The recognition sites range from about 30 nucleotide minimal sites to a few hundred nucleotides.

Any recognition site for a recombinase can be used, including naturally occurring sites, and variants. Variant recognition sites are known, see for example Hoess et al., (1986) *Nucleic Acids Res* 14:2287-300; Albert et al., (1995) *Plant J* 7:649-59; Thomson et al., (2003) *Genesis* 36:162-7; Huang et al., (1991) *Nucleic Acids Res* 19:443-8; Siebler and Bode, (1997) *Biochemistry* 36:1740-7; Schlake and Bode, (1994) *Biochemistry* 33:12746-51; Thygarajan et al., (2001) *Mol Cell Biol* 21:3926-34; Umlauf and Cox, (1988) *EMBO J* 7:1845-52; Lee and Saito, (1998) *Gene* 216:55-65; WO01/23545; WO99/25821; WO99/25851; WO01/11058; WO01/07572 and U.S. Pat. No. 5,888,732.

A recombinase can be provided via a polynucleotide that encodes the recombinase or it can be provided via a modified polynucleotide encoding the recombinase. For example, the polynucleotide (encoding a recombinase) can be modified to substitute codons having a higher frequency of usage in a plant, as compared to the naturally occurring polynucleotide sequence or it can be modified to substitute codons having a higher frequency of usage in a maize or soybean plant, as compared to the naturally occurring polynucleotide sequence.

TAL effector nucleases are a new class of sequence-specific nucleases that can be used to make double-strand breaks at specific target sequences in the genome of a plant or other organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) *PNAS* 10.1073/pnas.1013133107; Scholze & Boch (2010) *Virulence* 1:428-432; Christian et al. *Genetics* (2010) 186:757-761; Li et al. (2010) *Nuc. Acids Res*. (2010) doi:10.1093/nar/gkq704; and Miller et al. (2011) *Nature Biotechnology* 29:143-148; all of which are herein incorporated by reference.

Transposases are polypeptides that mediate transposition of a transposon from one location in the genome to another. Transposases typically induce double-strand breaks to excise the transposon, recognize subterminal repeats, and bring together the ends of the excised transposon, in some systems other proteins are also required to bring together the ends during transposition.

Examples of transposons and transposases include, but are not limited to, the Ac/Ds, Dt/rdt, Mu-M1/Mn, and Spm(En)/dSpm elements from maize, the Tam elements from snapdragon, the Mu transposon from bacteriophage, bacterial transposons (Tn) and insertion sequences (IS), Ty elements of yeast (retrotransposon), Ta1 elements from *Arabidopsis* (retrotransposon), the P element transposon from *Drosophila* (Gloor et al., (1991) Science 253:1110-1117), the Copia, Mariner and Minos elements from *Drosophila*, the Hermes elements from the housefly, the Piggy-Back elements from *Trichplusia* ni, Tc1 elements from *C. elegans*, and IAP elements from mice (retrotransposon). In some examples the transposase is provided via a polynucleotide that encodes the transposase.

It is possible to modify the polynucleotide encoding the transposase by substituting codons having a higher frequency of usage in a plant, as compared to the naturally occurring polynucleotide sequence of by substituting codons having a higher frequency of usage in a maize or soybean plant, as compared to the naturally occurring polynucleotide sequence.

DNA topoisomerases modulate DNA secondary and higher order structures and functions related primarily to replication, transcription, recombination and repair. Topoisomerases share two characteristics: (i) the ability to cleave and reseal the phosphodiester backbone of DNA in two successive transesterification reactions; and (ii) once a topoisomerase cleaved DNA intermediate is formed, the enzyme allows the severed DNA ends to come apart, allowing the passage of another single- or double-stranded DNA segment. DNA topoisomerases can be classified into three evolutionary independent families: type IA, type IB and type II.

Those that cleave one strand of DNA and allow single step changes in the linking number of circular DNA are defined as type I DNA topoisomerases. The *Escherichia coli* topoisomerase I and topoisomerase III, *Saccharomyces cerevisiae* topoisomerase III and reverse gyrase belong to the type IA or type I-5' subfamily as the protein link is to a 5' phosphate in the DNA. The prototype of type IB or I-3' enzymes are found in all eukaryotes and also in vaccinia virus topoisomerase I where the protein is attached to a 3' phosphate. Despite differences in mechanism and specificity between the bacterial and eukaryotic enzymes, yeast DNA topoisomerase I can complement a bacterial DNA topoisomerase I mutant (Bjornsti et al., (1987) *Proc. Natl. Acad. Sci. USA* 84:8971-5). Type IA topoisomerases relax negatively supercoiled DNA and require magnesium and a single-stranded region of DNA. Topoisomerases IB relax both positively and negatively supercoiled DNA with equal efficiency and do not require a single-stranded region of DNA or metal ions for function.

The type II family includes *E. coli* DNA gyrase, *E. coli* topoisomerase IV (par E), eukaryotic type II topoisomerases, and archaic topoisomerase VI. Type II enzymes are homodimeric (eukaryotic topoisomerase II) or tetrameric (gyrase), cleaving both strands of a duplex. Preferred cutting sites are known for available topoisomerases.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs consist of an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind a 18 nucleotide recognition sequence. A recognition sequence of 18 nucleotides is long enough to be unique in a mammalian genome ($4^{18}=6.9\times10^{10}$).

To date, designer zinc finger modules predominantly recognize GNN and ANN triplets (Dreier et al., (2001) *J Biol Chem* 276:29466-78; Dreier et al., (2000) *J Mol Biol* 303: 489-502; Liu et al., (2002) *J Biol Chem* 277:3850-6), but examples using CNN or TNN triplets are also known (Dreier et al., (2005) *J Biol Chem* 280:35588-97; Jamieson et al., (2003) *Nature Rev Drug Discov* 2:361-8). See also, Durai et al., (2005) *Nucleic Acids Res* 33:5978-90; Segal, (2002) *Methods* 26:76-83; Porteus and Carroll, (2005) *Nat Biotechnol* 23:967-73; zinc-finger consortium (website at www.zincfinger.org); Pabo et al., (2001) *Ann Rev Biochem* 70:313-40; Wolfe et al., (2000) *Ann Rev Biophys Biomol Struct* 29:183-212; Segal and Barbas, (2001) *Curr Opin Biotechnol* 12:632-7; Segal et al., (2003) *Biochemistry* 42:2137-48; Beerli and Barbas, (2002) *Nat Biotechnol* 20:135-41; Carroll et al., (2006) *Nature Protocols* 1:1329; Ordiz et al., (2002) *Proc. Natl. Acad. Sci. USA* 99:13290-5;

Guan et al., (2002) *Proc. Natl. Acad. Sci. USA* 99:13296-301; WO2002099084; WO00/42219; WO02/42459; WO2003062455; U.S. Patent Application Publication No. 20030059767; U.S. Patent Application Publication No. 2003/0108880; U.S. Pat. Nos. 6,140,466, 6,511,808 and 6,453,242.

Alternatively, engineered zinc finger DNA binding domains can be fused to other double-strand break inducing agents or derivatives thereof that retain DNA nicking/cleaving activity. For example, this type of fusion can be used to direct the double-strand break inducing agent to a different target site, to alter the location of the nick or cleavage site, to direct the inducing agent to a shorter target site, or to direct the inducing agent to a longer target site. In some examples a zinc finger DNA binding domain is fused to a site-specific recombinase, transposase, topoisomerase, or a derivative thereof that retains DNA nicking and/or cleaving activity.

It is possible to provide a zinc-finger nuclease via a polynucleotide that encodes the zinc-finger nuclease. This polynucleotide encoding the zinc-finger nuclease can be modified by substituting codons having a higher frequency of usage in a plant, as compared to the naturally occurring polynucleotide sequence or by substituting codons having a higher frequency of usage in a maize or soybean plant, as compared to the naturally occurring polynucleotide sequence.

Sufficient homology or sequence identity indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bp. The amount of homology can also described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) *Molecular Cloning: A Laboratory Manual*, (Cold Spring Harbor Laboratory Press, NY); *Current Protocols in Molecular Biology*, Ausubel et al., Eds (1994) Current Protocols, (Greene Publishing Associates, Inc. and John Wiley & Sons, Inc); and, Tijssen (1993) *Laboratory Techniques in Biochemistry and Molecular Biology—Hybridization with Nucleic Acid Probes*, (Elsevier, New York).

Any means can be used to bring together the various components needed to alter the genome of a dicot plant cell. For example, in in vitro systems, the double-strand-break-inducing agent and the polynucleotide(s) comprising the recognition site(s) can be provided by contacting the components under the appropriate conditions for DNA cleavage.

Alternatively a variety of methods are known for the introduction of nucleotide sequences and polypeptides into an organism, including, for example, transformation, sexual crossing, and the introduction of the polypeptide, DNA, or mRNA into the cell.

Methods for contacting, providing, and/or introducing a composition into various organisms are known and include but are not limited to, stable transformation methods, transient transformation methods, virus-mediated methods, and sexual breeding. Stable transformation indicates that the introduced polynucleotide integrates into the genome of the organism and is capable of being inherited by progeny thereof. Transient transformation indicates that the introduced composition is only temporarily expressed or present in the organism.

Protocols for introducing polynucleotides and polypeptides into plants may vary depending on the type of plant or plant cell targeted for transformation, such as monocot or dicot. Suitable methods of introducing polynucleotides and polypeptides into plant cells and subsequent insertion into the plant genome include microinjection (Crossway et al., (1986) *Biotechniques* 4:320-34 and U.S. Pat. No. 6,300,543), meristem transformation (U.S. Pat. No. 5,736,369), electroporation (Riggs et al., (1986) *Proc. Natl. Acad. Sci. USA* 83:5602-6, *Agrobacterium*-mediated transformation (U.S. Pat. Nos. 5,563,055 and 5,981,840), direct gene transfer (Paszkowski et al., (1984) *EMBO J* 3:2717-22), and ballistic particle acceleration (U.S. Pat. Nos. 4,945,050; 5,879,918; 5,886,244; 5,932,782; Tomes et al., (1995) "Direct DNA Transfer into Intact Plant Cells via Microprojectile Bombardment" in *Plant Cell, Tissue, and Organ Culture: Fundamental Methods*, ed. Gamborg & Phillips (Springer-Verlag, Berlin); McCabe et al., (1988) *Biotechnology* 6:923-6; Weissinger et al., (1988) *Ann Rev Genet* 22:421-77; Sanford et al., (1987) *Particulate Science and Technology* 5:27-37 (onion); Christou et al., (1988) *Plant Physiol* 87:671-4 (soybean); Finer and McMullen, (1991) *In Vitro Cell Dev Biol* 27P:175-82 (soybean); Singh et al., (1998) *Theor Appl Genet* 96:319-24 (soybean); Datta et al., (1990) *Biotechnology* 8:736-40 (rice); Klein et al., (1988) *Proc. Natl. Acad. Sci. USA* 85:4305-9 (maize); Klein et al., (1988) *Biotechnology* 6:559-63 (maize); U.S. Pat. Nos. 5,240,855; 5,322,783 and 5,324,646; Klein et al., (1988) *Plant Physiol* 91:440-4 (maize); Fromm et al., (1990) *Biotechnology* 8:833-9 (maize); Hooykaas-Van Slogteren et al., (1984) *Nature* 311:763-4; U.S. Pat. No. 5,736,369 (cereals); Bytebier et al., (1987) *Proc. Natl. Acad. Sci. USA* 84:5345-9 (Liliaceae); De Wet et al., (1985) in *The Experimental Manipulation of Ovule Tissues*, ed. Chapman et al., (Longman, N.Y.), pp. 197-209 (pollen); Kaeppler et al., (1990) *Plant Cell Rep* 9:415-8) and Kaeppler et al., (1992) *Theor Appl Genet* 84:560-6 (whisker-mediated transformation); D'Halluin et al., (1992) *Plant Cell* 4:1495-505 (electroporation); Li et al., (1993) *Plant Cell Rep* 12:250-5; Christou and Ford (1995) *Annals Botany* 75:407-13 (rice) and Osjoda et al., (1996) *Nat Biotechnol* 14:745-50 (maize via *Agrobacterium tumefaciens*).

Alternatively, polynucleotides may be introduced into plants by contacting plants with a virus or viral nucleic acids. Generally, such methods involve incorporating a polynucleotide within a viral DNA or RNA molecule. In some examples a polypeptide of interest may be initially synthesized as part of a viral polyprotein, which is later processed by proteolysis in vivo or in vitro to produce the desired recombinant protein. Methods for introducing polynucleotides into plants and expressing a protein encoded therein, involving viral DNA or RNA molecules, are known, see, for example, U.S. Pat. Nos. 5,889,191, 5,889,190, 5,866,785, 5,589,367 and 5,316,931. Transient transformation methods include, but are not limited to, the introduction of polypeptides, such as a double-strand break inducing agent, directly into the organism, the introduction of polynucleotides such as DNA and/or RNA polynucleotides, and the introduction of the RNA transcript, such as an mRNA encoding a double-strand break inducing agent, into the organism. Such methods include, for example, microinjection or particle bombardment. See, for example Crossway et al., (1986) *Mol Gen Genet* 202:179-85; Nomura et al., (1986) *Plant Sci* 44:53-8; Hepler et al., (1994) *Proc. Natl. Acad. Sci. USA* 91:2176-80; and, Hush et al., (1994) *J Cell Sci* 107:775-84.

Standard DNA isolation, purification, molecular cloning, vector construction, and verification/characterization methods are well established, see, for example Sambrook et al., (1989) *Molecular Cloning: A Laboratory Manual*, (Cold Spring Harbor Laboratory Press, NY). Vectors and constructs include circular plasmids, and linear polynucleotides, comprising a polynucleotide of interest and optionally other components including linkers, adapters, regulatory regions, introns, restriction sites, enhancers, insulators, selectable markers, nucleotide sequences of interest, promoters, and/or other sites that aid in vector construction or analysis. In some examples a recognition site and/or target site can be contained within an intron, coding sequence, 5' UTRs, 3' UTRs, and/or regulatory regions.

The present invention further provides expression constructs for expressing in a plant, plant cell, or plant part an endonuclease that is capable of binding to and creating a double strand break in a target site. The expression constructs of the invention comprise a promoter operably linked to a nucleotide sequence encoding an endonuclease of the present invention. The promoter is capable of driving expression of an operably linked nucleotide sequence in a plant cell. Any such promoter that is disclosed herein or known in the art can be used in the present invention. In one embodiment, the target site of the endonuclease is selected from the group consisting of TS21, TS14, TS30, TS5, TS7, TS4, TS22, and TS24 target sites of soybean, which have the nucleotide sequences set forth in SEQ ID NO:1, 2, 3, 4, 5, 6, 7, and 8, respectively. In another embodiment, the target site of the endonuclease is selected from the group consisting of MHP1, MHP14, MHP32, MHP42, MHP55, MHP67, MHP77, MHP98, MHP107, and MHP115 target sites of maize, which have the nucleotide sequences set forth in SEQ ID NO:68, 69, 70, 71, 72, 73, 74, 75, 76, and 77, respectively.

In certain embodiments, the expression constructs comprise a nucleotide sequence encoding the endonuclease that has been custom designed or engineered to cut at one the soybean target sites set forth above. Such nucleotide sequences include, for example, the nucleotide sequences set forth in SEQ ID NOS:9, 10, 11, 12, 13, 14, 15, and 16. Other nucleotide sequences of the invention include, but are not limited to, nucleotide sequences comprising a coding sequence of a DNA binding domain of an endonuclease, wherein the coding sequence is nucleotides 100-261 and nucleotides 850-1011 of SEQ ID NO:9, 10, 11, 12, 13, 14, 15 or 16 and degenerate coding sequences thereof. Such a degenerate coding sequence encodes the same amino acid sequence as that encoded by one of the coding sequences set forth in nucleotides 100-261 and nucleotides 850-1011 of SEQ ID NO:9, 10, 11, 12, 13, 14, 15 or 16 but differs in its nucleotide sequence due to the degeneracy of the genetic code.

In certain other embodiments, the expression constructs comprise a nucleotide sequence encoding the endonuclease that has been custom designed or engineered to cut at one the maize target sites set forth above. Such nucleotide sequences include, for example, the nucleotide sequences set forth in SEQ ID NOS: 78, 79, 80, 81, 82, and 83. Other nucleotide sequences of the invention include, but are not limited to, nucleotide sequences comprising a coding sequence of a DNA binding domain of an endonuclease, wherein the coding sequence comprises nucleotides 100-261 and nucleotides 850-1011 of SEQ ID NO: 80 and degenerate coding sequences thereof. Such a degenerate coding sequence encodes the same amino acid sequence as that encoded by one of the coding sequences set forth in nucleotides 100-261 and nucleotides 850-1011 of SEQ ID NO: 80 but differs in its nucleotide sequence due to the degeneracy of the genetic code. Other nucleotide sequences of the invention include, but are not limited to, nucleotide sequences comprising a coding sequence of a DNA binding domain of an endonuclease, wherein the coding sequence is nucleotides 100-261 and nucleotides 661-822 of SEQ ID NO: 78, 79, 81, 82 or 83 and degenerate coding sequences thereof. Such a degenerate coding sequence encodes the same amino acid sequence as that encoded by one of the coding sequences set forth in nucleotides 100-261 and nucleotides 661-822 of SEQ ID NO: 78, 79, 81, 82 or 83 but differs in its nucleotide sequence due to the degeneracy of the genetic code.

Any promoter can be used, and can be selected based on the desired outcome. A promoter is a region of DNA involved in recognition and binding of RNA polymerase and other proteins to initiate transcription. A plant promoter is a promoter capable of initiating transcription in a plant cell, for a review of plant promoters, see, Potenza et al., (2004) *In Vitro Cell Dev Biol* 40:1-22. Constitutive promoters include, for example, the core promoter of the Rsyn7 promoter and other constitutive promoters disclosed in WO99/43838 and U.S. Pat. No. 6,072,050; the core CaMV 35S promoter (Odell et al., (1985) *Nature* 313:810-2); rice actin (McElroy et al., (1990) *Plant Cell* 2:163-71); ubiquitin (Christensen et al., (1989) *Plant Mol Biol* 12:619-32; Christensen et al., (1992) *Plant Mol Biol* 18:675-89); pEMU (Last et al., (1991) *Theor Appl Genet* 81:581-8); MAS (Velten et al., (1984) *EMBO J* 3:2723-30); ALS promoter (U.S. Pat. No. 5,659,026), and the like. Other constitutive promoters are described in, for example, U.S. Pat. Nos. 5,608,149; 5,608,144; 5,604,121; 5,569,597; 5,466,785; 5,399,680; 5,268,463; 5,608,142 and 6,177,611. In some examples an inducible promoter may be used. Pathogen-inducible promoters induced following infection by a pathogen include, but are not limited to those regulating expression of PR proteins, SAR proteins, beta-1,3-glucanase, chitinase, etc.

Chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. Chemical-inducible promoters include, but are not limited to, the maize In2-2 promoter, activated by benzene sulfonamide herbicide safeners (De Veylder et al., (1997) *Plant Cell Physiol* 38:568-77), the maize GST promoter (GST-II-27, WO93/01294), activated by hydrophobic electrophilic compounds used as pre-emergent herbicides, and the tobacco PR-1a promoter (Ono et al., (2004) *Biosci Biotechnol Biochem* 68:803-7) activated by salicylic acid. Other chemical-regulated promoters include steroid-responsive promoters (see, for example, the glucocorticoid-inducible promoter (Schena et al., (1991) *Proc. Natl. Acad. Sci. USA* 88:10421-5; McNellis et al., (1998) *Plant J* 14:247-257); tetracycline-inducible and tetracycline-repressible promoters (Gatz et al., (1991) *Mol Gen Genet* 227:229-37; U.S. Pat. Nos. 5,814,618 and 5,789,156).

Tissue-preferred promoters can be utilized to target enhanced expression within a particular plant tissue. Tissue-preferred promoters include, for example, Kawamata et al., (1997) *Plant Cell Physiol* 38:792-803; Hansen et al., (1997) *Mol Gen Genet* 254:337-43; Russell et al., (1997) *Transgenic Res* 6:157-68; Rinehart et al., (1996) *Plant Physiol* 112:1331-41; Van Camp et al., (1996) *Plant Physiol* 112:525-35; Canevascini et al., (1996) *Plant Physiol* 112:513-524; Lam, (1994) *Results Probl Cell Differ* 20:181-96; and Guevara-Garcia et al., (1993) *Plant J* 4:495-505. Leaf-preferred promoters include, for example, Yamamoto et al., (1997) *Plant J* 12:255-65; Kwon et al., (1994) *Plant Physiol* 105:357-67; Yamamoto et al., (1994) *Plant Cell Physiol* 35:773-8; Gotor et al., (1993) *Plant J* 3:509-18; Orozco et al., (1993) *Plant Mol Biol* 23:1129-38; Matsuoka et al., (1993) *Proc. Natl. Acad. Sci. USA* 90:9586-90; Simpson et al., (1958) *EMBO J* 4:2723-9; Timko et al., (1988) *Nature* 318:57-8. Root-preferred promoters include, for example, Hire et al., (1992) *Plant Mol Biol* 20:207-18 (soybean root-specific glutamine synthase gene); Miao et al., (1991) *Plant Cell* 3:11-22 (cytosolic glutamine synthase (GS)); Keller and Baumgartner, (1991) *Plant Cell* 3:1051-61 (root-specific control element in the GRP 1.8 gene of French bean); Sanger et al., (1990) *Plant Mol Biol* 14:433-43 (root-specific promoter of *A. tumefaciens* mannopine synthase (MAS)); Bogusz et al., (1990) *Plant Cell* 2:633-41 (root-specific promoters isolated from *Parasponia andersonii* and *Trema tomentosa*); Leach and Aoyagi, (1991) *Plant Sci* 79:69-76 (*A. rhizogenes* roIC and roID root-inducing genes); Teeri et al., (1989) *EMBO J* 8:343-50 (*Agrobacterium* wound-induced TR1' and TR2' genes); VfENOD-GRP3 gene promoter (Kuster et al., (1995) *Plant Mol Biol* 29:759-72); and roIB promoter (Capana et al., (1994) *Plant Mol Biol* 25:681-91; phaseolin gene (Murai et al., (1983) *Science* 23:476-82; Sengopta-Gopalen et al., (1988) *Proc. Natl. Acad. Sci. USA* 82:3320-4). See also, U.S. Pat. Nos. 5,837,876; 5,750,386; 5,633,363; 5,459,252; 5,401,836; 5,110,732 and 5,023,179.

Seed-preferred promoters include both seed-specific promoters active during seed development, as well as seed-germinating promoters active during seed germination. See, Thompson et al., (1989) *BioEssays* 10:108. Seed-preferred promoters include, but are not limited to, Cim1 (cytokinin-induced message); cZ19B1 (maize 19 kDa zein); and milps (myo-inositol-1-phosphate synthase); (WO00/11177; and U.S. Pat. No. 6,225,529). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, and nuc1. See also, WO00/12733, where seed-preferred promoters from END1 and END2 genes are disclosed.

A phenotypic marker is screenable or selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichloro-phenoxyacetate (2,4-D). See for example, Yarranton, (1992) *Curr Opin Biotech* 3:506-11; Christopherson et al., (1992) *Proc. Natl. Acad. Sci. USA* 89:6314-8; Yao et al., (1992) *Cell* 71:63-72; Reznikoff, (1992) *Mol Microbiol* 6:2419-22; Hu et al., (1987) *Cell* 48:555-66; Brown et al., (1987) *Cell* 49:603-12; Figge et al., (1988) *Cell* 52:713-22; Deuschle et al., (1989) *Proc. Natl. Acad. Sci. USA* 86:5400-4; Fuerst et al., (1989) *Proc. Natl. Acad. Sci. USA* 86:2549-53; Deuschle et al., (1990) *Science* 248:480-3; Gossen, (1993) Ph.D. Thesis, University of Heidelberg; Reines et al., (1993) *Proc. Natl. Acad. Sci. USA* 90:1917-21; Labow et al., (1990) *Mol Cell Biol* 10:3343-56; Zambretti et al., (1992) *Proc. Natl. Acad. Sci. USA* 89:3952-6; Baim et al., (1991) *Proc. Natl. Acad. Sci. USA* 88:5072-6; Wyborski et al., (1991) *Nucleic Acids Res* 19:4647-53; Hillen and Wissman, (1989) *Topics Mol Struc Biol* 10:143-62; Degenkolb et al., (1991) *Antimicrob Agents Chemother* 35:1591-5; Kleinschnidt et al., (1988) *Biochemistry* 27:1094-104; Bonin, (1993) Ph.D. Thesis, University of Heidelberg; Gossen et al., (1992) *Proc. Natl. Acad. Sci. USA* 89:5547-51; Oliva et al., (1992) *Antimicrob Agents Chemother* 36:913-9; Hlavka et al., (1985) *Handbook of Experimental Pharmacology*, Vol. 78 (Springer-Verlag, Berlin); Gill et al., (1988) *Nature* 334:721-4.

The cells having the introduced sequence may be grown or regenerated into plants using conventional conditions, see for example, McCormick et al., (1986) *Plant Cell Rep* 5:81-4. These plants may then be grown, and either pollinated with the same transformed strain or with a different transformed or untransformed strain, and the resulting progeny having the desired characteristic and/or comprising the introduced polynucleotide or polypeptide identified. Two or more generations may be grown to ensure that the polynucleotide is stably maintained and inherited, and seeds harvested.

Any plant can be used, including moncot and dicot plants. Examples of monocot plants that can be used include, but are not limited to, corn (*Zea mays*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), wheat (*Triticum aestivum*), sugarcane (*Saccharum* spp.), oats (*Avena*), barley (*Hordeum*), switchgrass (*Panicum virgatum*), pineapple (*Ananas comosus*), banana (*Musa* spp.), palm, ornamentals, turfgrasses, and other grasses. Examples of dicot plants that can be used include, but are not limited to, soybean (*Glycine max*), canola (*Brassica napus* and *B. campestris*), alfalfa (*Medicago sativa*), tobacco (*Nicotiana tabacum*), Arabidopsis (*Arabidopsis thaliana*), sunflower (*Helianthus annuus*), cotton (*Gossypium arboreum*), and peanut (*Arachis hypogaea*), tomato (*Solanum lycopersicum*), potato (*Solanum tuberosum*) etc.

The transgenes, recombinant DNA molecules, DNA sequences of interest, and polynucleotides of interest can comprise one or more genes of interest. Such genes of interest can encode, for example, a protein that provides agronomic advantage to the plant. Genes of interest, including, but not limited to, those that encode proteins that provide agronomic advantage, can be reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); and the like.

Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene); glyphosate (e.g., the EPSPS gene and the GAT gene; see, for example, U.S. Publication No. 20040082770 and WO 03/092360); or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170:5837-5847) facilitate expression of polyhyroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

The transgenes, recombinant DNA molecules, DNA sequences of interest, and polynucleotides of interest can be comprise one or more DNA sequences for gene silencing. Methods for gene silencing involving the expression of DNA sequences in plant are known in the art include, but are not limited to, cosuppression, antisense suppression, double-stranded RNA (dsRNA) interference, hairpin RNA (hpRNA) interference, intron-containing hairpin RNA (ihpRNA) interference, transcriptional gene silencing, and micro RNA (miRNA) interference Cosuppression may be used to inhibit the expression of plant genes to produce plants having undetectable protein levels for the proteins encoded by these genes. See, for example, Broin et al. (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell et al. (1994) *Proc. Natl. Acad. Sci. USA* 91:3490-3496; Jorgensen et al. (1996) *Plant Mol. Biol.* 31:957-973; Johansen and Carrington (2001) *Plant Physiol.* 126:930-938; Broin et al. (2002) *Plant Cell* 14:1417-1432; Stoutjesdijk et al (2002) *Plant Physiol.* 129:1723-1731; Yu et al. (2003) *Phytochemistry* 63:753-763; and U.S. Pat. Nos. 5,034,323, 5,283,184, and 5,942,657; each of which is herein incorporated by reference. The efficiency of cosuppression may be increased by including a poly-dT region in the expression cassette at a position 3' to the sense sequence and 5' of the polyadenylation signal. See, U.S. Patent Publication No. 20020048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323; herein incorporated by reference.

Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550, or greater may be used. Methods for using antisense suppression to inhibit the expression of endogenous genes in plants are described, for example, in Liu et al (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, U.S. Patent Publication No. 20020048814, herein incorporated by reference.

Methods for using dsRNA interference to inhibit the expression of endogenous plant genes are described in Waterhouse et al. (1998) *Proc. Natl. Acad. Sci. USA* 95:13959-13964, Liu et al. (2002) *Plant Physiol.* 129:1732-1743, and WO 99/49029, WO 99/53050, WO 99/61631, and WO 00/49035; each of which is herein incorporated by reference.

Methods of hpRNA interference are described in Waterhouse and Helliwell (2003) *Nat. Rev. Genet.* 4:29-38 and the references cited therein. These methods are highly efficient at inhibiting the expression of endogenous genes. See, for example, Chuang and Meyerowitz (2000) *Proc. Natl. Acad. Sci. USA* 97:4985-4990; Stoutjesdijk et al. (2002) *Plant Physiol.* 129:1723-1731; and Waterhouse and Helliwell (2003) *Nat. Rev. Genet.* 4:29-38. Methods for using hpRNA interference to inhibit or silence the expression of genes are described, for example, in Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith et al. (2000) *Nature* 407:319-320. In fact, Smith et al. show 100% suppression of endogenous gene expression using ihpRNA-mediated interference. Methods for using ihpRNA interference to inhibit the expression of endogenous plant genes are described, for example, in Smith et al. (2000) *Nature* 407: 319-320; Wesley et al. (2001) *Plant J.* 27:581-590; Wang and Waterhouse (2001) *Curr. Opin. Plant Biol.* 5:146-150; Waterhouse and Helliwell (2003) *Nat. Rev. Genet.* 4:29-38; Helliwell and Waterhouse (2003) *Methods* 30:289-295, and U.S. Patent Publication No. 20030180945, each of which is herein incorporated by reference.

Transcriptional gene silencing (TGS) may be accomplished through use of hpRNA constructs wherein the inverted repeat of the hairpin shares sequence identity with the promoter region of a gene to be silenced. Processing of the hpRNA into short RNAs which can interact with the homologous promoter region may trigger degradation or methylation to result in silencing (Aufsatz et al. (2002) *PNAS* 99 (Suppl. 4):16499-16506; Mette et al. (2000) *EMBO J* 19(19):5194-5201).

The inhibition of the expression of a target protein may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier et al. (2003) *Nature* 425: 257-263, herein incorporated by reference. For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). miRNA molecules are highly efficient at inhibiting the expression of endogenous genes, and the RNA interference they induce is inherited by subsequent generations of plants.

The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events, the longer the region of homology, the greater the frequency. The length of the homology region needed to observe homologous recombination is also species-variable. In many cases, at least 5 kb of homology has been utilized, but homologous recombination has been observed with as little as 25-50 bp of homology. The minimum length of homology needed has been estimated at 20-50 bp in *E. coli* (Singer et al., (1982) *Cell* 31:25-33; Shen and Huang, (1986) *Genetics* 112:441-57; Watt et al., (1985) *Proc. Natl. Acad. Sci. USA* 82:4768-72), 63-89 bp in *Sacchromyces. cerevisaie* (Sugawara and Haber, (1992) *Mol Cell Biol* 12:563-75), and 163-300 bp in mammalian cells (Rubnitz and Subramani, (1984) *Mol Cell Biol* 4:2253-8; Ayares et al., (1986) *Proc. Natl. Acad. Sci. USA* 83:5199-203; Liskay et al., (1987) *Genetics* 115:161-7).

Homologous recombination has been demonstrated in insects. In *Drosophila*, Dray and Gloor found that as little as 3 kb of total template:target homology sufficed to copy a large non-homologous segment of DNA into the target with reasonable efficiency (Dray and Gloor, (1997) *Genetics* 147:689-99). Using FLP-mediated DNA integration at a target FRT in *Drosophila*, Golic et al., showed integration was approximately 10-fold more efficient when the donor and target shared 4.1 kb of homology as compared to 1.1 kb of homology (Golic et al., (1997) *Nucleic Acids Res* 25:3665). Data from *Drosophila* indicates that 2-4 kb of homology is sufficient for efficient targeting, but there is some evidence that much less homology may suffice, on the order of about 30 bp to about 100 bp (Nassif and Engels, (1993) *Proc. Natl. Acad. Sci. USA* 90:1262-6; Keeler and Gloor, (1997) *Mol Cell Biol* 17:627-34).

Homologous recombination has also been accomplished in other organisms. For example, at least 150-200 bp of homology was required for homologous recombination in the parasitic protozoan *Leishmania* (Papadopoulou and Dumas, (1997) *Nucleic Acids Res* 25:4278-86). In the filamentous fungus *Aspergillus nidulans*, gene replacement has been accomplished with as little as 50 bp flanking homology (Chaveroche et al., (2000) *Nucleic Acids Res* 28:e97). Targeted gene replacement has also been demonstrated in the ciliate *Tetrahymena thermophila* (Gaertig et al., (1994) *Nucleic Acids Res* 22:5391-8). In mammals, homologous recombination has been most successful in the mouse using pluripotent embryonic stem cell lines (ES) that can be grown in culture, transformed, selected and introduced into a mouse embryo. Embryos bearing inserted transgenic ES cells develop as genetically chimeric offspring. By interbreeding siblings, homozygous mice carrying the selected genes can be obtained. An overview of the process is provided in Watson et al., (1992) *Recombinant DNA*, 2nd Ed., (Scientific American Books distributed by WH Freeman & Co.); Capecchi, (1989) *Trends Genet* 5:70-6; and Bronson, (1994) *J Biol Chem* 269:27155-8. Homologous recombination in mammals other than mouse has been limited by the lack of stem cells capable of being transplanted to oocytes or developing embryos. However, McCreath et al., *Nature* 405:1066-9 (2000) reported successful homologous recombination in sheep by transformation and selection in primary embryo fibroblast cells.

Error-prone DNA repair mechanisms can produce mutations at double-strand break sites. The nonhomologous end-joining (NHEJ) pathways are the most common repair mechanism to bring the broken ends together (Bleuyard et al., (2006) *DNA Repair* 5:1-12). The structural integrity of chromosomes is typically preserved by the repair, but deletions, insertions, or other rearrangements are possible. The two ends of one double-strand break are the most prevalent substrates of NHEJ (Kirik et al., (2000) *EMBO J* 19:5562-6), however if two different double-strand breaks occur, the free ends from different breaks can be ligated and result in chromosomal deletions (Siebert and Puchta, (2002) *Plant Cell* 14:1121-31), or chromosomal translocations between different chromosomes (Pacher et al., (2007) *Genetics* 175: 21-9).

Episomal DNA molecules can also be ligated into the double-strand break, for example, integration of T-DNAs into chromosomal double-strand breaks (Chilton and Que, (2003) *Plant Physiol* 133:956-65; Salomon and Puchta, (1998) *EMBO J* 17:6086-95). Once the sequence around the double-strand breaks is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., (2004) *Plant Cell* 16:342-52). Ectopic and/or epigenic DNA sequences may also serve as a DNA repair template for homologous recombination (Puchta, (1999) *Genetics* 152: 1173-81).

Alteration of the genome of a plant cell, for example, through homologous recombination (HR), is a powerful tool for genetic engineering. Despite the low frequency of homologous recombination in higher plants, there are a few examples of successful homologous recombination of plant endogenous genes. The parameters for homologous recombination in plants have primarily been investigated by rescuing introduced truncated selectable marker genes. In these experiments, the homologous DNA fragments were typically between 0.3 kb to 2 kb. Observed frequencies for homologous recombination were on the order of $10^{-4}$ to $10^{-5}$. See, for example, Halfter et al., (1992) *Mol Gen Genet* 231:186-93; Offringa et al., (1990) *EMBO J* 9:3077-84; Offringa et al., (1993) *Proc. Natl. Acad. Sci. USA* 90:7346-50; Paszkowski et al., (1988) *EMBO J* 7:4021-6; Hourda and Paszkowski, (1994) *Mol Gen Genet* 243:106-11; and Risseeuw et al., (1995) *Plant J* 7:109-19.

An endogenous, non-selectable gene was targeted in *Arabidopsis* using a targeting vector containing a region of about 7 kb homologous to the target gene and the targeting frequency was estimated to be at least $3.9 \times 10^{-4}$ (Maio and Lam, (1995) *Plant J* 7:359-65). In another example, using a positive-negative selection scheme and a targeting vector containing up to 22.9 kb of sequence homologous to the target, homologous recombination was detected with a frequency less than $5.3 \times 10^{-5}$, despite the large flanking sequences available for recombination (Thykjr et al., (1997) *Plant Mol Biol* 35:523-30). In *Arabidopsis*, the AGL5 MADS-box gene was knocked out by homologous recombination using a targeting construct consisting of a kanamycin-resistance cassette inserted into the AGL5 sequence roughly 3 kb from the 5' end and 2 kb from the 3' end. Of the 750 kanamycin-resistant transgenic lines that were generated, one line contained the anticipated insertion (Kempin et al., (1997) *Nature* 389:802-3). Hanin et al., obtained homologous recombination events at a basal frequency of $7 \times 10^{-4}$ using 3 kb 5'-end and 2 kb 3'-end homology to the *Arabidopsis* PPO gene encoding protoporphyrinogen oxidase (Hanin et al., (2001) *Plant J* 28:671-7). Terada et al., targeted the Waxy locus in rice using an *Agrobacterium*-mediated transformation procedure. Negative selection, in the form of two copies of the diphteria toxin gene placed at both ends of T-DNA, was used to eliminate random integration of T-DNAs, allowing for enrichment of rare homologous recombination events in the selected material, and their transformation system generated thousands of events from just 150 rice seeds. The reported frequency of homologous recombination of the waxy gene in rice was $0.65\times10^{-3}$, without inclusion of elements to enhance homologous recombination (Terada et al., (2002) *Nat Biotech* 20:1030-4).

DNA double-strand breaks (DSBs) appear to be an effective factor to stimulate homologous recombination pathways in every organism tested to date (Puchta et al., (1995) *Plant Mol Biol* 28:281-92; Tzfira and White, (2005) *Trends Biotechnol* 23:567-9; Puchta, (2005) *J Exp Bot* 56:1-14). Using DNA-breaking agents, two- to nine-fold increase of homologous recombination was observed between artificially constructed homologous DNA repeats in plants (Puchta et al., (1995) *Plant Mol Biol* 28:281-92). In maize protoplasts, experiments with linear DNA molecules demonstrated enhanced homologous recombination between plasmids (Lyznik et al., (1991) *Mol Gen Genet* 230:209-18).

The effects of DSBs on homologous recombination have been investigated by using rare-cutting enzymes as well as transposons such as Ac and Mutator (Chiurazzi et al., (1996) *Plant Cell* 8:2057-66; Puchta et al., (1996) *Proc. Natl. Acad. Sci. USA* 93:5055-60; Xiao and Peterson, (2000) *Mol Gen Genet* 263:22-9; and Shalev and Levy (1997) *Genetics* 146:1143-51). Chiurazzi et al., (1996) *Plant Cell* 8:2057-66) introduced DSBs into an *Arabidopsis* chromosome using HO-endonuclease and observed 10-fold increase in the frequency of homologous recombination between repeats flanking the HO recognition site. Excision of Ac transposable elements also stimulated homologous recombination between repeats flanking the elements at an even higher frequency (Xiao and Peterson (2000) *Mol Gen Genet* 263: 22-9).

Puchta et al. reported that homologous recombination frequency at an artificial target locus was increased by up to two orders of magnitude when DSBs were generated using I-SceI (Puchta et al., (1996) *Proc. Natl. Acad. Sci. USA* 93:5055-60). In the experiment reported in Puchta et al., an I-SceI expression cassette was introduced into transgenic tobacco target lines together with targeting construct by co-inoculation with the two respective *Agrobacterium* strains. Homologous recombination between T-DNA containing the targeting construct and the target site reconstituted the kanamycin-resistance gene (nptII). There was an apparent correlation between frequency of homologous recombination and the amount of I-SceI expression cassette, suggesting that more DSBs yielded higher homologous recombination frequency.

High frequency of homologous recombination at a pre-introduced artificial target site was obtained using a zinc-finger nuclease (ZFN) in tobacco (Wright et al., (2005) *Plant J* 44:693-705). The zinc-finger nuclease expression cassette and donor DNA were introduced into protoplasts by co-electroporation and targeted modification was monitored by kanamycin resistance and GUS activity. One modified event was observed in approximately every 10 transformants, however, only 20% of the modified events contained the desired homologous recombination products as indicated by Southern blot analysis.

Zinc finger nucleases are engineered endonucleases with altered specificities, for example by fusion of an engineered DNA binding domain to an endonuclease, for example, FokI (Durai et al., (2005) *Nucleic Acids Res* 33:5978-90; Mani et al., (2005) *Biochem Biophys Res Comm* 335:447-57). Wright et al., and Lloyd et al., reported a high frequency mutagenesis at a DNA target site integrated into tobacco or *Arabidopsis* chromosomal DNA using zinc-finger nucleases (Wright et al., (2005) *Plant J* 44:693-705; Lloyd et al., (2005) *Proc. Natl. Acad. Sci. USA* 102:2232-7). Using a designed zinc-finger nuclease recognizing a tobacco endogenous acetolactate synthase (ALS) gene locus, a mutated ALS gene known to confer resistance to imidazolinone and sulphonylurea herbicides was introduced to replace the endogenous ALS gene at frequencies exceeding 2% of transformed cells (Townsend et al., (2009) *Nature* 459:442-5). The knock-out of an endogenous gene and the expression of a transgene can be achieved simultaneously by gene targeting. The IPK1 gene, which encodes inositol-1,3,4,5,6-pentakisphosphate 2-kinase needed in the final step of phytate biosynthesis in maize seeds, was targeted using a designed zinc-finger nuclease to insert via homologous recombination a PAT gene, which encodes phosphinothricin acetyl transferase tolerance to glufosinate ammonium herbicides such as bialaphos. The disruption of the IPK1 gene with the insertion of the PAT gene resulted in both herbicide tolerance and the expected alteration of the inositol phosphate profile in developing seeds (Shukla et al., (2009) *Nature* 459:437-41).

Members of the serine family of recombinases produce double-strand breaks at the recombination sites as a part of their catalytic activities (Grindley et al., (2006) *Ann Rev Biochem* 16:16). The R/RS system in sweet orange appeared to induce mutations of RS sites leading to chromosomal deletions not associated with site-specific recombination reactions per se (Ballester et al., (2006) *Plant Cell Rep* 26:39-45).

Another approach uses protein engineering of existing homing endonucleases to alter their target specificities. Homing endonucleases, such as I-SceI or I-CreI, bind to and cleave relatively long DNA recognition sequences (18 bp and 22 bp, respectively). These sequences are predicted to naturally occur infrequently in a genome, typically only 1 or 2 sites/genome. The cleavage specificity of a homing endonuclease can be changed by rational design of amino acid substitutions at the DNA binding domain and/or combinatorial assembly and selection of mutated monomers (see, for example, Arnould et al., (2006) *J Mol Biol* 355:443-58; Ashworth et al., (2006) *Nature* 441:656-9; Doyon et al., (2006) *J Am Chem Soc* 128:2477-84; Rosen et al., (2006) *Nucleic Acids Res* 34:4791-800; and Smith et al., (2006) *Nucleic Acids Res* 34:e149; Lyznik et al., (2009) U.S. Patent Application Publication No. 20090133152A1; Smith et al., (2007) U.S. Patent Application Publication No. 20070117128A1). Engineered meganucleases have been demonstrated that can cleave cognate mutant sites without broadening their specificity. An artificial recognition site specific to the wild type yeast I-SceI homing nuclease was introduced in maize genome and mutations of the recognition sequence were detected in 1% of analyzed F1 plants when a transgenic I-SceI was introduced by crossing and activated by gene excision (Yang et al., (2009) *Plant Mol Biol* 70:669-79). More practically, the maize liguleless locus was targeted using an engineered single-chain endonuclease designed based on the I-CreI meganuclease sequence. Mutations of the selected liguleless locus recognition sequence were detected in 3% of the T0 transgenic plants when the designed homing nuclease was introduced by *Agrobacterium*-mediated transformation of immature embryos (Gao et al., (2010) *Plant J* 61:176-87).

EXAMPLES

The present invention is further defined in the following Examples, in which parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Such modifications are also intended to fall within the scope of the appended claims.

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kb" means kilobase(s).

The DNA repair mechanisms of cells are the basis of transformation to introduce extraneous DNA or induce mutations on endogenous genes. DNA homologous recombination is a specialized way of DNA repair that the cells repair DNA damages using a homologous sequence. In plants, DNA homologous recombination happens at frequencies too low to be used in transformation until it has been found that the process can be stimulated by DNA double-strand breaks (Bibikova et al., (2001) *Mol. Cell. Biol.* 21:289-297; Puchta and Baltimore, (2003) *Science* 300:763; Wright et al., (2005) *Plant J.* 44:693-705).

Example 1

DNA Double-Strand-Break-Induced Alteration of an Endogenous Target Site

When a DNA double-strand-break-inducing agent recognizes and cleaves the specific recognition sequence at a target site in the genome, a DNA double-strand break is formed triggering the cell DNA repair mechanisms to mobilize to repair the damage that could be fatal to the cell. The process can be utilized in plant transformation to introduce mutations specifically at the target site to knock out the gene residing at the target site or to insert a donor DNA of interest at the target site. Once the DNA double-strand break is formed, depending on the designs of the DNA constructs involved and the actual processes of DNA repair, different outcomes can be obtained serving different transformation purposes.

For simple site-specific gene mutations, a target site containing a recognition sequence (FIG. 1A) and a DNA double-strand break agent such as a endonuclease (FIG. 1B) that recognizes specifically the recognition sequence have to be present in the same cell. After the endonuclease recognizes and cuts the DNA, the two free ends can be repaired through end joining by the cell DNA repair machinery without the intervention of any external factors. The two ends can be repaired to its original state so no change can be detected or they can be altered before being repaired resulting detectable changes after they are connected again such as the deletion of one or more nucleotides of the recognition sequence and possibly extra surrounding sequences (FIG. 1F). Mutations are introduced at the target site by the latter process.

To achieve site-specific DNA insertions, a donor DNA containing the DNA of interest has to be simultaneously present in the cell in addition to the target site and the endonuclease. The donor DNA can contain the same DNA sequences that flank the target site to flank the gene of interest, i.e., the homologous sequences (FIG. 1C). The DNA of interest can be inserted at the target site by homologous recombination (FIG. 1E), a process that is stimulated by the DNA double-strand break at the target site. The donor DNA can also contain only the DNA of interest without any flanking homologous sequences (FIG. 1D). The DNA of interest can still be inserted at the target site though in a less predictable fashion through non-homologous recombination. Similarly, any unrelated DNA that happens to be present when the DNA ends are repaired can be inserted at the target site (FIG. 1G). The different outcomes (FIGS. 1E-G) can be obtained simultaneously in the same transformation experiment.

Any means to make a DNA double-strand break in vivo can be used as the DNA double-strand-break-inducing agent such as the most commonly used meganucleases which recognize >18 bp sequences, which are long enough to be unique in most genomes. Even numerous meganucleases have been found and characterized to recognize many different sequences, but such sequences are often not naturally present in important crops such as soybean or maize and even if similar sequences can be found in crop genomes, the limited numbers of these sequences are still too small to be useful. Certain meganucleases such as I-CreI can be modified by protein engineering in such a way that it will no longer preferentially recognize the recognition sequence of wild type I-CreI and instead will preferentially recognize specifically selected sequences of interest. Taking advantage of the flexibility of the I-CreI endonuclease, one can design and make a modified I-CreI to cleave a target site of our choice in the genome and subsequently introduce mutations or insert genes of interest at the selected target site. The precise genetic engineering that this methodology provides will solve many problems that traditional plant transformation methods such as *Agrobacterium* infection and biolistic bombardment currently face, such as unpredictable integration, unwanted endogenous gene interruption, unpredicted transgene expression, etc.

In one embodiment of the invention, we used engineered I-CreI-like meganucleases that recognize selected different endogenous target sites in the soybean genome and produced mutations and insertions at the selected target sites.

Example 2

Production of a Complex Trait Locus in the Soybean Genome Near a Transgenic Event for Oil Quality Using Engineered Meganucleases Soybean lines comprising an endogenous target recognition sequence in their genome were contacted with a custom designed meganuclease, derived from I CreI, which is designed to specifically recognize and create a double-strand break in the endogenous target sequence. Soybean embryos comprising an endogenous target site were contacted with the components described below, events selected and characterized.

A. TS21, TS14, TS30 and TS5 Target Sites

Sequence analyses were done for about 500000 bp genomic region in soybean near a transgenic event of interest (event DP-305423-1, U.S. Patent Application Publication No. 2008/0312082 A1, published Dec. 18, 2008). A series of soybean genomic endogenous target recognition sequences, referred to as TS21, TS14, TS30 and TS5, were selected for design of custom double-strand break inducing agents derived from I-CreI meganuclease. Each of these target recognition sequences is a unique 22 bp polynucleotide. The target recognition sites have the following sequences:

```
TS21 target
                                   (SEQ ID NO: 1)
GGCACTCTCGTGT▼GTGATTAAA TS14 target
                                   (SEQ ID NO: 2)
CAGACGTACGCAA▼GTAGCTTTG TS30 target
                                   (SEQ ID NO: 3)
GAGTCCCACGCAA▼GAGCATAAA TS5 target
                                   (SEQ ID NO: 4)
AAGACTTACGTGT▼GTACTCGTG
```

The double-strand break sites and overhang regions are shown in bold, the enzyme cuts after C13, as indicated by the solid triangle.

Within the soybean genome, TS5 is about 600 kbp upstream of, and on the same chromosome as, the transgenic event of interest. TS30, TS21 and TS14 are on the same chromosome as TS5 and are 120 kbp, 125 kbp and 500 kbp downstream of the transgenic event of interest (FIG. 2).

B. TS21, TS14, TS30, and TS5 Meganucleases

The I-CreI meganuclease was modified to produce the TS21, TS14, TS30 and TS5 meganucleases, which are designed to recognize their corresponding target sequences, under a contract with Precision Biosciences (Durham, N.C. USA). Wild-type I-CreI meganuclease is a homodimer. In order to recognize their target sequences, different substitutions were made to each monomer. The coding sequences for each monomer were joined by a linker sequence to produce single-chain fusion polypeptides. Genes encoding the designed meganucleases were optimized for expression in plants. SEQ ID NO: 9 is the plant-optimized nucleotide sequence of the TS21 meganuclease. SEQ ID NO: 10 is the plant-optimized nucleotide sequence of the TS14 meganuclease. SEQ ID NO: 11 is the plant-optimized nucleotide sequence of the TS30 meganuclease. SEQ ID NO: 12 is the plant-optimized nucleotide sequence of the TS5 meganuclease. These genes include a nucleus localization signal from the SV40 virus (SEQ ID NO: 34) and an intron from the potato ST-LS1 gene. The intron prevents expression of the genes in bacteria during the cloning process, but is not necessary for expression in plant cells. In these plant-optimized nucleotide sequences (SEQ ID NOs: 9-16) nucleotides 1-30 encode an SV40 nucleus localization amino acid sequence, nucleotides 100-261 and nucleotides 850-1011 encode the 1st half and 2nd half target site binding amino acid sequences, respectively, nucleotides 403-591 are the potato ST-LS1 intron, and nucleotides 685-798 encode the amino acid sequence of the polypeptide that links the two re-engineered I-CreI monomers into a single chain.

Plant optimized nucleotide sequences without the ST-LS1 intron encoding the engineered meganucleases were constructed as well (see, SEQ ID NO: 33 for example).

C. Vector Construction for Plant Expression Vectors of the Meganuclease Genes and Repair DNAs for Transgene Integration by Homologous Recombination Vectors comprising expression cassettes for the appropriate meganuclease were constructed using standard molecular biological techniques. All custom designed meganucleases were tested including TS21, TS14, TS30 and TS5. For each of the meganucleases, a plant expression vector comprising a polynucleotide encoding one of the meganuclease genes was operably linked to a soybean constitutive promoter.

The following meganuclease plant expression vectors were made:

RTW317 (SEQ ID NO: 35, GM-EF1A pro::TS21::pinII) expression cassette contains the TS21 meganuclease plant optimized sequence without an intron and driven by soybean EF1A promoter.

RTW322 (SEQ ID NO: 36, GM-EF1A pro::TS21 with ST-LS1 intron2::pinII) expression cassette contains the TS21 meganuclease plant optimized sequence with an intron and driven by soybean EF1A promoter. Other expression cassettes were made in a similar manner as RT317 and RTW322, but contained a different promoter, or meganuclease, such as: RTW319 (GM-EF1A pro::TS14::pinII), RTW324 (GM-EF1A pro::TS14 with ST-LS1 intron2:: pinII), RTW323 (GM-EF1A pro::TS5 with ST-LS1 intron2:: pinII), RTW325 (GM-EF1A pro::TS30 with ST-LS1 intron2::pinII), RTW345 (GM-UBQ pro::TS21::pinII), RTW334 (GM-UBQ pro::TS21 with ST-LS1 intron2::pinII), RTW351 (GM-MTH1 pro::TS21::pinII), RTW339 (GM-MTH1 pro::TS21 with ST-LS1 intron2::pinII), wherein GM-ETF1A is the soybean ETF1A promoter, GM-UBQ is the soybean ubiquitin promoter, GM-MTH1 is the soybean MTH1 promoter, and pinII is the pinII terminator.

To achieve site-specific DNA insertions, a repair DNA (donor DNA) containing the gene of interest has to be simultaneously present in the cell in addition to the target site and the endonuclease. The gene of interest was flanked by two homologous recombination fragments (HR1 and HR2), which were 1 to 3 kb long genomic DNA sequences flanking the meganuclease target sites. The gene of interest can be inserted at the target site by DNA homologous recombination, a process that is stimulated by the DNA double-strand break at the target site.

A repair DNA (or donor DNA) fragment, Rep-RTW328A (SEQ ID NO: 37) was made for gene integration at TS21 target site in the soybean genome. The RTW328 repair DNA consists of a 1020 bp TS21 HR1 fragment (SEQ ID NO:17), a hygromycin selection marker cassette and a 1000 bp TS21 HR2 fragment (SEQ ID NO:18). The hygromycin selection marker was driven by a SCP1 promoter and a NOS terminator (U.S. Pat. No. 6,072,050; Suzuki et al., Gene (2000) 242(1-2):331-336). Similar repair DNA vectors were made for TS14, TS30, and TS5 target sites in soybean genome. The Rep-TS14 repair DNA vector consists of a 1000 bp TS14 HR1 fragment (SEQ ID NO:19, the same hygromycin selection marker cassette and a 928 bp TS14 HR2 fragment (SEQ ID NO:20). The Rep-TS30 repair DNA vector (consists of a 1000 bp TS0 HR1 fragment (SEQ ID NO:21), the same hygromycin selection marker cassette and a 1009 bp TS30 HR2 fragment (SEQ ID NO:22). The Rep-TS5 repair DNA vector consists of a 1006 bp TS5 HR1 fragment (SEQ ID NO:23), the same hygromycin selection marker cassette and a 1007 bp TS5 HR2 fragment (SEQ ID NO:24).

A DNA double-strand break agent was simultaneously introduced with the repair DNA to facilitate homologous DNA recombination. It is convenient to transiently express the custom designed meganuclease by co-bombardment of a meganuclease expression vector with its corresponding repair DNA in soybean transformation. The presence or absence of an ST-LS1 intron in the DNA nucleotide sequence encoding a meganuclease did not affect the functionality of the meganuclease. Alterations at the target site were observed when expression of the meganuclease with both a DNA sequence that included or excluded the ST-LS1 intron in the expression cassette.

D. Genomic Sequence Modifications and Transgene Integration at Endogenous Target Sites with Custom Designed Meganucleases PCR and qPCR assays were done following established protocols using gene-specific primers and probes (Li et al., (2007) *Plant Mol Biol* 65:329-41; Li et al., (2009) *Plant Physiol* 151:1087-95). qPCR assays specific to the TS21, TS14, TS30, and TS5 target sequences were developed to identify sequence changes that happen in the region. The primers and probe were designed as below and tested.

TS21 qPCR:
Mega21-190F (SEQ ID NO:38)
Mega21-301R (SEQ ID NO:39)
Mega21-250T (SEQ ID NO:40)
TS14 qPCR:
Mega14-13F (SEQ ID NO:41)
Mega14-128R (SEQ ID NO:42)
Mega14-85T (SEQ ID NO:43)
TS30 qPCR:
Mega30-30F (SEQ ID NO:44)
Mega21-87R (SEQ ID NO:45)
Mega21-52T (SEQ ID NO:46)
TS5 qPCR:
Mega5-F1 (SEQ ID NO:47)
Mega5-R1 (SEQ ID NO:48)
Mega5-T1 (SEQ ID NO:49)

All hygromycin resistant soybean transgenic events were first analyzed by qPCR assays of the meganuclease target site. Changes in the meganuclease target sequence caused by DNA cleavage and repair result in the copy number reduction of the meganuclease target site from two copies in wild type soybean genome to either one or zero copies in the transgenic events. These "qPCR hit" events with reduced target site copy numbers were chosen for further genomic PCR and sequencing analyses. From qPCR analyses of the TS21, TS14, TS30 and TS5 target sites, it was shown that the copy numbers of the target sites in most of the positive transgenic events were reduced by half, indicating one allele of the target sites in soybean genome was disrupted by meganuclease cutting/DNA repair mechanism.

Two groups of genomic PCR amplifications were carried out to further characterize these candidate events from qPCR assay to understand the genomic sequence modifications and transgene integrations. The first group of genomic PCRs were designed to identify mutations in the meganuclease target sites, by amplifying genomic fragments containing the TS21 target site using a primer that anneals in HR1 and another primer that anneals in HR2. For example, for TS21, the primer set WOL133 and WOL134 (SEQ ID NO:50 and 51) were used to amplify genomic fragments containing the TS21 target site (FIG. 3A). The PCR products were cloned and sequenced to identify mutations at the TS21 target site. In some cases, a meganuclease in vitro cutting assay to cut the PCR product of an unmodified target site was used to test if the target site had been modified. In the in vitro cutting assay, the PCR products amplified using primers directed to the target site were digested with the meganuclease at 37° C. overnight. Samples with meganuclease enzyme were treated with proteinase K and SDS to denature the protein. The digestion products were separated on a 1.5 to 2% agarose gel. Undigested products indicate that the target site was modified. The undigested PCR products were then cloned and sequenced to verify the genome sequence modification. An example of the soybean genome sequence modification on TS21 target site is shown in FIG. 3B.

With this approach, soybean genome sequence modifications were detected at TS5, TS14 and TS30 target sites (FIG. 4 and Table 1).

TABLE 1 qPCR copy number analyses of TS30 target sites, pinII (representing the meganuclease cassette) and Hygro (representing the repair DNA cassette)

| Clone ID | TS30 qPCR Copy# | pinII qPCR copy# | Hygro qPCR copy# |
|---|---|---|---|
| A 7052.2.5 | 0.56 | 0.00 | 1.98 |
| A 7052.10.26 | 0.55 | 0.00 | 1.55 |
| A 7052.10.28 | 0.54 | 0.00 | 1.96 |
| A 7034.1.11 | 0.53 | 0.00 | 2.98 |
| A 7034.3.1 | 0.54 | 1.70 | 3.41 |
| A 7034.3.15 | 0.52 | 0.96 | 4.54 |
| WT control | 0.96 | 2.23 | 5.19 |

The copy numbers of the TS30 target sites in positive transgenic events were reduced by half, indicating one allele of the target sites in soybean genome was disrupted by meganuclease cutting/DNA repair mechanism. These results demonstrate that introduction of the meganuclease gene into the plant cell leads to modifications in the genomic region of interest.

Both wild type soybean and transgenic embryos have been used in the soybean transformation. The target modification rate (qPCR) with TS21 is the same in wild type soybean and the transgenic event. These results demonstrated that we can directly introduce genome modifications in the transgenic event or introduce genome modifications to the same locus in wild type soybean.

The second group of genomic PCR amplifications was more focused on transgene integration with border specific PCR. For example, for TS21 (FIG. 3A), the primer set WOL190 (SEQ ID NO:52) and WOL242 (SEQ ID NO:53) were designed and used to amplify the left border DNA fragment that results from transgene integration. WOL190 is a sequence specific primer located in soybean genome 5' beyond the TS21 HR1 region and WOL242 is a sequence specific primer to the 5' hygromycin-resistance marker gene coding sequence in the reverse orientation. An 1860 bp PCR product can only be obtained when the RTW328A repair DNA is integrated by homologous recombination facilitated by a double-strand break introduced at the genomic target site by TS21 meganuclease. Another set of primers, WOL153 (SEQ ID NO:54) and WOL247 (SEQ ID NO: 55), was also designed and used to amplify the right border DNA fragment that results from transgene integration. WOL153 is the sense primer from the NOS terminator and the WOL247 is a sequence specific primer located in soybean genome 3' beyond the TS21 HR2 region. A 1727 bp PCR product can only be obtained when the RTW328A repair DNA is integrated by homologous recombination facilitated by a double-strand break introduced at the genomic target site by TS21 meganuclease. Similar genomic PCR primers have been designed and tested for other custom designed meganuclease.

TS21 qPCR
Target site primers
WOL133 (SEQ ID NO:50)
WOL134 (SEQ ID NO:51)
Left border primers
WOL190 (SEQ ID NO:52)
WOL242 (SEQ ID NO:53)

Right border primers
    WOL153 (SEQ ID NO:54)
    WOL247 (SEQ ID NO:55)
TS14 qPCR
Target site primers
    WOL121 (SEQ ID NO:56)
    WOL150 (SEQ ID NO:57)
Left border primers
    WOL192 (SEQ ID NO:58)
    WOL242 (SEQ ID NO:53)
Right border primers
    WOL153 (SEQ ID NO:54)
    WOL193 (SEQ ID NO:59)
TS30 qPCR
Target site primers
    WOL113 (SEQ ID NO:60)
    WOL114 (SEQ ID NO:61)
Left border primers
    WOL194 (SEQ ID NO:62)
    WOL242 (SEQ ID NO:53)
Right border primers
    WOL153 (SEQ ID NO:54)
    WOL195 (SEQ ID NO:63)
TS5 qPCR
Target site primers
    WOL105 (SEQ ID NO:64)
    WOL144 (SEQ ID NO:65)
Left border primers
    WOL196 (SEQ ID NO:66)
    WOL242 (SEQ ID NO:53)
Right border primers
    WOL153 (SEQ ID NO:54)
    WOL197 (SEQ ID NO:67)

Primer pairs were designed with one primer capable of annealing to either the 5' or 3' sequence flanking a target site and another primer capable of annealing to a sequence within the potential insert (i.e., the transgene). For the TS14 target site, 18 qPCR positive events were identified from total 68 events by qPCR analyses. Out of the 18 qPCR positive events, three events were confirmed to be perfect TS14 meganuclease mediated transgene integration events by homologous recombination.

Figure 5:
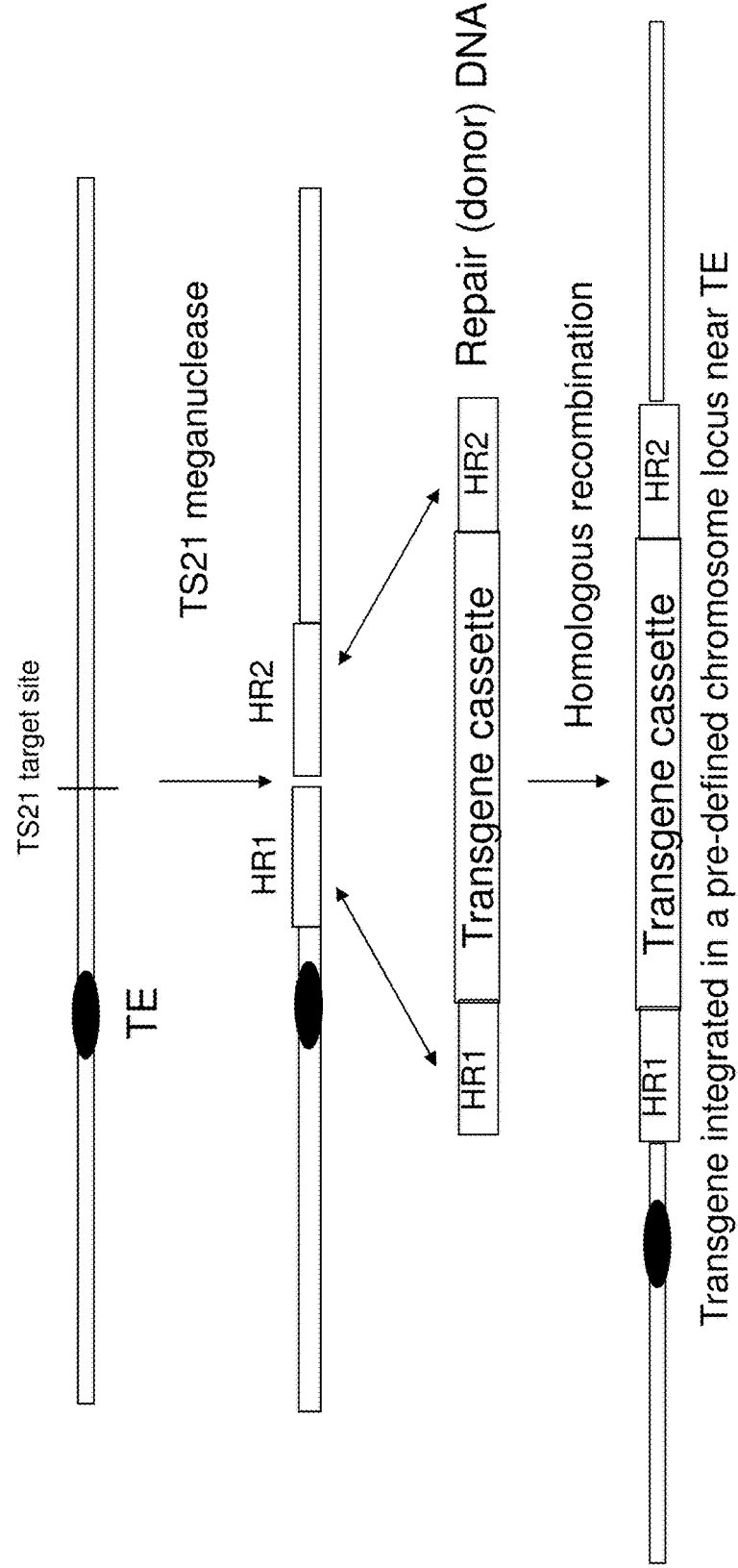

These results demonstrate that soybean cells possess natural DNA repair machinery that can repair DNA double-strand break ends by simple end joining or by homologous recombination. It is thus expected that similar rates of site-directed mutagenesis and gene insertion via homologous recombination can be achieved at any target sites in the soybean genome using proper double-strand break inducing agents specific to the target recognition sequences. Using a simple PCR screening procedure described herein, it is practical to identify such insertion and mutation events. A perfect transgene integration event can be identified when both left border PCR and right border PCR indicate insertion at the target site. Transgene integration at the pre-defined target sites within a genomic region of interest provides a novel gene stacking technology. FIG. 5 is a schematic example of stacking new trait genes into a single target site in close proximity to a transgenic event of interest.

Example 3

Production of a Complex Trait Locus in the Soybean Genome Near a Herbicide Resistance Transgenic Event Using Engineered Meganucleases A. TS7, TS4, TS22 and TS24 Target Sites The transgene border analyses of a herbicide resistance transgenic event (Event 3560.4.3.5 described in U.S. Patent Application Publication Nos. 2010/0184079, 2009/0036308, and 2008/0051288) showed that the transgene was inserted in a soybean chromosome about 12 cM away from three disease resistance markers based on molecular marker analyses (FIG. 6). Sequence analyses were done for about 400000 bp in this genomic region of interest and four meganuclease target sites (TS7, TS4, TS22 and TS24) were identified with desirable genetic distances between these target sites and nearby disease resistance markers, and a herbicide resistance transgenic event. Each of these target recognition sequences is a unique 22 bp polynucleotide. The target recognition sites have the following sequences:

```
TS7 target
                                        (SEQ ID NO: 5)
GACATTGTCGTGA▼GAAAAGAGA TS4 target
                                        (SEQ ID NO: 6)
AAATCTGTCTTGC▼GAAACGGCA TS22 target
                                        (SEQ ID NO: 7)
TATTCTCTCATAA▼ATAAACTTT TS24 target
                                        (SEQ ID NO: 8)
GGAATGGACATAA▼GAGAACTGT
```

The double-strand break sites and overhang regions are shown in bold, the enzyme cuts after C13, as indicated by the solid triangle.

B. TS7, TS4, TS22 and TS24 Meganucleases

The I-CreI meganuclease was modified to produce the TS7, TS4, TS22 and TS24 meganucleases, which are designed to recognize their corresponding target sequences, under a contract with Precision Biosciences (Durham, N.C. USA). Wild-type I-CreI meganuclease is a homodimer. In order to recognize their target sequences, different substitutions were made to each monomer. The coding sequences for each monomer were joined by a linker sequence to produce single-chain fusion polypeptides All these target sites are about 1 to 10 cM away from the cluster of the three disease resistance markers.

The plant optimized nucleotide sequence encoding the TS7 meganuclease (SEQ ID NO: 13), TS4 meganuclease (SEQ ID NO:14), TS22 meganuclease (SEQ ID NO:15) and TS24 meganuclease (SEQ ID NO:16) includes a DNA fragment (from by 1-30) encoding an SV40 nuclear localization signal (MAPKKKRKVH; SEQ ID NO: 34) as well as a ST-LS1 intron (from by 403 to by 591 of SEQ ID 13-16) in order to eliminate expression in *E. coli* and *Agrobacterium*. Nucleotides 685-798 of SEQ ID NOs:13-16 encode the amino acid sequence of the polypeptide that links the two engineered I-CreI monomers into a single chain. Nucleotides 100-261 of SEQ ID NOs:13-16 and nucleotides 850-1011 of SEQ ID NOs:13-16 encode the first half and the second half target site binding amino acid sequences, respectively.

C. Vector Construction for Plant Expression Vectors of the Meganuclease Genes and Repair DNAs for Transgene Integration by Homologous Recombination Vectors comprising expression cassettes for the appropriate meganuclease were constructed using standard molecular biological techniques. All custom designed meganucleases were tested including TS7, TS4, TS22 and TS24. For each of the meganucleases, a plant expression vector comprising a polynucleotide encoding one of the meganuclease genes was operably linked to a soybean constitutive promoter.

To achieve site-specific DNA insertions, a repair DNA (donor DNA) containing the DNA of interest has to be simultaneously present in the cell in addition to the target site and the endonuclease. The DNA of interest was flanked by two homologous recombination fragments (HR1 and HR2), which were 1 to 3 kb long genomic DNA sequences flanking the meganuclease target sites. The DNA of interest can be inserted at the target site by DNA homologous recombination, a process that is stimulated by the DNA double-strand break at the target site.

The HR1 and HR2 domains for TS7, TS4, TS22 and TS24 are SEQ ID NOs: 25 and 26, SEQ ID NOs: 27 and 28, SEQ ID NOs: 29 and 30 and SEQ ID NOs: 31 and 32, respectively.

Repair DNA vectors were made as described in Example 2C.

A DNA double-strand break agent was simultaneously introduced with the repair DNA to facilitate homologous DNA recombination. It is convenient to transiently express the custom designed meganuclease by co-bombardment of a meganuclease expression vector with its corresponding repair DNA in soybean transformation.

Example 4

Cluster of Meganuclease Target Sites in a Short Region of the Soybean Genome for Stacking of Multiple Trait Genes As shown in FIG. 7, a series of meganuclease target sites can be identified with desirable genetic distances between these target sites. Custom designed meganucleases can be used to target a series of trait genes into this defined genome locus either by sequential transformation or by genetic crosses with individual trait genes. Using this method depicted in FIG. 7, multiple traits can be stacked in a genomic region of interest that comprises, for example, a transgene or native gene of interest, and other transgenic traits or native trait loci such as disease resistance markers.

Example 5

Production of a Complex Trait Locus at a Maize Endogenous Locus by Engineered Meganucleases A. MHP Target Sites A genomic region encompassing about 1.8 million nucleotides and representing a genetic region of approximately 4.3 centimorgans (cM) on a maize chromosome was chosen as a target region for generation of a complex trait locus. The genomic region was scanned for 22-mer sequences that could serve as target sites containing recognition sequences for double-strand-break inducing meganucleases and be useful for insertion of additional transgenes in order to create a complex trait locus. A series of 35 putative target sites (SEQ ID NOs: 68-77) were selected in a 2 cM region (FIG. 8) in close proximity of the transgene insertion site for design of custom double-strand break inducing agents derived from I-CreI meganuclease. FIG. 8 show the genetic and physical location of the MHP target sites relative to each other and the transgene of interest.

B. MHP Meganucleases

The I-CreI meganuclease was modified to produce endonucleases, which were designed to recognize their corresponding target sequences, (SEQ ID NOs: 68-77). The design of custom made meganucleases has been described in United States Patent Application Publication No. US 2007/0117128 A1.

Genes encoding the designed meganucleases were optimized for expression in plants. The engineered endonuclease expression cassettes contained the maize codon-optimized nucleotide sequences for better performance in maize cells. The endonuclease gene sequences were also supplemented with DNA sequences encoding a SV40 nuclear localization signal (SEQ ID NO: 34). The maize ubiquitin promoter and the potato proteinase inhibitor II gene terminator sequences completed the endonuclease gene designs. The MHP55 (SEQ ID NO:80) expression cassette was additionally modified by addition of the ST-LS1 intron to the coding sequence of the first monomer in order to eliminate its expression in E. coli and Agrobacterium. SEQ ID NO:82 is the plant-optimized nucleotide sequence of MHP55-2 containing a nuclear localization signal and without an intron. SEQ ID NO: 78 is the plant-optimized nucleotide sequence of the MHP14 meganuclease. A custom designed meganuclease, referred to as MHP14+ was made as well. SEQ ID NO: 79 is the plant-optimized nucleotide sequence of the MHP14+ meganuclease. SEQ ID NO: 83 is the plant-optimized nucleotide sequence of the MHP77 meganuclease C. Vector Construction for Plant Expression Vectors of the Meganuclease Genes and Repair (donor) DNAs for Transgene Integration by Homologous Recombination Vectors comprising expression cassettes for the appropriate meganuclease were constructed using standard molecular biological techniques. For each of the meganucleases, a plant expression vector comprising a polynucleotide encoding one of the meganuclease genes was operably linked to a maize constitutive promoter.

To achieve site-specific DNA insertions, a repair DNA (donor DNA) containing the gene of interest has to be simultaneously present in the cell in addition to the target site and the meganuclease. A vector (PHP44285, SEQ ID NO:104), or PHP44779, SEQ ID NO:105) containing a polynucleotide encoding the engineered meganuclease MHP14, or the optimized meganuclease MHP14+, and a donor DNA was constructed using standard molecular biology techniques. The donor DNA contained an herbicide resistance gene used as the selection marker for transformation. The herbicide resistance gene MoPAT encodes a phosphinothricin acetyltransferase, and was flanked by two homologous recombination fragments, HR1 (SEQ ID NO: 84) and HR2 (SEQ ID NO: 85), which were about 1 kb long genomic DNA sequences flanking the meganuclease target sites. Each vector PHP44285 or PHP44779 contained the meganuclease cassette, the donor DNA and the homology sequences HR1 and HR2.

Maize immature embryos 9-12 DAP (days after pollination, approximately 1.5-2.0 mm in size) from a maize transformable line were used for gene transformation by bombardment (Example 6). The immature embryos were placed on 560Y medium for 4 hours at 26° C. or alternatively, immature embryos were incubated at temperatures ranging from 26° C. to 37° C. for 8 to 24 hours prior to placing on 560Y preceding bombardment (as described in Example 6). Developmental genes ODP2 (AP2 domain transcription factor ODP2 (Ovule development protein 2); US20090328252 A1) and Wushel were included in the experiments through co-bombardment (Example 7). Maize immature embryos were transformed with the vectors PHP44285 or PHP44779.

D. Genomic Sequence Modifications and Transgene Integration at Endogenous Target Sites with Custom Designed Meganuclease Successful delivery of the MHP14 donor vector (PHP44285 or PHP44779) conferred bialaphos herbicide resistance, and was used to identify putative events by callus selection on herbicide containing media. Callus tissues and/or plants regenerated from stable transformants using standard culture and regeneration conditions were screened for modification of the endogenous MHP14 target site.

Real time PCR (qPCR) was used to determine the target site copy number. Two copies of the target site indicate that both alleles are wild type and that no modification occurred at the target site. One copy means one allele of the target site has changed during repair of the double strand break generated by the MHP14 or MHP14+, while absence of the target site (null) is the result of both alleles modified. The copy number can also be in between 1 and 2 due to chimeric nature of callus samples. The probe sequence for qPCR of MHP14 target site was CAGATTCACGTCAGATTT (SEQ ID NO: 106), the MHPTS14_forward primer was AGCGACATAGTGGTGTATAAAAGGAA (SEQ ID NO: 107) and MHPTS14_reverse primer was TGGATTGTAATATGTGTACCTCATGCT (SEQ ID NO: 108). The amplicon was approximately 100 bp.

To examine whether increased temperature would increase the rate of target site modification, maize embryos were incubated at different temperatures following bombardment with several meganucleases. Table 2 shows the effect of temperature on the meganuclease activity of MHP14 as determined by target site modification. Table 2 indicates that increased temperature results in increased target site mutation rate.

TABLE 2

Effect of incubating maize embryos at increased temperature post-bombardment on target site mutation rate of meganucleases

| Meganuclease | Temperature (° C.) | Target Site Mutation Rate |
|---|---|---|
| MHP14 | 28 | 14% |
| MHP14 | 32 | 46% |

Following bombardment, embryos were incubated on 560P (maintenance medium) for 12 to 48 hours at 28° C. or 32° C. and then placed at 28° C. Herbicide-resistant events were screened for modification at the target site by measuring target site copy-number using qPCR. Target site mutation rate indirectly measures the meganuclease activity. TSMutRate (target site mutation rate) indicated the modification rate of the MHP14 or LIG3/4 target site (#events with modification/#events*100%). As shown in Table 2, target site mutation rate for both MHP14 and LIG34 was approximately 3× higher when embryos were placed at 32° C. for 48 hours after bombardment compared to no temperature elevation treatment.

Maize calli were also screened for integration of the transgene cassette from the donor DNA (PHP44285 or PHP44779) at the MHP14 target site through junction PCR and selected callus events were regenerated into T0 plants. FIG. 9A shows an outline of PCR screening for integration of the donor DNA fragment via homologous recombination at MHP14 target site (PHP44779 donor). Arrows indicate primer locations. FIG. 9B shows PCR of MHP14 callus events: B1-B12 Junction PCR with primers 146773/146775; b1-b12 Junction PCR with primers 146772/146778. Two events (B2 and B5) yielded the predicted 1-1.2 kb PCR fragments that result from integration by homologous recombination for both junctions. PCR products from T0 plants derived from these callus events were sequenced to verify the callus results. PCR screening revealed integration of the herbicide resistance transgene cassette at MHP14 target site. Primers were from the genomic region outside of the homology of donor vector and from the transgene cassette close to the end of the homology.

FIG. 10A shows a schematic outline of long fragment PCR reactions used to confirm UBI:moPAT:PinII cassette integration at the endogenous MHP14 target. FIG. 10B: shows the results of long fragment PCR on T0 plants from three events where integration occurred at the target site. The plant A5 was from event #1, A6-A8 event #2, and C4-C6 event #3. 10B-left shows the long junction fragment PCR on the HR1 side using genomic primer (146775) and moPAT primer (mopatR2); 10B-right shows the long junction fragment PCR on HR2 side (mopatF2/146772). Arrows indicated PCR primer locations. Primer set 146772/mopatF2 amplified a 4 kb fragment, spanning from moPAT gene through the UBI intron, UBI promoter, and the HR2 sequence to the adjacent genomic region. Primer set 146775/mopatR2 amplified a 2.2 kb fragment, spanning from the moPAT gene through the HR1 to the adjacent genomic region. These two fragments overlapped and covered the whole insert at MHP14 target site. The sizes of the two long PCR products indicate a perfect integration of the donor gene cassette at MHP14 target site To determine the segregation pattern of the integration events in progeny, T1 seeds from selfed T0 plants were planted in flats and T1 plants genotyped by using PCR and/or qPCR. The segregation ratio of integration genotypes fit 1:2:1 for wild type (no integration), heterozygous (one allele having integration and the other wild-type) and homozygous integration of the transgene at the MHP14 target site, demonstrating Mendelian inheritance. No visible phenotype was observed in the homozygous or heterozygous integration plants.

The entire inserted fragment of UBI:moPAT:PinII was obtained by using PCR on DNA from homozygous T1 plants with primers in the genomic region outside of the HR1 and HR2 (146772/146775). A PCR product of 5 kb was amplified from homozygous plants as expected. A 2 kb PCR product was amplified from the unmodified intact genomic sequence from wild-type plants.

Trait gene cassettes can be introduced at other target sites of the complex trait locus through homologous recombination mediated by engineered meganucleases. Engineered meganucleases were designed to direct double strand breaks a two other MHP target sites, MHP55 (SEQ ID NO: 72) and MHP77 (SEQ ID NO: 74) within the complex trait locus. Target site modification was determined using qPCR. The probe sequence for qPCR screening of the MHP55 target site was AACCGTCGTGAGACCT (SEQ ID NO: 115), the MHPTS55_Forward_MGBprimer sequence was AAGGCGCAGCCGTTGAG (SEQ ID NO: 116), and MHP55_reverse_MGB primer was CTACCGGTTTCGCGTGCTCT (SEQ ID NO: 117). The probe sequence for qPCR of MHP77 target site was TAGTAT- GACATACATACCGCC (SEQ ID NO: 118), the MHPTS77_Forward_MGB primer sequence was TCCT-TAGGGCGGTATGTATGTCA (SEQ ID NO: 119), and MHP77_reverse_MGB primer was CATCGGT-CAAAAAACACATAAACTTT (SEQ ID NO: 120). The trait gene cassettes encoding MHP14, MHP55 and MHP77 were introduced into maize somatic embryos via transformation techniques using bombardment and following bombardment, embryos were incubated on 560P (maintenance medium) for 48 hours at. As shown in Table 3, maize callus containing the MHP55 target site bombarded with PHP45782 or PHP46924 which include genes encoding MHP55 or MHP55.2 meganucleases, respectively, also lead to an observed increase in the target site mutation rate modified MHP55.2 variant. In addition, maize callus containing a MHP77 target site bombarded with vectors PHP45970 or PHP50238 which include genes encoding MHP77 or MHP77.3 meganucleases, respectively, showed a higher frequency of mutated target sites from callus bombarded with the modified variant MHP77.3. Taken together, like MHP14, these meganucleases directed mutations to their corresponding target sites and modified versions lead to an increase in the target site mutation rate (approx 2 to 10-fold increase when compared to their original versions) suggesting the newly designed versions of the meganucleases were more active than the original nucleases.

TABLE 3

Meganuclease activity (defined as target site mutation rate) of original and modified meganucleases

| Meganuclease | Target Site Mutation Rate |
| --- | --- |
| MHP55 | 0% |
| MHP55-2 | 5% |
| MHP77 | 1% |
| MHP77-3 | 11% |
| MHP14 | 29% |
| MHP14+ | 40% |

The mutations observed at these target sites indicated that the engineered meganucleases were functional and that the target sites can be used for integration of additional trait genes.

E. Production of a Complex Trait Locus at a Maize Endogenous Locus by Crossing

A maize event obtained through random integration containing a transgene DNA of interest was identified and MHP14, MHP55 and MHP77 target sites surrounding the transgenic DNA of interest were identified as described above. Other maize events containing a modification at the MHP14, MHP55 and MHP77 target site (through addition of herbicide resistance gene as described above) were also identified.

Plants homozygous for the integration of a herbicide resistance gene at the MHP14 target site were crossed with homozygous maize plants containing the transgene DNA of interest. The cross resulted in fertile plants producing F1 seeds. The F1 seeds were planted and out-crossed with Elite inbred line plants and screened for the stacked phenotype. Additional trait genes can be added to the complex trait locus by crossing one transgenic event containing n-transgenes with other trangenic events containing the additional trait gene at the additional target site, and progeny can be screened for the presence of n+1 transgenes. This process can be repeated as many times as the amount of target sites are present in the complex trait locus.

F. Production of a Complex Trait Locus at a Maize Endogenous Locus by Serial Transformation A complex trait locus can be also be created by serial transformation. A first transformed line containing a first trait gene integrated at a first MHP target site can be used to supply embryos. The first transformed line can be retransformed with a second trait gene and a vector encoding a second engineered meganuclease; resulting in the second trait gene being integrated at a second MHP target site through homologous recombination mediated by the second engineered meganuclease. The homozygous integration plants containing a selectable marker at the MHP14 target site can be used to supply embryos. Two rounds of transformations will create two traits at the MHP locus. A transformed line that is homozygous for integration events with two trait genes at MHP target sites can be used to supply embryos for another retransformation, and a third trait gene can be introduced to a third target site.

Example 6

Transformation of Maize Immature Embryos

Transformation can be accomplished by various methods known to be effective in plants, including particle-mediated delivery, *Agrobacterium*-mediated transformation, PEG-mediated delivery, and electroporation.

a. Particle-Mediated Delivery

Transformation of maize immature embryos using particle delivery is performed as follows. Media recipes follow below.

The ears are husked and surface sterilized in 30% Clorox bleach plus 0.5% Micro detergent for 20 minutes, and rinsed two times with sterile water. The immature embryos are isolated and placed embryo axis side down (scutellum side up), 25 embryos per plate, on 560Y medium for 4 hours and then aligned within the 2.5-cm target zone in preparation for bombardment. Alternatively, isolated embryos are placed on 560L (Initiation medium) and placed in the dark at temperatures ranging from 26° C. to 37° C. for 8 to 24 hours prior to placing on 560Y for 4 hours at 26° C. prior to bombardment as described above.

A plasmid comprising the Zm-BBM (also referred to as Zm-ODP2) coding sequence (set forth in SEQ ID NO: 9) operably linked to a promoter is constructed. This could be a weak promoter such as nos, a tissue-specific promoter, such as globulin-1 or oleosin, an inducible promoter such as In2, or a strong promoter such as ubiquitin plus a plasmid containing the selectable marker gene phosphinothricin N-acetyltransferase (PAT; Wohlleben et al. (1988) *Gene* 70:25 37) that confers resistance to the herbicide bialaphos. Furthermore, plasmids containing the double strand brake inducing agent and donor DNA such as PHP44285 or PHP44779 are constructed as described above and co-bombareded with the plasmids containing the developmental genes ODP2 (AP2 domain transcription factor ODP2 (Ovule development protein 2); US20090328252 A1) and Wushel.

The plasmids are precipitated onto 1.1 μm (average diameter) tungsten pellets using a calcium chloride (CaCl$_2$) precipitation procedure by mixing 100 μl prepared tungsten particles in water, 10 μl (1 μg) DNA in Tris EDTA buffer (1 μg total DNA), 100 μl 2.5 M CaCl$_2$, and 10 μl 0.1 M spermidine. Each reagent is added sequentially to the tungsten particle suspension, with mixing. The final mixture is sonicated briefly and allowed to incubate under constant vortexing for 10 minutes. After the precipitation period, the tubes are centrifuged briefly, liquid is removed, and the particles are washed with 500 ml 100% ethanol, followed by a 30 second centrifugation. Again, the liquid is removed, and 105 µl 100% ethanol is added to the final tungsten particle pellet. For particle gun bombardment, the tungsten/DNA particles are briefly sonicated. 10 µl of the tungsten/DNA particles is spotted onto the center of each macrocarrier, after which the spotted particles are allowed to dry about 2 minutes before bombardment.

The sample plates are bombarded at level #4 with a Biorad Helium Gun. All samples receive a single shot at 450 PSI, with a total of ten aliquots taken from each tube of prepared particles/DNA.

Following bombardment, the embryos are incubated on 560P (maintenance medium) for 12 to 48 hours at temperatures ranging from 26 C to 37 C, and then placed at 26 C. After 5 to 7 days the embryos are transferred to 560R selection medium containing 3 mg/liter Bialaphos, and subcultured every 2 weeks at 26 C. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to a lighted culture room. Approximately 7-10 days later, developing plantlets are transferred to 272V hormone-free medium in tubes for 7-10 days until plantlets are well established. Plants are then transferred to inserts in flats (equivalent to a 2.5" pot) containing potting soil and grown for 1 week in a growth chamber, subsequently grown an additional 1-2 weeks in the greenhouse, then transferred to Classic 600 pots (1.6 gallon) and grown to maturity. Plants are monitored and scored for transformation efficiency, and/or modification of regenerative capabilities.

Initiation medium (560L) comprises 4.0 g/l N6 basal salts (SIGMA C-1416), 1.0 ml/l Eriksson's Vitamin Mix (1000× SIGMA-1511), 0.5 mg/l thiamine HCl, 20.0 g/l sucrose, 1.0 mg/l 2,4-D, and 2.88 g/l L-proline (brought to volume with D-I H2O following adjustment to pH 5.8 with KOH); 2.0 g/l Gelrite (added after bringing to volume with D-I H2O); and 8.5 mg/l silver nitrate (added after sterilizing the medium and cooling to room temperature).

Maintenance medium (560P) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, 2.0 mg/l 2,4-D, and 0.69 g/l L-proline (brought to volume with D-I H2O following adjustment to pH 5.8 with KOH); 3.0 g/l Gelrite (added after bringing to volume with D-I H2O); and 0.85 mg/l silver nitrate (added after sterilizing the medium and cooling to room temperature).

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I H2O following adjustment to pH 5.8 with KOH); 2.0 g/l Gelrite (added after bringing to volume with D-I H2O); and 8.5 mg/l silver nitrate (added after sterilizing the medium and cooling to room temperature).

Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I H2O following adjustment to pH 5.8 with KOH); 3.0 g/l Gelrite (added after bringing to volume with D-I H2O); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H2O) (Murashige and Skoog (1962) Physiol. Plant. 15:473), 100 mg/l myo-inositol, 0.5 mg/l zeatin, 60 g/l sucrose, and 1.0 ml/l of 0.1 mM abscisic acid (brought to volume with polished D-I H2O after adjusting to pH 5.6); 3.0 g/l Gelrite (added after bringing to volume with D-I H2O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H2O), 0.1 g/l myo-inositol, and 40.0 g/l sucrose (brought to volume with polished D-I H2O after adjusting pH to 5.6); and 6 g/l bacto-agar (added after bringing to volume with polished D-I H2O), sterilized and cooled to 60° C.

b. *Agrobacterium*-Mediated Transformation

*Agrobacterium*-mediated transformation was performed essentially as described in Djukanovic et al. (2006) *Plant Biotech J* 4:345-57. Briefly, 10-12 day old immature embryos (0.8-2.5 mm in size) were dissected from sterilized kernels and placed into liquid medium (4.0 g/L N6 Basal Salts (Sigma C-1416), 1.0 ml/L Eriksson's Vitamin Mix (Sigma E-1511), 1.0 mg/L thiamine HCl, 1.5 mg/L 2,4-D, 0.690 g/L L-proline, 68.5 g/L sucrose, 36.0 g/L glucose, pH 5.2). After embryo collection, the medium was replaced with 1 ml *Agrobacterium* at a concentration of 0.35-0.45 OD550. Maize embryos were incubated with *Agrobacterium* for 5 min at room temperature, then the mixture was poured onto a media plate containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2,4-D, 0.690 g/L L-proline, 30.0 g/L sucrose, 0.85 mg/L silver nitrate, 0.1 nM acetosyringone, and 3.0 g/L Gelrite, pH 5.8. Embryos were incubated axis down, in the dark for 3 days at 20° C., then incubated 4 days in the dark at 28° C., then transferred onto new media plates containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2,4-D, 0.69 g/L L-proline, 30.0 g/L sucrose, 0.5 g/L MES buffer, 0.85 mg/L silver nitrate, 3.0 mg/L Bialaphos, 100 mg/L carbenicillin, and 6.0 g/L agar, pH 5.8. Embryos were subcultured every three weeks until transgenic events were identified. Somatic embryogenesis was induced by transferring a small amount of tissue onto regeneration medium (4.3 g/L MS salts (Gibco 11117), 5.0 ml/L MS Vitamins Stock Solution, 100 mg/L myo-inositol, 0.1 µM ABA, 1 mg/L IAA, 0.5 mg/L zeatin, 60.0 g/L sucrose, 1.5 mg/L Bialaphos, 100 mg/L carbenicillin, 3.0 g/L Gelrite, pH 5.6) and incubation in the dark for two weeks at 28° C. All material with visible shoots and roots were transferred onto media containing 4.3 g/L MS salts (Gibco 11117), 5.0 ml/L MS Vitamins Stock Solution, 100 mg/L myo-inositol, 40.0 g/L sucrose, 1.5 g/L Gelrite, pH 5.6, and incubated under artificial light at 28° C. One week later, plantlets were moved into glass tubes containing the same medium and grown until they were sampled and/or transplanted into soil.

Example 7

Transient Expression of BBM Enhances Transformation

Parameters of the transformation protocol can be modified to ensure that the BBM activity is transient. One such method involves precipitating the BBM-containing plasmid in a manner that allows for transcription and expression, but precludes subsequent release of the DNA, for example, by using the chemical PEI. In one example, the BBM plasmid is precipitated onto gold particles with PEI, while the transgenic expression cassette (UBI::moPAT~GFPm::PinII; moPAT is the maize optimized PAT gene) to be integrated is precipitated onto gold particles using the standard calcium chloride method.

Briefly, gold particles were coated with PEI as follows. First, the gold particles were washed. Thirty-five mg of gold particles, 1.0 in average diameter (A.S.I. #162-0010), were weighed out in a microcentrifuge tube, and 1.2 ml absolute EtOH was added and vortexed for one minute. The tube was incubated for 15 minutes at room temperature and then centrifuged at high speed using a microfuge for 15 minutes at 4° C. The supernatant was discarded and a fresh 1.2 ml aliquot of ethanol (EtOH) was added, vortexed for one minute, centrifuged for one minute, and the supernatant again discarded (this is repeated twice). A fresh 1.2 ml aliquot of EtOH was added, and this suspension (gold particles in EtOH) was stored at −20° C. for weeks. To coat particles with polyethylimine (PEI; Sigma #P3143), 250 µl of the washed gold particle/EtOH mix was centrifuged and the EtOH discarded. The particles were washed once in 100 µl ddH2O to remove residual ethanol, 250 µl of 0.25 mM PEI was added, followed by a pulse-sonication to suspend the particles and then the tube was plunged into a dry ice/EtOH bath to flash-freeze the suspension, which was then lyophilized overnight. At this point, dry, coated particles could be stored at −80° C. for at least 3 weeks. Before use, the particles were rinsed 3 times with 250 µl aliquots of 2.5 mM HEPES buffer, pH 7.1, with 1× pulse-sonication, and then a quick vortex before each centrifugation. The particles were then suspended in a final volume of 250 µl HEPES buffer. A 25 µl aliquot of the particles was added to fresh tubes before attaching DNA. To attach uncoated DNA, the particles were pulse-sonicated, then 1 µg of DNA (in 5 µl water) was added, followed by mixing by pipetting up and down a few times with a Pipetteman and incubated for 10 minutes. The particles were spun briefly (i.e. 10 seconds), the supernatant removed, and 60 µl EtOH added. The particles with PEI-precipitated DNA-1 were washed twice in 60 µl of EtOH. The particles were centrifuged, the supernatant discarded, and the particles were resuspended in 45 µl water. To attach the second DNA (DNA-2), precipitation using TFX-50 was used. The 45 µl of particles/DNA-1 suspension was briefly sonicated, and then 5 µl of 100 ng/µl of DNA-2 and 2.5 µl of TFX-50 were added. The solution was placed on a rotary shaker for 10 minutes, centrifuged at 10,000 g for 1 minute. The supernatant was removed, and the particles resuspended in 60 µl of EtOH. The solution was spotted onto macrocarriers and the gold particles onto which DNA-1 and DNA-2 had been sequentially attached were delivered into scutellar cells of 10 DAP Hi-II immature embryos using a standard protocol for the PDS-1000. For this experiment, the DNA-1 plasmid contained a UBI::RFP::pinII expression cassette, and DNA-2 contained a UBI::CFP::pinII expression cassette. Two days after bombardment, transient expression of both the CFP and RFP fluorescent markers was observed as numerous red & blue cells on the surface of the immature embryo. The embryos were then placed on non-selective culture medium and allowed to grow for 3 weeks before scoring for stable colonies. After this 3-week period, 10 multicellular, stably-expressing blue colonies were observed, in comparison to only one red colony. This demonstrated that PEI-precipitation could be used to effectively introduce DNA for transient expression while dramatically reducing integration of the PEI-introduced DNA and thus reducing the recovery of RFP-expressing transgenic events. In this manner, PEI-precipitation can be used to deliver transient expression of BBM and/or WUS2.

For example, the particles are first coated with UBI::BBM::pinII using PEI, then coated with UBI::moPAT~YFP using TFX-50, and then bombarded into scutellar cells on the surface of immature embryos. PEI-mediated precipitation results in a high frequency of transiently expressing cells on the surface of the immature embryo and extremely low frequencies of recovery of stable transformants (relative to the TFX-50 method). Thus, it is expected that the PEI-precipitated BBM cassette expresses transiently and stimulates a burst of embryogenic growth on the bombarded surface of the tissue (i.e. the scutellar surface), but this plasmid will not integrate. The PAT~GFP plasmid released from the Ca++/gold particles is expected to integrate and express the selectable marker at a frequency that results in substantially improved recovery of transgenic events. As a control treatment, PEI-precipitated particles containing a UBI::GUS::pinII (instead of BBM) are mixed with the PAT~GFP/Ca++ particles. Immature embryos from both treatments are moved onto culture medium containing 3 mg/l bialaphos. After 6-8 weeks, it is expected that GFP+, bialaphos-resistant calli will be observed in the PEI/BBM treatment at a much higher frequency relative to the control treatment (PEI/GUS).

As an alternative method, the BBM plasmid is precipitated onto gold particles with PEI, and then introduced into scutellar cells on the surface of immature embryos, and subsequent transient expression of the BBM gene elicits a rapid proliferation of embryogenic growth. During this period of induced growth, the explants are treated with *Agrobacterium* using standard methods for maize (see Example 1), with T-DNA delivery into the cell introducing a transgenic expression cassette such as UBI::moPAT~GFPm::pinII. After co-cultivation, explants are allowed to recover on normal culture medium, and then are moved onto culture medium containing 3 mg/l bialaphos. After 6-8 weeks, it is expected that GFP+, bialaphos-resistant calli will be observed in the PEI/BBM treatment at a much higher frequency relative to the control treatment (PEI/GUS).

It may be desirable to "kick start" callus growth by transiently expressing the BBM and/or WUS2 polynucleotide products. This can be done by delivering BBM and WUS2 5'-capped polyadenylated RNA, expression cassettes containing BBM and WUS2 DNA, or BBM and/or WUS2 proteins. All of these molecules can be delivered using a biolistics particle gun. For example 5'-capped polyadenylated BBM and/or WUS2 RNA can easily be made in vitro using Ambion's mMessage mMachine kit. RNA is co-delivered along with DNA containing a polynucleotide of interest and a marker used for selection/screening such as Ubi::moPAT~GFPm::PinII. It is expected that the cells receiving the RNA will immediately begin dividing more rapidly and a large portion of these will have integrated the agronomic gene. These events can further be validated as being transgenic clonal colonies because they will also express the PAT~GFP fusion protein (and thus will display green fluorescence under appropriate illumination). Plants regenerated from these embryos can then be screened for the presence of the polynucleotide of interest.

Although the foregoing invention has been described in some detail by way of illustration and example for purposes of clarity of understanding, it will be obvious that certain changes and modifications may be practiced within the scope of the appended claims.

That which is claimed:

1. A maize plant comprising a complex transgenic trait locus, the trait locus comprising at least first and second altered target sequences, wherein the first altered target sequence originated from a first endogenous target sequence that is recognized and cleaved by a first engineered double-strand-break-inducing agent and the second altered target sequence originated from a second endogenous target sequence that is recognized and cleaved by a second engineered double-strand break-inducing agent, wherein each of said altered target sequences differ from their corresponding endogenous target sequence, wherein the first and second endogenous target sequences are located on the same arm of the same chromosome, wherein each of the alterations comprises a transgene, and wherein at least one of the endogenous target sequences is selected from the group consisting of SEQ ID NOs: 69 and 72.

2. The maize plant of claim 1, wherein the transgene is selected from the group consisting of DNA for gene silencing, DNA encoding a phenotypic marker and DNA encoding a protein providing an agronomic advantage.

3. A seed of the maize plant of claim 1, comprising said complex transgenic trait locus.

* * * * *